US012151050B2

(12) United States Patent
Williams et al.

(10) Patent No.: US 12,151,050 B2
(45) Date of Patent: Nov. 26, 2024

(54) MEDICAL DEVICES CONTAINING COMPOSITIONS OF POLY(BUTYLENE SUCCINATE) AND COPOLYMERS THEREOF

(71) Applicant: Tepha, Inc., Lexington, MA (US)

(72) Inventors: Simon F. Williams, Cambridge, MA (US); Said Rizk, Windham, NH (US); David P. Martin, Arlington, MA (US); Skander Limem, Lynnfield, MA (US); Kai Guo, Belmont, MA (US); Amit Ganatra, Attleboro, MA (US); German Oswaldo Hohl Lopez, Lexington, MA (US)

(73) Assignee: Tepha, Inc., Lexington, MA (US)

( * ) Notice: Subject to any disclaimer, the term of this patent is extended or adjusted under 35 U.S.C. 154(b) by 1096 days.

(21) Appl. No.: 17/006,712

(22) Filed: Aug. 28, 2020

(65) Prior Publication Data
US 2021/0046212 A1    Feb. 18, 2021

Related U.S. Application Data

(63) Continuation-in-part of application No. 16/290,718, filed on Mar. 1, 2019.
(Continued)

(51) Int. Cl.
*A61L 31/06* (2006.01)
*A61B 17/04* (2006.01)
*A61B 17/72* (2006.01)
*A61B 17/80* (2006.01)
*A61B 17/86* (2006.01)
*A61F 2/00* (2006.01)
*A61F 2/12* (2006.01)
*A61F 2/30* (2006.01)
*A61L 17/10* (2006.01)
*A61L 27/18* (2006.01)
*A61L 27/56* (2006.01)
*A61L 27/58* (2006.01)
*A61L 31/14* (2006.01)
*B29C 45/00* (2006.01)
(Continued)

(52) U.S. Cl.
CPC .......... *A61L 31/06* (2013.01); *A61B 17/0401* (2013.01); *A61B 17/72* (2013.01); *A61B 17/80* (2013.01); *A61B 17/8095* (2013.01); *A61B 17/866* (2013.01); *A61F 2/0063* (2013.01); *A61F 2/12* (2013.01); *A61F 2/30756* (2013.01); *A61L 17/105* (2013.01); *A61L 27/18* (2013.01); *A61L 27/56* (2013.01); *A61L 27/58* (2013.01); *A61L 31/146* (2013.01); *B29C 45/0001* (2013.01); *B29C 48/022* (2019.02); *B29C 48/05* (2019.02); *B29C 48/08* (2019.02); *B29C 70/52* (2013.01); *B33Y 10/00* (2014.12); *B33Y 80/00* (2014.12); *C08G 63/16* (2013.01); *C08G 63/85* (2013.01); *C08J 5/02* (2013.01); *C08L 67/02* (2013.01); *D01D 5/08* (2013.01); *D01D 5/082* (2013.01); *D04B 1/16* (2013.01); *D04B 1/22* (2013.01); *A61B 2017/00526* (2013.01); *A61F 2240/001* (2013.01); *A61L 2430/02* (2013.01); *A61L 2430/04* (2013.01); *A61L 2430/06* (2013.01); *A61L 2430/10* (2013.01); *A61L 2430/34* (2013.01); *B29K 2067/00* (2013.01); *B29K 2105/0085* (2013.01); *B29L 2031/7532* (2013.01); *B29L 2031/7546* (2013.01); *C08J 2367/02* (2013.01); *D10B 2331/04* (2013.01); *D10B 2509/04* (2013.01)

(58) Field of Classification Search
None
See application file for complete search history.

(56) References Cited

U.S. PATENT DOCUMENTS 5,349,028 A    9/1994    Takahashi
7,317,069 B2   1/2008    Aoshima
(Continued)

FOREIGN PATENT DOCUMENTS

CN    105903073    8/2016
CN    106957434    7/2017
(Continued)

OTHER PUBLICATIONS

International Search Report and Written Opinion mailed Jul. 3, 2019 for International Application No. PCT/US2019/020348.
(Continued)

*Primary Examiner* — Nannette Holloman
(74) *Attorney, Agent, or Firm* — Wolf, Greenfield & Sacks, P.C.

(57) ABSTRACT

Resorbable implants, coverings and receptacles comprising poly(butylene succinate) and copolymers thereof have been developed. The implants are preferably sterilized, and contain less than 20 endotoxin units per device as determined by the limulus amebocyte lysate (LAL) assay, and are particularly suitable for use in procedures where prolonged strength retention is necessary, and can include one or more bioactive agents. The implants may be made from fibers and meshes of poly(butylene succinate) and copolymers thereof, or by 3d printing molding, pultrusion or other melt or solvent processing method. The implants, or the fibers preset therein, may be oriented. These coverings and receptacles may be used to hold, or partially/fully cover, devices such as pacemakers and neurostimulators. The coverings, receptacles and implants described herein, may be made from meshes, webs, lattices, non-wovens, films, fibers, foams, molded, pultruded, machined and 3D printed forms.

16 Claims, 16 Drawing Sheets

Related U.S. Application Data

(60) Provisional application No. 62/893,565, filed on Aug. 29, 2019, provisional application No. 62/733,384, filed on Sep. 19, 2018, provisional application No. 62/636,930, filed on Mar. 1, 2018.

(51) Int. Cl.

| | | |
|---|---|---|
| *B29C 48/00* | (2019.01) | |
| *B29C 48/05* | (2019.01) | |
| *B29C 48/08* | (2019.01) | |
| *B29C 70/52* | (2006.01) | |
| *B33Y 10/00* | (2015.01) | |
| *B33Y 80/00* | (2015.01) | |
| *C08G 63/16* | (2006.01) | |
| *C08G 63/85* | (2006.01) | |
| *C08J 5/02* | (2006.01) | |
| *C08L 67/02* | (2006.01) | |
| *D01D 5/08* | (2006.01) | |
| *D04B 1/16* | (2006.01) | |
| *D04B 1/22* | (2006.01) | |
| *A61B 17/00* | (2006.01) | |
| *B29K 67/00* | (2006.01) | |
| *B29K 105/00* | (2006.01) | |
| *B29L 31/00* | (2006.01) | |

(56) References Cited

U.S. PATENT DOCUMENTS

| | | | |
|---|---|---|---|
| 7,700,500 | B2 | 4/2010 | Jordan |
| 7,972,692 | B2 | 7/2011 | Chakravarty |
| 8,680,229 | B2 | 3/2014 | Maeda |
| 8,747,974 | B2 | 6/2014 | Nakano |
| 10,058,639 | B2 | 8/2018 | Zhang |
| 10,595,983 | B1 | 3/2020 | Ferguson |
| 10,689,498 | B2 | 6/2020 | Connelly et al. |
| 10,994,057 | B2 | 5/2021 | Williams et al. |
| 11,292,885 | B1 | 4/2022 | Connelly et al. |
| 11,786,632 | B2 | 10/2023 | Williams et al. |
| 11,878,087 | B2 | 1/2024 | Williams et al. |
| 2005/0027098 | A1 | 2/2005 | Hayes |
| 2008/0147165 | A1 | 6/2008 | Hossainy |
| 2008/0287024 | A1 | 11/2008 | Chakravarty et al. |
| 2009/0171037 | A1 | 7/2009 | Aoshima |
| 2010/0249332 | A1 | 9/2010 | Ferguson |
| 2010/0249361 | A1 | 9/2010 | Wang |
| 2011/0293685 | A1 | 12/2011 | Kuo et al. |
| 2012/0283826 | A1 | 11/2012 | Moses |
| 2013/0090521 | A1 | 4/2013 | Lau |
| 2013/0267972 | A1 | 10/2013 | Peniston et al. |
| 2014/0276995 | A1 | 9/2014 | Lau |
| 2015/0148514 | A1 | 5/2015 | Makal |
| 2015/0258238 | A1 | 9/2015 | Ferguson |
| 2016/0166727 | A1 | 6/2016 | Ganatra et al. |
| 2019/0269815 | A1 | 9/2019 | Williams et al. |
| 2019/0269816 | A1 | 9/2019 | Williams |
| 2019/0269817 | A1 | 9/2019 | Williams et al. |
| 2019/0269822 | A1 | 9/2019 | Williams et al. |
| 2020/0390933 | A1 | 12/2020 | Williams et al. |
| 2020/0390944 | A1 | 12/2020 | Williams et al. |
| 2021/0047484 | A1 | 2/2021 | Williams et al. |
| 2021/0244860 | A1 | 8/2021 | Williams et al. |
| 2022/0202988 | A1 | 6/2022 | Williams et al. |
| 2023/0414829 | A1 | 12/2023 | Williams et al. |

FOREIGN PATENT DOCUMENTS

| | | |
|---|---|---|
| IN | 201641013616 | 4/2016 |
| JP | H07-011517 A | 1/1995 |
| JP | H07-173715 A | 7/1995 |
| JP | H08-134719 A | 5/1996 |
| JP | H08-158154 A | 6/1996 |
| JP | H09-41220 A | 2/1997 |
| JP | H09-195122 A | 7/1997 |
| JP | H10-99424 A | 4/1998 |
| JP | 2000-282357 A | 10/2000 |
| JP | 2007-92048 A | 4/2007 |
| JP | 2007-215803 A | 8/2007 |
| JP | 2007-222277 A | 9/2007 |
| JP | 2008-95212 A | 4/2008 |
| JP | 2013-042914 A | 3/2013 |
| JP | 2016124935 | 7/2016 |
| WO | 2006/115226 A1 | 11/2006 |
| WO | 2014173055 | 10/2014 |
| WO | 2016192632 | 12/2016 |

OTHER PUBLICATIONS

International Search Report and Written Opinion mailed Dec. 10, 2020 for International Application No. PCT/US2020/048773.

International Preliminary Report on Patentability mailed Nov. 12, 2021 for International Application No. PCT/US2020/048773.

Ji et al., Morphology, rheology, crystallization behavior, and mechanical properties of poly(lactic acid)/poly(butylene succinate)/dicumyl peroxide reactive blends. J App Polym Sci. Sep. 9, 2013;131(3):39580. doi: /10.1002/app.39580.

Costa-Pinto, et al., "Chitosan-poly(butylene succinate) scaffolds and human bone marrow stromal cells induce bone repair in a mouse calvaria model", J. of Tissue Eng. and Regen. Med., 6:21-28 (2012).

De Geyter, et al., "Non-Thermal Plasma Surface Modification of Biodegradable polymers", Biomedical Science, Engineering and Technology, 10:225-248 (2012).

Gigli, et al., "Poly (butylene succinate)-based polyesters for biomedical applications: A review", Eur. Polym. J., 75:431-460 (2016).

International Search Report for PCT/US2019/020348 dated Jul. 3, 2019.

International Search Report for PCT/US2020/048773 dated Dec. 10, 2020.

Kun, et al., "Biocompatibility of a Novel Poly (butyl succinate) and Polylactic Acid Blend", ASAIO Journal, 58:262-267 (2012).

Li, et al., "in vitro Evaluation of Biodegradable Poly (butylene succinate) as a Novel Biomaterial", Macromol. Biosci., 5:433-440 (2005).

Manavitehrani, et al., "Biomedical Applications of Biodegradable Polyesters", Polymers, 8:20-52 (2016).

Vandesteene, et al., "Synthesis of Branched Poly (butylene succinate): Structure Properties Relationship", Chin. J. Polym. Sci., 34(7):873-888 (2016).

Wang, et al., "Biocompatibility and bioactivity of plasma-treated biodegradable poly (butylene succinate)", Acta Biomaterialia, 5(1):279-287 (2009).

Xu, et al., "Poly(butylene succinate) and its copolymers: Research, development and industrialization", Biotechnol. J. 5:1149-1163 (2010).

Definition of "mastopexy". Accessed online on Feb. 10, 2021 at https://www.plasticsurgery.org. (Year: 2021)*A.

Definition of "orient". Accessed online on Feb. 10, 2021 at https://www.collinsdictionary.com. (Year: 2021).

Definition of "Rhytidectomy". Accessed online on Feb. 10, 2021 at https://www.plasticsurgery.org. (Year: 2021).

Food and Drug Administration's Guidance for Industry Pyrogen and Endotoxins Testing: Questions and Answers (Jun. 2012) accessed online on Feb. 11, 2021 at https://www.fda.gov. (Year: 2012).

Jacquel, et al., "Synthesis and Properties of Poly(butylene succinate): Efficiency of Different Transesterification Catalysts", Journal of Polymer Science, Part A: Polymer Chemistry, 48:5301-5312, (2011).

Ojansivu et al. "Knitted 3D Scaffolds of Polybutylene Succinate Support Human Mesenchymal Stem Cell Growth and Osteogenesis", Stem Cells International, vol. 2018, Article ID 5928935, 11 pages, May 2018. (Year: 2018).

Polybutylene Succinate, polymer properties database. Accessed online on Feb. 12, 2021 at https://polymerdatabase.com (Year: 2021).

(56) References Cited

OTHER PUBLICATIONS

Ribeiro, et al., "Evaluation of Novel 3D Architectures Based on Knitting Technologies for Engineering Biological Tissues", International Conference on Medical Textiles and Healthcare Products, MedTex13, Raleigh, NC, USA (2013).
U.S. Appl. No. 17/006,705 filed Aug. 28, 2020, Williams.

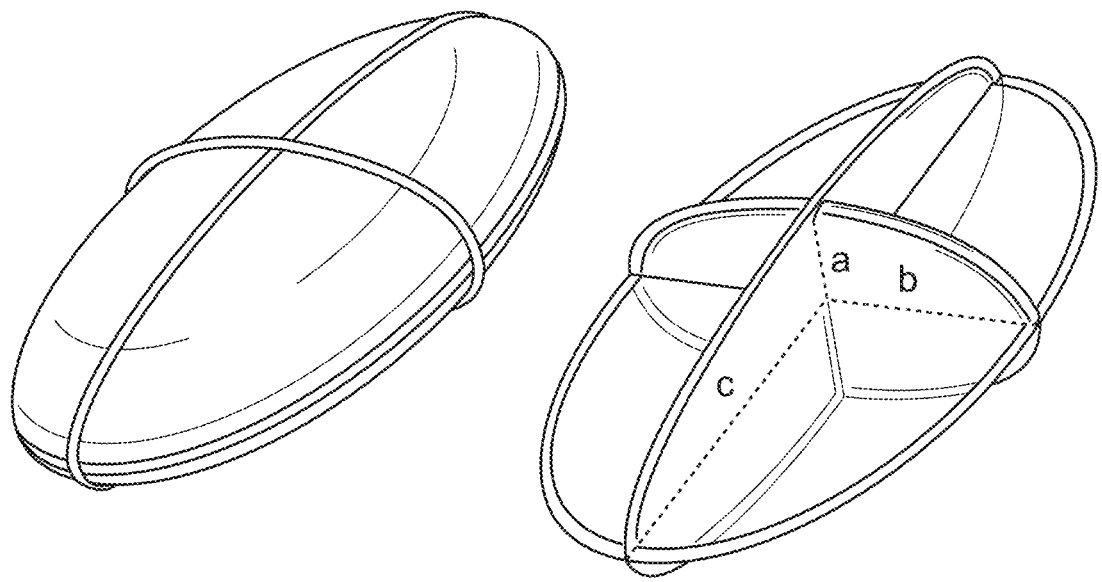
FIG. 9A  FIG. 9B
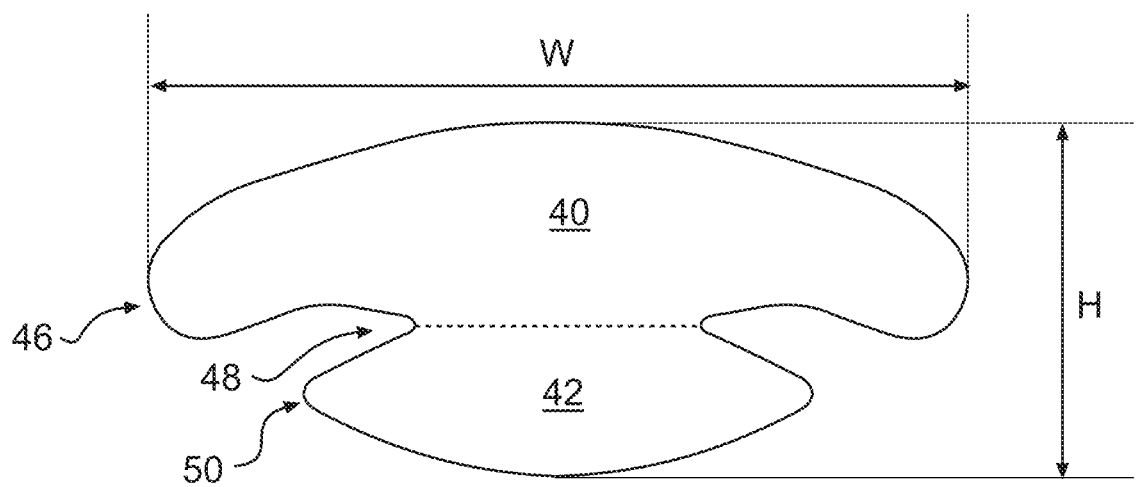
FIG. 10

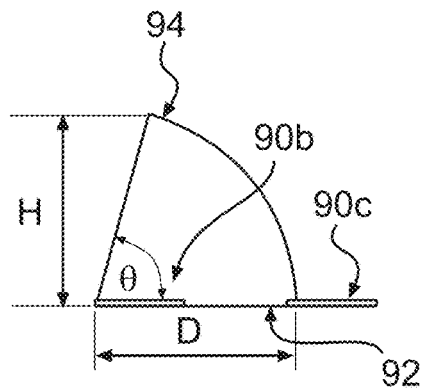
FIG. 16D
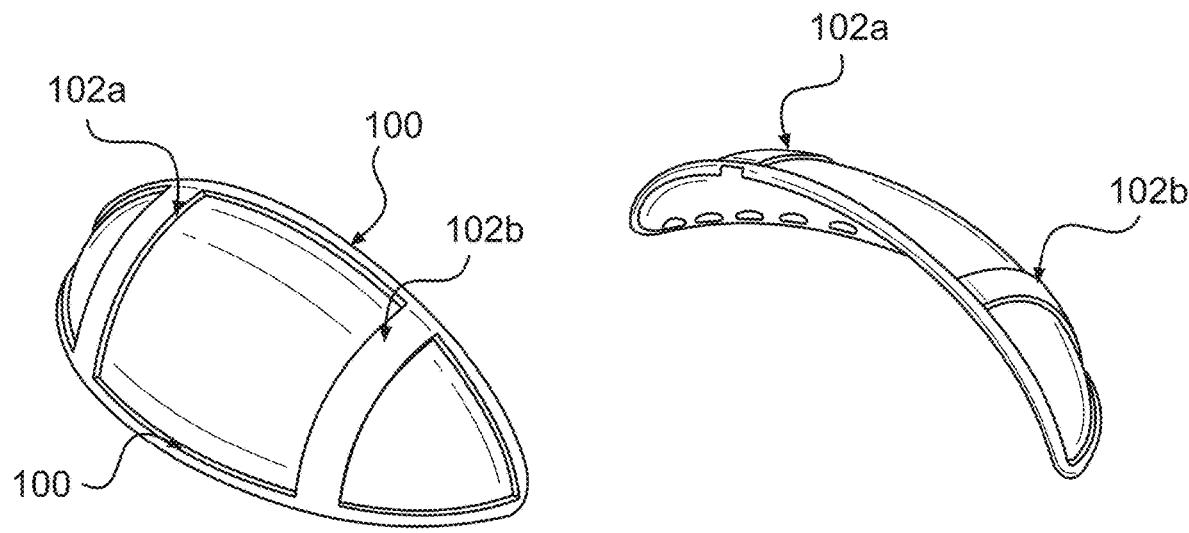
FIG. 17A
FIG. 17B

MEDICAL DEVICES CONTAINING COMPOSITIONS OF POLY(BUTYLENE SUCCINATE) AND COPOLYMERS THEREOF

CROSS REFERENCE TO RELATED APPLICATIONS

This application claims benefit of U.S. Provisional Application No. 62/893,565, filed Aug. 29, 2019, and is a continuation-in-part of U.S. application Ser. No. 16/290,718, filed Mar. 1, 2019, which claims the benefit of and priority to U.S. Application No. 62/636,930, filed Mar. 1, 2018 and U.S. Application No. 62/733,384, filed on Sep. 19, 2018, all of which which are hereby incorporated herein by reference in their entirety.

FIELD OF THE INVENTION

The present invention generally relates to resorbable polymeric compositions that can be processed into implants or coverings and receptacles for implants. The implants contain poly(butylene succinate) and copolymers thereof.

BACKGROUND OF THE INVENTION

Multifilament products made from resorbable polymers, such as copolymers of glycolide and lactide, and monofilament products made from resorbable polymers, such as polydioxanone (PDO), are well known in the prior art, and widely used in wound closure and general surgery. However, these products undergo rapid loss of strength retention in vivo, which limits their application primarily to fast healing repairs, and repairs where prolonged strength retention is not necessary. For example, while a surgeon may use a resorbable multifilament suture to approximate soft tissue that is not under significant tension, a surgeon will generally not use a resorbable suture when loads on the suture can be very high and remain high for a prolonged period, such as in rotator cuff repairs. Instead, surgeons will typically use permanent sutures for rotator cuff repairs even though it would be desirable to use a suture that is completely resorbed once healing is complete. Similarly, a surgeon may use a resorbable monofilament suture or mesh to approximate soft tissue that is not under significant tension, but will generally not use a resorbable monofilament suture or mesh when loads on the device can be very high and remain high for a prolonged period, such as in hernia repair. Instead, surgeons will typically use permanent (e.g. polypropylene) meshes for hernia repairs even though it would be desirable to use devices that completely resorb after healing is complete.

Recently, an aliphatic polyester, poly(butylene succinate) (PBS) has been commercialized for use in industrial applications such as paper coatings, packaging, and mulch films (U.S. Pat. No. 7,317,069 to Aoshima, U.S. Pat. No. 8,680,229 to Maeda, U.S. Pat. No. 8,747,974 to Nakano, WO2014173055A1 to Xu, and US Patent Application 20100249332 to Ferguson.). The industrial polymer is produced through condensation polymerization from readily available starting materials, succinic acid and 1,4-butanediol. Xu and Guo, *Biotechnol. J.* 5:1149-1163 (2010) have reviewed the industrialization of the PBS polymer, Li et al. have evaluated poly(butylene succinate) in vitro (Li et al. *Macromol. Biosci.* 5:433-440 (2005)), Vandesteene et al. *Chin. J. Polym. Sci.*, 34(7):873-888 (2016) have studied the structure-property relationships of the polymer. Kun et al. *ASAIO Journal,* 58:262-267 (2012) have studied the biocompatibility of blends of PBS with polylactic acid, and Gigli et al. *Eur. Polym. J.,* 75:431-460 (2016) have reviewed the polymer's in vitro biocompatibility. WO2016192632 to Du et al. disclosed bone plates with three-dimensional structures. WO2014173055 to Xu et al. disclosed yarns produced with an orientation ratio of 1.2 to 1.85×, apparently in the context of making fabrics for garments. However, no FDA-approved implants containing poly(butylene succinate) or copolymers thereof have been successfully developed.

One reason that progress in developing implants made from PBS and copolymers thereof has been prevented is that the mechanical properties of the polymers were unsatisfactory, particularly when compared to alternative medical grade polymers. Low molecular weights of PBS and copolymers thereof were mainly responsible for the poor mechanical properties. In order to increase molecular weight, new methods of polymer synthesis have more recently been successfully developed, and industrial products made from PBS and copolymers thereof have now been introduced. These advances in improving molecular weight relied upon the use of isocyanate chemistry to increase the molecular weight of PBS, and provide polymers with good mechanical properties (U.S. Pat. No. 5,349,028). Unfortunately, this approach is not a good option for the development of biocompatible degradable implants due to the toxicity associated with isocyanate chemistry.

In the practice of surgery there currently exists a need for resorbable fibers, films and other polymeric articles with high tensile strength and prolonged strength retention. These fibers, including multifilament yarns and monofilament fibers, as wells as films and other polymeric articles would allow the surgeon to use resorbable devices instead of permanent devices when high strength is initially required, or when prolonged strength retention is necessary. For example, monofilament resorbable fibers with high strength and prolonged strength retention could be used to make monofilament surgical meshes suitable for hernia repair, breast reconstruction and mastopexy, treatment of stress urinary incontinence, and pelvic floor reconstruction and other applications for soft tissue support and reinforcement. Pelvic floor reconstruction includes treatment of pelvic organ prolapse, cystocele, urethrocele, uterine prolapse, vaginal fault prolapse, enterocele and rectocele. And multifilament yarns with high tenacity and prolonged strength retention could be used, for example, in the repair of the rotator cuff and other ligaments and tendons, as well as for hernia repair or breast lift procedures. Resorbable films with high strength and prolonged strength retention (including porous films with these characteristics) could be used for similar medical indications, including hernia repair, breast reconstruction, mastopexy, treatment of stress urinary incontinence, pelvic floor reconstruction, repair of the rotator cuff and other ligaments and tendons. Other processing techniques, such as 3D printing, including fused filament fabrication, could also be used to make implants with prolonged strength retention, including lattices and other porous constructs, suitable for use in, for example, hernia repair, breast reconstruction and mastopexy, treatment of stress urinary incontinence, and pelvic floor reconstruction.

There is thus a need to develop resorbable implants with prolonged strength retention and preferably high initial tensile strength that also have good biocompatibility, can be produced economically, and degrade to non-toxic degradation products.

It is an object of the present invention to provide biocompatible implants of poly(butylene succinate) and copolymers thereof with prolonged strength retention.

It is a further object of the present invention to provide implants of poly(butylene succinate) and copolymers thereof that are made from oriented fibers, including monofilament and multifilament fibers.

It is yet a further object of the present invention to provide implants of poly(butylene succinate) and copolymers thereof that are made from films, including porous films, in particular, films that have been oriented in one or more directions.

It is yet a further object of the present invention to provide implants of poly(butylene succinate) and copolymers thereof that are made by 3D printing.

It is another object of the present invention to provide processes to produce oriented implants and 3D printed implants of poly(butylene succinate) and copolymers thereof.

It is still another object of the invention to provide methods for implantation of implants made from poly(butylene succinate) and copolymers thereof.

SUMMARY OF THE INVENTION

Resorbable biocompatible implants comprising poly(butylene succinate) and copolymers thereof have been developed. These implants are made using poly(butylene succinate), copolymers, or blends thereof, and are produced so that the implants are biocompatible, contain less than 20 endotoxin units per device as determined by the limulus amebocyte lysate (LAL) assay, and are sterile.

The poly(butylene succinate) polymer comprises succinic acid and 1,4-butanediol, which are also hydrolytic degradation products of poly(butylene succinate) that are converted enzymatically to natural metabolites in vivo, and which degrade by known metabolic/catabolic pathways to carbon dioxide and water without the formation of toxic metabolites.

The poly(butylene succinate) and copolymers thereof are also made without the use of crosslinking agents that can result in toxic metabolites being released from the implants as the polymers degrade.

The implants are particularly suitable for use in procedures where prolonged strength retention is necessary, such as hernia repair, soft tissue reinforcement, breast reconstruction and augmentation, mastopexy, orthopedic repairs, wound management, pelvic floor reconstruction, treatment of stress urinary incontinence, stenting, heart valve surgeries, dental procedures and other plastic surgeries. Such implants of poly(butylene succinate) and copolymers thereof include but are not limited to implants:
  (i) that are made from oriented fibers, including monofilament and multifilament fibers:
  (ii) that are made from films, including porous films, in particular, films that have been oriented in one or more directions; or
  (iii) that are made by 3D printing.

The preparation of the implants avoids the use of production technologies that produce endotoxin, or require the use of antibiotics.

Preferably, the implants are made from polymeric compositions of poly(butylene succinate) and copolymers thereof, wherein the melting temperatures of the compositions are between 105 and 120° C., and thus the implants are stable during transportation in hot climates as well as in storage.

The polymeric compositions used to prepare the implants preferably exclude the use of poly(butylene succinate) and copolymers thereof that have been prepared with the use of isocyanates.

In a preferred embodiment, the implants comprise polymeric compositions comprising 1,4-butanediol and succinic acid units copolymerized with one or more hydroxycarboxylic acid units, even more preferably wherein the hydroxycarboxylic acid units are malic acid, citric acid, or tartaric acid. In a particularly preferred embodiment, the implants comprise succinic acid-1,4-butanediol-malic acid copolyester. In another embodiment, the implants comprise polymeric compositions comprising 1,4-butanediol and succinic acid units copolymerized with maleic acid, fumaric acid, or combinations thereof. These polymeric compositions may further comprise other monomers, including malic acid, citric acid or tartaric acid.

In an embodiment, the implants are made from fibers and meshes comprising poly(butylene succinate) and copolymers thereof. In a preferred embodiment, the fibers are oriented.

It has been discovered that the oriented fibers do not curl when uneven forces are applied to their surfaces during implantation. For example, these fibers do not curl, or form pig tail structures, when used as sutures and tension is applied unevenly to the suture's surfaces. Pig tailing of suture fibers is undesirable because it makes the handling or knot tying of surgical sutures very difficult during implantation.

It has also been discovered that oriented fibers of poly(butylene succinate) and copolymers thereof can be prepared that are not pitted during degradation after implantation in vivo. This fiber property provides a predictable degradation profile in vivo, and is particularly important for the performance of small diameter fibers and multifilament fibers. Pitting of the surface of a small diameter fiber, or uneven erosion of the fiber surface, can result in the premature loss of strength retention of the fiber leading to early failure of the fiber in vivo. Premature loss of strength retention results from the introduction of defects and the effective cross-section of the fiber being decreased by pitting.

The absence of pitting of the fibers is particularly important in all fiber-based implants, and especially important in implants where prolonged strength retention is desirable like resorbable wound closure materials such as sutures and staples, surgical meshes, hernia meshes, breast reconstruction meshes, implants for soft tissue reinforcement, mastopexy meshes, and slings. Pitting can be visualized using SEM as indents, micropores or hollowing of the surface of the fiber.

In one embodiment, oriented monofilament and multifilament fibers, and other oriented articles, of poly(butylene succinate) and copolymers have been developed with very high tensile strengths, but that still degrade in vivo over time. As discussed in Manavitehrani et al, 2016, *Polymers*, 8: 20-52 (see Table 1 thereof), PBS generally has a tensile strength of about 17.5 MPa whereas Wang et al, 2009, *Acta Biomaterialia*, 5(1): 279-287 (see Table 1 thereof) reported that PBS has a tensile strength of 58 MPa. However, as reported in the present application, oriented monofilament and multifilament fibers of poly(butylene succinate) and copolymers have been developed with much higher tensile strengths than those previously reported, for example, greater than 400 MPa, 500 MPa, 600 MPa, 700 MPa, or 800 MPa, but less than 2,000 Pa, and more preferably between 400 MPa and 1,200 MPa. It has been discovered that these fibers can be prepared using multi-stage orientation in combination with heated conductive liquid chambers. Furthermore, it has been discovered that orientation can be used to modify the degradation characteristics of articles formed from poly(butylene succinate) and copolymers. For example, the present application shows that oriented PBS articles can retain 83.1% of initial weight average molecular weight (Mw) after 12 weeks incubation in phosphate buffered saline (see Example 13, Table 6) and 72.5% after implantation in vivo after 12 weeks (Example 15, Table 12). In contrast, Li et al. evaluated poly(butylene succinate) articles formed by hot compression molding (a method which does not provide orientation), by incubation in vitro in phosphate buffered saline over several weeks and showed that the article retained only about 40% of the initial Mw after 12 weeks incubation and only about 12.5% of the initial Mw after 15 weeks incubation (Li et al. *Macromol. Biosci.* 5:433-440 (2005); FIG. 4. This demonstrates the important benefits that orientation can provide to the resilience of implants formed from poly(butylene succinate) and copolymers, when in use over time. The high tensile strengths of these fibers, and improved resilience, make them suitable for use in resorbable implant applications requiring high tensile strength and prolonged strength retention.

Such applications include hernia repair, breast reconstruction, treatment of urinary incontinence with slings, resorbable wound closure materials such as suturing and stapling materials, mesh suturing, and ligament and tendon repair.

In another embodiment, it has been discovered that this new method of fiber formation can also be used to prepare oriented monofilament and multifilament fibers of poly (butylene succinate) and copolymers that are relatively stiff with Young's Modulus values between 1 and 5 GPa, for example between 2 and 3 GPa. In contrast Manavitehrani et al, supra (see Table 1 thereof) reports that PBS generally has a modulus of 0.7 GPa, whereas Wang et al, 2009, supra (see Table 1 thereof) reported that PBS has a tensile strength of 0.67 GPa. The high stiffness of the fibers provided by this embodiment of the present invention can be particularly advantageous in the preparation, handling, and performance of resorbable implantable wound closure materials such as sutures and staples, and also of surgical meshes.

In another embodiment, it has been discovered that this new method of fiber formation can also be used to prepare absorbable devices and oriented monofilament and multifilament fibers of poly(butylene succinate) and copolymers that have degradation products of low acidity. For example, the two acid dissociation constants (pKa) of succinic acid, which is a hydrolytic degradation product of poly(butylene succinate) and copolymers thereof are approximately 4.21 and 5.64. These values of pKa are higher (less acidic) than the pKa values for the monomers used in many other absorbable polymers, such as polyglycolic acid (PGA), polylactic acid (PLA), poly-L-lactic acid (PLLA), poly-lactic-co-glycolic acid copolymer (PLGA) and the like, since the pKa's of glycolic acid and lactic acid are approximately 3.83 and 3.86, respectively. Thus, the disclosed implants have major advantages over prior approaches that have used absorbable polygalactin 910 (PLGA) or other similar meshes containing monomers with lower pKa values than succinic acid. Upon hydrolysis, the latter meshes release hydrolytic degradation products that are more acidic than succinic acid and 1,4-butanediol. Acidic degradation products can cause local tissue irritation, toxicity, aseptic sinus formation, tissue damage or necrosis at the site of the implant and it is preferred to have less acidic degradation products such as succinic acid and 1,4-butanediol to avoid such adverse tissue reactions.

It has also been found that the poly(butylene succinate) and copolymer compositions can be used to prepare orthopedic implants with sufficient stiffness and torsional strengths to make them useful in resorbable implants such as interference screws, bone screws and suture anchors.

It has also been discovered that surgical meshes can be prepared from poly(butylene succinate) and copolymers thereof that are dimensionally stable when implanted in vivo, and do not shrink for at least 4 weeks, or at least 12 weeks, following implantation. i.e., the width and length of the mesh do not decrease in size substantially, or significantly. Table 8 shows that the relative area of the mesh does not shrink. The width and length remain relatively constant. Whereas data for the GalaFLEX mesh is given in Table 9, and the area of the mesh and dimensions decrease. Accordingly, in this embodiment, the area of the mesh decreases by less than 6%, for example, less than 5%, less than 4%, less than 2% and less than 1% by 12 weeks compared to its initial area, and the area of the mesh decreases by less than 4%, preferably, less than 2% and even more preferably between 0 and 1% at 4 weeks post implantation, compared to its initial area. The term "area of the mesh" in this context preferably refers to the uniplanar surface area, i.e. the product of the width and length of the mesh.

The surgical meshes prepared from oriented fibers of poly(butylene succinate) and copolymers thereof are described herein. The improved meshes prevent additional tension being placed on tissues at the implant site, and maintain the original area of reinforcement or repair. Furthermore, it has also been discovered that the meshes do not curl along their edges after implantation, and continue to contour to the patient's anatomy. Curling of implantable mesh along its edges is undesirable because it can expose neighboring tissue to mesh edges and result in tissue damage.

In a further embodiment, the implants are made by 3D printing compositions comprising poly(butylene succinate) and copolymers thereof. In a particularly preferred embodiment, the implants made by 3D printing have porous structures, and even more preferably lattice structures. It has been discovered that certain compositions of poly(butylene succinate) and copolymers thereof can be 3D printed to produce implants where surprisingly the printed polymers have a higher weight average molecular weight than the compositions from which they are derived. This increase in weight average molecular weight may be the result of chain extension reactions above the melting point of the composition.

In another embodiment, the implants contain one or more antimicrobial agents to prevent colonization of the implants, and reduce or prevent the occurrence of infection following implantation in a patient.

Coverings and receptacles made from forms of poly (butylene succinate) and copolymers thereof have also been developed for use with cardiac rhythm management devices and other implantable devices. These coverings and receptacles may be used to hold, or partially or fully cover, devices such as pacemakers, breast implants, and neurostimulators. In a preferred embodiment, the coverings and receptacles are made from meshes, non-wovens, films, fibers, foams, 3D printed objects, and contain antibiotics such as rifampin and minocycline.

The implants comprising poly(butylene succinate) and copolymers thereof can be sterilized, for example by irradiation, but are more preferably sterilized by ethylene oxide gas or cold ethylene oxide gas.

BRIEF DESCRIPTION OF THE DRAWINGS

FIG. 9A is a diagram of a hemi-ellipsoid implant shape. FIG. 9B is a schematic of the implant with the cross-section dimensions of its three-dimensional shape defined by tri-axial dimensions "a", "b" and "c".

FIG. 10 is a diagram of an implant for breast reconstruction with a wide upper span (40) to facilitate sling support and encompass the breast mound, and an extra-large bottom tab (42) to support the breast vertical pillar and shape the IMF. The two-dimensional implant shape is designed to minimize bunching or folding of the implant during breast reconstruction.

FIG. 15A shows a partial dome shape of the implant, which is designed to contour and add shape to the breast mound. FIG. 15B shows the width (W) of the partial dome, and (80) shows the arch or edge of the dome viewed looking inside the dome. FIG. 15C shows the height (H), depth (D), and angle (θ) between the base (or floor) (84) of the partial dome and the edge (82) of the partial dome at its highest point (86).

FIG. 16A shows a three-dimensional partial dome shaped implant with three tabs (90a, 90b, 90c) for breast reconstruction that is designed to contour and add shape to the breast mound. FIG. 16B shows the width (W) of the partial dome and placement of the tabs (90a, 90b, 90c). FIG. 16C shows the view of the implant looking from above the partial dome. FIG. 16D shows the height (H), depth (D), and angle (θ) between the base (or floor) (92) of the partial dome and the edge of the partial dome at its highest point (94).

FIG. 17A shows an example of how a three-dimensional partial dome shaped implant, viewed from above, can be reinforced with body ribbing (100) around the edge and body ribbing in the mid-dome region (102a and 102b) of the implant. FIG. 17B shows the same three-dimensional implant as FIG. 17A, except viewed from above and looking partially inside the dome.

DETAILED DESCRIPTION OF THE INVENTION

Figure 1:
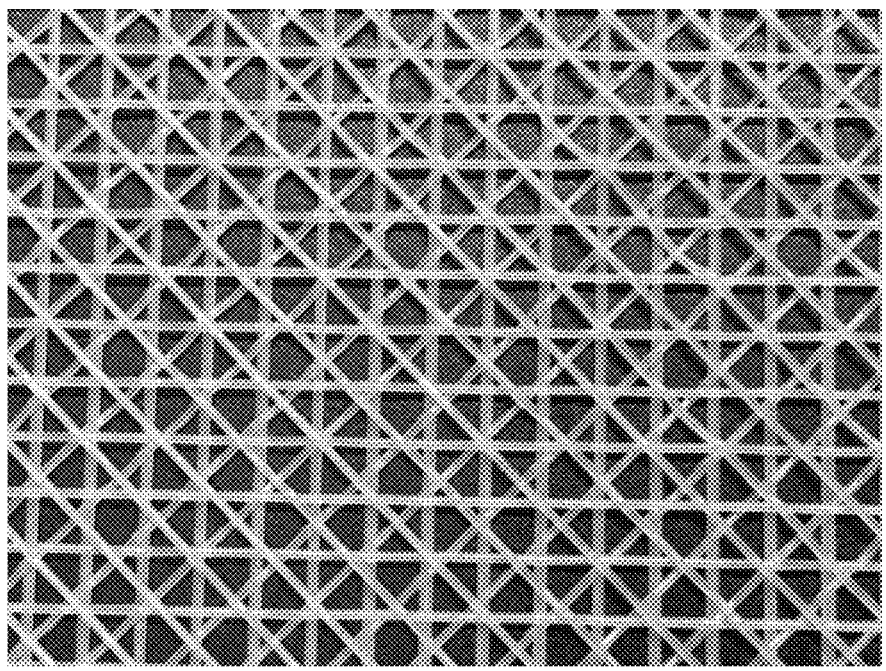
FIG. 1 is an image showing a 3D printed mesh produced by melt extrusion deposition (MED) of succinic acid-1,4-butanediol-malic acid copolyester.
Figure 2:
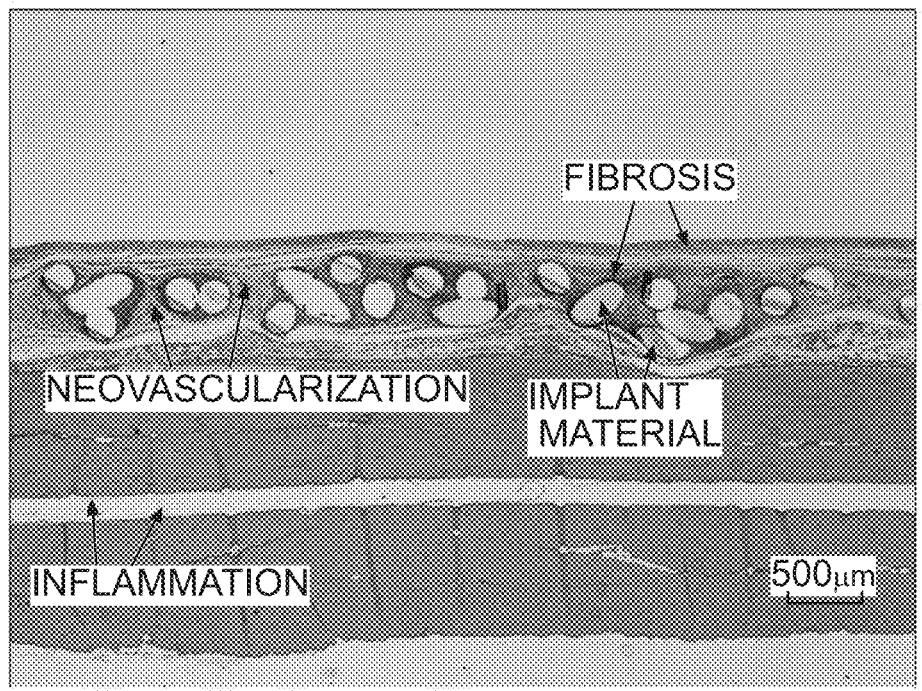
FIG. 2 is an image of a paraffin-embedded tissue slide showing the histology of a PBS mesh after subcutaneous implantation in a rabbit for a 4-week period using an H&E stain at a magnification of 20×.
Figure 3:
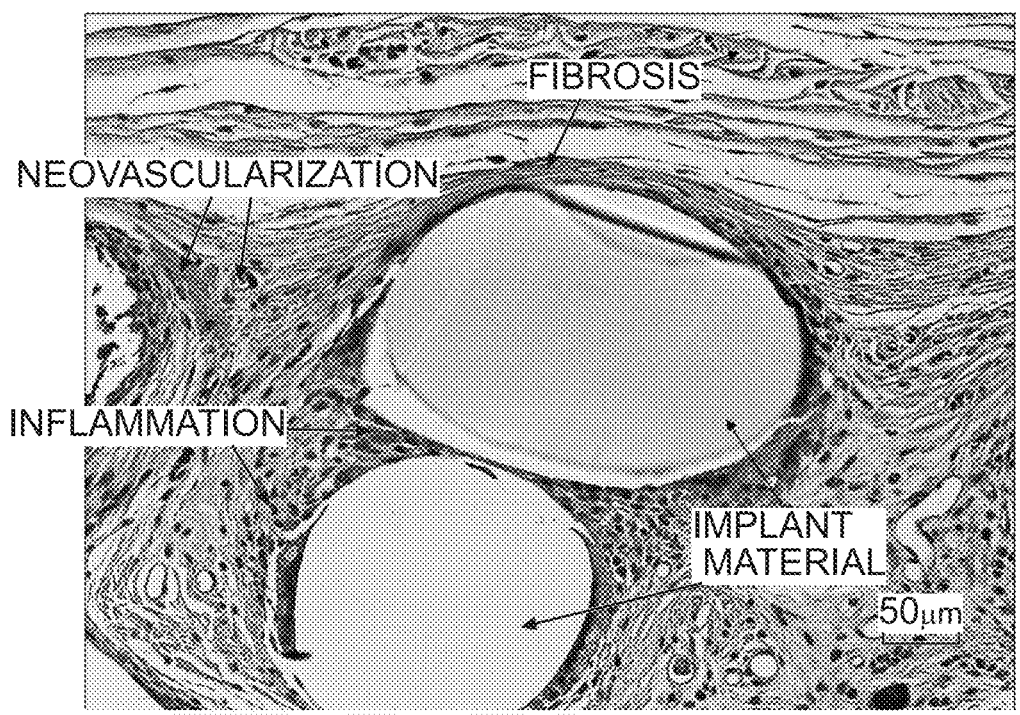
FIG. 3 is an image of a paraffin-embedded tissue slide, showing the histology of a PBS mesh after subcutaneous implantation in a rabbit for a 4-week period using an H&E stain at a magnification of 200×.

Methods have been developed to prepare resorbable implants with prolonged strength retention that contain poly(butylene succinate) or copolymer thereof.

These implants preferably have high initial strength, and preferably contain less than 20 endotoxin units per device as determined by the limulus amebocyte lysate (LAL) assay.

After implantation, the implants degrade slowly providing sufficient time for healing before the strength of the implant is lost.

In certain embodiments, the implants comprise micropores and/or are in the form of scaffolds, which allow tissue ingrowth to occur over a prolonged period of time on account of the prolonged strength retention.

The implants may contain one or more antimicrobial agents to prevent colonization of the implants by microorganisms, and reduce or prevent the occurrence of infection following implantation in a patient. After implantation, the implants may be designed to release the antimicrobial agents.

The implants may be coated on one or more surfaces to prevent adhesions forming to the coated surfaces.

In another embodiment, biomedical implants and other medical devices and articles may be coated with the compositions of poly(butylene succinate) or copolymer thereof as described herein.

In another embodiment, biomedical implants and other medical devices and articles (such as, but not limited to, a stent, such as a metallic stent) is coated with a base coating containing poly(butylene succinate) or copolymer thereof, blended with one or more other polymers, optionally a top coat which may, for example, contain either poly(butylene succinate) or copolymer thereof or the same composition as the base coat. Optionally, the base coat has a thickness of about 10 microns to about 50 microns, more preferably from about 15 microns to about 25 microns. In one embodiment, the base coat has a thickness of about 20 microns. Optionally, the top coat has a thickness of about 10 microns to about 40 microns, preferably from about 10 microns to 20 microns. In one embodiment, the top coat has a thickness of about 15 microns. Preferably, the base coat and/or top coat has an elongation to break that is, or is at least, within the range of 10% to 50%. Preferably the base coat and/or top coat has a Young's modulus that is less than 5.0 GPa; and optionally at least or greater than 600 MPa, at least or greater than 700 MPa, at least or greater than 800 MPa, at least or greater than 1 GPa, or at least or greater than 2 GPa, but less than 5 GPa. In one option, the base coat and/or top coat, or the biomedical implant, device or article as a whole, is plastically expandable at body temperature.

Optionally, the biomedical implant of the present invention (in one embodiment, at least in the context of stents) does comprise a triblock copolymer that contains 1,4-butanediol, succinic acid, and MPEG units.

In one embodiment, the implants may be delivered minimally invasively, and the implants may also be three-dimensional with or without the ability to resume their original shapes after being deformed for delivery.

The implants are particularly suitable for use in procedures where prolonged strength retention is required, such as hernia repair, including abdominal, ventral, incisional, umbilical, inguinal, femoral, hiatal and paraesophageal hernia, soft tissue reinforcement, breast reconstruction and augmentation, mastopexy, orthopedic repairs including ligament and tendon repair, wound management, resorbable wound closure materials such as suturing and stapling materials, pelvic floor reconstruction, treatment of stress urinary incontinence, stenting, heart valve surgeries, dental procedures and other plastic surgeries. Such implants of poly(butylene succinate) and copolymers thereof include but are not limited to implants:

(i) that are made from oriented fibers, including monofilament and multifilament fibers:
(ii) that are made from films, including porous films, in particular, films that have been oriented in one or more directions; or
(iii) that are made by 3D printing.

In one preferred embodiment, methods have been developed to produce implants with highly oriented fibers and meshes of poly(butylene succinate) and copolymers thereof. In this context a highly oriented fiber is a fiber that has been produced by a process that imparts an orientation ratio of at least 2, 3, 4, 5, 6, 7, 8 or more. A highly oriented mesh is a mesh comprising, or formed from, one or more highly oriented fibers. Maintenance of the high degree of orientation of these fibers and meshes is essential to their physical function in vivo.

The high degree of orientation of the fibers and meshes allows these devices to retain strength in the body for prolonged periods ("prolonged strength retention"), and therefore provide critical support to tissues during reconstruction and repair procedures.

If orientation is lost during preparation of the implants containing these fibers and meshes, the resulting products will have lower strength and strength retention, and be unable to provide the necessary reinforcement and configuration required for healing. For example, spray coating or dip coating of oriented poly(butylene succinate) fibers using many solvents may plasticize or dissolve the polymer and result in loss of fiber orientation and loss of strength retention.

Methods have been developed that allow fibers and meshes of poly(butylene succinate) and copolymers thereof to be prepared without substantial loss of orientation of the fibers, and therefore without substantial loss of strength and strength retention.

Optionally, these implants may also incorporate other bioactive agents, such as antibiotics, antimicrobials, and anti-adhesion agents. For example, oriented resorbable implants made from PBS and copolymers thereof, have been developed that contain one or more anti-microbial agents to prevent colonization of the implants by microorganisms, and reduce or prevent the occurrence of infection following implantation in a patient. These oriented implants are particularly suitable for use in procedures where prolonged strength retention is necessary and where there is a risk of infection, such as hernia repair, breast reconstruction and augmentation, mastopexy, orthopedic repairs, wound management, pelvic floor reconstruction, treatment of pelvic organ prolapse, including treatment of cystocele, urethrocele, uterine prolapse, vaginal fault prolapse, enterocele and rectocele, stenting, heart valve surgeries, dental procedures and other plastic surgeries.

In another preferred embodiment, methods have been developed to produce implants of poly(butylene succinate) and copolymers by 3D printing, including free deposition modeling, including fused filament fabrication, fused pellet deposition, and melt extrusion deposition, selective laser melting, and solution printing. A particularly preferred 3D printing method is fused filament fabrication. In a preferred embodiment, the implants comprising poly(butylene succinate) and copolymers produced by 3D printing are porous, and in a particularly preferred embodiment the implants may be lattices, including meshes containing struts or fibers.

Methods have also been developed to prepare resorbable enclosures, pouches, holders, covers, meshes, non-wovens, films, foams, clamshells, casings, and other receptacles made from poly(butylene succinate) and copolymers thereof that partially or fully encase, surround or hold implantable medical devices, and optionally wherein the poly(butylene succinate) and copolymers thereof contain and release one or more antimicrobial agents to prevent colonization of the implants and/or reduce or prevent infection. Implantable medical devices that can be partially or fully encased include cardiac rhythm management (CRM) devices (including pacemakers, defibrillators, and pulse generators), implantable access systems, neurostimulators, ventricular access devices, infusion pumps, devices for delivery of medication and hydration solutions, intrathecal delivery systems, pain pumps, breast implants, and other devices to provide drugs or electrical stimulation to a body part.

In one embodiment, the methods disclosed herein are based upon the discovery that oriented implants and 3D printed implants of poly(butylene succinate) and copolymers thereof retain their strength longer than copolymers of glycolide and lactide, and monofilament products made from polydioxanone (PDO). The oriented and 3D printed implants of poly(butylene succinate) and copolymers thereof can also be prepared with high initial strength.

Methods have also been developed to prepare resorbable implants comprising poly(butylene succinate) and copolymers thereof that may be used for soft and hard tissue repair, regeneration, and replacement. These implants include, but not limited to: suture, barbed suture, braided suture, monofilament suture, hybrid suture of monofilament and multifilament fibers, braids, ligatures, knitted or woven meshes, surgical meshes for soft tissue implants for reinforcement of soft tissue, for the bridging of fascial defects, for a trachea or other organ patch, for organ salvage, for dural grafting material, for wound or burn dressing, or for a hemostatic tamponade, surgical mesh in the form of a mesh plug, knitted tubes, tubes suitable for the passage of bodily fluid, catheters, monofilament meshes, multifilament meshes, patches (such as, but not limited to, hernial patches and/or repair patches for the repair of abdominal and thoracic wall defects, inguinal, paracolostomy, ventral, paraumbilical, scrotal or femoral hernias, for muscle flap reinforcement, for reinforcement of staple lines and long incisions, for reconstruction of pelvic floor, for repair of pelvic floor prolapse, including rectal or vaginal prolapse, treatment of cystocele, urethrocele, uterine prolapse, and enterocele, for suture and staple bolsters, for urinary or bladder repair, or for pledgets), soft tissue reinforcement implants, wound healing device, bandage, wound dressing, burn dressing, ulcer dressing, skin substitute, hemostat, tracheal reconstruction device, organ salvage device, dural substitute, dural patch, nerve guide, nerve regeneration or repair device, hernia repair device, hernia mesh, hernia plug, device for temporary wound or tissue support, tissue engineering device, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, sphincter bulking material for use in the treatment of adult incontinence, injectable particles, injectable microspheres, microparticles, bulking or filling device, filling agent for use in plastic surgery to fill in defects, bone marrow scaffold, clip, clamp, screw, bone screw, pin, nail, medullary cavity nail, bone plate, bone plug, cranioplasty plug, interference screw, tack, fastener, suture fastener, rivet, staple, fixation device for an implant, bone graft substitute, bone void filler, bone putty, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, meniscus anchors, articular cartilage repair device, osteochondral repair device, spinal fusion device, spinal fusion cage, interosseous wedge, intramedullary rod, antibiotic beads for treatment or prevention of a bone infection, joint spacer, device for treatment of osteoarthritis, viscosupplement, stent, including coronary, cardiovascular, peripheral, ureteric, urethral, urology, gastroenterology, nasal, ocular, or neurology stents, stent coatings, stent graft, devices with vascular applications, cardiovascular patch, intracardiac patching or for patch closure after endarterectomy, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, targeted delivery devices, diagnostic devices, rods, devices with biocompatible coatings, prosthetics, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, device for facial scar revision, and foams. The present application also discloses the use of poly(butylene succinate) and copolymers thereof for use in the preparation of a coating for an implant or other medical device, such as any one or more of the implants listed above. In a particularly preferred embodiment, these implants comprise polymeric compositions comprising 1,4-butanediol and succinic acid units copolymerized with one or more hydroxycarboxylic acid units, even more preferably wherein the hydroxycarboxylic acid units are malic acid, citric acid, or tartaric acid. In a particularly preferred embodiment, these implants comprise succinic acid-1,4-butanediol-malic acid copolyester. In another embodiment, the implants comprise polymeric compositions comprising 1,4-butanediol and succinic acid units copolymerized with maleic acid, fumaric acid, or combinations thereof. These polymeric compositions may further comprise other monomers, including malic acid, citric acid or tartaric acid.

I. Definitions

"Absorbable" is used herein to describe a polymer or device which undergoes hydrolytic and/or enzymatic driven chain scission, generating degradation products that are then absorbed by the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Bioactive agent" is used herein to refer to therapeutic, prophylactic, and/or diagnostic agents. "Bioactive agent" includes a single such agent and is also intended to include a plurality.

"Biocompatible" as generally used herein means the biological response to the material or device being appropriate for the device's intended application in vivo. Any metabolites or degradation products of these materials should also be biocompatible.

"Bicomponent" as generally used herein means a structure containing two or more materials.

"Blend" as generally used herein means a physical combination of different polymers, as opposed to a copolymer comprised of two or more different monomers.

"Burst strength" as used herein unless otherwise stated is determined by test method based on ASTM D6797-02 "Standard test method for bursting strength of fabrics constant rate of extension (CRE) ball burst test," using a MTS Q-Test Elite universal testing machine or similar device. However, the testing fixture uses a ⅜ inch diameter ball and the opening is ½ inch diameter.

"Copolymers of poly(butylene succinate)" as generally used herein means any polymer of succinic acid and 1,4-butanediol monomers incorporating one or more additional monomers. Examples of copolymers of poly(butylene succinate) include poly(butylene succinate-co-adipate), poly(butylene succinate-co-terephthalate), poly(butylene succinate-co-ethylene succinate), and poly(butylene succinate-co-propylene succinate). Poly(butylene succinate-co-adipate), for example, may be made by condensation polymerization from succinic acid, adipic acid and 1,4-butanediol. Copolymers of poly(butylene succinate) include polymers comprising (i) succinic acid and 1,4-butanediol units, and (ii) one or more of the following additional units, such as: chain extenders, cross-linking agents, and branching agents. Examples of these copolymers include: succinic acid-1,4-butanediol-malic acid copolyester, succinic acid-1,4-butanediol-citric acid copolyester, succinic acid-1,4-butanediol-tartaric acid copolyester, succinic acid-1,4-butanediol-malic acid copolyester further comprising citric acid, tartaric acid, or a combination thereof, succinic acid-adipic acid-1,4-butanediol-malic acid copolyester, succinic acid-adipic acid-1,4-butanediol-citric acid copolyester, succinic acid-adipic acid-1,4-butanediol-tartaric acid copolyester, or succinic acid-adipic acid-1,4-butanediol-malic acid copolyester further comprising citric acid, tartaric acid, or combinations thereof. Copolymers of poly(butylene succinate) also include polymers comprising succinic acid and 1,4-butanediol units and one or more hydroxycarboxylic acid unit. The copolymers may also comprise maleic or fumaric acid units, or combinations thereof.

"Diameter" as generally used herein is determined according to the US Pharmacopeia (USP) standard for diameter of surgical sutures (USP 861).

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993). Elongation at 16 N/cm is measured using ASTM D6797-15, Standard Test Method for Bursting Strength of Fabrics Constant-Rate-of-Extension (CRE) Ball Burst Test.

"Endotoxin content" as used herein refers to the amount of endotoxin present in a sample, and is determined by the limulus amebocyte lysate (LAL) assay.

"Filament length" as used herein, unless otherwise specified, refers to the mean length of filaments in a monofilament fiber or multifilament fiber.

"Full contour breast implant" as used herein refers to an implant that can be used to contour both the upper pole and the lower pole of the breast, wherein at least part of the implant covers the upper and lower poles of the breast.

"Knot pull tensile strength" (or "knot strength") as used herein is determined using a universal mechanical tester according to the procedures described in the US Pharmacopeia (USP) standard for testing tensile properties of surgical sutures (USP 881).

"Lower pole" as generally used herein means the part of the breast located between the inframammary fold (IMF) and the nipple meridian reference, and protruding away from the chest wall.

"Lower pole volume" as generally used herein means the volume of tissue in the lower pole of the breast. The volume is contained within the boundaries defined by the lower pole curve, the chest wall and nipple projection line.

"Mesh suture" as used herein means a device including a needle and a mesh component that can be used to re-appose soft tissue. The mesh suture is designed to be threaded through soft tissue, and the mesh component anchored under tension to re-appose soft tissue. The mesh component helps to prevent the suture from cutting through the tissues (suture pullout or cheese-wiring), and increases the strength of the repair, when compared to conventional monofilament and multifilament sutures.

"Micropores" as use herein refers to holes or voids which may be present in the polymer, particularly within the body of a fiber. It is preferred that the term "micropores" does not refer to pores in a mesh, i.e. the region between fibers in such a product.

"Molecular weight" as used herein, unless otherwise specified, refers to the weight average molecular weight (Mw), not number average molecular weight (Mn), and is measured by gel permeation chromatography (GPC) in chloroform relative to polystyrene standards. Where number average molecular weight is used herein, this is measured by gel permeation chromatography (GPC) relative to polystyrene standards.

"Nipple meridian reference" is the plane drawn horizontally through the nipple to the chest wall.

"Nipple projection line" is the line drawn perpendicular to the chest wall and through the nipple.

"Nitrogen content" as used herein refers to the mass percentage of elemental nitrogen in a sample, and is determined by the Kjeldahl method of nitrogen analysis, or other suitable analytical method for trace elemental nitrogen analysis, and is expressed in parts per million (ppm).

"Non-sacrificial element, fiber or strut" as generally used herein means an element, fiber or strut of an implant that retains strength longer than a sacrificial element, fiber or strut, however, the non-sacrificial element, fiber or strut may eventually be broken, stretched or completely degraded.

"Orientation" as generally used herein refers to the alignment of polymer chains within a material or construct. For example, oriented fibers means that some or all of the polymer chains within a fiber have been aligned.

"Orientation ratio" as used herein is the ratio of the output speed to the input speed of two godets (or rollers) used to orient the multifilament yarn or monofilament fiber. For example, the orientation ratio would be 3 if the output speed of the multifilament yarn or monofilament fiber is 6 meters per minute, and the input speed of the multifilament yarn or monofilament fiber is 2 meters per minute.

"PBS" as used herein means poly(butylene succinate).

"Phosphate buffered saline" as used herein is prepared by diluting a 10× Phosphate Buffered Saline, Ultra Pure Grade (Product #J373-4L, from VWR) to 1× with deionized water and adding 0.05 wt % sodium azide (NaN3, Product #14314 from Alfa Aesar) as a biocide. The resulting 1× buffer solution contains 137 mM NaCl, 2.7 mM KCl, 9.8 mM phosphate and 0.05 wt % sodium azide and has pH 7.4 at 25° C. The prepared solution is filtered through a 0.45 μm filter (VWR Product #10040-470) prior to use.

"Physiological conditions", "in vivo" and/or "physiological conditions in vivo" can, in one embodiment, refer to sub-cutaneous implantation in a subject, such as a human or an animal. The animal may, for example, be a New Zealand White rabbit, and optionally the procedure for sub-cutaneous implantation and/or (if relevant) recovery of an implanted item, may follow the procedure indicated in Example 15 of the present application. The same definition may apply to a determination of the properties of items after "implantation".

"Poly(butylene succinate)" as generally used herein means an aliphatic polyester containing succinic acid and 1,4-butanediol units, and may be made by condensation polymerization from succinic acid and 1,4-butanediol. Poly (butylene succinate) may be abbreviated as "PBS". Poly (butylene succinate) includes polymers of (i) succinic acid and 1,4-butanediol units, and (ii) one or more additional monomers, including the following: chain extenders, cross-linking agents, and branching agents.

"Pore size" as generally used herein is calculated using open source 25 ImageJ software available at https://imagej.nih.gov/ij/index.html.

"Pre-pectoral" as used herein in the context of breast implant placement means that the implant is placed in the breast above the pectoral muscle.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Sacrificial element, fiber or strut" as generally used herein means an element, fiber or strut of an implant that is present initially in the implant, but degrades, yields, or breaks prior to the degradation, stretching or breakage of a non-sacrificial element, fiber or strut in the implant.

"Self-reinforced" as used herein describes a property of the implant in which the outer rim is strengthened such that the implant can be squeezed, pulled, rolled, folded, or otherwise temporarily deformed by the user to facilitate its insertion in the body, and that allows the implant to recover its initial shape after insertion in the body.

"Shape Memory" as used herein describes a property of the implant that allows the user to squeeze, pull, roll up, fold up, or otherwise deform the implant temporarily in order to facilitate its insertion in the body wherein the device recovers its preformed shape after insertion in the body.

"Split metal form" is used herein interchangeably with "split metal mold".

"Strength retention" refers to the amount of time that a material maintains a particular mechanical property following implantation into a human or animal. For example, if the tensile strength of a resorbable fiber decreased by half over 3 months when implanted into an animal, the fiber's strength retention at 3 months would be 50%.

"Sub-glandular" as used herein in the context of breast implant placement means the implant is placed beneath the glands of the breast, but superficial to the pectoral muscle.

"Sub-pectoral" as used herein in the context of breast implant placement means the implant is placed beneath the pectoral muscle of the chest.

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails.

"Support rib" is used herein interchangeably with "ribbing" and "ring" to refer to reinforcement around the edge of the implant.

"Taber Stiffness Unit" or (TSU) is defined as the bending moment of ⅕ of a gram applied to a 1½" (3.81 cm) wide specimen at a 5-centimeter test length, flexing it to an angle of 15°, and is measured using a Taber V-5 Stiffness Tester Model 150-B or 150-E. The TABER® V-5 Stiffness Tester—Model 150-B or 150-E is used to evaluate stiffness and resiliency properties of materials up to 10,000 Taber Stiffness Units. This precision instrument provides accurate test measurement to ±1.0% for specimens 0.004" to 0.219" thickness. One Taber Stiffness Unit is equal to 1 gram cm (g cm) or 10.2 milliNewton meters (mN m). Taber Stiffness Units can be converted to Genuine Gurley™ Stiffness Units with the equation: $S_T=0.01419 S_G-0.935$, where $S_T$ is the stiffness in Taber Stiffness Units and $S_G$ is the stiffness in Gurley Stiffness Units. To convert Taber Stiffness Units to milliNewton Meters, use the equation: $X=S_T \cdot 0.098067$, where X is the stiffness in milliNewton Meters. When explants do not meet the size requirements for the Taber test due to limitations in the available testing sizes for implantation in an experimental animal, the values may be used to determine changes in the relative stiffness or provide comparative values between samples of the same size.

"Tear Resistance" as used herein is measured using ASTM-D1938 (Standard Test Method for Tear Resistance of Plastic Film and Thin Sheeting by a Single-Tear Method).

"Tenacity" means the strength of a yarn or a filament for its given size, and is measured as the grams of breaking force per denier unit of yarn or filament and expressed as grams per denier (gpd).

"Tensile modulus" is the ratio of stress to strain for a given material within its proportional limit.

"Tensile strength" as used herein means the maximum stress that a material can withstand while being stretched or pulled before failing or breaking.

"Upper pole" as generally used herein means the top part of the breast located between the nipple meridian reference and the position at the top of the breast where the breast takes off from the chest wall, and protruding away from the chest wall.

"Upper pole volume" as generally used herein means the volume of tissue in the upper pole of the breast. The volume of tissue is contained within the boundaries defined by the upper pole curve, the chest wall, and the nipple projection line.

"USP Size" as used herein means the suture size as defined by the United States Pharmacopeia.

"Yarn" as used herein means a continuous strand of textile fibers, or filaments. The yarn may be twisted, not twisted, or substantially parallel strands.

II. Compositions

Methods have been developed to produce resorbable implants comprising poly(butylene succinate) and copolymers thereof. The resorbable implants may be used for soft and hard tissue repair, regeneration, and replacement.

In one embodiment, the implants comprise fibers with prolonged strength retention. The fibers may be monofilament or multifilament fibers, and are preferably oriented. The fibers preferably have an in vivo tensile strength retention of at least 70% at 4 weeks, and more preferably at least 80% or 90% tensile strength retention at 4 weeks. The fibers preferably have an in vivo tensile strength retention of at least 50% at 12 weeks, and more preferably at least 65% tensile strength retention at 12 weeks. These properties make the fibers suitable for use in implants requiring prolonged strength retention, such as hernia meshes, soft tissue reinforcement implants, meshes, lattices and textiles, breast reconstruction meshes, resorbable wound closure materials such as sutures and staples, slings for treatment of stress urinary incontinence, mesh sutures, and pelvic floor reconstruction devices, including devices for treatment of pelvic organ prolapse, including treatment of cystocele, urethrocele, uterine prolapse, vaginal fault prolapse, enterocele and rectocele. In addition to having prolonged strength retention, these fibers preferably have one or more of the following properties: (i) tensile strengths greater than 400 MPa, 500 MPa, 600 MPa, 700 MPa, or 800 MPa, but less than 2,000 MPa, and more preferably between 400 MPa and 1,200 MPa, (ii) Young's Modulus greater than 600 MPa, 700 MPa, 800 MPa, 900 MPa, 1 GPa, or 2 GPa, but less than 5 GPa, and (iii) elongation to break of 10-150%, more preferably 10-50%.

Methods have also been developed to produce implants comprising PBS or copolymer thereof that can partially or fully encase, surround or hold implantable medical devices, and wherein the PBS or copolymers thereof release one or more antimicrobial agents to prevent colonization of the implantable medical devices by microorganisms and/or reduce or prevent infection in the patient. Suitable implants comprising PBS or copolymers thereof include pouches, holders, covers, meshes (including, but not limited to surgical meshes for soft tissue implants for reinforcement of soft tissue, for the bridging of fascial defects, for a trachea or other organ patch, for organ salvage, for dural grafting material, for wound or burn dressing, or for a hemostatic tamponade; or surgical mesh in the form of a mesh plug), non-wovens, lattices, webs, films, clamshells, casings, and receptacles.

In another embodiment, methods are described to prepare implants comprising PBS and copolymers thereof that are relatively stiff. In one embodiment, the polymeric compositions of PBS and copolymers thereof can be used to prepare orthopedic implants. These implants have sufficient stiffness and torsional strength to make them suitable for use in resorbable implants such as interference screws, bone screws, suture anchors, bone anchors, clips, clamps, screws, pins, nails, medullary cavity nails, bone plates, interference screw, tacks, fasteners, suture fastener, rivets, staples, fixation devices for an implant, and bone void fillers.

Methods to process PBS and copolymers thereof by 3D printing into resorbable implants are also described. The methods are particularly suitable for making meshes, void fillers, lattices, tissue scaffolds and complex 3D shapes for use as implants.

A. Poly(Butylene Succinate) and Copolymers

The methods described herein can typically be used to produce resorbable implants and resorbable enclosures, pouches, holders, covers, meshes, non-wovens, webs, lattices, films, clamshells, casings, and other receptacles from poly(butylene succinate) and copolymers thereof. Copolymers contain other diols and diacids in addition to the 1,4-butanediol and succinate monomers, and may alternatively or additionally contain branching agents, coupling agents, cross-linking agents and chain extenders. Examples of diols and diacids that can be included are: 1,3-propanediol, ethylene glycol, 1,5-pentanediol, 2,3-butanediol, glutaric acid, adipic acid, terephthalic acid, malonic acid, and oxalic acid. The copolymers may contain one or more additional diols and diacids in addition to 1,4-butanediol and succinic acid. Copolymers include, but are not limited to, poly(butylene succinate-co-adipate), poly(butylene succinate-co-terephthalate), poly(butylene succinate-co-butylene methylsuccinate), poly(butylene succinate-co-butylene dimethylsuccinate), poly(butylene succinate-co-ethylene succinate) and poly(butylene succinate-co-propylene succinate).

The resorbable implants described herein may be produced from poly(butylene succinate) and copolymers thereof wherein the polymer or copolymer has been produced using one or more of the following: chain extenders or coupling agents, cross-linking agents, and branching agents. In a preferred embodiment, the poly(butylene succinate) has been prepared with a chain-extender, and greater than 10, 20, 30, 40, 50, 60, 70, 80, 90% of the polymer chains have been extended with a chain-extender. Poly(butylene succinate) or copolymer thereof may be chain extended, branched, or cross-linked by adding one or more of the following agents: malic acid, trimethylol propane, trimesic acid, citric acid, glycerol propoxylate, and tartaric acid. Particularly preferred agents for branching, chain-extending, or cross-linking are hydroxycarboxylic acid units. Preferably the hydroxycarboxylic acid unit has two carboxyl groups and one hydroxyl group, two hydroxyl groups and one carboxyl group, three carboxyl groups and one hydroxyl group, or two hydroxyl groups and two carboxyl groups. In one preferred embodiment, the implants are prepared from poly(butylene succinate) comprising malic acid as a branching, chain extending or cross-linking agent. The composition may be referred to as poly(1,4-butylene glycol-co-succinic acid), cross-linked or chain extended with malic acid, poly(butylene succinate), cross-linked or chain extended with malic acid, or succinic acid-1,4-butanediol-malic acid copolyester. In a preferred embodiment, the poly(butylene succinate) is chain-extended with malic acid such that greater than 10, 20, 30, 40, 50, 60, 70, 80 or 90% of the poly(butylene succinate) polymer chains have been chain extended. It should be noted that the malic acid may dehydrate at high temperature, for example during melt extrusion, into maleic or fumaric acid units. It is intended that references herein to PBS copolymers comprising malic acid include implants where the malic acid in the PBS copolymer has undergone further reaction during processing, for example, to form maleic or fumaric acid or another compound. Thus, implants comprising poly(butylene succinate)-malic acid copolymer refer to implants prepared from copolymers comprising succinic acid, 1,4-butanediol and malic acid. The implants may comprise a composition of poly(butylene succinate) copolymer wherein greater than 20, 30, 40, 50, 60, 70, 80, or 90% of the polymer chains of the composition have been chain extended with malic acid. In another preferred embodiment, malic acid may be used as a branching or cross-linking agent to prepare a copolymer of poly(butylene succinate) with adipate, which may be referred to as poly [(butylenesuccinate)-co-adipate] cross-linked with malic acid. The malic acid disclosed herein may be the L-enantiomer, D-enantiomer, a combination therefore, but in one preferred embodiment the poly (butylene succinate) is prepared using L-malic acid, such that poly(1,4-butylene glycol-co-succinic acid), cross-linked or chain extended with L-malic acid is one particularly preferred composition.

Agents that may be used to chain extend poly(butylene succinate) or copolymer thereof also include epoxides, isocyanates, diisocyanates, oxazolines, diepoxy compounds, acid anhydrides, carbonates, silicate esters, and carbodiimides. Additional monomers may also be included that can be cross-linked, for example, maleic, fumaric, and itaconic acids can be incorporated and chains extended by the addition of peroxide. In one embodiment, copolymers with long-chain branching are preferred. It should be noted however that the use of isocyanates and diisocyanates is not preferred due to the toxicity associated with the use of these cross-linking chemistries. In one embodiment, the PBS and copolymer polymeric compositions exclude compositions prepared with isocyanates or diisocyanates. In another embodiment, the PBS and copolymer polymeric compositions exclude compositions prepared with urethane linkages. In a particularly preferred composition, the PBS and copolymer polymeric compositions used herein to prepare the implants are prepared only from monomers that have one or more of the following groups: hydroxy groups and carboxylic acid groups. In another embodiment, the PBS and copolymer thereof polymeric compositions exclude ether linkages.

In a preferred embodiment, the poly(butylene succinate) and copolymers thereof contain at least 70%, more preferably 80%, and even more preferably 90% by weight succinic acid and 1,4-butanediol units.

In another embodiment, the poly(butylene succinate) and copolymers thereof disclosed herein include polymers and copolymers which contain a small quantity of unreacted or partially reacted monomer. For example, succinic acid (or dimethyl succinate) and 1,4-butanediol units may be present in small quantities in the poly(butylene succinate) and copolymers thereof prior to converting these compositions into resorbable implants. In embodiments, the poly(butylene succinate) and copolymers thereof may comprise one or more side reaction products derived from succinic acid or 1,4-butanediol, such as tetrahydrofuran. It is preferred that the quantity of unreacted monomer or side reaction product is minimized, particularly in the polymer or copolymer prior to conversion into an implant. In one embodiment, the poly(butylene succinate) or copolymer thereof contains up to 0.5 wt %, more preferably up to 0.2 wt %, succinic acid or dimethyl succinate. In another embodiment, the poly (butylene succinate) or copolymer thereof contains up to 0.5 wt %, more preferably 0.2 wt %, 1,4-butanediol. In another embodiment, the poly(butylene succinate) or copolymer thereof contains up to 0.5 wt %, more preferably up to 0.2 wt %, tetrahydrofuran. In a further embodiment, the poly (butylene succinate) or copolymer thereof contains up to 5 wt %, preferably up to 0.5 wt %, and more preferably up to 0.1 wt %, malic acid.

In another embodiment, the poly(butylene succinate) and copolymers thereof disclosed herein include polymers and copolymers in which known isotopes of hydrogen, carbon and/or oxygen are enriched. Hydrogen has three naturally occurring isotopes, which include $^1$H (protium), $^2$H (deuterium) and $^3$H (tritium), the most common of which is the $^1$H isotope. The isotopic content of the polymer or copolymer can be enriched for example, so that the polymer or copolymer contains a higher than natural ratio of a specific isotope or isotopes. The carbon and oxygen content of the polymer or copolymer can also be enriched to contain higher than natural ratios of isotopes of carbon and oxygen, including, but not limited to $^{13}$C, $^{14}$C, $^{17}$O or $^{18}$O. Other isotopes of carbon, hydrogen and oxygen are known to one of ordinary skill in the art.

A preferred hydrogen isotope enriched in poly(butylene succinate) or copolymer thereof is deuterium, i.e., deuterated poly(butylene succinate) or copolymer thereof. The percent deuteration can be up to at least 1% and up to 5, 10, 15, 20, 25, 30, 35, 40, 45, 50, 55, 60, 65, 70, 75, 80, or 85% or greater.

Accordingly, the present application discloses a composition comprising PBS or copolymer thereof, wherein the isotopes of hydrogen, carbon and/or oxygen in the polymer have been enriched, and the use of such a composition in accordance with the other disclosures of the present application.

For example, the abundance of deuterium in the PBS or copolymer thereof may exceed 0.0115% of all elemental hydrogen present in the PBS or copolymer, and/or the PBS or copolymer may contain tritium. Additionally, or alternatively, the abundance of carbon-13 in the PBS or copolymer may exceed 1.07% of all elemental carbon present in the PBS or copolymer, and/or the PBS or copolymer may contain carbon-14. Additionally, or alternatively, the abundance of oxygen-17 in the PBS or copolymer may exceed 0.038% of all elemental oxygen present in the PBS or copolymer, and/or the abundance of oxygen-18 in the PBS or copolymer exceeds 0.205%. Optionally, the abundance of deuterium in the polymer exceeds 1, 5, 10, 15, 20, 25, 30, 35, 40, 45, 50, 55, 60, 65, 70, 75, 80, or 85% of the elemental hydrogen present in the PBS or copolymer.

The poly(butylene succinate) and copolymers thereof disclosed herein may be formed from monomers and additives which are themselves produced by chemical or biological processes. In the manufacture of implants using polymers, it is desirable that the polymeric materials have the lowest levels of impurities possible in order to prevent or minimize the reaction of the body to the impurities. Relevant impurities include organic impurities. The purification of polymers to a level where they are suitable for use in implants involves purification processes that remove a range of impurities, including, for example, lipids, proteins, peptides, polysaccharides, nucleic acids, amino acids and cell wall components. Where biological processes are used to produce one or more of the monomers and additives, those processes may result in said monomers and additives containing residual quantities of nitrogen-containing matter, such as nitrogen containing monomers, proteins, peptides, etc. In one embodiment, the poly(butylene succinate) and copolymers thereof disclosed herein include polymers and copolymers in which the nitrogen content is reduced so that it is present at 0 PPM or 0.01 PPM to 500 PPM. The nitrogen content is preferably up to 100 PPM, and more preferably up to 50 PPM.

Preferred polymers and copolymers have a weight average molecular weight (Mw) of 10,000 to 400,000, more preferably 50,000 to 300,000 and even more preferably 100,000 to 200,000 based on gel permeation chromatography (GPC) in chloroform solution relative to polystyrene standards. In a particularly preferred embodiment the polymers and copolymers have a weight average molecular weight of 50,000 to 300,000, and more preferably 130,000 to 250,000.

The poly(butylene succinate) and copolymers thereof disclosed herein preferably have a polydispersity in the range of from 1 to 10, such as from 3 to 10 (e.g. from 4 to 7, or 3 to 8).

Preferred polymers and copolymers have a number average molecular weight (Mn) of 1,000 to 150,000, preferably 5,000 to 100,000 or 10,000 to 100,000 and even more preferably 10,000-60,000 or 20,000-60,000 Da. For example, the polymers and copolymers may have a number average molecular weight (Mn) of from 1,000 to 50,000, 10,000 to 70,000 or from 70,000 to 150,000 Da. In a further embodiment, the polymers and copolymers may have a number average molecular weight (Mn) of from 1 to 150 kDa based on gel permeation chromatography (GPC) relative to polystyrene standards, and a PDI ranging from 2 to 10. In another embodiment, the polymers and copolymers have a number average molecular weight (Mn) of from 20 to 60 kDa based on GPC relative to polystyrene standards, and a PDI ranging from 3 to 8.

In a preferred embodiment, the tensile strength of an unoriented form of poly(butylene succinate) or copolymer thereof that is used to make the implants should be at least 1 MPa, preferably 10 MPa, more preferably 35 MPa, and even more preferably up to 70 MPa or higher. A particularly preferred tensile range for unoriented forms is 35-60 MPa. The Young's modulus of an unoriented form of poly(butylene succinate) or copolymer thereof that is used to make the implants should preferably be in the range of 30-700 MPa, and more preferably 300-500 MPa depending on its crystallinity. It is also preferable that the polymer or copolymer has a melting point of at least 80° C., preferably 90° C., and even more preferably greater than 100° C. In a preferred embodiment, the melting point of the poly(butylene succinate) or copolymer thereof that is used to make the implants is 115° C.±20° C., and more preferably between 105° C. and 120° C. A higher melting point (over 100° C.) is preferable to provide improved stability of the implants particularly during sterilization, shipping and storage.

In one preferred embodiment, the poly(butylene succinate) or copolymer thereof used to make the implants has one or more, or all of the following properties: density of 1.23-1.26 g/cm$^3$, glass transition temperature of −31° C. to −35° C., melting point of 113° C. to 117° C., melt flow rate (MFR) at 190° C./2.16 kgf of 2 to 10 g/10 min, and tensile strength of 30 to 60 MPa.

In a further embodiment, the poly(butylene succinate) or copolymer thereof used to make the implants may contain micropores. Micropores typically have an average diameter in the range from 10 µm to 1 mm. Preferably, the micropores have an average diameter larger than 50 µm or 75 µm, to provide suitably sized pores to encourage tissue in-growth. Optionally the average diameter of micropores is selected to be from 50 to 500 µm.

For example, one object of this invention is to manipulate the microporosity of the poly(butylene succinate) or copolymer thereof, for the purpose of controlling the rates of degradation of articles, in particular medical implants, formed from, comprising, consisting essentially of, or consisting of, poly(butylene succinate) or copolymer thereof and/or controlling the rates of degradation of the element(s) of those articles, in particular medical implants, made from the poly(butylene succinate) or copolymer thereof.

The introduction of micropores in the poly(butylene succinate) polymer or copolymer thereof can permit the polymer or copolymer to degrade more readily in the environment and/or in vivo (for example, after implantation).

Accordingly, the present invention also provides methods for manufacturing implants (in particular, the implants described elsewhere in the present application) which increase microporosity and/or exposed surface area of the poly(butylene succinate) polymer or copolymer thereof, in order to alter degradability.

For example, microporous poly(butylene succinate) polymer or copolymer thereof can be made using methods that create pores, voids, or interstitial spacing, such as an emulsion or spray drying technique, or which incorporate gaseous, liquid leachable or lyophilizable particles within the polymer or copolymer. Examples including fibers (including monofilaments, and multifilaments), foams, coatings, meshes, microparticles and other articles (e.g. as described elsewhere in the present application).

Optionally, the rate of degradation of articles formed from poly(butylene succinate) polymer or copolymer thereof may be enhanced by forming the article from such polymer or copolymer that includes additives which form micropores therein.

Pore forming agents are generally added as particulates and include water soluble compounds such as inorganic salts and sugars which can be removed by leaching. However, gaseous or liquid pore forming agents may also be used. Suitable particles include salt crystals, proteins such as gelatin and agarose, starches, polysaccharides such as alginate and other polymers. The average diameters of the particles may be suitably sized to provide micropores having an average diameter in the ranges discussed above. Gaseous pore forming agents include carbon dioxide, steam, or super critical carbon dioxide or other gases and liquids, which can be added to the polymer or molten polymer under pressure. After the pressure is released, the gaseous additive may expand and preferentially evaporate to leave pores within the polymer or device.

Pore forming agents useful for the production of microporous poly(butylene succinate) polymer or copolymer thereof may be lyophilizable. Lyophilizable liquids include water or dioxane, while lyophilizable solids include ammonium chloride or ammonium acetate.

Pore forming agents used for the production of microporous poly(butylene succinate) polymer or copolymer thereof can be included, for example, in an amount of between 0.01% and 90% weight to volume, preferably at a level between one and thirty percent (w/w, polymer), to increase micropore formation in the poly(butylene succinate) polymer or copolymer thereof.

In one option, after the poly(butylene succinate) polymer or copolymer thereof is formed comprising the pore forming agents, it may be treated to remove the pore forming agents (e.g. by leaching, evaporation, or lyophilization), thereby producing microporous poly(butylene succinate) polymer or copolymer thereof. The removal of the pore forming agent may occur before, during, or after, the poly(butylene succinate) polymer or copolymer thereof has been structurally configured into the form (e.g. shape, size, etc.) present in a finished medical implant.

In a particularly preferred embodiment, it is important that the poly(butylene succinate) or copolymer thereof, has a low moisture content during processing and storage. This is necessary to ensure that the implants can be produced with high tensile strength, prolonged strength retention, and good shelf life. In a preferred embodiment, the polymers and copolymers that are used to prepare the implants have a moisture content of less than 1,000 ppm (0.1 wt %), less than 500 ppm (0.05 wt %), less than 300 ppm (0.03 wt %), more preferably less than 100 ppm (0.01 wt %), and even more preferably less than 50 ppm (0.005 wt %).

The compositions used to prepare the implants must have a low endotoxin content. The endotoxin content must be low enough so that the implants produced from the poly(butylene succinate) or copolymer thereof have an endotoxin content of less than 20 endotoxin units per device as determined by the limulus amebocyte lysate (LAL) assay. In one embodiment, the compositions have an endotoxin content of <2.5 EU/g of PBS or copolymer thereof.

Optionally, the resorbable implants and other articles produced from a polymeric composition comprising poly (butylene succinate) polymer or copolymer thereof according to the present invention may be implants and articles that comprise, consist essentially of, or consist of components made of the polymeric composition. For example, the polymeric composition may be present in the resorbable implants and other articles of the present invention in an amount of at least, or greater than, about 5 wt %, 10 wt %, 15 wt %, 20 wt %, 30 wt %, 40 wt %, 50 wt %, 60 wt %, 70 wt %, 80 wt %, 85 wt %, 90 wt %, 95 wt %, 96 wt %, 97 wt %, 98 wt %, 99 wt %, or substantially 100 wt % the remainder (if any) of which may, for example and without limitation, be other components in the resorbable implants and other articles which may be other resorbable or non-resorbable parts thereof, bioactive agents, or any other components of the resorbable implants and other articles.

B. Additives and Other Polymers

Certain additives may be incorporated into poly(butylene succinate) and copolymers thereof prior to converting these compositions into resorbable implants. Preferably, these additives are incorporated during the compounding process to produce pellets that can be subsequently processed into implants. For example, additives may be compounded with poly(butylene succinate) or copolymer thereof, the compounded poly(butylene succinate) or copolymer thereof extruded into pellets, and the pellets 3D printed or extruded into fibers suitable for making implantable surgical meshes (including, but not limited to, surgical meshes for soft tissue implants for reinforcement of soft tissue, for the bridging of fascial defects, for a trachea or other organ patch, for organ salvage, for dural grafting material, for wound or burn dressing, for breast reconstruction, for hernia repair, or for a hemostatic tamponade; or surgical mesh in the form of a mesh plug), for example by knitting, weaving or 3D printing. In another embodiment, the additives may be incorporated using a solution-based process. In a preferred embodiment of the invention, the additives are biocompatible, and even more preferably the additives are both biocompatible and resorbable.

In one embodiment of the invention, the additives may be nucleating agents, dyes or colorants, processing aids, and/or plasticizers. These additives may be added in sufficient quantity to produce the desired result. In general, these additives may be added in amounts of up to 20% by weight.

Nucleating agents may be incorporated to increase the rate of crystallization or increase the crystallization temperature of the poly(butylene succinate) or copolymer thereof. Such agents may be used, for example, to improve the mechanical properties of fibers and meshes, as well as the implants, and to reduce cycle times. Preferred nucleating agents include, but are not limited to, salts of organic acids such as calcium citrate, polymers or oligomers of poly(butylene succinate) polymers and copolymers, high melting polymers such as polyglycolic and polylactic acids, alpha-cyclodextrin, talc, micronized mica, calcium carbonate, ammonium chloride, and aromatic amino acids such as tyrosine and phenylalanine or salts of these.

Plasticizers that may be incorporated into the compositions include, but are not limited to, polyethylene glycol, polypropylene glycol, polybutylene glycol, copolymers of ethylene glycol, propylene glycol and or butylene glycol, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment of the invention, the additives are contrast agents, radiopaque markers and radioactive substances. These additives may also be incorporated into poly(butylene succinate) or copolymer thereof either before preparing the implants, such as fibers, meshes or 3D printed objects, or after they are prepared.

In another embodiment, the additives are dyes. Preferred dyes include D&C Blue No. 9 (as defined by the US Code of Federal Regulations (CFR) Part 74.1109, principally 7,16-dichloro-6,15-dihydro-5,9,14,18-anthrazine-tetrone), D&C Green No. 5 (as defined by CFR Part 74.1205, principally the disodium salt of 2,2'-[(9,10-dihydro-9,10-dioxo-1,4-anthracenediyl)diimino]bis-[5-methylbenzenesulfonic acid] (CAS Reg. No. 4403-90-1), FD&C Blue No. 2 (as defined by the CFR Part 74.3102), D&C Blue No. 6 (as defined by the CFR Part 74.3106, and principally [A2,2'-biindoline]-3,3' dione (CAS Reg. No. 482-89-3), D&C Green No. 6 (as defined by the CFR Part 74.3206), and D&C Violet No. 2 (as defined by the CFR Part 74.3602). In embodiments, dyes are blended with the poly(butylene succinate) or copolymers thereof prior to melt processing or melt compounded. In embodiments, dyes are dry blended with poly(butylene succinate) or copolymers thereof (e.g. the dye is spread over polymer pellets), or the dye is melt compounded with poly(butylene succinate) or copolymer thereof. In embodiments, one or more dyes may be blended with poly(butylene succinate) or copolymer thereof, and the dyed blend extruded to form dyed fiber, such as dyed monofilament or multifilament fiber, or the blend melt processed to form a dyed non-woven, film, injection molded construct, foam, thermoform, laminate, pultruded construct, extruded tube, or 3D printed construct. Dyed fiber may be further processed, for example, by knitting, weaving, crocheting, or braiding to form dyed knitted mesh, woven mesh, braid, and other dyed textiles. In other embodiments, a dye and the poly(butylene succinate) or copolymer thereof may be solution blended to form a dyed object, such as a dyed fiber or dyed non-woven. In embodiments, a solution of dye and poly(butylene succinate) or copolymer thereof may be electrospun to form a dyed non-woven. In embodiments, dyes are blended or mixed with poly(butylene succinate) or copolymer thereof to form blends, objects or constructs with a dye concentration of 0.001 to 1 wt %, more preferably between 0.01 to 0.08 wt %.

In yet another embodiment of the invention, the additives are other polymers, preferably other resorbable polymers. Examples of other resorbable polymers that can be incorporated into the compositions used to make the implants are: polymers and copolymers of glycolic acid, lactic acid, 1,4-dioxanone, trimethylene carbonate, ε-caprolactone, 3-hydroxybutyrate, 4-hydroxybutyrate, including polyglycolic acid, polylactic acid, polydioxanone, polycaprolactone, poly-4-hydroxybutyrate and copolymers thereof, poly-3-hydroxybutyrate, copolymers of glycolic and lactic acids, such as VICRYL® polymer, MAXON® and MONOCRYL® polymers, and including poly(lactide-co-caprolactones); poly(orthoesters); polyanhydrides; poly(phosphazenes); synthetically or biologically prepared polyesters; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO); polypropylene glycol, polypropylene oxide and copolymers of ethylene and propylene oxide, polybutylene glycol, polytetrahydrofuran); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); silk, including recombinant silks, and silk derivatives and analogs; cellulose, including bacterial cellulose, and recombinant cellulose; chitin; chitosan; modified chitosan; biocompatible polysaccharides; hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or poly-caprolcatone and copolymers thereof, including random copolymers and block copolymers thereof. In embodiments, these polymers are blended with PBS or copolymer thereof so that the content of the polymer in the PBS or copolymer thereof is 0.1 wt % to 99.9 wt %, more preferably 0.1 wt % to 30 wt %, and even more preferably 0.1 wt % to 20 wt %. In embodiments, the polymers are blended with PBS or copolymer thereof by solution blending, melt blending. In an embodiment, the polymers are blended using a twin screw extruder.

In one embodiment, the PBS or copolymer thereof polymeric composition is not blended with another polymer.

In another embodiment, the PBS or copolymer thereof polymeric composition is not blended with polylactic acid (PLA), which may be poly-L-lactic acid (PLLA), poly-D-lactic acid (PDLA), or poly-D,L-lactic acid (PDLLA).

In another embodiment, the PBS or copolymer thereof polymeric composition may be blended with PLA (which may optionally be PLLA, PDLA, or PDLLA), wherein it may be preferred that: (i) the blend contain no other polymers other than the PBS or copolymer thereof and the PLA; or (ii) the blend contain at least, or greater than, 40 wt %, 50 wt %, 60 wt %, 70 wt %, or 80 wt % PBS or copolymer thereof, such as greater than 85 wt %, 90 wt %, 95 wt %, 96 wt %, 97 wt %, 98 wt %, or 99 wt %, the remainder of which may be PLA alone or along with any other components of a blend.

In another embodiment, the PBS or copolymer thereof polymeric composition is not blended with poly-caprolactone (PCL) and/or if it is blended with PCL then the blend does not contain polyanhydride and/or any other polymer.

In another embodiment, the PBS or copolymer thereof polymeric composition is not blended with chitosan and/or if it is blended with chitosan, then then the blend contains greater than 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with polyglycolic acid, and the blend contains greater than 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with polydioxanone, and the blend contains greater than 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a copolymer comprising glycolic acid and trimethylene carbonate, and the blend contains greater than 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with poly-4-hydroxybutyrate (P4HB), and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof. In embodiments, PBS or copolymer thereof is blended with P4HB, and the blend contains 0.1-25 wt % PBS or copolymer thereof. Blending 0.1-25 wt % PBS or copolymer thereof with P4HB has been found to increase crystallization rate of P4HB, and increase the crystallization temperature. These changes in crystallization rate and time are particularly useful in melt processing, for example, in the formation of fibers, including monofilament and multifilament fibers, films, non-wovens and other textiles. In embodiments, P4HB is blended with PBS or copolymer thereof, and the blend contains 0.1-25 wt % P4HB. Blending 0.1-25 wt % P4HB with PBS or copolymer thereof may be useful for increasing the rate of degradation of PBS or copolymer thereof.

In an embodiment, the PBS or copolymer thereof polymeric composition is blended with poly-3-hydroxybutyrate-co-4-hydroxybutyrate, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a polymer comprising 3-hydroxybutyrate, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a polymer comprising 3-hydroxybutyrate and 3-hydroxyhexanoate, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a polymer comprising 3-hydroxyoctanoate, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a polymer comprising glycolic acid and ε-caprolactone, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with polymer comprising lactic acid, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof. In embodiments, the PBS or copolymer thereof polymeric composition is blended with a copolymer comprising lactic acid, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In an embodiment, the PBS or copolymer thereof polymeric composition is blended with a polymer comprising glycolic acid and lactic acid, and the blend contains greater than 5 wt %, 10 wt %, 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

In embodiments, the polymers described above may be blended with PBS or copolymers thereof by solution blending or melt blending. In a preferred embodiment, blends are prepared using a twin screw extruder.

In embodiments, the additives are hydrogels.

C. Bioactive Agents

If desired, the implants of polybutylene succinate and/or copolymers thereof may incorporate one or more bioactive agents, including one or more drugs, for example in order to form a drug delivery device.

Useful bioactive agents include without limitation, physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body, and preferably include agents that promote healing and the regeneration of host tissue, and also therapeutic agents that prevent, inhibit or eliminate infection. Examples can include, but are not limited to, small-molecule drugs, peptides, proteins, antibodies, antimicrobials, antibiotics, antiparasitic agents, sugars, polysaccharides, nucleotides, oligonucleotides, hyaluronic acid and derivatives thereof, aptamers, siRNA, nucleic acids, and combinations thereof.

In certain exemplary embodiments, these bioactive agents may be added during the formulation process, during pelletization or blending, or may be added later to the implants.

In one embodiment, the one or more bioactive agents or drugs are dispersed uniformly in the polybutylene succinate and/or copolymers.

The percentage loading of the one or more bioactive agents or drugs will depend on the specific treatment and the desired release kinetics. The polybutylene succinate polymers and/or copolymer are suitable for loadings of the one or more bioactive agents or drugs to at least 33 wt % (i.e. polymer to drug ratios of 2:1). Higher loadings of up to 1:1 also can be used. The desired release kinetics will also depend upon the specific treatment.

In a preferred embodiment, the device is characterized by linear or zero-order release of the one or more bioactive agents or drugs. In a more preferred embodiment, the device does not release a burst of the one or more bioactive agents or drugs.

The one or more bioactive agents or drugs will typically be released over a period of at least 3 days, 7 days, 21 days, at least one month, at least three months, or at least six months. In general a linear release of the one or more bioactive agents or drugs is preferred. The length of time for the one or more bioactive agents or drugs release can be controlled by selection of the one or more bioactive agents or drugs, varying the loading and/or the shape and configuration of the device. Modifications in device porosity and/or microporosity may also be used to modify the release kinetics of the one or more bioactive agents or drugs. Optionally, less than 5, 10, 20, 30, 40, 50, 60, 70, 80 or 90 wt % of the one or more bioactive agents or drugs is released when the device is incubated in vitro in 0.1 M, pH 7.4, phosphate buffer at 37° C. after 10 days.

Examples of bioactive agents that can be incorporated into the implants of poly(butylene succinate) or copolymer thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, antibiotics, antimicrobials, growth factors, fibronectin, laminin, vitronectin, integrins, steroids, hydroxyapatite, silver particles or silver ions, vitamins, non-steroidal anti-inflammatory drugs, chitosan and derivatives thereof, alginate and derivatives thereof, collagen, sugars, polysaccharides, nucleotides, oligonucleotides, lipids, lipoproteins, anti-adhesion agents, hyaluronic acid and derivatives thereof, allograft material, xenograft material, ceramics, medical glass, bio-active glass, nucleic acid molecules, antisense molecules, aptamers, siRNA, nucleic acids, and combinations thereof. In a particularly preferred embodiment, the implants designed to allow tissue in-growth on one surface of the implant, and prevent tissue in-growth on another surface may be coated on the surfaces where tissue in-growth is not desired with a Sepra® hydrogel barrier. Such implants may be used, for example, in hernia repair to minimize tissue attachment to the visceral side of the implant following intraabdominal placement.

Antimicrobial agents that may be incorporated into the implants of poly(butylene succinate) and copolymers thereof, include, but are not limited to, antibacterial drugs, antiviral agents, antifungal agents, and antiparasitic drugs. Antimicrobial agents include substances that kill or inhibit the growth of microbes such as microbicidal and microbiostatic agents. Antimicrobial agents that may be incorporated into the implants of poly(butylene succinate) and copolymers thereof, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof; clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes. In a preferred embodiment, the antimicrobial agents incorporated into the implants are (i) rifampin and (ii) minocycline and its hydrochloride, sulfate, or phosphate salt. In a particularly preferred embodiment the implants of poly(butylene succinate) and copolymer thereof comprise rifampin and minocycline or its hydrochloride, sulfate, or phosphate salt.

Methods have been developed to prepare oriented resorbable implants that contain one or more antimicrobial agents to prevent colonization of the implants, and reduce or prevent the occurrence of infection following implantation in a patient. After implantation, the implants are designed to release the antimicrobial agents. The resorbable implants comprise oriented PBS and/or copolymers thereof. In one embodiment, the implant releases antimicrobial agent for at least 2-3 days. The implants are particularly suitable for use in procedures where there is a risk of infection, such as hernia repair, breast reconstruction and augmentation, mastopexy, orthopedic repairs, wound management, pelvic floor reconstruction, including treatment of pelvic organ prolapse, including treatment of cystocele, urethrocele, uterine prolapse, vaginal fault prolapse, enterocele and rectocele, surgical treatments for incontinence, stenting, heart valve surgeries, dental procedures and other surgical procedures or plastic surgeries. In a preferred embodiment, methods have been developed to produce medical implants comprising highly oriented fibers, meshes and/or films or other articles of PBS and/or copolymers thereof that contain the antimicrobial agents. Maintenance of the high degree of orientation of these fibers, meshes and/or films can be essential to their physical function in vivo. The high degree of orientation of the fibers, meshes and/or films allows these devices to retain strength in the body for prolonged periods ("prolonged strength retention"), and therefore provide critical support to tissues during reconstruction and repair procedures. If orientation is lost during preparation of the antimicrobial-containing fibers and meshes, the resulting products will have lower strength and strength retention, and be unable to provide the necessary reinforcement and configuration required for healing. For example, spray coating or dip coating of oriented fibers using many solvents may result in loss of fiber orientation and loss of strength retention. Methods have been developed that allow fibers, meshes and/or films of PBS and copolymers thereof containing antimicrobials to be prepared without substantial loss of orientation, and therefore without substantial loss of strength and strength retention.

Methods have also been developed to prepare resorbable enclosures, pouches, holders, covers, meshes, non-wovens, films, clamshells, casings, and other receptacles made from PBS and copolymers thereof that partially or fully encase, surround or hold implantable medical devices, and wherein the PBS and copolymers thereof contain and release one or more antimicrobial agents to prevent colonization of the implants and/or reduce or prevent infection. Implantable medical devices that can be partially or fully encased include cardiac rhythm management (CRM) devices (including pacemakers, defibrillators, and pulse generators), implantable access systems, neurostimulators, ventricular access devices, infusion pumps, devices for delivery of medication and hydration solutions, intrathecal delivery systems, pain pumps, and other devices to provide drugs or electrical stimulation to a body part.

In one embodiment, the methods disclosed herein are based upon the discovery that certain solvents and solvent mixtures can be used to apply antimicrobial agents to oriented constructs of PBS and copolymers thereof, such as fibers and meshes, without causing de-orientation of the constructs. The solvents and solvent mixtures are essentially non-solvents or poor solvents for oriented constructs of PBS and copolymers thereof, but can dissolve the antimicrobial agents. Furthermore, upon application to the constructs of PBS and copolymers thereof, the solvents either evaporate, can be removed by washing with another non-solvent for the construct, or can be readily dried, and leave behind the antimicrobial agents on the constructs. Suitable solvents for applying antimicrobial agents to oriented constructs of PBS and copolymers thereof, must therefore be (i) non-solvents or poor solvents for the constructs, (ii) capable of dissolving the antimicrobial agents in suitable concentrations, (iii) volatile or easily removed from the construct using, for example, low heat or another non-solvent for the construct, and (iv) non-reactive and non-toxic. Examples of suitable non-solvents include hexane, ethyl acetate, methanol, ethanol, isopropanol, water, and combinations thereof.

Accordingly, the present application also provides: An implant comprising an oriented form of PBS or copolymer thereof and one or more antimicrobial agents. In one embodiment, the oriented form may comprise fiber, mesh, woven, non-woven, film, patch, tube, laminate, or pultruded profile. Optionally, the fiber is monofilament, multifilament, braided, or barbed. Optionally, the mesh, woven and non-woven forms are knitted mesh, woven mesh, monofilament mesh, or multifilament mesh. Without limitation, the antimicrobial agents may be selected from one or more of the following: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes.

Optionally, the oriented form may have been monoaxially or biaxially oriented, and more preferably the oriented form may have one or more of the following properties: tensile strength between 400 MPa and 1200 MPa, a Young's Modulus of less than 5.0 GPa (e.g. at least 600 MPa, at least 1 GPa, or at least 2 GPa, but less than 5 GPa), an elongation at break between 15% and 50%, and a melt temperature between 105 and 120° C. In one option, the implant may contain rifampin and minocycline, or its hydrochloride, sulfate, or phosphate salt.

The one or more antimicrobial agents may, for example, be released from the implant for at least 2 days. In some embodiments, the implant may be a monofilament mesh with one or more of the following properties: suture pull out strength of at least 10 N, or at least 20 N, ball burst strength measured using a ⅜ inch ball of at least 22 lb. force, fiber diameters ranging from 10 μm to 1 mm, pore diameters of at least 50 μm, and a Taber stiffness between 0.01 and 10 Taber stiffness units or between 0.1 and 1 Taber stiffness units. In other embodiments, the implant may be a monofilament mesh and, for example, may have a suture pull out strength of at least 5 kgf, and a ball burst strength measured using a ⅜ inch ball of at least 44 lb. force. Optionally, the implants are used for soft or hard tissue repair, regeneration or replacement. Optionally, the implant is selected from the group: suture, barbed suture, wound closure device, patch, wound healing device, wound dressing, burn dressing, ulcer dressing, skin substitute, hemostat, tracheal reconstruction device, organ salvage device, dural patch or substitute, nerve regeneration or repair device, hernia repair device, hernia mesh, hernia plug, device for temporary wound or tissue support, tissue engineering scaffold, guided tissue repair/regeneration device, anti-adhesion membrane or barrier, tissue separation membrane, retention membrane, sling, device for pelvic floor reconstruction, including treatment of pelvic organ prolapse, including treatment of cystocele, urethrocele, uterine prolapse, vaginal fault prolapse, enterocele and rectocele, urethral suspension device, device for treatment of urinary incontinence, bladder repair device, bulking or filling device, bone marrow scaffold, bone plate, fixation device for an implant, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision. Optionally, the implant further comprises one or more of the following: processing aid, plasticizer, nucleant, dye, medical marker, therapeutic agent, diagnostic agent, prophylactic agent, protein, peptide, polysaccharide, glycoprotein, lipid, lipoprotein, nucleic acid molecule, inorganic or organic synthetic molecule, contrast agent, radiopaque marker, radioactive substance, hyaluronic acid or derivative thereof, collagen, hydroxyapatite, or absorbable polymer comprising one or more the following monomeric units: glycolic acid, lactic acid, trimethylene carbonate, p-dioxanone, and caprolactone. In some embodiments, the oriented form of PBS or copolymer thereof is a resorbable enclosure, pouch, holder, cover, mesh, non-woven, film, clamshell, casing, or other receptacle designed to partially or fully encase, surround or hold an implantable medical device, and wherein the implantable medical device that can be partially or fully encased is selected from one of the following: cardiac rhythm management (CRM) device (including pacemaker, defibrillator, and generator), implantable access system, neurostimulator, ventricular access device, infusion pump, device for delivery of medication and hydration solution, intrathecal delivery system, pain pump, or other device that provides drug(s) or electrical stimulation to a body part. Optionally, the implant contains rifampin and minocycline, or its hydrochloride, sulfate, or phosphate salt and further optionally the antimicrobial agent may be released from the implant for at least 2 days.

In one embodiment, the bioactive agent may be applied as a coating in several layers, such as spray coating multiple different layers onto the device or on selected areas of the device, or by applying a layer-by-layer approach using alternating layers of bioactive agents, coating or additives. These layers may differ in the amount or concentration of additive, or in type of coating material, or in the counter ion or charge of the coating material or additive. In a preferred embodiment, the layers are designed to degrade, dissolve or erode in a controlled way, thus prolonging the time of release of the active agent or the release kinetics of the active agent. For instance, multiple alternating layers of charged polymers (e.g. positively charged polylysine and negatively charged polyaspartic acid) may be used to create a coating that contains bioactive agents by the layer-by-layer approach. The release of the bioactive agent will depend on the rate of degradation, dissolution or erosion of the layers in the target tissue.

D. Reactive Blending

In embodiments, implants or compositions to form implants are prepared by reactive blending of PBS or copolymer thereof. In embodiments, the PBS or copolymer thereof comprises residual active catalyst from its preparation, or active catalyst is added to the PBS or copolymer thereof to catalyze reactive blending. When blended with another polyester, oligomer or monomer, the residual active catalyst or added catalyst may catalyze reactive blending of the polyester, oligomer or monomer with PBS or copolymer thereof resulting in transesterification between the polyester, oligomer or monomer and PBS or copolymer thereof. Reactive blending in this manner may be used to create block copolymers of the polyester and PBS or copolymer thereof or introduce new monomeric units. In embodiments, reactive blending is used to catalyze transesterification of PBS or copolymer thereof with another polyester, oligomer or monomer. In further embodiments, reactive blending is used to catalyze esterification or transesterification of PBS or copolymer thereof with one or more of the following: another polyester, oligomer or monomer containing ester groups or hydroxyl groups or a monomer present as a lactone.

In embodiments, the catalyst used for reactive blending is a metal-based catalyst. When a metal compound is used as a reactive blending catalyst, the amount of catalyst used to prepare the blend of poly(butylene succinate) or copolymer thereof is preferably 0.1 ppm or more, preferably 0.5 ppm or more, more preferably 1 ppm or more, and less than 30,000 ppm, preferably less than 1,000 ppm, more preferably less than 250 ppm, and more preferably less than 130 ppm. In embodiments, the catalyst comprises one or more of the following metals: scandium, yttrium, titanium, zirconium, vanadium, molybdenum, tungsten, zinc, iron, tin and germanium. Preferred catalysts for reactive blending include titanium catalysts. A particularly preferred catalyst for reactive blending is a titanium alkoxide. The titanium catalyst may either be present in a residual amount in the PBS polymer or copolymer, or may be added to the polymer or copolymer.

In embodiments, units or blocks of a more hydrolytically degradable polymer, oligomer or monomer are introduced into the polymer backbone of PBS or copolymer thereof by reactive blending in order to increase the rate of degradation of the PBS polymer or copolymer. In embodiments, blends prepared by reactive blending of PBS or copolymer thereof comprise a hydrolytically degradable polymer, oligomer or monomer. In embodiments, the hydrolytically degradable polymer or oligomer is a polyester. In embodiments, the hydrolytically degradable polymer, oligomer, or monomer may comprise one or more of the following monomers: glycolic acid, lactic acid, p-dioxanone, trimethylene carbonate, 4-hydroxybutyric acid or ester thereof, 3-hydroxybutyric acid or ester thereof, and ε-caprolactone. In embodiments, blends of PBS or copolymer thereof are formed by reactive blending PBS or copolymer thereof with one or more of the following polyesters: polyglycolic acid, polylactic acid, polyglycolic acid-co-lactic acid, polydioxanone, poly-4-hydroxybutyrate, poly-3-hydroxybutyrate, a copolymer comprising glycolic acid and ε-caprolactone, and poly-ε-caprolactone. In embodiments, a blend of PBS or copolymer thereof formed by reactive blending comprises 1-99 wt % of a hydrolytically degradable polymer, oligomer, or monomer and more preferably the blend comprises greater than 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof. In embodiments, a blend of PBS or copolymer thereof formed by reactive blending comprises 1-99 wt % of a polymer, oligomer or monomer comprising one or more of the following monomers: glycolic acid, lactic acid, p-dioxanone, trimethylene carbonate, 4-hydroxybutyric acid, 3-hydroxybutyric acid, and ε-caprolactone. In embodiments, the blends formed by reactive blending further comprise a metal catalyst, and preferably a titanium catalyst. In embodiments, a blend of PBS or copolymer thereof formed by reactive blending comprises a titanium catalyst, and 1-99 wt % of a polymer comprising one or more of the following monomers: glycolic acid, lactic acid, p-dioxanone, trimethylene carbonate, 4-hydroxybutyric acid, 3-hydroxybutyric acid, and ε-caprolactone. In embodiments, a blend of PBS or copolymer thereof formed by reactive blending comprises a titanium catalyst, and 1-99 wt % of a combination of polymer, oligomers and monomers comprising one or more of the following monomers: glycolic acid, lactic acid, p-dioxanone, trimethylene carbonate, 4-hydroxybutyric acid, 3-hydroxybutyric acid, and ε-caprolactone.

In embodiments, blends of PBS or copolymer thereof with other polymers, including those listed in Section II. B, may be prepared by reactive blending with a radical initiator. Suitable radical initiators are organic peroxide, azo compounds, or organic peroxy compounds. In embodiments, the radical initiator is dicumyl peroxide, di-(2-tert-butyl-peroxyisopropyl)benzene, or azobisisobutyronitrile (AIBN). Suitable concentrations of the initiator include 0.01-1 phr (part per hundred), and more preferably 0.1-0.5 phr.

Accordingly, in the context of reactive blending of PBS or copolymers thereof the present invention also provides subject matter defined by the following numbered paragraphs:

Paragraph 1. An implant comprising a polymeric composition comprising a 1,4-butanediol unit and a succinic acid unit, wherein the implant is formed by a process comprising reactive blending, wherein the polymeric composition is reactively blended with another polyester, oligomer or monomer, wherein the polymeric composition further comprises a residual catalyst or added catalyst, and wherein the oligomer or monomer comprise one or more hydroxy, ester or lactone groups.

Paragraph 2. The implant of Paragraph 1, wherein the catalyst used for reactive blending is a metal-based catalyst.

Paragraph 3. The implant of Paragraph 2, wherein the metal-based catalyst comprises one or more of the following metals: scandium, yttrium, titanium, zirconium, vanadium, molybdenum, tungsten, zinc, iron, tin and germanium.

Paragraph 4. The implant of Paragraph 3, wherein the metal catalyst is a titanium catalyst, including a titanium alkoxide.

Paragraph 5. The implant of Paragraph 3, wherein the catalyst is present in the polymeric composition in a residual amount or is added to the polymeric composition.

Paragraph 6. The implant of Paragraphs 2 to 5, wherein the metal catalyst is present in the polymeric composition at a level of 0.1 ppm or more, preferably 0.5 ppm or more, more preferably 1 ppm or more, and less than 30,000 ppm, preferably less than 1,000 ppm, more preferably less than 250 ppm, and more preferably less than 130 ppm.

Paragraph 7. The implant of Paragraphs 1 to 6, wherein the polyester, oligomer or monomer reactively blended with the polymeric composition is hydrolytically degradable.

Paragraph 8. The implant of Paragraph 7, wherein the polyester, oligomer or monomer comprise one or more of the following: glycolic acid, lactic acid, glycolide, lactide, p-dioxanone, trimethylene carbonate, 4-hydroxybutyric acid or ester thereof, 3-hydroxybutyric acid or ester thereof, and ε-caprolactone.

Paragraph 9. The implant of Paragraph 7, wherein the polyester is selected from one or more of the following: polyglycolic acid, polylactic acid, polyglycolic acid-co-lactic acid, polydioxanone, poly-4-hydroxybutyrate, poly-3-hydroxybutyrate, a copolymer comprising glycolic acid and ε-caprolactone, and poly-ε-caprolactone.

Paragraph 10. The implant of Paragraphs 1-9, wherein the implant is formed by reactive blending and comprises 1-99 wt % of a hydrolytically degradable polyester, oligomer, or monomer and more preferably the reactive blend comprises greater than 20 wt %, 30 wt %, 40 wt %, 50 wt %, 60 wt %, 70 wt %, 80 wt %, 90 wt %, 95 wt %, 96 wt %, 97 wt %, 98 wt %, or 99 wt % of PBS or copolymer thereof.

Paragraph 11. The implant of Paragraph 10, wherein the implant is formed by reactive blending with 1-99 wt % of a polyester, oligomer or monomer comprising one or more of the following monomers: glycolic acid, lactic acid, p-dioxanone, trimethylene carbonate, 4-hydroxybutyric acid, 3-hydroxybutyric acid, and ε-caprolactone.

Paragraph 12. The implant of Paragraphs 1-11, wherein the reactive blend comprises a blend of PBS or copolymer thereof, a titanium catalyst, and 1-99 wt % of a polymer comprising one or more of the following monomers: glycolic acid, lactic acid, lactide, glycolide, p-dioxanone, trimethylene carbonate, 4-hydroxybutyric acid, 3-hydroxybutyric acid, and Ω-caprolactone.

Paragraph 13. The implant of Paragraphs 1-11, wherein the reactive blend comprises a blend of PBS or copolymer thereof, a titanium catalyst, and 1-99 wt % of one or more polyesters, oligomers and monomers comprising one or more of the following monomers: glycolic acid, lactic acid, lactide, glycolide, p-dioxanone, trimethylene carbonate, 4-hydroxybutyric acid, 3-hydroxybutyric acid, and □-caprolactone.

Paragraph 14. The implant of Paragraph 1, wherein the process further comprises adding a radical initiator.

E. Compositions of PBS or Copolymer Thereof with Catalysts to Increase Polymer or Copolymer Weight Average Molecular Weight During Melt Processing Preventing loss of weight average molecular weight during melt processing of PBS or copolymers thereof is important in maximizing tensile strength and strength retention of implants derived from these polymers. It has been discovered that certain compositions of PBS or copolymers thereof can be melt processed without loss of weight average molecular weight, and in fact it has been possible to produce compositions of PBS or copolymers thereof wherein the weight average molecular weight of the polymers increases during melt processing. An increase in molecular weight can be particularly advantageous in some implant applications. For example, increasing the weight average molecular weight can result in prolonged strength retention of the implant. In embodiments, implants are formed with chain extension of PBS or copolymers thereof during melt processing.

In embodiments, compositions of PBS or copolymer thereof are provided wherein the weight average molecular weights of PBS or copolymer thereof increase when the polymer or copolymer is melt processed to form an implant. In embodiments, these compositions comprise a catalyst. The catalyst may be residual catalyst remaining in the polymer after synthesis of the polymer, or the catalyst may be added to a composition of PBS or copolymer thereof. In embodiments, the catalyst may comprise one of the following metals: scandium, yttrium, titanium, zirconium, vanadium, molybdenum, tungsten, zinc, iron, tin and germanium. A preferred catalyst comprises titanium. A particularly preferred catalyst is a titanium alkoxide. In embodiments, the catalyst is present in the PBS or copolymer at a level of 0.1-1,000 ppm, more preferably 1-1,000 ppm, and even more preferably 1-100 ppm or 5-100 ppm. In embodiments, the weight average molecular weight of PBS or copolymer thereof comprising the catalyst increases during melt processing by 1 to 100%, more preferably by 2 to 60%, and even more preferably by 2 to 31%. In embodiments, the weight average molecular weight of PBS or copolymer thereof comprising the catalyst increases during melt processing at temperatures ranging from 150 to 250° C., and more preferably 180 to 230° C. In embodiments, a composition comprising PBS or copolymer thereof with 1-100 ppm of a titanium catalyst is melt processed at temperatures in the range of 100 to 250°, or 100 to 230° C., to form an implant wherein the weight average molecular weight of the PBS or copolymer thereof in the implant is higher than the weight average molecular weight of the PBS or copolymer thereof prior to melt processing. In embodiments, the thermal processing range reaches peak temperatures of 180 to 250° C. or 180 to 230° C. In embodiments, these compositions may be processed by melt processing methods, including melt extrusion, injection molding, melt foaming, film melt extrusion, melt blowing, melt spinning, compression molding, lamination, thermoforming, molding, spun-bonding, nonwoven fabrication, tube melt extrusion, fiber melt extrusion, 3D printing by melt extrusion deposition (MED), fused pellet deposition (FPD), fused filament fabrication (FFF), and selective laser melting (SLM). Implants that may be formed from these compositions include: fibers, meshes including meshes for hernia repair and for breast reconstruction or breast lift, breast implants, scaffolds, monofilament fiber, multifilament fiber, non-wovens, films, injection molded implants, 3D printed implants, tubes, foams, screws, bone screws, interference screws, pins, ACL screws, clips, clamps, nails, medullary cavity nails, bone plates, bone substitutes, tacks, fasteners, suture fastener, rivets, staples, fixation devices, suture anchors, bone anchors, meniscus anchors, meniscal implants, intramedullary rods and nails, joint spacers, interosseous wedge implants, osteochondral repair devices, spinal fusion devices, spinal fusion cage, bone plugs, cranioplasty plugs, and plugs to fill or cover trephination burr holes and other orthopedic implants. In an embodiment, implants comprising PBS and copolymers thereof, may be formed by melt processing with weight average molecular weights that are between 1-100%, more preferably 1-50%, and even more preferably 5-30%, higher than the weight average molecular weights of the PBS or copolymer thereof used to prepare the implants.

The increase in weight average molecular weight of a PBS copolymer containing a titanium catalyst during melt processing is described in Example 18, and results are shown in Table 17. In this example, the PBS copolymer contains 56 ppm titanium, and has a starting weight average molecular weight of 160.4 kDa. When the copolymer is processed at temperatures of 100 to 230° C. with peak temperatures ranging from 180 to 230° C., the weight average molecular weight of the implant formed by melt processing of the copolymer ranged from 164.5 to 209.4 kDa representing an increase in weight average molecular weight of up to 31%.

Accordingly, in the context of compositions of PBS or copolymer thereof with catalysts to increase polymer or copolymer weight average molecular weight during melt processing the present invention also provides subject matter defined by the following numbered paragraphs:

Paragraph 1. An implant comprising a polymeric composition comprising a 1,4-butanediol unit and a succinic acid unit, wherein the implant is formed by melt processing, and wherein the weight average molecular weight of the polymeric composition increases during melt processing.

Paragraph 2. The implant of paragraph 1, wherein the polymeric composition prior to melt processing further comprises a catalyst.

Paragraph 3. The implant of paragraph 2, wherein the catalyst comprises one or more of the following metals: scandium, yttrium, titanium, zirconium, vanadium, molybdenum, tungsten, zinc, iron, tin and germanium.

Paragraph 4. The implant of paragraph 3, wherein the catalyst is a titanium alkoxide.

Paragraph 5. The implant of paragraphs 3 and 4, wherein the catalyst is present at a level of 0.1 to 1,000 ppm.

Paragraph 6. The implant of paragraph 1, wherein the weight average molecular weight increases during melt processing by 1 to 100%.

Paragraph 7. The implant of paragraph 1, wherein the polymeric composition is heated to a temperature between 150° C. and 250° C. during melt processing.

Paragraph 8. The implant of paragraph 1, wherein the implant is melt processed by melt extrusion, injection molding, melt foaming, film extrusion, melt blowing, melt spinning, compression molding, lamination, thermoforming, molding, spun-bonding, non-woven fabrication, tube extrusion, fiber extrusion, 3D printing by melt extrusion deposition, fused pellet deposition, fused filament fabrication, and selective laser melting.

Paragraph 9. The implant of paragraph 1, wherein the implant is a fiber, suture, mesh, including mesh for hernia repair, breast reconstruction, and breast lift, breast implant, tissue scaffold, monofilament fiber, multifilament fiber, non-woven, film, injection molded implant, 3D printed implant, tube, foam, screw, bone screw, interference screw, pin, ACL screw, clip, clamp, nail, medullary cavity nail, bone plate, bone substitute, tack, fastener, suture fastener, rivet, staple, fixation device, suture anchor, bone anchor, meniscus anchors, meniscal implant, intramedullary rod and nail, joint spacer, interosseous wedge implant, osteochondral repair device, spinal fusion device, spinal fusion cage, bone plug, cranioplasty plug, and plug to fill or cover trephination burr holes.

Paragraph 10. The implant of paragraph 1, wherein the polymeric composition is melt processed to form a fiber, and wherein the fiber has one or more of the following properties: (i) tensile strength of 400 MPa to 2,000 MPa, (ii) Young's Modulus of 600 MPa to 5 GPa, and (iii) elongation to break of 10 to 150%.

Paragraph 11. The implant of paragraph 10, wherein the fiber is knitted, woven or braided.

Paragraph 12. The implant of paragraph 11, wherein the implant is a mesh.

Paragraph 13. A method of forming the implant of any one of paragraphs 1-12, wherein the implant is produced by a method comprising the steps of: (a) preparing a polymeric composition comprising a polymer or copolymer of 1,4-butanediol unit, a succinic acid unit, and a metal catalyst, wherein the metal catalyst comprises scandium, yttrium, titanium, zirconium, vanadium, molybdenum, tungsten, zinc, iron, tin or germanium, and (b) forming the implant by a process comprising melt processing of the polymeric composition.

Paragraph 14. The method of paragraph 13, wherein the catalyst is present at a level of 0.1 to 1,000 ppm Paragraph 15. The method of paragraph 13, wherein the implant is formed by a process comprising one of the following melt processing processes: melt extrusion, injection molding, melt foaming, film extrusion, melt blowing, melt spinning, compression molding, lamination, thermoforming, molding, spun-bonding, non-woven fabrication, tube extrusion, fiber extrusion, 3D printing by melt extrusion deposition, fused pellet deposition, fused filament fabrication, and selective laser melting.

Paragraph 16. The method of paragraph 13, wherein the polymeric composition is heated to a temperature between 150° C. and 250° C. during melt processing.

Paragraph 17. The method of paragraph 13, wherein the weight average molecular weight increases during melt processing by 1 to 100%.

Paragraph 18. The method of paragraph 13, wherein the implant is a fiber, suture, mesh, including mesh for hernia repair, breast reconstruction, and breast lift, breast implant, tissue scaffold, monofilament fiber, multifilament fiber, non-woven, film, injection molded implant, 3D printed implant, tube, foam, screw, bone screw, interference screw, pin, ACL screw, clip, clamp, nail, medullary cavity nail, bone plate, bone substitute, tack, fastener, suture fastener, rivet, staple, fixation device, suture anchor, bone anchor, meniscus anchors, meniscal implant, intramedullary rod and nail, joint spacer, interosseous wedge implant, osteochondral repair device, spinal fusion device, spinal fusion cage, bone plug, cranioplasty plug, and plug to fill or cover trephination burr holes.

Paragraph 19. The method of paragraph 13, wherein the polymeric composition is melt processed to form a fiber, and wherein the fiber has one or more of the following properties: (i) tensile strength of 400 MPa to 2,000 MPa, (ii) Young's Modulus of 600 MPa to 5 GPa, and (iii) elongation to break of 10 to 150%.

Paragraph 20. The implant of paragraph 13, wherein the fiber is knitted, woven, braided, or formed into a mesh.

III. Methods of Synthesizing and Processing Implants of Poly(Butylene Succinate) and Copolymers Thereof A. Poly(Butylene Succinate) and Copolymers Thereof Poly(butylene succinate) and copolymers thereof may be synthesized by any suitable method. A suitable method must provide a biocompatible polymeric composition of PBS and copolymer thereof. In an embodiment, poly(butylene succinate) can be synthesized by (i) condensation or esterification of succinic acid and 1,4-butanediol or transesterification of dimethyl succinate and 1,4-butanediol to obtain oligomers, and (ii) polycondensation of the oligomers to form high weight average molecular weight poly(butylene succinate).

In one method, poly(butylene succinate) may be prepared by charging a suitable vessel with succinic acid (or dimethyl succinate) and 1,4-butanediol in a 1:1 ratio (or with a small excess of 1,4-butanediol). The reactants are heated to 130-190° C., more preferably 160-190° C., under an inert atmosphere, to melt the acid component and distill off water (or methanol). Once the distillation is completed, the pressure in the vessel is reduced using a high vacuum, and a suitable high weight average molecular weight poly(butylene succinate) is produced by polycondensation preferably at a temperature of 220-240° C. in the presence of a catalyst, with or without the addition of a co-catalyst.

Suitable catalysts for the synthesis of poly(butylene succinate) include p-toluenesulfonic acid, tin (II) chloride, monobutyl tin oxide, tetrabutyl titanate, titanium isopropoxide, tetraisopropyl titanate, lanthanide triflates, and distannoxane. Catalysts may include metal elements of the Groups 1 to 14 of the periodic table. Preferred catalysts have metal elements that are scandium, yttrium, titanium, zirconium, vanadium, molybdenum, tungsten, zinc, iron and germanium. Titanium and zirconium catalysts are particularly preferred for preparing poly(butylene succinate) and copolymers thereof. Tetraalkyl titanates are preferred catalysts. Specifically, tetra-n-propyl titanate, tetraisopropyl titanate, tetra-n-butyl titanate, tetra-t-butyl titanate, tetraphenyl titanate, tetracyclohexyl titanate, tetrabenzyl titanate, and mixed titanates thereof are preferred. In addition, titanium (oxy)acetylacetonate, titanium tetraacetylacetonate, titanium (diisopropoxide) acetylacetonate, titanium bis(ammonium lactate) dihydroxide, titanium bis(ethylacetoacetate) diisopropoxide, titanium (triethanolaminate) isopropoxide, polyhydroxytitanium stearate, titanium lactate, titanium triethanolaminate, butyl titanate dimer, are also preferred catalysts. Of these, tetra-n-propyl titanate, tetraisopropyl titanate, and tetra-n-butyl titanate, titanium (oxy) acetylacetonate, titanium tetraacetylacetonate, titanium bis (ammonium lactate) dihydroxide, polyhydroxytitanium stearate, titanium lactate, and butyl titanate dimer are preferred, and tetra-n-butyl titanate, titanium (oxy)acetylacetonate, titanium tetraacetylacetonate, polyhydroxytitanium stearate, titanium lactate, and butyl titanate dimer are more preferred. Particularly, tetra-n-butyl titanate, titanium butoxide, titanium isopropoxide, tetrisopropyl titanate, polyhydroxytitanium stearate, titanium (oxy)acetylacetonate, and titanium tetraacetylacetonate are preferred. In embodiments, a preferred catalyst is a titanium alkoxide. Zirconium catalysts that may be used to prepare the polymer or copolymer include zirconium tetraacetate, zirconium acetate hydroxide, zirconium tris(butoxy) stearate, zirconyl diacetate, zirconium oxalate, zirconyl oxalate, zirconium potassium oxalate, polyhydroxyzirconium stearate, zirconium ethoxide, zirconium tetra-n-propoxide, zirconium tetraisopropoxide, zirconium tetra-n-butoxide, zirconium tetra-t-butoxide, zirconium tributoxy acetylacetonate, and mixtures thereof. Of these, zirconyl diacetate, zirconium tris(butoxy) stearate, zirconium tetraacetate, zirconium acetate hydroxide, zirconium ammonium oxalate, zirconium potassium oxalate, polyhydroxyzirconium stearate, zirconium tetra-n-propoxide, zirconium tetraisopropoxide, zirconium tetra-n-butoxide, and zirconium tetra-t-butoxide are preferred, and zirconyl diacetate, zirconium tetraacetate, zirconium acetate hydroxide, zirconium tris(butoxy) stearate, zirconium ammonium oxalate, zirconium tetra-n-propoxide, and zirconium tetra-n-butoxide are more preferred. Particularly, zirconium tris(butoxy) stearate is preferred. Germanium catalysts that may be used include inorganic germanium compounds such as germanium oxide and germanium chloride and organic germanium compounds such as tetraalkoxygermanium. Germanium oxide, tetraethoxygermanium, tetrabutoxygermanium, and the like are preferred. Other metal-containing catalysts that can be used include scandium compounds such as scandium carbonate, scandium acetate, scandium chloride, and scandium acetylacetonate, yttrium compounds such as yttrium carbonate, yttrium chloride, yttrium acetate, and yttrium acetylacetonate, vanadium compounds such as vanadium chloride, vanadium oxide trichloride, vanadium acetylacetonate, and vanadium acetylacetonate oxide, molybdenum compounds such as molybdenum chloride and molybdenum acetate, tungsten compounds such as tungsten chloride, tungsten acetate, tungstenic acid, lanthanoid compounds such as cerium chloride, samarium chloride, and ytterbium chloride.

When a metal compound is used as a catalyst, the amount of catalyst used to prepare poly(butylene succinate) or copolymer thereof is preferably 0.1 ppm or more, preferably 0.5 ppm or more, more preferably 1 ppm or more, and less than 30,000 ppm, preferably less than 1,000 ppm, more preferably less than 250 ppm, and more preferably less than 130 ppm.

In embodiments, a phosphorous compound may be included in the polymerization process. In embodiments, the phosphorous compound may be a co-catalyst. In embodiments, the one phosphorus compound may be a heat stabilizer. In embodiments, the phosphorus compounds may be a proton-releasing compound. In embodiments, the phosphorous compound may be an organic phosphinic acid, organic phosphonic acid, inorganic phosphoric acid, or hydrogen phosphate salt. In embodiments, the phosphorus compound may be: polyphosphoric acid, phosphoric acid, hypophosphorous acid, pyrophosphorous acid, phosphorous acid, metaphosphoric acid, peroxophosphoric acid, ammonium hydrogen phosphate, magnesium hydrogen phosphate, calcium hydrogen phosphate, ammonium hydrogen polyphosphate, magnesium hydrogen polyphosphate, calcium hydrogen polyphosphate, tributyl phosphate, triphenyl phosphate, phenylphosphonic acid, benzylphosphonic acid, methylphosphonic acid, n-butylphosphonic acid, cyclophosphonic acid, diphenylphosphinic acid, phenyl phosphinic acid, benzylphosphinic acid, methylphosphinic acid, n-butylphosphinic acid, cyclohexylphosphinic acid, sodium phenylphosphinate. In embodiments, the phosphorus containing compound is present in the PBS or copolymer thereof at a concentration of 0.001-10 wt %, and more preferably 0.001-1 wt %, and even more preferably 0.01-0.1 wt %. In embodiments, the phosphorus co-catalyst is used with a metal catalyst to produce PBS or copolymer thereof, wherein the atomic ratio of the phosphorus (P) to metal (M), P/M, is 0.01-0.8, and more preferably 0.2-0.5.

After completion of the polycondensation, the polymer can be purified by dissolution in a solvent, filtering, and precipitation. For example, the polymer can be dissolved in chloroform, filtered, and precipitated with an alcohol such as methanol or ethanol. If desired, the polymer may be further purified by washing, for example with diethyl ether. Preferably the amount of metal in the poly(butylene succinate) or copolymer thereof is less than 100 ppm, and more preferably less than 50 ppm. A preferred metal content in the poly(butylene succinate) or copolymer thereof is 0.1-100 ppm, and more preferably 1-50 ppm.

After completion of the polycondensation, the polymer can be purified by washing with a non-solvent such as methanol, ethanol, isopropanol, butanol, ethyl acetate, water or mixtures thereof to remove side reaction products such as tetrahydrofuran, unreacted monomer or oligomers. For example, the polymer can be suspended in methanol, ethanol, water, or mixtures thereof, for a period of time at ambient temperature or elevated temperature and then collected by a solid-liquid separation step such as filtration or centrifugation. Residual washing solvents may be removed by drying, evaporation or under vacuum. Such washing steps may also be performed to remove, hydrolyze or inactivate the residual catalysts.

In an embodiment, the polymeric compositions of PBS and copolymer thereof used to prepare the implants comprise 1-500 ppm of one or more of the following: silicon, titanium and zinc. Preferably, the polymeric compositions comprise less than 100 ppm or less than 50 ppm of silicon, titanium and zinc. In another embodiment, the polymeric compositions used to make the implants do not comprise metals other than silicon, titanium and zinc or catalysts and co-catalysts in detectable quantities by PIXE analysis or in detectable quantities above 10 ppm by ICP-MS analysis. In a particularly preferred embodiment, the polymeric compositions used to make the implants exclude tin.

Copolymers of poly(butylene succinate) may be formed by copolymerization with different comonomer units, preferably dicarboxylic acids and diols, including for example, adipic acid, terephthalic acid, fumaric acid, ethylene glycol and 1,3-propanediol. Other suitable diol and dicarboxylic acid comonomer units include 1,2-propanediol, 1,2-butanediol, 2,3-butanediol, 1,3-butanediol, 2,3-butanediol, 1,5-pentane diol, 1,2-pentanediol, 2,4-pentanediol, 1,6-hexanediol, 1,2-hexanediol, malonic acid, glutaric acid, suberic acid, sebacic acid, azelaic acid, decanedicarboxylic acid, dodecanedicarboxylic acid, and octadecanedicarboxylic acid. In a preferred embodiment, the content of comonomer units is less than 30%, more preferably less than 20% and even more preferably less than 15%. In another preferred embodiment, the comonomer content of the copolymer is less than 15%, and the melting point of the copolymer is more than 100° C. Preferably, the melting point of the PBS copolymer is between 105° C. and 120° C.

In yet another embodiment, the polymers and copolymers of succinic acid and 1,4-butanediol may contain chain branches or chain extenders, most preferably chain branches or chain extensions formed with aliphatic oxycarboxylic acids. Preferred chain branching and/or chain extending agents are trifunctional and tetrafunctional aliphatic oxycarboxylic acids. Preferred trifunctional oxycarboxylic acid chain branching agents and/or chain extending may have (i) two carboxyl groups and one hydroxyl group in the same molecule (such as malic acid), or (ii) one carboxyl group and two hydroxyl groups in the same molecule. Preferred tetrafunctional oxycarboxylic acid chain branching and/or chain extending agents may have (i) three carboxyl groups and one hydroxyl group in the same molecule (such as citric acid), (ii) two carboxyl groups and two hydroxyl groups in the same molecule (such as tartaric acid), or (iii) three hydroxyl groups and one carboxyl group in the same molecule. Other chain branching and/or chain extending agents that may be incorporated include hydroxyglutaric acid, hydroxymethylglutaric acid, hydroxyisophthalic acid, and hydroxyterephthalic acid. Malic acid, tartaric acid and citric acid are particularly preferred chain branching and/or chain extending agents. Chain branching agents, cross-linking agents, coupling agents and chain extending agents are preferably incorporated into the poly(butylene succinate) and copolymer thereof in amounts of 0.001 to 5.0 mol %, or 0.01 to 5.0 mol %, more preferably 0.01 to 2.5 mol %, and most preferably 0.01 to 0.5 mol % or 0.1 to 0.5 mol %. In one embodiment, the chain branching and/or chain extending agent is malic acid. In a preferred embodiment, malic acid is incorporated in the poly(butylene succinate) polymer or copolymer in an amount of 0.001-5.0 mol % or 0.01-5.0 mol %, more preferably 0.01-0.5 mol % or 0.1-0.5 mol %, or in an amount of 0.01-1 part by weight, more preferably 0.1-0.5 parts by weight. In a preferred embodiment, greater than 1, 10, 20, 30, 40, 50, 60, 70, 80 or 90% of the polymer chains of poly(butylene succinate) are chain extended with malic acid. When malic acid is used as a trifunctional oxycarboxylic acid serving as the copolymerizable component, examples of the copolyester include succinic acid-1,4-butanediol-malic acid copolyester, succinic acid-adipic acid-1,4-butanediol-malic acid copolyester, succinic acid-1,4-butanediol-malic acid-tartaric acid copolyester, succinic acid-adipic acid-1,4-butanediol-malic acid-tartaric acid copolyester, succinic acid-1,4-butanediol-malic acid-citric acid copolyester, and succinic acid-adipic acid-1,4-butanediol-malic acid-citric acid copolyester. Malic acid may be present as the L-enantiomer, D-enantiomer, or both, but L-malic acid is preferred. During exposure to heat, or further processing, the malic acid monomers in the copolymer may dehydrate to produce fumaric and or maleic acids monomers in the copolymer. Thus, the implant disclosed herein may also comprise fumaric and maleic acid units, or combinations thereof.

Branching, chain extending, and cross-linking of polymer chains may be detected and quantified using methods that are known in the art, such as laser light scattering.

B. Spinning of Poly(Butylene Succinate) and Copolymers Thereof

Poly(butylene succinate) and copolymers thereof may be processed and oriented to provide implants with high tensile strength and prolonged strength retention. The polymers may be processed in the melt or in solution. In one preferred embodiment, poly(butylene succinate) and copolymers thereof are melt processed.

In melt processing of poly(butylene succinate) and copolymers thereof it is important to prevent hydrolysis of the polymers by residual moisture. Therefore, it is important that the polymers are dried prior to melt processing. In a preferred embodiment, the poly(butylene succinate) and copolymers are dried prior to melt processing so that they have a moisture content of less than 0.1 wt. %, preferably less than 0.05 wt. %, more preferably less than 0.01 wt. %, and even more preferably less than 0.005 wt. %. The polymers may be dried with hot air and under vacuum prior to melt processing. In a preferred embodiment, the polymers are dried under vacuum at 30-90° C., more preferably 60-90° C. Further, to prevent moisture pickup after drying, it is important to protect the polymer from exposure to moisture during processing and to process the polymer under dry conditions. Preferably, the polymer is kept under a blanket of dry, inert gas prior to and during extrusion, as well as at the extruder outlet.

In order to obtain implants with high tensile strength and prolonged strength retention, it is important to prevent loss of weight average molecular weight during melt processing of poly(butylene succinate) and copolymers thereof. At temperatures in excess of 200° C., the shear viscosity of poly(butylene succinate) can decrease significantly. The magnitude of the loss increases as the temperature rises above 200° C. and as the exposure time increases. In order to make implants with the highest tensile strength and prolonged strength retention, it is therefore important to minimize the time the polymers are exposed to high processing temperatures as well as the presence of moisture in the polymers. In an embodiment, the implants are melt extruded with a temperature profile of 60-230° C., more preferably 80-180° C., and even more preferably 80-170° C.

Examples 1 and 2 described herein compare two different methods of melt extruding poly(butylene succinate) and copolymers thereof. In some embodiments, fibers are melt extruded using standard heat convection chambers as described in Example 1. The monofilament fiber is oriented in this embodiment with 2-6 stages of orientation, and more preferably with 3, 4 or 5 stages of orientation. In this embodiment (i.e., orientation using standard heat convection chambers), the fiber can be oriented in line or, preferably, off line, at least one day after extrusion, for example, 1, 2, 3, 4, 5, 6, 7, 8, 9, 10, 11, 12, 13, 14 or 15 days after extrusion.

Additionally, it has been discovered that the method disclosed in Example 2 yields fibers with substantially higher tensile strengths than those obtained by the method described in Example 1. Thus, the method disclosed in Example 2 is preferred for making implants comprising fibers when it is desirable for the fibers to have high tensile strength and prolonged strength retention.

Using the method disclosed in Example 2, fibers were obtained with tensile strengths of 779-883 MPa compared to tensile strengths of 434-518 MPa produced by the method disclosed in Example 1 for the same monofilament diameter. In contrast to the method of Example 1, the use of multi-stage incremental orientation of the fiber and use of conductive chambers, instead of standard heat convection chambers used in Example 1, resulted in fiber with surprisingly higher tensile strengths. Preferably, the monofilament fiber is oriented with 2-6 stages of orientation, and more preferably with 3, 4 or 5 stages of orientation.

In a preferred embodiment, monofilament or multifilament fiber comprising poly(butylene succinate) and copolymers thereof is produced by a method comprising the steps of: (a) spinning multifilament or monofilament fiber comprising the polymer composition, (b) one or more stages of drawing the multifilament or monofilament fiber with an orientation ratio of at least 3.5 at a temperature of 50-70° C., (c) one or more stages of drawing the multifilament or monofilament fiber with an orientation ratio of at least 2.0 at a temperature of 65-75° C., and (d) drawing the multifilament or monofilament fiber with an orientation ratio greater than 1.0 at a temperature of 70-75° C. Preferably, the sum of the orientation ratios is over 6.0, 6.5, 7.0, 7.5 or 8.0.

In an even more preferred embodiment, the fibers are drawn in a conductive liquid chamber. Prior to drawing the fibers, melt extruded polymer is preferably quenched in a conductive liquid bath. The temperature of the bath is preferably from 50° to 70° C. Further cooling of the fiber after it is quenched may be desired, and can be achieved by passing the fiber between two godets. In an embodiment, the temperature range for extrusion of PBS or copolymer thereof to form high strength fibers is from 60-230° C., or 75-220° C., but is more preferably from 75-200° C., 80-180° C., 80-175° C., or 80-170° C. Example 3 discloses specific examples of a method using multi-stage incremental orientation and the use of conductive chambers to prepare multifilament fibers of PBS and copolymers thereof. Examples of multifilament fibers with tenacities of 8.3-12.5 g/d are shown. Preferably, the monofilament fiber is oriented with 2-6 stages of orientation, and more preferably with 3, 4 or 5 stages of orientation.

If desired, the oriented fibers may be annealed. In one embodiment, the oriented fibers may be annealed using temperatures of 80° C. to 120° C., and more preferably 105° C.±10° C.

In an embodiment, the oriented monofilament fibers have diameters ranging from 0.01 to 1.00 mm. In a particularly preferred embodiment, the diameters of the monofilament fibers range from 0.07 to 0.7 mm. In another embodiment, the monofilament fibers may optionally meet the USP standards for absorbable monofilament sutures.

In an embodiment, the monofilament fibers of PBS and copolymers thereof have a tensile strength of 400 MPa to 2,000 MPa, and more preferably a tensile strength greater than 500 MPa, 600 MPa, 700 MPa or 800 MPa, but less than 1,200 MPa. In another embodiment, the monofilament fibers of PBS and copolymer thereof have a Young's Modulus of at least 600 MPa, and less than 5 GPa, but more preferably greater than 800 MPa, 1 GPa, 1.5 GPa, and 2 GPa. In a further embodiment, the monofilament fibers of PBS and copolymer thereof have an elongation to break of 10-150%, and more preferably 10-50%. In yet another embodiment, the monofilament fibers of PBS and copolymers thereof have knot pull tensile strengths of 200 MPa to 1,000 MPa, and more preferably knot pull tensile strength greater than 300 MPa, 400 MPa and 500 MPa, but less than 800 MPa. In an even more preferred embodiment, the knot pull tensile strengths of the monofilament fibers of PBS and copolymers thereof are from 300 MPa to 600 MPa.

In yet another embodiment, the multifilament fibers of PBS and copolymers thereof have a tenacity greater than 4 grams per denier, but less than 14 grams per denier. Preferably, the multifilament fibers have an elongation to break of between 15% and 50%.

The yarns and monofilament fibers of poly(butylene succinate) and copolymers thereof may be used to prepare knitted and woven meshes, non-woven meshes, suture tapes, mesh sutures, surgical meshes (including but not limited to surgical meshes for soft tissue implants for reinforcement of soft tissue, for the bridging of fascial defects, for a trachea or other organ patch, for organ salvage, for dural grafting material, for wound or burn dressing, for breast reconstruction, for hernia repair, or for a hemostatic tamponade; or surgical mesh in the form of a mesh plug), webs, patches (such as, but not limited to, hernial patches and/or repair patches for the repair of abdominal and thoracic wall defects, inguinal, paracolostomy, ventral, paraumbilical, scrotal or femoral hernias, for muscle flap reinforcement, for reinforcement of staple lines and long incisions, for reconstruction of pelvic floor, for treatment of pelvic organ prolapse, including treatment of cystocele, urethrocele, uterine prolapse, enterocele, repair of rectal or vaginal prolapse, for suture and staple bolsters, for urinary or bladder repair, or for pledgets) and resorbable wound closure materials such as suturing and stapling materials. These mesh, web, and patch products are particularly useful for soft tissue repair, hernia repair, breast lifts, breast reconstructions, face and neck lifts, pelvic floor reconstruction, including treatment of pelvic organ prolapse, including treatment of cystocele, urethrocele, uterine prolapse, vaginal fault prolapse, enterocele and rectocele, treatment of stress urinary incontinence, organ salvage, lift and suspension procedures, and for making enclosures, pouches, holders, covers, clamshells, and casings to hold implantable medical devices.

In one embodiment, a mesh, web or patch prepared using a yarn or monofilament fiber of poly(butylene succinate) or copolymer thereof may have a total filament length of 10 to 400 cm per $cm^2$ of mesh, web or patch, for example from 20 to 100 cm per $cm^2$ of mesh, web or patch. In another embodiment, a mesh, web or patch prepared using a yarn or monofilament fiber of poly(butylene succinate) or copolymer thereof may have a total length of 3 to 1,200 meters. Filament length can be measured for example, by winding the fiber on a spool with a counter that measures its length (for example, the number of rotations of the spool).

The meshes, webs and patches described herein may comprise monofilament and/or multifilament fibers, with each fiber having an external surface which contributes to the total fiber surface area. In an embodiment, the total fiber surface area in such a mesh, web or patch is from 0.1 to 125 $cm^2$ per $cm^2$ of mesh, web or patch, such as from 1 to 10 $cm^2$ per $cm^2$ of mesh, web or patch.

In view of their mechanical properties, the yarns and monofilament fibers disclosed herein may also be used to prepare medical devices including sutures, braided sutures, hybrid sutures of monofilament and multifilament fibers, barbed sutures, suture tapes, mesh sutures, surgical meshes (including but not limited to surgical meshes for soft tissue implants for reinforcement of soft tissue, for the bridging of fascial defects, for a trachea or other organ patch, for organ salvage, for dural grafting material, for wound or burn dressing, for breast reconstruction, for hernia repair, or for a hemostatic tamponade; surgical mesh in the form of a mesh plug), braids, ligatures, tapes, knitted or woven meshes, knitted tubes, tubes suitable for the passage of bodily fluid, multifilament meshes, patches (such as, but not limited to, hernial patches and/or repair patches for the repair of abdominal and thoracic wall defects, inguinal, paracolostomy, ventral, paraumbilical, scrotal or femoral hernias, for muscle flap reinforcement, for reinforcement of staple lines and long incisions, for reconstruction of pelvic floor, for repair of rectal or vaginal prolapse and treatment of pelvic organ prolapse, including treatment of cystocele, urethrocele, uterine prolapse, and enterocele, for suture and staple bolsters, for urinary or bladder repair, or for pledgets), wound healing devices, bandages, wound dressings, burn dressings, ulcer dressings, skin substitutes, hemostats, tracheal reconstruction devices, organ salvage devices, dural substitutes, dural patches, nerve regeneration or repair devices, hernia repair devices, hernia meshes, hernia plugs, device for temporary wound or tissue support, tissue engineering device, tissue engineering scaffolds, guided tissue repair/regeneration devices, anti-adhesion membranes, adhesion barriers, tissue separation membranes, retention membranes, slings, devices for pelvic floor reconstruction, urethral suspension devices, devices for treatment of urinary incontinence, including stress urinary incontinence, devices for treatment of vesicoureteral reflux, bladder repair devices, sphincter muscle repair devices, sphincter bulking material for use in the treatment of adult incontinence, suture anchors, soft suture anchors, bone anchors, ligament repair devices, ligament augmentation devices, ligament grafts, anterior cruciate ligament repair devices, tendon repair devices, tendon grafts, tendon augmentation devices, rotator cuff repair devices, meniscus repair devices, meniscus regeneration devices, articular cartilage repair devices, osteochondral repair devices, spinal fusion devices, spinal fusion cages, stents, including coronary, cardiovascular, peripheral, ureteric, urethral, urology, gastroenterology, nasal, ocular, or neurology stents, stent grafts, devices with vascular applications, cardiovascular patches, intracardiac patching for patch closure after endarterectomy, vascular closure devices, intracardiac septal defect repair devices, including but not limited to atrial septal defect repair devices and PFO (patent foramen ovale) closure devices, left atrial appendage (LAA) closure devices, pericardial patches, vein valves, heart valves, vascular grafts, myocardial regeneration devices, periodontal meshes, guided tissue regeneration membranes for periodontal tissue, embolization devices, anastomosis devices, cell seeded devices, controlled release devices, drug delivery devices, plastic surgery devices, breast lift devices, mastopexy devices, breast reconstruction devices, breast augmentation devices (including devices for use with breast implants), breast reduction devices (including devices for removal, reshaping and reorienting breast tissue), devices for breast reconstruction following mastectomy with or without breast implants, facial reconstructive devices, forehead lift devices, brow lift devices, eyelid lift devices, face lift devices, rhytidectomy devices, thread lift devices (to lift and support sagging areas of the face, brow and neck), rhinoplasty devices, device for malar augmentations, otoplasty devices, neck lift devices, mentoplasty devices, buttock lift devices, cosmetic repair devices, devices for facial scar revision, and enclosures, pouches, holders, covers, clamshells, casings to hold implantable medical devices.

C. 3D Printing of Implants

In another preferred embodiment, the implants may be prepared by 3D printing. Methods that can be used to 3D print poly(butylene succinate) and copolymers thereof include fused filament fabrication (FFF), fused deposition modeling, fused pellet deposition, melt extrusion deposition (MED), selective laser melting, and solution printing. A particularly preferred method of 3D printing implants is melt extrusion deposition.

In embodiments, a method of 3D printing poly(butylene succinate) and copolymers thereof is to feed a filament of the polymer or copolymer to a FFF printer. In FFF of poly (butylene succinate) and copolymers it is important to prevent hydrolysis of the polymers by residual moisture. Therefore, it is important that the filament used in FFF has a low moisture content, preferably less than 0.1 wt. %, preferably less than 0.05 wt. %, more preferably less than 0.01 wt. %, and even more preferably less than 0.005 wt. %. The filament may be dried with hot air and under vacuum prior to printing. In a preferred embodiment, the polymers are dried under vacuum at 30-90° C., more preferably 60-90° C. Preferably, the polymer is kept dry, the filament is protected from moisture, and moisture re-uptake during processing is prevented.

In order to obtain 3D printed implants with high tensile strength and prolonged strength retention, it is important to prevent loss of weight average molecular weight during melt processing of poly(butylene succinate) and copolymers thereof. The magnitude of the molecular weight loss increases as the temperature rises above 200° C. and as the exposure time increases. In order to make implants with the highest tensile strength and prolonged strength retention, it is therefore important to minimize the time the polymers are exposed to high processing temperatures during 3D printing as well as the presence of moisture in the polymer or copolymer. The temperature of the hot end, including the printer nozzle, may be set to temperatures ranging from 120° C. to 300° C., more preferably 130° C. to 230° C., and even more preferably 150° C. to 200° C.

Methods of 3D Printing of PBS and copolymers thereof are shown in Examples 9 and 10. The 3D Printing of a PBS-malic acid copolymer by MED using different thermal conditions is shown in Example 18, and the properties of the implants obtained shown in Table 17. Surprisingly, the weight average molecular weight of the PBS polymer was found to increase as the processing temperature was raised from 180° C. to 220° C. (At 230° C., the weight average molecular weight decreased from the peak at 220° C.) In embodiments, 3D printed implants are formed with chain extension of PBS or copolymers thereof during 3D printing. An increase in molecular weight can be particularly advantageous in some implant applications. For example, increasing the weight average molecular weight can result in prolonged strength retention of the implant. In an embodiment, implants comprising PBS and copolymers thereof, are produced with weight average molecular weights that exceed the weight average molecular weights of the composition used to prepare the implants. The implants may be formed by 3D Printing, including fused filament fabrication, fused pellet deposition, melt extrusion deposition, and selective laser melting, but also using other thermal processing techniques, such as melt processing, melt extrusion, melt-blowing, melt spinning, injection molding, compression molding, lamination, foaming, film extrusion, thermoforming, pultrusion, molding, tube extrusion, spun-bonding, non-woven fabrication. In an embodiment, implants comprising PBS and copolymers thereof, may be formed by melt processing with weight average molecular weights that are between 1-50%, more preferably 5-30%, higher than the weight average molecular weights of the PBS and copolymers resins used to prepare the implants.

In an embodiment, implants comprising PBS and copolymers thereof can be prepared by 3D printing that do not incorporate knots or interlaced fibers, including meshes and lattices. In a particularly preferred embodiment, knotless meshes comprising PBS and copolymers thereof may be prepared by 3D printing. These knotless meshes may be used, for example, in hernia repair, breast reconstruction, plastic surgery, treatment of stress urinary incontinence, soft tissue reinforcement and pelvic floor reconstruction, including treatment of pelvic organ prolapse, including treatment of cystocele, urethrocele, uterine prolapse, vaginal fault prolapse, enterocele and rectocele.

In other embodiments, implants comprising PBS and copolymers thereof can be prepared by 3D printing that are completely unoriented or only partially oriented. In a particularly preferred embodiment, unoriented meshes comprising PBS and copolymers thereof may be prepared by 3D printing. These unoriented meshes may be used, for example, in hernia repair, breast reconstruction, plastic surgery, treatment of stress urinary incontinence, soft tissue reinforcement and pelvic floor reconstruction, including treatment of pelvic organ prolapse, including treatment of cystocele, urethrocele, uterine prolapse, vaginal fault prolapse, enterocele and rectocele. In another embodiment, unoriented knotless meshes comprising PBS or copolymer thereof may be prepared by 3D printing.

In a particularly preferred embodiment, implants for hernia repair, soft tissue reinforcement, breast surgery, including breast reconstruction and mastopexy, pelvic floor reconstruction, including treatment of pelvic organ prolapse, including treatment of cystocele, urethrocele, uterine prolapse, vaginal fault prolapse, enterocele and rectocele, and treatment of stress urinary incontinence, are prepared by 3D printing. These 3D printed products include 3D printed hernia repair lattices, 3D printed breast implant lattices, 3D printed mastopexy lattices, 3D printed breast reconstruction lattices, slings comprising 3D printed lattices for breast lift procedures, 3D printed lattices for treatment of stress urinary incontinence, and 3D printed lattices for pelvic floor reconstruction. An example of a 3D printed lattice is given in Example 9 (3D printed implantable mesh). Lattices prepared using the method of Example 9 may be used for hernia repair, soft tissue reinforcement, breast surgery, including breast reconstruction and mastopexy, pelvic floor reconstruction, including treatment of pelvic organ prolapse, including treatment of cystocele, urethrocele, uterine prolapse, vaginal fault prolapse, enterocele and rectocele, and treatment of stress urinary incontinence.

D. Methods of Manufacturing Films

In another preferred embodiment, the implants may be prepared by forming films made from a polymeric composition, comprising a 1,4-butanediol unit and a succinic acid unit as described herein. Such films may, in themselves, be suitable for use as implants, or may be further modified to form implants. Any suitable method for the formation of films may be used, including for example, by solvent casting or melt extrusion. Such films may be characterized by their thinness, which may be less than 100 μm, and even less than 50 μm.

(i) Method of Making Films by Solvent Casting

In a preferred method, a film of PBS polymer or copolymer thereof may be prepared by solution casting as follows. A homogeneous solution of PBS polymer or copolymer in a suitable solvent is prepared. The polymer solution is pumped through a slot die with a suitable die gap onto a moving web, for example, of aluminum foil. The web speed may, for example, be approximately 0.5 m/min and it may travel 5 m before being collected on a collection roller. The speed is adjusted to ensure evaporation of the solvent. One or more separate air drying zones set at a suitable temperature are employed to remove solvent from the polymer film before collection on the final roll. A number of parameters can be varied to control the film thickness including, but not limited to, the pump speed, the die gap and width, the polymer concentration and the web speed.

A method of forming a PBS copolymer film by casting and melt pressing is given in Example 21 and properties of the film are shown in Table 19. The cast film produced by this method had a tensile modulus of 487 MPa, stress of 33 MPa, and elongation at break of 51%.

Also shown in Example 21 and Table 19 are films produced by casting films of the PBS copolymer blended with poly-4-hydroxybutyrate (P4HB). As is evident from Table 19, the tensile modulus of the P4HB/PBS copolymer blends increased as the percentage of PBS copolymer in the blend increased. Breaking strength of the blends generally decreased as the percentage of PBS copolymer in the blend was increased, although the change was small when lower amounts of the PBS copolymer were present in the blend. Elongation at break of the films decreased as the percentage of the PBS copolymer in the blended film was increased. In addition to the results shown in Table 19, the following results were also observed: (i) a slight depression of the melting temperature of PBS copolymer and P4HB was observed in blends when the PBS copolymer was added to P4HB or vice versa, and (ii) crystallization of P4HB occurred faster and at a higher temperature when 10% PBS copolymer was added to P4HB. The results demonstrate that addition of PBS or copolymer thereof increases the crystallization rate of P4HB, which is useful in processing P4HB, for example, by film melt extrusion, melt spinning or injection molding.

Accordingly, the present invention also provides the subject matter disclosed by the following numbered paragraphs:

Paragraph 1. A film comprising a blend of PBS or copolymer thereof with poly-4-hydroxybutyrate (P4HB), wherein the weight percent of P4HB present in the film is from 10 wt. % to 90 wt. %, and wherein the Young's modulus of the film is from 333 MPa to 287 MPa.

Paragraph 2. The film of Paragraph 1, wherein the stress at break of the film is from 36 to 49 MPa.

Paragraph 3. The film of Paragraph 1, wherein the extension at break of the film is from 95 to 165%.

(ii) Method of Making Films by Melt Processing Through Melt Extrusion

Films can also be prepared by melt-extrusion methods. Preferred methods are a T-die extrusion method or an inflation method.

In the formation of the film by melt-extrusion, suitable barrel and T-die temperatures for carrying out the formation are selected to ensure melting of the PBS polymer or copolymer thereof but not so high as to cause unacceptable thermal decomposition. However, the site of the barrel directly below a hopper may have a temperature of less than the melting temperature of the PBS polymer or copolymer thereof. The molten film exits the T-die and is cast over a chilled moving surface preferably, one or more rotating cylindrical cast rollers with surface temperature maintained at a temperature of less than the melting temperature of the PBS polymer or copolymer thereof. This step is followed by a take-up step to wind up the extruded film. Film thickness can be varied by changing the gap of the T-die slit, polymer flow rate, and cast roll speed.

In embodiments, a film of PBS or copolymer thereof is extruded by a process comprising the following steps: (i) drying the PBS polymer or copolymer thereof to a moisture content of less than 0.01 wt % water; (ii) feeding the dried polymer or copolymer into an extruder barrel with a film extrusion die, wherein the heating zones of the extruder and the die are set at temperatures between 60° C. and 240° C., and more preferably between 70° C. and 220° C., and (iii) casting the extrudate on a chilled roll stack set at a temperature below the melt temperature of the PBS polymer or copolymer, and more preferably at a temperature between 5° C. and 50° C. In embodiments, unoriented extruded films of PBS or copolymer thereof have one or more of the following properties: (i) a tensile stress of 30 to 60 MPa, an elongation to break of 40-200%, and (iii) Young's Modulus of 400 MPa to 1.5 GPa. In embodiments, oriented extruded films of PBS or copolymer thereof have a tensile stress of 61 to 300 MPa.

Example 23 describes melt extrusion of a PBS copolymer. The PBS copolymer had a melt temperature of 115° C. The copolymer was extruded with a temperature profile of 75-180° C. with a die temperature of 210° C. The extruded films were collected using three horizontal chilled rolls set at a temperature of 20° C. The extruded films had the following tensile properties: tensile stress 43-47 MPa, elongation at breast 86-146%, and Young's Modulus of 949-989 MPa.

In the formation of film by the inflation method, an inflation molding circular die is used instead of a T-die to extrude cylindrical film of PBS polymer or copolymer thereof. The molten cylindrical film is cooled and solidified by blowing it up with cold air blown from the central portion of the circular die, and the cylindrical film which had been blown up is collected with a take-up machine. Film thickness can be varied by changing the gap of the inflation die slit, polymer flow rate, cooling air pressure and temperature and take-up speed.

(iii) Orientation of Films

Films formed from PBS polymer or copolymer thereof, such as the melt-extrusion films and solvent cast films, can show improved mechanical properties when stretched. The melt-extrusion film may be stretched by several methods such as a roll stretching and/or a stretching method using a tenter frame. The melt-extrusion film can be stretched at a stretch ratio of 0.25 to 15. The stretching may be monoaxial stretching for forming a monoaxially oriented film, consecutive biaxial stretching for forming a biaxially oriented film and simultaneous biaxial stretching for forming a plane-oriented film. When the melt-extrusion film is stretched, the physical properties in the direction in which the film is stretched can be modified, for example, the tensile strength in the direction in which the film is stretched is increased. Optionally, the film is stretched in one or more directions to provide a tensile strength between 400 MPa and 1200 MPa in each direction of stretching; wherein the stretch ratio in each direction of stretching may be the same or different, and then resultant tensile strength in each direction of stretching may be the same or different. For example, a biaxially oriented film may be oriented by the same stretch ratio in each direction of stretch and have the same tensile strength in each direction of stretch. Alternatively, a biaxially oriented film may be oriented by a different stretch ratio in each direction of stretch and have a different tensile strength in each direction of stretch.

Accordingly, in the context of films, the present invention also provides an implant comprising a polymeric composition, wherein the polymeric composition comprises a 1,4-butanediol unit and a succinic acid unit, wherein the implant comprises an oriented film of the polymeric composition, and optionally, the polymeric compositions are isotopically enriched. Optionally, the oriented film has been monoaxially or biaxially oriented.

E. Methods of Manufacturing Ultrafine Fibers of PBS and Copolymers Thereof and Three Dimensional Structures Methods are provided for manufacturing ultrafine fibers of PBS and copolymers as well as three dimensional structures containing the ultrafine fibers, by electrospinning, and medical implants comprising the ultrafine fibers.

(i) Method of Making PBS Polymer or Copolymer Ultrafine Fibers by Electrospinning In a preferred method, ultrafine fibers of PBS polymer or copolymer thereof may be prepared as follows. The PBS polymer or copolymer is dissolved in a solvent to make a polymer solution. A suitable electrospinning device consists of a high voltage power supply with a positive lead connected to a copper wire. The copper wire is inserted into a nozzle, such as a glass capillary, from which the polymer solution is electrospun. The glass capillary is either filled with the polymer solution, or alternatively the polymer solution can be pumped through the capillary (with for example a precision pump). A collector is positioned at a desired distance from the nozzle or capillary, and the collector is connected to the negative lead (i.e. ground) of the power supply. Charged jets of polymer are consistently shot to the collector due to the applied electrical potential. Solvent evaporates during the time the jet of polymer hits the collector due to the high surface to volume ratio of the strands coupled with the humidity and temperature.

A number of parameters can be varied to control the sizes of the ultrafine fibers. These include, but are not limited to, solution flow rate (ml/min), distance between the nozzle and the collector, needle configuration (including needle diameter and needle extrusion distance), temperature, humidity, choice of solvent, polymer molecular weight, collection time, electric potential, and use of compressed gas to attenuate the fibers.

There are no particular restrictions on the solvent that can be used except it must be capable of dissolving the selected PBS or copolymers thereof, and evaporate during the spinning stage to allow the formation of the electrospun ultrafine fibers. If necessary, reduced pressure conditions can be used during the fiber drawing stage if the solvent evaporation is insufficient, as well as temperatures that are selected according to the evaporation behavior of the solvent and stability of the polymer. Volatile solvents that are liquid at room temperature, and have boiling points no higher than 200° C. are particularly preferred. Examples of volatile solvents include methylene chloride, chloroform, dichloroethane, tetrachloroethane, trichloroethane, dibromomethane, bromoform, acetone, acetonitrile, tetrahydrofuran, 1,4-dioxane, 1,1,1,3,3,3-hexafluoroisopropanol, toluene, xylene, dimethylformamide (DMF), and dimethylsulfoxide. These solvents may be used alone, or two or more solvents may be combined for use as a mixed solvent system. Particularly preferred solvents include methylene chloride, chloroform, dichloroethane, tetrachloroethane, trichloroethane, dibromomethane, bromoform, tetrahydrofuran, acetone, dimethylformamide, and 1,4-dioxane.

Alternatively, the PBS polymer can be electrospun without the use of solvent in a process called melt electrospinning or melt electro-writing. This method is similar to solution electro-spinning, however, the molecular weight of the polymer and the spinning temperature are chosen so that the melt viscosity of the polymer is low enough that it flows under the electrostatic forces of the electro-spinning equipment. A voltage differential is maintained between the spinning nozzle and the collector and the molten polymer can be pumped through the nozzle connected to a positive voltage. A collector is positioned at a desired distance from the spinning nozzle or capillary, and the collector is connected to the negative lead (i.e. ground) of a power supply. Charged jets of polymer are consistently shot to the collector due to the applied electrical potential. The molten jet of polymer hits the collector and solidifies. The electric field can be modified to direct the charged molten polymer fibers to specific locations or in specific patterns on the collector. The nozzle or collector may be moved independent of one another using computer controllers to control the special pattern of fibers on the collector.

(ii) Method of Making Three-Dimensional PBS Polymer or Copolymer Structures by Electrospinning A particular advantage of the electrospinning method over melt blown fiber spinning methods is that the ultrafine fibers can be spun directly onto scaffolding structures. The method may also be used to make three-dimensional structures. This is achieved by either positioning the scaffold at the fiber collection plate and rotating the scaffolding structure during fiber collection, or alternatively, rotating the nozzle around the scaffold. Alternatively, the electric field may be changed to alter the deposition of the spun fibers.

In a preferred embodiment, the ultrafine fibers are electrospun onto a collector that has been sprayed or coated with an anti-static agent, such as static guard. The use of an anti-static (or conductive) coating can alter the deposition of the ultrafine fibers on the collector plate, and improve the coating of the collector material with the ultrafine fibers. In a particularly preferred embodiment, the ultrafine fibers are electrospun onto the following collectors that have been sprayed or coated with an anti-static (or conductive) coating: monofilament mesh, a multifilament mesh, a nonwoven fabric, a woven fabric, a foam, or a film, or any combinations thereof. One particular advantage of using an anti-static agent to coat these collector materials is that it allows the ultrafine fibers to become in intimate contact with these collector materials, for example, invading pores of meshes, fabrics and foams. This results in a greater proportion of the substrate being covered by the ultrafine fibers, and is particularly useful in the preparation of scaffolds for tissue repair and regeneration. In a particularly preferred embodiment, the ultrafine fibers cover more than 25% of the surface area of the collector material (such as a monofilament mesh, a multifilament mesh, a nonwoven fabric, a woven fabric, foam, or a film) that has been treated with an anti-static agent.

Accordingly, the present application also provides a medical device or medical implant (such as an implant disclosed elsewhere in the present application) comprising ultrafine fibers of a polymeric composition that comprises a 1,4-butanediol unit and a succinic acid unit or copolymer thereof, wherein the ultrafine fibers are preferably produced by electrospinning or melt electrospinning, and preferably have an average diameter of from 10 nm to 10 µm and more preferably from 50 nm to 5 µm. For example, the average diameter may be greater than 10 nm, 50 nm, 100 nm, 200 nm, 300 nm, 400 nm, 500 nm, 600 nm, 700 nm, 800 nm, 900 nm, 1 µm, 2 µm, 3 µm, or 4 µm but less than 10 µm, 9 µm, 8 µm, 7 µm, 6 µm or 5 µm. The mean fiber diameter of the fiber can be measured by selecting random locations on the fiber (for example, between 100-120 random locations) taking photographs of the surface of the fibers structure at high magnification using a scanning electron microscope, and calculating the average based on the number of locations measured. Optionally, the medical device or medical implant comprises ultrafine fibers with a fiber diameter less than 900 nm. Optionally, the medical device or medical implant comprises ultrafine fibers with a fiber diameter not exceeding 25 µm. In one preferred embodiment, the medical device or medical implant comprises ultrafine fibers that have been deposited on a monofilament mesh, a multifilament mesh, a nonwoven fabric, a woven fabric, a foam, or a film.

F. Coatings and Spin Finishes

Biocompatible coatings and spin finishes can be applied to PBS and copolymers thereof, and medical devices made from PBS and copolymers thereof.

The spin finishes can be applied to fibers formed from PBS and copolymers thereof to facilitate their manufacture, and also for their conversion to other products, including medical textiles. The spin finishes protect the multifilament fiber bundles, keeping them intact following extrusion, and imparting lubricity to the fiber bundles and monofilament fibers so that they are not damaged in subsequent processing steps, particularly in textile processing. In the preferred embodiment, the coatings and spin finish are applied to the PBS or copolymers thereof.

These coatings include wax, natural and synthetic polymers such as polyvinyl alcohol, and spin finishes including polyethylene glycol sorbitan monolaurate, and polymers or oligomers of ethylene oxide, propylene oxide, copolymers of ethylene oxide and propylene oxide, PEG400, PEG40 Stearate, Dacospin and Filapan. These coatings are preferably applied so the coated item has a coating weight of less than 6 wt. %, more preferably less than 3 wt. %, and even more preferably less than 2 wt. %. It is preferred that the coatings readily leave the surface of the coated item or fiber-based device in vivo, for example, by degradation or dissolution (for example if the coating is water-soluble.)

The spin finish is preferably a liquid at the fiber processing temperature. For example, if the PBS or copolymer thereof is processed at or near room temperature, the spin finish is preferably a liquid at room temperature. In other embodiments, the polyalkylene oxides can be wetted with water or solvent to provide a liquid solution at the processing temperature. A particularly preferred embodiment is where the spin finish is polyethylene glycol (PEG) with an average molecular weight of approximately 400 Daltons (PEG 400) to 2000 daltons (PEG 2000) applied to a PBS polymer or copolymer thereof. PEG with an average molecular weight of approximately 400 Daltons (PEG 400) to 1000 daltons (PEG 1000) is preferred for polymers being processed at or near room temperature. Higher molecular weights can be preferable for polymers being processed at higher temperatures.

In another preferred embodiment for the processing of monofilament fibers of PBS or copolymer thereof into textiles, the spin finish is polyethylene glycol sorbitan monolaurate (e.g., a polysorbate detergent available under the brand Tween® 20). A particularly preferred embodiment is where the spin finish, Tween® 20, is applied to monofilament fiber of PBS or copolymer thereof and knitted or woven into a textile construct.

The preferred coating weight for a spin finish will depend on the fiber being processed. Monofilaments require less spin finish than multifilaments, due to the smaller total surface area of a monofilament fiber. So a preferred coating weight on a monofilament may be less than 2 wt %, preferably less than 1 wt %, while for multifilament it may be less than 10 wt %, preferably less than 8 wt %.

Spin finishes can be removed by a scouring process to prevent cytotoxicity or poor biocompatibility. In preferred embodiments, the residual content of the spin finish (such as Tween® 20) after scouring is less than about 0.5 wt %, including less than about 0.4, 0.3, 0.2, 0.1, 0.09, 0.08, 0.07, 0.06, 0.05, 0.04, or 0.03 wt %. In preferred embodiments, the residual content of PEG 400 after scouring is less than about 2 wt %, including less than about 1, 0.5, 0.4, 0.3, 0.2, or 0.1 wt %.

The textile construct produced from the coated fibers of PBS or copolymer thereof may be further coated, impregnated, covered, or encapsulated by or contain collagen. Other coatings disclosed herein include wax, as well as natural and synthetic polymers such as polyvinyl alcohol.

The coatings preferably impart good lubricity to PBS and/or copolymers thereof, particularly to fibers and braids made from these materials, making the coatings ideal for use on medical devices such as braided sutures. Braided monofilament fibers or multifilament yarns are provided that are coated with polymers or oligomers of ethylene oxide, polymers or oligomers of propylene oxide, polyvinyl alcohol, or combinations thereof.

In a preferred embodiment, the coating is polyethylene glycol (PEG) with an average molecular weight of approximately 1000 Daltons (PEG 1000) to 10,000 daltons (PEG 10000) applied to devices, such as braided sutures, derived from PBS or copolymers thereof.

In another embodiment, the coating is polyvinyl alcohol (PVOH). A particularly preferred embodiment is where the coating is polyvinyl alcohol applied to a PBS polymer or copolymer thereof or applied to devices, such as braided sutures, derived from PBS or copolymers thereof.

In preferred embodiments, the biocompatible coating is present on the PBS polymer or copolymer or the medical devices made from PBS polymers or copolymer in a coating weight of about 0.1 wt % to 10 wt %, including about 0.1, 0.2, 0.3, 0.4, 0.5, 0.6, 0.7, 0.8, 0.9, 1, 2, 3, 4, 5, 6, 7, 8, 9, and 10 wt %. For example, PEG2000 is preferably present on the polymers or the medical devices made from the polymers in a coating weight of less than 10 wt %, more preferably less than 7 wt %, even more preferably less than 5 wt %. For example, PVA is preferably present on the polymers or the medical devices made from the polymers in a coating weight of less than 6 wt %, more preferably less than 4 wt %, even more preferably less than 3 wt %.

A method of reducing the tissue drag force of a braided suture formed from filaments formed from PBS or copolymers thereof is also provided. This method can involve coating the braided suture with polymers or oligomers of ethylene oxide, polymers or oligomers of propylene oxide, polyvinyl alcohol, or combinations of copolymers thereof.

Accordingly, the present invention also provides the subject matter disclosed by the following numbered paragraphs:

Paragraph 1. A monofilament fiber or multifilament yarn comprising a polymer composition, wherein the polymeric composition is coated with a spin finish comprising a coating material as described herein, wherein the polymeric composition comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The monofilament fiber or multifilament yarn of Paragraph 1, wherein the polymer composition comprises PBS.

Paragraph 3. The monofilament fiber or multifilament yarn of Paragraph 1, wherein the coating material is selected from polyethylene glycol sorbitan monolaurate, polymers or oligomers of ethylene oxide, propylene oxide, copolymers of ethylene and propylene oxide, PEG400, PEG40 Stearate, Dacospin, Filapan and combinations thereof.

Paragraph 4. The monofilament fiber or multifilament yarn of paragraph 3, wherein the polymer is polyethylene glycol having an average molecular weight of 100 to 1000 daltons in a spin finish or polyethylene glycol having an average molecular weight of 1000 to 10,000 in a coating.

Paragraph 5. The monofilament fiber or multifilament yarn of Paragraph 1, wherein the coating material is polyethylene glycol sorbitan monolaurate.

Paragraph 6. A medical device formed from the monofilament fiber or multifilament yarn of any one of Paragraphs 1 to 5.

Paragraph 7. The device of Paragraph 6 that has been scoured to remove substantially all the spin finish.

Paragraph 8. The device of Paragraph 7, wherein the device is selected from the group consisting of barbed sutures, braided sutures, monofilament sutures, ligatures, hybrid sutures of monofilament and multifilament fibers, braids, knitted or woven meshes, monofilament meshes, multifilament meshes, knitted tubes, stents, stent grafts, drug delivery devices, devices for temporary wound or tissue support, devices for soft tissue repair, devices for replacement or regeneration, repair patches, tissue engineering scaffolds, retention membranes, anti-adhesion membranes, tissue separation membranes, hernia repair devices, breast reconstruction devices, devices for blepharoplasty, devices for facial scar revisions, devices for forehead lifts, devices for mentoplasty, devices for malar augmentation, devices for otoplasty, devices for rhinoplasty, devices for neck lift surgery, devices for rhytidectomy, threadlift devices to lift and support sagging areas of the face, brow, and neck, fixation devices, cardiovascular patches, vascular closure devices, vascular grafts, slings, biocompatible coatings, rotator cuff repair devices, meniscus repair devices, adhesion barriers, guided tissue repair/regeneration devices, articular cartilage repair devices, nerve guides, tendon repair devices, ligament repair devices, intracardiac septal defect repair devices, left atrial appendage (LAA) closure devices, pericardial patches, bulking and filling agents, vein valves, heart valves, bone marrow scaffolds, meniscus regeneration devices, ligament and tendon graft, ocular cell implants, spinal fusion devices, imaging devices, skin substitutes, dural substitutes, bone graft substitutes, wound dressings, and hemostats, or any other device disclosed in the present application.

Paragraph 9. The device of Paragraph 8, wherein the breast reconstruction device is selected from the group consisting of devices for breast augmentation, devices for mastopexy, devices for breast reduction, devices for breast positioning and shaping, and devices for breast reconstruction following mastectomy.

Paragraph 10. The device of Paragraph 8, comprising a braided suture wherein the suture comprises an outer multifilament sheath optionally formed of PBS or copolymer thereof and an inner monofilament core optionally formed of PBS or a copolymer thereof.

Paragraph 11. The device of Paragraph 10, comprising a suture wherein the suture comprises an outer multifilament and monofilament sheath comprising the PBS polymer or copolymer, and an inner monofilament core comprising the PBS polymer or copolymer.

Paragraph 12. The device of Paragraph 10, wherein the inner monofilament core is barbed, or is made from a non-degradable polymer.

Paragraph 13. The device of any one of Paragraphs 6 to 12, wherein the device comprises one or more additional components selected from the group consisting of plasticizer, nucleant, collagen, crosslinked collagen, hyaluronic acid or derivate thereof, ceramic, medical glass, bioactive glass, polyhydroxyalkanoate, poly-4-hydroxybutyrate, polymer or copolymer of lactic acid, glycolic acid, caprolactone, p-dioxanone, or trimethylene carbonate, polymer additive, dye, compatibilizer, filler, therapeutic agent, antimicrobial agent, diagnostic agent, and prophylactic agent.

Paragraph 14. The device of Paragraph 6, wherein the device is a suture and contains at least one or more fibers with contrasting dye to provide an identifiable color trace in the suture strand.

Paragraph 15. The device of Paragraph 6, wherein the device is a suture used for ligament and tendon repair.

Paragraph 16. The device of Paragraph 6, wherein the device is a surgical mesh.

Paragraph 17. The device of Paragraph 16, wherein the surgical mesh comprises fiber formed from PBS or a copolymer thereof and a permanent fiber.

Paragraph 18. The device of Paragraph 17, wherein the permanent fiber is polypropylene, a polyester, or a combination thereof.

Paragraph 19. The device of Paragraph 16, wherein the surgical mesh comprises monofilament fibers.

Paragraph 20. The device of Paragraph 16, wherein the surgical mesh has been coated or encapsulated with collagen.

Paragraph 21. The device of Paragraph 20, wherein the porosity of the collagen is at least 5 µm in diameter.

Paragraph 22. A method of producing the device of Paragraph 20 or 21, wherein the PBS or copolymer component is, optionally treated with plasma gas, coated or encapsulated with collagen, the collagen is crosslinked, and the device is sterilized with ethylene oxide or by irradiation.

Paragraph 23. A method of using the device of Paragraph 8, comprising implanting or administering the device at a site in or on a patient in need thereof.

Paragraph 24. The device of Paragraph 7, or any Paragraph dependent thereon, the device passes cytotoxicity testing using the ISO Elution Method (1×MEM Extract).

Paragraph 25. A method of producing a monofilament fiber or multifilament yarn comprising PBS polymer or copolymer wherein the PBS polymer or copolymer is coated with a coating material is selected from polyethylene glycol sorbitan monolaurate, polymers or oligomers of ethylene oxide, propylene oxide, PEG400, PEG40 Stearate, Dacospin, Filapan and combinations thereof, the method comprising deriving the monofilament fiber or multifilament yarn by melt-extrusion processing of the PBS polymer or copolymer, allowing the PBS polymer or copolymer to cool and solidify and applying the coating material to the fiber or yarn by passage through a spin finish applicator either inline or offline.

Paragraph 26. A braided monofilament fiber or multifilament yarn, comprising filaments formed from PBS polymer or copolymer and coated with a coating material selected from polyethylene glycol sorbitan monolaurate, polymers or oligomers of ethylene oxide, propylene oxide, PEG400, PEG40 Stearate, Dacospin, Filapan and combinations thereof.

Paragraph 27. The braided monofilament fiber or multifilament yarn of Paragraph 26, wherein the coating material is polyethylene glycol, wherein the polyethylene glycol has an average molecular weight of 1000 to 10,000 daltons.

Paragraph 28. The braided monofilament fiber or multifilament yarn of Paragraph 26 or 27, wherein the average tissue drag force of the coated braid is reduced at least 10% relative to the uncoated braid.

G. Other Methods of Manufacturing Implants

Implants comprising poly(butylene succinate) and copolymers thereof may also be prepared by casting, solvent casting, solution spinning, solution bonding of fibers, melt processing, extrusion, melt extrusion, melt spinning, fiber spinning, orientation, relaxation, annealing, injection molding, compression molding, machining, machining of extrudate, lamination, particle formation, microparticle, macroparticle and nanoparticle formation, foaming, dry spinning, knitting, weaving, crocheting, melt-blowing, film formation, film blowing, film casting, membrane forming, electrospinning, thermoforming, pultrusion, centrifugal spinning, molding, tube extrusion, spunbonding, spunlaiding, nonwoven fabrication, entangling of staple fibers, fiber knitting, weaving and crocheting, mesh fabrication, coating, dip coating, laser cutting, barbing, barbing of fibers, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, and printing using a binding solution and granules of powder.

In an embodiment, implants comprising PBS and copolymers thereof may be prepared by solution processing, including methods disclosed herein, using, for example, the following solvents: methylene chloride, chloroform, dichloroethane, tetrachloroethane, trichloroethane, dibromomethane, bromoform, tetrahydrofuran, acetone, THF, ethyl acetate, dimethylformamide, 1,4-dioxane, DMF and DMSO and combinations thereof.

In embodiments, the implants comprising PBS and copolymers thereof are sponges or foams, and preferably are highly porous. Highly porous sponges or foams comprising PBS and copolymers thereof are particularly desirable for use in tissue engineering applications. For example, in applications where it is desirable for cells to invade the implant to form new tissue. In embodiments, the PBS and copolymers thereof may be used as coatings on other polymers and materials to form coated sponges and foams. For example, other polymers described herein may be formed into sponges or foams, and coated with PBS and copolymers thereof.

As discussed above, in one option, implants comprising poly(butylene succinate) and/or copolymers thereof may also be prepared by pultrusion. In contrast to melt extrusion processing (where polymer powder or pellets are melt extruded and oriented by stretching of the extrudate to form crystalline structures), pultrusion is a process whereby un-oriented polymeric rods are pulled through a series of profile dies to provide a reduced profile with high modulus and tensile strength. It is possible to use pultrusion to substantially increase the orientation of articles formed from PBS or copolymers thereof, resulting in increased modulus and tensile strength of the polymer, and a decrease in elongation to break of the processed polymer and devices made with the processed polymer, compared to the same polymer prior to orientation. Pultrusion is quite different from melt extrusion and orientation of polymeric fibers.

The present application also discloses micro-fiber webs containing fibers of poly(butylene succinate) and/or copolymers thereof, and methods for producing them. The micro-fibers have average diameters ranging from 0.01 to 100 µm. Micro-fiber webs with higher elongation to break values can be made by centrifugal spinning. The micro-fiber webs may contain crimped fibers, unlike fibers typically derived by melt-blown extrusion, dry spinning and electrospinning. The micro-fiber webs also have higher elongation to break values than nonwovens produced by melt-blown extrusion, dry spinning and electrospinning.

Also disclosed are methods for making micro-fiber webs from PBS and copolymers thereof. The methods allow the micro-fiber webs to be produced without substantial loss of the polymer weight average molecular weight. The micro-fiber webs containing/including micro-fibers of PBS or copolymer thereof, are preferably derived by centrifugal spinning. In one embodiment, the PBS polymer or copolymer is dissolved in a solvent, the polymer solution is pumped through a rotating spinneret, and fibers are collected as a web. The equipment for centrifugal spinning typically includes one or more spinnerets incorporating one or more orifices, fed by a polymer melt or a solution of PBS or copolymer thereof, which can be rotated at high speed. Rotation of a spinneret at high speed applies a centrifugal force to the polymer solution and causes it to be drawn from the orifice of the spinneret and released as a polymer jet. Evaporation of the solvent from the polymer jet results in the formation of fiber, and the fiber is collected to form a micro-fiber web. The average diameter of the fibers in the micro-fiber web ranges from 0.01 to 100 microns.

Medical implants and other medical devices and articles described herein may be coated with the compositions of poly(butylene succinate) or copolymer thereof as described herein. Optionally, the poly(butylene succinate) or copolymer thereof can be formed into latex or emulsions, and used to coat medical implants and other medical devices and articles. For example, an emulsion may be prepared by water-in-oil or oil-in water methods. In one exemplary embodiment, a PBS:Solvent:Oleic Acid:Triethanolamine:Water (10:40:4:6:30 g) emulsion may be used.

Also disclosed is a method of forming a perforated implant, the method comprising the steps of: positioning needles through the pores of a surgical mesh that is formed from a polymeric composition, coating the surgical mesh with a collagen solution, freezing the coated mesh, removing the needles from the pores of the frozen coated mesh, and drying the coated mesh, wherein the polymeric composition comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Perforated collagen coated meshes that can be used in vivo for soft or hard tissue repair, regeneration, or remodeling are thus described herein. At least as a result of the method used to make the meshes, the perforated collagen coated meshes do not have a significant percentage of partially closed or occluded perforations.

"Perforation" as used herein in connection with the disclosed perforated collagen mesh is distinct from "pores" which may additionally be present in the disclosed perforated mesh. "Perforated" is used to refer to pores that span the thickness of the collagen coated mesh, which are distinct from pores that may be present on the collagen-coated mesh, but do not span the thickness of the mesh and do not create open channels from one side of the implant to the other side of the implant (obtained, for example, by just applying a collagen coating onto a polymeric mesh for example). The perforated collagen meshes disclosed herein include pores that are perforations and pores that are not perforations.

In one embodiment, at least 70% of the perforations through the implant are not occluded by any mesh fiber or collagen, and more preferably greater than 75%, 80%, 85%, 90%, 95% or 100% of the perforations are not partially occluded by either collagen or mesh fiber.

The methods provide a means to manufacture perforated collagen coated meshes without damaging the surface of the mesh. The methods also allow perforated collagen coated meshes to be produced with a wide range of thicknesses that would be difficult to produce by standard coating techniques. The ability to produce these perforated collagen coated meshes has been made possible by the process wherein needles are inserted into the pores of the mesh prior to coating the mesh with collagen. During the process the needles prevent collagen from entering the pores, and the needles also make it possible to produce long perforations, of selected diameters, through thick collagen coatings that have been applied to the mesh. Importantly, the method yields a perforated collagen coated mesh where the perforations have not become occluded with collagen, and the mesh surface has not been damaged.

The collagen used to coat the mesh may be derived from a natural source or it may be produced using a recombinant DNA technology. In one embodiment, the collagen may be derived from an equine, porcine, ovine, bovine, sheep, marine, or human source. In a preferred embodiment, the collagen is derived from a bovine source, and more preferably a bovine source certified to be free of bovine spongiform encephalopathy (BSE).

The collagen may be of the same fibrillar type, or a mixture of fibrillar types, including any of types I to XIII. In a preferred embodiment, it may be a mixture of types I to III. In a particularly preferred embodiment, the collagen is predominantly type I, or solely type I.

The collagen used to coat the mesh is preferably in the form of a solution, slurry, or gel. The collagen may, for example, be in a neutral salt solution or dilute acid solution. In a preferred embodiment, the collagen is in a dilute acid solution. Examples of suitable solutions include collagen in acetic acid, citrate buffer or hydrochloric acid. Dilute solutions are generally preferred, such as acetic acid (0.5 M), or hydrochloric acid pH 2-3.5. A particularly preferred solution is 1% acid swollen bovine collagen gel produced by Devro Pty Ltd (Kelso, NSW, Australia). This solution has a pH of 2.9-3.1, fat content of ≤7%, ash content of ≤1%, and endotoxin content of ≤10 EU/mL.

The collagen may be processed by treatment with alkali or enzymes. These reagents may be used to cleave crosslinks and to suspend or dissolve acid-insoluble collagen structures. For example, the collagen may be processed using approximately 10% sodium hydroxide and 10% sodium sulfate. Or, the collagen may be treated with pepsin to provide collagen that can be swollen and solubilized. The collagen may also be subjected to treatments by denaturing agents and mechanical fragmentation, or subjected to chemical modification and derivatization, for example, by succinylation, acetylation, methylation or attachment of other polymers or chemical entities.

Other proteins may be added to the collagen solution, including both fibrous and globular proteins. In a preferred embodiment, gelatin can be added to the collagen solution.

The perforated collagen coated meshes may comprise bioactive agents. These agents may be present in the mesh or collagen, or both the mesh and collagen, or may be present on the surface of the mesh or collagen, or both surfaces.

The bioactive agents may be used, for example, to improve wettability, water contact angle, cell attachment, tissue in-growth, or tissue maturation of the perforated collagen coated mesh. The bioactive agents may also be incorporated for the purposes of delivering bioactive agents in vivo. In a particularly preferred embodiment, the bioactive agents are delivered in the vicinity of the perforated collagen coated mesh.

Optionally, in the method of forming a perforated implant described above, the surgical mesh with needles through the pores of the mesh may be brought into contact with a collagen solution on one side of the surgical mesh to encase that side of the mesh with collagen, and optionally additional collagen solution is added to the other side of the mesh to fully encase the mesh with collagen.

The method may further comprising heating the needles before removing the needles from the pores of the coated mesh. Optionally, the coated mesh is dried by freeze-drying. Optionally, the method further comprises heat setting the mesh after positioning the needles through the pores of the surgical mesh and, for example, the heat set mesh may be removed from the needles and subsequently relocated in the same position on the needles. Optionally, the method further comprises cross-linking the collagen.

The perforated implant produced by this process may optionally have one or more of the following properties: average thickness between 0.1 mm and 25 mm, perforations with diameters from 0.1 mm to 10 mm, density of perforations from 1 to 50 per square cm, and burst strength between 1 kgf and 100 kgf.

Optionally, the needles are tapered. Optionally, the perforations in the implant are located in a random, ordered, or patterned manner. Optionally, the shape of the perforations in the implant may be bounded by curved or straight borders, or combinations thereof, for example, the shape of the perforations in the implant may be circles, ellipses, triangles, squares, and polygons.

Optionally, the perforated implant is formed using an assembly comprising a needle plate consisting of a pattern of needles fit onto a back plate, a base plate with holes that match the needle pattern on the needle plate, frame plates that attach to the base plate to form a container for the collagen solution, a spacer rim plate to adjust the thickness of the implant, and a perforated separation plate with holes that match the needle pattern on the needle base plate. In one preferred option, (i) the needles of the needle plate are positioned through the pores of the surgical mesh, and the mesh is optionally heat set on the needle plate, (ii) the mesh is removed from the needle plate, and the needle plate is inserted into the base plate until it is flush against one side of the base plate and the needles protrude from the other side of the base plate, (iii) the frame plates are attached to each side of the base plate to form a container, (iv) the spacer rim plate is placed on top of the base plate and inside the container formed by the frame plates so that it is located between the needles and the inside wall of the frame plates, (v) a collagen solution is poured to cover the base plate to the desired depth, (vi) the mesh is replaced on the needles in the same orientation as previously used for heat setting and the mesh is moved over the needles until it is in contact with the collagen solution, (vii) optionally, a collagen solution is poured on top of the surgical mesh so that it covers the mesh, and the mesh is completely encapsulated by collagen, (viii) the perforated separation plate is slid down the needles of the needle plate until it contacts the spacer rim plate, (ix) the entire assembly containing the collagen coated mesh is frozen, (x) the needles of the needle plate are heated, and the assembly is disassembled to release the perforated frozen collagen coated mesh, and (xi) the perforated collagen coated mesh is freeze-dried. For example, the method may further comprise cross-linking the perforated collagen coated mesh with formaldehyde, glutaraldehyde, grape seed extract, genepin or other suitable cross-linking agent, and/or may further comprise one or more of the following steps: adding graduated markings to the perforated collagen coated mesh, cutting the perforated collagen coated mesh; packaging the perforated collagen coated mesh and sterilizing the perforated collagen coated mesh. Optionally, the mesh is sterilized with ethylene oxide. The method may further comprise keeping the perforated collagen mesh flat while it is freeze-dried. The perforated collagen coated mesh may be frozen to a temperature of $-40°$ C.$\pm 10°$ C., and freeze-dried using a lyophilizer over a period of 5 to 20 hours.

Optionally, the mesh may be made from monofilament or multifilament, or combinations thereof. Optionally, the implant is dimensioned for use as an implant, and/or the implant is trimmable to a predetermined shape. The implant may optionally have one or more of the following properties that are within 20% of the value of the uncoated mesh: (i) burst strength, (ii) suture pullout strength, and (iii) tensile strength.

The present application also discloses a perforated implant obtainable by the foregoing method comprising a perforated collagen coated mesh with one or more of the following properties: an average thickness between 0.1 mm and 25 mm, perforations with diameters from 0.01 mm to 10 mm, density of perforations from 1 to 50 per square cm, and burst strength between 1 kgf and 100 kgf, wherein the mesh is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

The implant may have at least 65% of the burst strength of the non-collagen coated mesh. The mesh may be made from monofilament fibers formed from the polymeric composition, with average diameters between 0.001 mm and 1.0 mm. The implant may be made from a knitted monofilament mesh. The collagen may be cross-linked.

The present application also discloses a perforated implant comprising a perforated collagen coated mesh wherein the perforations are aligned with the pores of the mesh such that the perforations in the implant are formed through the pores of the mesh, wherein the mesh is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application. The mesh may be a monofilament knitted mesh.

Also disclosed is a method of using a perforated implant as disclosed above, wherein the implant is implanted in the body or applied topically to the surface of the body. For example, the implant may be used for soft or hard tissue repair. Optionally, the implant is used in plastic surgery, mastopexy, breast reconstruction, hernia repair, treatment of urinary incontinence, pelvic floor reconstruction, ligament and tendon repair, or lift procedures including face lift, neck lift, eyebrow lift and breast lift.

H. Orientation

The present application provides an implant comprising a polymeric composition, wherein the polymeric composition comprises a 1,4-butanediol unit and a succinic acid unit, wherein the implant comprises an oriented form of the polymeric composition, and optionally, the polymeric compositions are isotopically enriched.

Orientation can be used to modify numerous physical characteristics of such polymeric compositions, and implants prepared therefrom, including but not limited to degree of crystallinity, tensile strength, Young's modulus, elongation to break and tenacity, as well as the degradation characteristics, for example retention of tensile strength, retention of mass, and/or retention of weight average molecular weight after implantation in vivo and/or under physiological conditions in vitro (such as at 37° C. in phosphate buffered saline) over a measured period of time, such as 4 weeks, 8 weeks, 12 weeks, 24 weeks or longer; wherein the point of comparison is a non-oriented form of the same polymeric composition or implant prepared therefrom which differs from the oriented form only in terms of the absence of the use of orientation in its production.

Any form of the polymeric composition can be selected for orientation, and/or to include an oriented form of a PBS polymeric composition. For example, the form may be a form of the polymeric composition that has been prepared by casting, solvent casting, solution spinning, solution bonding of fibers, melt processing, extrusion, melt extrusion, melt spinning, fiber spinning, injection molding, compression molding, machining, machining of extrudate, lamination, foaming, dry spinning, wet spinning, knitting, weaving, crocheting, melt-blowing, film formation, film blowing, film casting, membrane forming, electrospinning, melt electrospinning, melt electrowriting, thermoforming, pultrusion, centrifugal spinning, molding, tube extrusion, spunbonding, spunlaiding, nonwoven fabrication, entangling of staple fibers, fiber knitting, weaving and crocheting, mesh fabrication, coating, dip coating, laser cutting, barbing, barbing of fibers, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, and printing using a binding solution and granules of powder. Additionally, or alternatively, an already-oriented form of the polymeric composition can be used in any of the foregoing methods of preparing polymeric articles.

Optionally, the oriented form comprises fiber, mesh, woven, non-woven, film, molded object, patch, tube, laminate or pultruded profile. In a particularly preferred embodiment, the oriented form is a fiber selected from a monofilament, multifilament, braided fiber, or barbed fiber. In another particularly preferred embodiment, the oriented form is a mesh, which may be selected from woven and non-woven forms, including knitted mesh, woven mesh, monofilament mesh, or multifilament mesh.

The oriented form may, for example, have been monoaxially or biaxially oriented.

The orientation process used to produce the oriented form may additionally include either, or both, of relaxation and annealing steps.

Properties of the oriented form can be modified by the addition of a relaxation step following orientation and/or an annealing step. The relaxation step can be carried out at a temperature suitable for the relaxation of the selected PBS polymer or copolymer, for example from 30 to 150° C. and/or the annealing step can be carried out at a temperature suitable for annealing of the selected PBS polymer or copolymer, for example from 80° C. to 120° C., and more preferably 105° C.±10° C.

Introduction of an annealing process and relaxation step during the process of orientation of a fiber, for example, can further enhance the handling properties of the resulting fibers. The relaxation step allows the oriented form to shrink and elongation is allowed to increase by as much as 25% followed by an annealing step either on or offline to further control and fine tune elongation, modulus and strength.

The PBS or copolymer thereof may additionally be combined with absorbable additives then processed through relaxation and/or annealing to further enhance properties of the oriented form.

As discussed elsewhere in the present application, a spin finish may be applied to the polymeric composition and be present for the duration of the orientation, relaxation and/or annealing steps, and optionally be removed by scouring thereafter.

Orientation of an article formed from the polymeric composition, to produce an oriented form of the article, may comprise one or more stages of drawing the article. Preferably, the monofilament fiber is oriented with 2-6 stages of orientation, and more preferably with 3, 4 or 5 stages of orientation.

A suitable sum of the orientation ratios over the one or more stages of drawing may, without limitation, be about, or at least, 2.0, 2.5, 3.0, 3.5, 4.0, 4.5, 5.0, 5.5, 6.0, 6.5, 7.0, 7.5, 8.0 or more.

One example of a multi-stage drawing process can include the steps of: (a) drawing the article with an orientation ratio of at least 3.5, at a temperature of 50-70° C., (b) one or more stages of drawing the article with an orientation ratio of at least 2.0 at a temperature of 65-75° C., and (c) drawing the article with an orientation ratio greater than 1.0 at a temperature of 70-75° C. Preferably, the sum of the orientation ratios over a multi-stage drawing process is over 6.0, 6.5, 7.0, 7.5 or 8.0.

In another option, an article formed from the polymeric composition may be drawn in a conductive liquid chamber. Prior to drawing the article, melt extruded polymer is preferably quenched in a conductive liquid bath. The temperature of the bath is preferably from 50° C. to 70° C. Further cooling of the article after it is quenched may be desired, and can be achieved (for example, by passing the article between two godets). In an embodiment, the temperature range for extrusion of PBS or copolymer thereof to form high strength articles is from 60-230° C., or 75-220° C., but is more preferably from 75-200° C., 80-180° C., 80-175° C., or 80-170° C. Example 3 discloses specific examples of a method using multi-stage incremental orientation and the use of conductive chambers to prepare multifilament fibers of PBS and copolymers thereof. Examples of multifilament fibers with tenacities of 8.3-12.5 g/d are shown.

Also disclosed herein are methods that further improve the production of monofilament fibers of a polymeric composition comprising PBS or copolymers thereof, wherein the monofilament fibers are cold drawn and then hot drawn at temperatures above the melt temperature of the polymeric composition. This process can provide even higher break strengths. In accordance with this embodiment, the polymeric composition should not be drawn immediately after it leaves the molten state. Further, the fiber extrudate is preferably not drawn under tension from the extruder.

The method generally includes the following steps: (i) spin the polymeric composition into fibers (multifilament or monofilament), (ii) allow the fibers time to crystalize, (iii) cold draw, and (iv) one or more orientation steps of hot drawing.

In some embodiments, the last hot drawing orientation step is followed by a relaxation step (also sometimes referred to as "hot stretching").

In an embodiment, the articles formed from PBS and copolymers thereof that have been oriented and, optionally have been subject to relaxation and/or annealing, have a tensile strength of 400 MPa to 2,000 MPa, and more preferably a tensile strength greater than 500 MPa, 600 MPa, 700 MPa or 800 MPa, but less than 1,200 MPa.

In another embodiment, the articles formed from PBS and copolymers thereof that have been oriented and, optionally have been subject to relaxation and/or annealing, have a Young's Modulus of at least 400 MPa, and less than 5 GPa, but more preferably greater than 600 MPa, 800 MPa, 1 GPa, 1.5 GPa, and 2 GPa.

In a further embodiment, the articles formed from PBS and copolymers thereof that have been oriented and, optionally have been subject to relaxation and/or annealing, have an elongation to break of 10-150%, and more preferably 10-50%, for example between 15% and 50%.

In yet another embodiment, the articles formed from PBS and copolymers thereof that have been oriented and, optionally have been subject to relaxation and/or annealing, have a tenacity greater than 4 grams per denier, but less than 14 grams per denier. Preferably, the multifilament fibers have an elongation to break of between 15% and 50%.

The present application also discloses the subject matter as described in the following numbered paragraphs:

Paragraph 1. A polymeric composition in the form of an implantable medical device or a component thereof, the polymeric composition comprising PBS or a copolymers thereof, having:
 (i) have a tensile strength of 400 MPa to 2,000 MPa,
 (ii) an elongation to break of 10-150%, and/or
 (iii) a Young's modulus of at least 400 MPa, and less than 5 GPa,
wherein the polymeric composition is producible by extrusion and orientation, and optionally further by relaxation and/or annealing.

Paragraph 2. A polymeric composition in the form of an implantable medical device or a component thereof according to Paragraph 1, wherein the filament has:
 (i) an elongation to break from 10-50%, for example between 15% and 50%.
 (ii) a Young's modulus greater than 600 MPa, 800 MPa, 1 GPa, 1.5 GPa, or 2 GPa, and less than 5 GPa; and/or
 (iii) a tensile strength greater than 500 MPa, 600 MPa, 700 MPa or 800 MPa, but less than 1,200 MPa
wherein the polymeric composition is producible by extrusion and orientation, and optionally further by relaxation and/or annealing.

Paragraph 3. A polymeric composition in the form of an implantable medical device or a component thereof according to Paragraph 2 wherein it is produced by extrusion, orientation by drawing the extruded polymeric composition to between six and eleven times its original length, relaxation to shrink and elongate the filament and annealing.

Paragraph 4. The polymeric composition in the form of an implantable medical device or a component thereof according to any of Paragraphs 1 to 3 in the form of a suture, a monofilament fiber, or a multifilament fiber or yarn.

Paragraph 5. The polymeric composition in the form of an implantable medical device or a component thereof according to any of Paragraphs 1 to 3 in the form of a mesh.

Paragraph 6. The polymeric composition in the form of an implantable medical device or a component thereof according to any of Paragraphs 1 to 3 in the form of a device for repair of tendons or ligaments or any other medical device as disclosed in the present application or claims.

I. Antimicrobial Coatings

In an embodiment, the implants comprising poly(butylene succinate) and copolymers thereof, may be coated with solutions of antimicrobial agents dissolved in poor solvents for poly(butylene succinate) and copolymers thereof. These poor solvents do not cause significant loss of orientation, if any, of the poly(butylene succinate) or copolymer thereof. However, these poor solvents allow the antimicrobial agents to slightly soften and penetrate the surfaces of the implants. This has two main advantages. First, it allows the implants to be coated with higher concentrations of antimicrobial agents, and second it allows the antimicrobial agents to diffuse into the implants. Diffusion of the antimicrobial agents into the implants results in a more prolonged release profile, and an increased ability of the implant to prevent colonization of the implants, and reduce or prevent the occurrence of infection following implantation in a patient. A suitable poor solvent that can dissolve antimicrobial agents, but not cause loss of orientation of the implants, is an aqueous or alcoholic solution of tetrahydrofuran (THF).

Alcohols that may be combined with this solvent include methanol and ethanol. The concentration of the antimicrobial agent(s) in the poor solvent can range from about 0.1 mg/mL to about 100 mg/mL, preferably from about 1 mg/mL to about 30 mg/mL. The amount (density of coverage) of each antimicrobial coated on the implant can range from about 1 $\mu g/cm^2$ to about 1000 $\mu g/cm^2$, or preferably, from about 50 $\mu g/cm^2$ to about 200 $\mu g/cm^2$. In various embodiments, the amount ranges from about 10 $\mu g/cm^2$ to about 175 $\mu g/cm^2$, or from about 10 $\mu g/cm^2$ to about 150 $\mu g/cm^2$, or from about 10 $\mu g/cm^2$ to about 100 $\mu g/cm^2$, or from about 10 $\mu g/cm^2$ to about 75 $mg/cm^2$, or from about 20 $\mu g/cm^2$ to about 200 $\mu g/cm^2$ or from about 50 $\mu g/cm^2$ to about 200 $\mu g/cm^2$, or from about 75 $\mu g/cm^2$ to about 200 $\mu g/cm^2$ or from about 100 $\mu g/cm^2$ to about 200 $\mu g/cm^2$, or from about 150 $\mu g/cm^2$ to about 200 $\mu g/cm^2$.

In a preferred embodiment of the invention, the implants of poly(butylene succinate) and copolymers thereof, are coated with rifampin and minocycline (including its hydrochloride, sulfate, or phosphate salt) dissolved in poor solvents for poly(butylene succinate) and copolymers thereof. The antimicrobial agents may be applied to the oriented implants individually using the same or different poor solvents, or from a single solution containing both antimicrobial agents in a poor solvent. In one embodiment, rifampin may be applied to the implants of poly(butylene succinate) and copolymers thereof from solutions of the following poor solvents (i) THF, (ii) DMSO, (iii) DMF and (iv) DMA each mixed with one or more of the following: water, methanol and/or ethanol. In another embodiment, minocycline may be applied to the oriented implants of poly(butylene succinate) and copolymers thereof from solutions in the following poor solvents: THF/water, THF/methanol, and THF/ethanol. In a preferred embodiment, rifampin and minocycline (including its hydrochloride, sulfate, or phosphate salt forms) are dissolved in a solution of THF/water, THF/ethanol or THF/ethanol, and applied to the implants.

J. Sterilization of the Implants

Implants made from the high tenacity yarns and monofilament fibers of poly(butylene succinate) and copolymers thereof, or other implants made from of poly(butylene succinate) and copolymers thereof, may be sterilized using ethylene oxide gas, and even more preferably using an ethylene oxide cold cycle. In another preferred embodiment, the implants may be sterilized with electron-beam irradiation or gamma-irradiation. In another embodiment, the implants may be sterilized using alcohol, hypochlorous acid, or gaseous hydrogen peroxide, nitrogen dioxide, chlorine dioxide or peracetic acid.

The sterility of the devices may be maintained by packaging of the devices in packages designed to protect the devices from contamination and maintain sterility. In a preferred embodiment, the implants comprising poly(butylene succinate) or copolymer thereof are sterilized using ethylene oxide. The use of ethylene oxide is preferred since it has been found that implants can be sterilized without a significant loss of weight average molecular weight. In a particularly preferred embodiment, the implants sterilized by ethylene oxide maintain at least 80%, more preferably at least 90%, and even more preferably at least 95% of their weight average molecular weight during sterilization.

K. Microparticle Compositions

In embodiments, poly(butylene succinate) and copolymers thereof may be formed into microparticle compositions. The microparticle compositions may be delivered to perform a multitude of purposes ranging from medical device applications to drug-delivery or pharmaceutical purposes.

In embodiments, the microparticle compositions include particles having a diameter from about 1 nanometer (nm) to about 1000 microns ($\mu$m), or from 10 nm to 1,000 $\mu$m. In general, microparticle compositions may be prepared within this size range that are of a suitable size, or range of sizes, for use in a variety of medical, surgical, clinical, cosmetic, medical device, pharmaceutical and/or drug-delivery applications. In embodiments, the microparticles have a size in the range of from about 250 to about 1000 microns. In another embodiment, the microparticles have a size in the range of from about 100 to about 250 microns. In another embodiment, as in the case of microparticle compositions typically used for subcutaneous (SC) or intramuscular (IM) administration, the microparticles have a diameter in the range from about 20 microns to about 150 microns. In some embodiments, the microparticles have a diameter in the range of about 20 microns to about 50 microns, preferably from about 20 microns to about 40 microns. In other embodiments, the microparticles have a diameter in the range from about 1 micron to about 30 microns, preferably from about 1 micron to about 20 microns, more preferably from about 1 micron to about 10 microns. In an embodiment, the microparticles are less than 10 microns in size. In still another embodiment, the microparticles are less than 1 micron in size. Further embodiments include microparticles in the range of about 500-1000 nm or in the range of 200-500 nm. Still further embodiments may include particles with sizes largely in the range of 100-200 nm and particles with size ranges of 10-100 nm or 1-100 nm.

The microparticle compositions described herein may be prepared by a variety of methods including spray-drying; fluid-bed techniques; techniques that utilize spraying of solutions through nozzles (or jets) either into air or into liquids in order to prepare microparticles; cryogenic spray techniques; ultrasonic spraying through nozzles (or jets) without or with the presence of applied electrical potential (e.g., electrostatic spraying); supercritical fluid techniques for the preparation of microparticle compositions; or any of the general techniques involving polymer precipitation or phase separation or coacervation and any combinations therein.

The following are representative methods for forming microparticles comprising poly(butylene succinate) or copolymer thereof, and a core material to be encapsulated. The core material may be omitted if no core material is to be encapsulated in the microparticles. The core material may be a bioactive agent, or other additive or polymer, including a diagnostic or imaging agent. As used herein, "core material" means a material that is incorporated into the microparticle, and includes material incorporated anywhere in the microparticle, and is not limited to the core or center of the microparticle.

Spray Drying

In spray drying, the core material to be encapsulated may be dispersed or dissolved in a solution containing poly(butylene succinate) or copolymer thereof. The solution or dispersion may then be pumped through a micronizing nozzle driven by a flow of compressed gas, and the resulting aerosol suspended in a heated cyclone of air, allowing the solvent to evaporate from the microdroplets. The solidified microparticles comprising poly(butylene succinate) or copolymer thereof pass into a second chamber and are trapped in a collection flask.

Hot Melt Encapsulation

In hot melt microencapsulation, the core material to be encapsulated may be added to molten poly(butylene succinate) or copolymer thereof. This mixture may then be suspended as molten droplets in a nonsolvent for the polymer which has been heated to approximately 10° C. above the melting point of the polymer. The emulsion is maintained with vigorous stirring while the nonsolvent is quickly cooled below the glass transition of the polymer, causing the molten droplets to solidify and entrap the core material.

Solvent Evaporation Microencapsulation

In solvent evaporation microencapsulation, the poly(butylene succinate) or copolymer thereof may be dissolved in a water immiscible organic solvent and the core material to be encapsulated is added to the polymer solution as a suspension or solution in an organic solvent. An emulsion may be formed by adding this suspension or solution to a beaker of vigorously stirred water (which may contain a surface active agent, for example, polyethylene glycol or polyvinyl alcohol, to stabilize the emulsion). The organic solvent is then evaporated while continuing to stir. Evaporation results in precipitation of the polymer, forming solid microcapsules containing the core material.

The solvent evaporation process can be used to entrap a liquid core material in microcapsules of poly(butylene succinate) or copolymer thereof. The polymer may be dissolved in a miscible mixture of solvent and nonsolvent, at a nonsolvent concentration which is immediately below the concentration which would produce phase separation (i.e., cloud point). The liquid core material may be added to this solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution may then be transferred into an agitated volume of nonsolvent, causing any remaining dissolved polymer to precipitate and extracting any residual solvent from the formed membrane. This process may be used to form microcapsules composed of a polymer shell of poly(butylene succinate) or copolymer thereof with a core of liquid material.

In embodiments, microparticles comprising poly(butylene succinate) or copolymer thereof are prepared using an emulsion-based methodology. These methods may include emulsion-solvent extraction methods, emulsion-solvent evaporation methods, or combinations of extraction and evaporation techniques. In these methods of preparing microparticle compositions, a polymer solution is typically prepared by dissolving the polybutylene succinate or copolymer thereof in a suitable solvent. The solvent can be a single solvent or a co-solvent. A single solvent or an admixture of two or more solvents may be referred to as a "solvent system." The core material may typically be added to the polymer solution, either as a solid or as a solution or suspension. The core material may or may not be soluble in the polymer solution. In some embodiments, the core material can be added after first dissolving or suspending the core material in a solvent system (the "first solvent") then adding this solution or suspension into the polymer solution comprising poly(butylene succinate) or copolymer thereof. The core material can be dissolved in the first solvent and, upon adding this solution to the polymer solution comprising poly(butylene succinate) or copolymer thereof, the core material can remain dissolved in the resulting polymer solution. Alternatively, the addition of the solution containing the core material to the polymer solution can result in the core material precipitating out of solution to a greater or lesser extent, depending on the overall solubility of the core material in the resulting solution. The first solvent (i.e., the solvent system used to dissolve or suspend the core material) can be fully soluble in the polymer solution comprising poly(butylene succinate) or copolymer thereof. In another embodiment, the first solvent can be only partially soluble (or miscible) in the resulting polymer solution and a liquid-liquid emulsion may be formed. In another embodiment, the first solvent can be only slightly soluble in the polymer solution; alternatively, the solvent can be nearly or virtually insoluble in the polymer solution. In situations when the first solvent is not fully soluble in the polymer solution comprising poly(butylene succinate) or copolymer thereof, then a liquid-liquid emulsion will form. This emulsion can be either an oil-in-water emulsion or a water-in-oil emulsion depending on the particular solvent systems used to prepare the polymer and core material solutions. Preparing polymer solutions in the form of an emulsion is often described as the "double-emulsion" technique for preparing microparticle compositions.

The core material may be distributed homogeneously throughout the microparticle. Alternatively, the core material may be distributed heterogeneously in the microparticle matrix, i.e. encapsulated within (e.g., in the interior) of the microparticle or the exterior regions of the microparticle.

Solvent Removal Microencapsulation

In solvent removal microencapsulation, the poly(butylene succinate) or copolymer thereof may be dissolved in an oil miscible organic solvent and the core material to be encapsulated added to the polymer solution as a suspension, dissolved in water, or as a solution in an organic solvent. Surface active agents may be added to improve the dispersion of the core material to be encapsulated. An emulsion may be formed by adding the suspension or solution to an oil with stirring, in which the oil is a nonsolvent for the polymer and the polymer/solvent solution is immiscible in the oil. The organic solvent may be removed by diffusion into the oil phase while continuing to stir. Solvent removal results in precipitation of the polymer, forming solid microcapsules/microparticles containing the core material.

Phase Separation Microencapsulation

In phase separation microencapsulation, the core material to be encapsulated may be dispersed in a polymer solution comprising poly(butylene succinate) or copolymer thereof with stirring. While continually stirring to uniformly suspend the core material, a nonsolvent for the polymer is slowly added to the solution to decrease the polymer's solubility. Depending on the solubility of the polymer in the solvent and nonsolvent, the polymer may either precipitate or phase separate into a polymer rich and a polymer poor phase. In embodiments, the polymer in the polymer rich phase will migrate to the interface with the continuous phase, encapsulating the core material in a droplet with an outer polymer shell comprising poly(butylene succinate) or copolymer thereof.

Spontaneous Emulsification

In spontaneous emulsification, emulsified liquid polymer droplets comprising poly(butylene succinate) or copolymer thereof, are solidified by changing temperature, evaporating solvent, or adding chemical cross-linking agents.

Coacervation

In coacervation, poly(butylene succinate) or copolymer thereof may be used to encapsulate a core material. Coacervation is a process involving separation of colloidal solutions into two or more immiscible liquid layers. Through the process of coacervation compositions comprised of two or more phases and known as coacervates may be produced. The ingredients that comprise the two phase coacervate system are present in both phases; however, the colloid rich phase has a greater concentration of the components than the colloid poor phase.

Phase Inversion Nanoencapsulation ("PIN")

In embodiments, microparticles comprising poly(butylene succinate) or copolymer thereof are formed by PIN. In PIN, the poly(butylene succinate) or copolymer thereof may be dissolved in an effective amount of a solvent. The core material to be encapsulated may also be dissolved or dispersed in an effective amount of the solvent. The polymer, the core material, and the solvent together form a mixture having a continuous phase, wherein the solvent is the continuous phase. The mixture may then be introduced into an effective amount of a nonsolvent to cause the spontaneous formation of the microencapsulated core material, wherein the solvent and the nonsolvent are miscible. In embodiments, a hydrophobic core material is dissolved in an effective amount of a first solvent that is free of polymer. The hydrophobic agent and the solvent form a mixture having a continuous phase. A second solvent comprising poly(butylene succinate) or copolymer thereof and then an aqueous solution are then introduced into the mixture. The introduction of the aqueous solution causes precipitation of the hydrophobic core material and produces a composition of micronized hydrophobic core material having an average particle size of 1 micron or less.

Melt-Solvent Evaporation Method

In the melt-solvent evaporation method, the poly(butylene succinate) or copolymer thereof is heated above its melting point to a point of sufficient fluidity to allow ease of manipulation (for example, stirring with a spatula). The core material is then added to the molten polymer and physically mixed while maintaining the temperature. This preferably results in melting of the core material in the polymer and/or dispersion of the core material in the polymer. The mixture is then allowed to cool to room temperature and harden. The mixture may then be used to form microparticles using solvent based methods described herein, such as the double-emulsion technique. In embodiments, the core material dispersed in the poly(butylene succinate) or copolymer thereof, prepared for example as described above, is dissolved or dispersed in an organic solvent composition; with or without non-ionic surfactants of various hydrophilic-lipophilic ratios. The composition is then introduced into an aqueous solution that contains a surfactant, for example, PVA (polyvinylalcohol). The water-insoluble solvent forms an oil phase (inner phase) and may be stirred into the aqueous solution or water phase (outer phase). The O/W (oil/water) emulsion is then combined with fresh water that contains PVA and is stirred to help facilitate solvent evaporation and formation of the microparticles.

In the methods described above for forming microparticles, one or more other polymers described herein may be used to form microparticles comprising blends of poly (butylene succinate) or copolymer thereof with one or more other polymers disclosed herein.

Injection Vehicles for Microparticle Compositions

In embodiments, the microparticle compositions are incorporated into injection vehicles or liquid phases. The injection vehicle or liquid phase may be aqueous or nonaqueous. Preferably, the injection vehicle is selected with a viscosity and density such that the resulting suspension formed from the microparticle composition is stable in suspension and of suitable viscosity to be passed through a needle used to administer the microparticles to a human or animal. Suitable aqueous injection vehicles include, but are not limited to, saline solution and solutions of contrast agents suitable for injection. Suitable nonaqueous injection vehicles include, but are not limited to, fluorinated liquid vehicles such as polyfluoroalkylmethylsiloxanes, Miglyol or other pharmaceutically acceptable oils and oil-based vehicles.

The injection vehicle may contain one or more viscosity-modifying agents and/or surfactants. Other suitable additives include, but are not limited to, buffers, osmotic agents, and preservatives. Examples of viscosity-modifying agents include, but are not limited to, synthetic polymers, such as poloxamers, Pluronics, or polyvinyl pyrrolidone; polysaccharides, such as sodium carboxymethyl cellulose (CMC); natural polymers, such as gelatin, hyaluronic acid, or collagen. The viscosity-modifying agent may be used in any concentration range that provides sufficient flow through the needle for administration. As such, the injection vehicle may be a low viscosity solution with or without a surfactant; further, the injection vehicle may be a medium or high viscosity solution. Suitable surfactants include anionic, cationic, amphiphilic, or nonionic surfactants. Examples of surfactants that may be included in the injection vehicle include, but are not limited to, Tween 20, Tween 80, sodium dodecylsulfate, or sodium laurylsulfate.

Since the density of the poly(butylene succinate) or copolymer may be greater than of saline for injection, the injection vehicle may need to be optimized to match the density of the microparticles and may contain one or more density-modifying agents and/or surfactants. Examples of density-modifying agents include, but are not limited to, synthetic polymers, contrast agents for imaging, or iodine containing compounds such as iopamidol (Isovue), iohexol (Omnipaque), iopromide (Ultravist), ioversol (Optiray) and/or ioxilan (Oxilan). The density of aqueous solutions for injection of iopamidol, for example, increases with its concentration, such that 41, 51, 61 and 76 wt % solutions have densities (specific gravities) of 1.23, 1.28, 1.34 and 1.41 g/ml at 37° C. Thus, such a contrast agent can be added to an aqueous suspension of microparticles to modify the solution density to match that of the microparticle to prevent the microparticles from floating or settling out of suspension.

Specific examples of injection vehicles include, but are not limited to, those that are identical or similar to those vehicles that are used in commercial pharmaceutical formulations or contrast agents used in imaging.

In embodiments, the injection vehicle contains carboxymethyl cellulose (CMC) as a viscosity-modifying agent in a concentration range of from about 0.05 wt % to about 25 wt %, preferably from 0.05 wt % to 3 wt %, more preferably from 3 wt % to 6 wt %., even more preferably from 6 wt % to 10 wt %, most preferably from 10 to 25 wt %. In embodiments, the injection vehicle may contain a surfactant, for example Tween 20 or Tween 80, in a concentration range of about 0.05 wt % to 0.5 wt %. In other embodiments, an injection vehicle may be prepared using the viscosity modifying agent poloxamer (or Pluronics) in a concentration range of from 0.5 wt % to 50 wt %; 0.05 wt % to 5 wt %, 5 wt % to 20 wt %; or 20 wt % to 50 wt %. In an embodiment, the injection vehicle requires little or no surfactant. In embodiments, the injection vehicle may also contain polyvinylpyrrolidone (PVP) as a viscosity-modifying agent in the range of 0.1 wt % to 10 wt %. In embodiments, the injection vehicle may contain other additives such as osmotic agents, for example, to make the osmolality of the microparticle formulation close to that of physiological environments. In embodiments, the injection vehicle may comprise mannitol; for example, injection vehicles can contain mannitol in the range of about 0.5 wt % to 15 wt %, 0.5 to 5 wt %, or 5 wt % to 15 wt %. In further embodiments, a density modifying agent, such as a contrast agent, may be added to the injection vehicle in the range of about 5 wt % to 70 wt %, 20 to 60 wt %, or 30 wt % to 50 wt %.

In embodiments, the microparticle compositions may be dispersed into or suspended in the injection vehicle. The concentration of the microparticle composition solids that is added to and dispersed into or suspended in a particular volume of injection vehicle can range from dilute to concentrated. As used herein, the concentration of the microparticles refers to the solids loading of the microparticles comprising poly(butylene succinate) or copolymer thereof in the liquid injection vehicle. The required concentration of solids in the suspension may be determined by the application or by the strength or activity of the bioactive agent or both. In an embodiment, the concentration of solids in the suspension is from about 0.1 wt % to about 75 wt %. Preferred solids contents of the microparticle compositions dispersed or suspended in the injection vehicle include from about 0.1 wt % to about 1 wt %, from about 1 wt % to about 10 wt %, from about 5 wt % to about 50 wt %, or from about 50 wt % to about 75 wt %.

In embodiments, the microparticle compositions may be suspended in aqueous-based vehicles. In embodiments, the aqueous vehicles may contain a viscosity-modifying agent, a density modifying agent, and/or a surfactant. In embodiments, the suspensions of the microparticle composition in the aqueous vehicles may have a concentration level in the range of about 10-40 wt % (percent solids).

Microparticles Comprising Core Materials

In embodiments, the microparticles may be used to deliver one or more core materials that is a bioactive agent, additive, or therapeutic, diagnostic, or prophylactic agent. The core material can be associated, affixed, adhered, or otherwise physically or chemically bound to the surface of the microparticle. The core material may be a small molecule (for example, less than 1000 daltons) or macromolecule (for example, equal to or greater than 1000 daltons); and the core material may be from a biological source or can be synthetically prepared or optionally the core material may be from a biological source that has subsequently been modified synthetically. The microparticles can be prepared with the core material, such as a bioactive agent, encapsulated in, associated with, or otherwise attached (e.g., covalently, non-covalently, ionically) to the surface of the microparticles in some manner. In embodiments, the microparticle composition may contain no core material.

The core material may be a liquid or solid bioactive agent that can be incorporated in the delivery systems described herein. In embodiments, the core material may be at least very slightly water soluble, or moderately water soluble. In embodiments, the core material is diffusible through the polymeric composition. In embodiments, the core material may be an acidic, basic, or amphoteric salt. In embodiments, the core material may be administered as a free acid or base or as a pharmaceutically acceptable salt. In embodiments, the core material may be included in the microparticles in the form of, for example, an uncharged molecule, a molecular complex, a salt, an ether, an ester, an amide, polymer-drug conjugate, a pre-drug, or other form to provide the desired effective biological or physiological activity.

Examples of bioactive agents that can be incorporated into the microparticles as core materials include those described in Section II.C, and also include, but are not limited to, peptides, proteins such as hormones, enzymes, antibodies and the like, nucleic acids such as aptamers, iRNA, siRNA, DNA, RNA, antisense nucleic acid or the like, antisense nucleic acid analogs or the like, low-molecular weight compounds, or high-molecular-weight compounds. Bioactive agents contemplated for use in the microparticle compositions also include anabolic agents, antacids, anti-asthmatic agents, analeptic agents, anti-cholesterolemic and anti-lipid and antihyperlipidemic agents, anticholinergic agents, anti-coagulants, anti-convulsants, antidiabetic agents; anti-diarrheals, anti-edema agents; anti-emetics, antihelminthic agents; anti-infective agents including antibacterial and antimicrobial agents, anti-inflammatory agents, anti-manic agents, antimetabolite agents, anti-migraine agents; anti-nauseants, anti-neoplastic agents, anti-obesity agents and anorexic agents; antipruritic agents; anti-pyretic and analgesic agents, anti-smoking (smoking cessation) agents and anti-alcohol agents; anti-spasmodic agents, anti-thrombotic agents, antitubercular agents; anti-tussive agents, anti-uricemic agents, anti-anginal agents, antihistamines, anxiolytic agents; appetite suppressants and anorexic agents; attention deficit disorder and attention deficit hyperactivity disorder drugs; biologicals, cerebral dilators, coronary dilators, bronchiodilators, cytotoxic agents, decongestants, diuretics, diagnostic agents, erythropoietic agents, expectorants, gastrointestinal sedatives, central nervous system ("CNS") agents, CNS stimulants, hyperglycemic agents, hypnotics, hypoglycemic agents, immunomodulating agents, immunosuppressive agents, muscle relaxants, nicotine, parasympatholytics; sialagogues, ion-exchange resins, laxatives, mineral supplements, mucolytic agents, neuromuscular drugs, vasodialators, peripheral vasodilators, beta-agonists; tocolytic agents; psychotropics, psychostimulants, sedatives, stimulants, thyroid and anti-thyroid agents, tissue growth agents, uterine relaxants, vitamins, or antigenic materials. Representative classes of drugs or bioactive agents that can be incorporated as a core material in the microparticle compositions include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, steroids, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, anti-alzheimers agents, antihypertensive agents, beta-adrenergic blocking agents, alpha-adrenergic blocking agents, nutritional agents, and the benzophenanthridine alkaloids. The bioactive agent can further be a substance capable of acting as a stimulant, sedative, hypnotic, analgesic, anticonvulsant.

Suitable diagnostic agents that can be incorporated into the microparticles as core materials include medical imaging and diagnostic agents including, for example, MRI-based imaging such as iron oxide particles (including, for example superparamagnetic iron oxide, or SPIO, particles) and gadolinium-containing agents. The microparticle core materials may also include dyes, contrast agents, fluorescent markers, imaging agents, radio-opaque agents, and radiologic agents used in medical diagnostic and imaging technologies.

In embodiments, the microparticle compositions may contain one or more core materials having a concentration from about 0 to 99.9 weight percent (wt. %) of the microparticle composition. In an embodiment, the microparticle is a placebo with zero wt. % core material. In another embodiment, microparticle compositions intended for the delivery of vaccine antigens may only be required to deliver very small or trace quantities of the core material in this case, the vaccine antigen. Loading levels of the antigen in such cases may be less than 1 wt % in the microparticles, or may be below 0.1 wt %. In other embodiments, the loading of the core material may be larger, for example, from about 1 to about 90 wt %, preferably from about 1 to about 50 wt %, more preferably from about 1 to about 10%. For the incorporation of one or more bioactive peptides as core materials into the microparticles, the bioactive peptide may be present in the microparticle composition at levels from about 1 to about 10 wt %. In other embodiments, a bioactive peptide with all of its associated soluble salts can be present in the microparticle composition at loading levels of about 40 wt % or higher. The percent loading is dependent on many factors including, but not limited to, the particular application, the choice and attributes of the core material itself, and the size and structure of the microparticle composition.

In embodiments, the microparticle compositions may comprise one or more pharmaceutically acceptable excipients, carriers, and additives. As used herein, the "carrier" is all components present in the pharmaceutical formulation other than the active ingredient or ingredients. The term "carrier" includes, but is not limited to, solvents, suspending agents, stabilizing agents, colorants, anti-oxidants, dispersants, buffers, pH modifying agents, isotonicity modifying agents, preservatives, antimicrobial agents, and combinations thereof. Other additives that may be included in the microparticles include those useful for processing or preparation of the microparticles, those additives that can aid in the incorporation or stability of a microparticle bioactive agent, or those additives that can be useful in modifying performance of the microparticle composition, including, for example, modifying the rate of drug release, drug stability, water uptake, or polymer degradation.

The microparticle compositions may comprise other excipients including any number of other medically or pharmaceutically acceptable agents such as preservatives, lipids, fatty acids, waxes, surfactants, plasticizers, porosigens, antioxidants, bulking agents, buffering agents, chelating agents, co-solvents, water-soluble agents, insoluble agents, metal cations, anions, salts, osmotic agents, synthetic polymers, biological polymers, hydrophilic polymers, polysaccharides, sugars, hydrophobic polymers, hydrophilic block copolymers, hydrophobic block copolymers, block copolymers containing hydrophilic and hydrophobic blocks. Such excipients may be used singly or in combinations of two or more excipients when preparing the microparticles. The excipients may be useful in order to alter or affect drug release, water uptake, polymer degradation, or stability of the bioactive agent.

In embodiments, the one or more excipients may be incorporated into the microparticle by mixing first with the poly(butylene succinate) or copolymer thereof. In other embodiments, the excipients may be added separately into a solution of poly(butylene succinate) or copolymer thereof. In other embodiments, the excipients may be incorporated into a first solution consisting of a core material, for example a bioactive agent, dissolved or dispersed into a first solvent. In embodiments, the excipients may be added into a solution of poly(butylene succinate) or copolymer thereof before, during, or after the core biomaterial, e.g. bioactive agent, is added into the polymer solution. In embodiments, such excipients may be used in the preparation of microparticles that contain no core material, for example, no bioactive agent. In embodiments, excipients may be added directly into a polymer solution of poly(butylene succinate) or copolymer, or alternatively, the excipients may first be dissolved or dispersed in a solvent which is then added into the polymer solution. Examples of water soluble and hydrophilic excipients include poly(vinyl pyrrolidone) or PVP and copolymers containing one or more blocks of PVP along with blocks of other biocompatible polymers (for example, poly(lactide) or poly(lactide-co-glycolide) or polycaprolactone); poly(ethylene glycol) or PEG and copolymers containing blocks of PEG along with blocks of other biocompatible polymers (for example, poly(lactide) or poly(lactide-co-glycolide) or polycaprolactone); poly(ethylene oxide) or PEO, and copolymers containing one or more blocks of PEO along with blocks of other biocompatible polymers (for example, poly(lactide) or poly(lactide-co-glycolide) or polycaprolactone) as well as block copolymers containing PEO and poly(propylene oxide) or PPO such as the triblock copolymers of PEO—PPO-PEO (such as Poloxamers™, Pluronics™); and, modified copolymers of PPO and PEO containing ethylene diamine (Poloxamines™ and Tetronics™). In embodiments, the microparticles may be prepared containing one or more bioactive agents or one or more excipients or combinations thereof.

In embodiments, the one or more excipients may be incorporated into the microparticles at a concentration from about 1% to about 90% by weight of the microparticle composition. In embodiments, the microparticle composition may contain greater than 80% or 90% or 99% of the excipient and, correspondingly, the microparticles contain very little poly(butylene succinate) or copolymer thereof.

IV. Implants of Poly(Butylene Succinate) and Copolymers Thereof

The compositions of poly(butylene succinate) and copolymers thereof described herein are suitable for preparing implants for soft and hard tissue repair, regeneration, and replacement.

Implants of oriented forms of poly(butylene succinate) and copolymers thereof are particularly suitable for use in applications requiring prolonged strength retention. The multifilament yarns and monofilament fibers disclosed herein have prolonged strength in vivo making them suitable for soft tissue repairs where high strength is required and where strength needs to be maintained for a prolonged period. Other examples of applications for the high strength yarn and monofilament fibers include soft and hard tissue repair, replacement, remodeling, and regeneration include wound closure, breast reconstruction and breast lift, including mastopexy procedures, lift procedures performed on the face such as face-lifts, neck lifts, and brow lifts, ligament and other tendon repair procedures, abdominal closure, hernia repairs, anastomosis, slings for lifting tissues, slings for treatment of stress urinary incontinence, and pelvic floor reconstruction, including treatment of pelvic organ prolapse, including treatment of cystocele, urethrocele, uterine prolapse, vaginal fault prolapse, enterocele and rectocele.

A. Sutures and Braids

Figure 5:
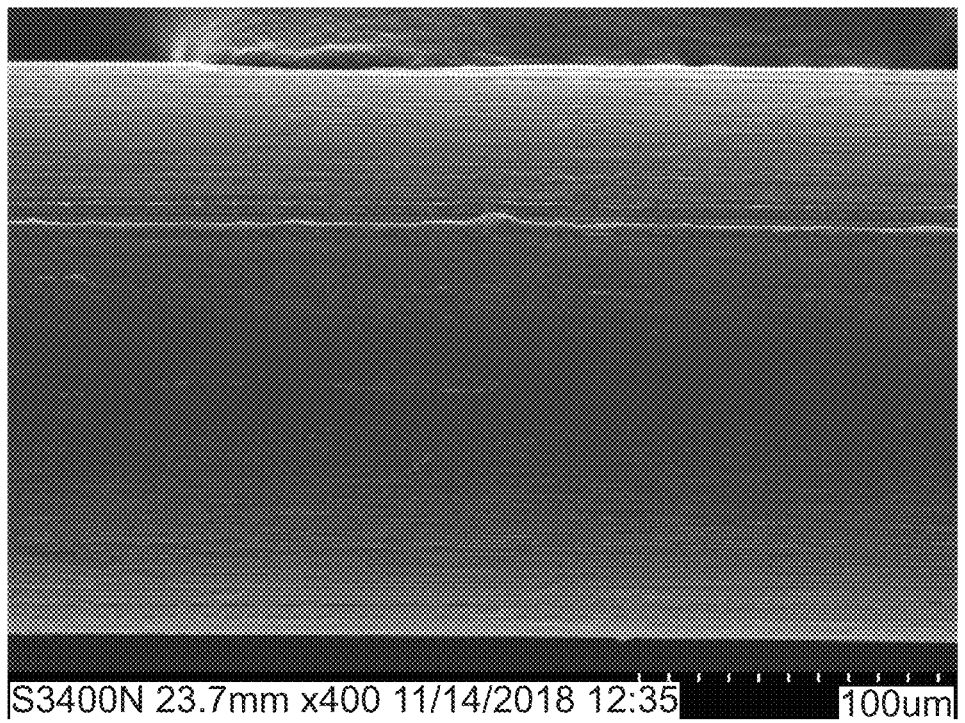
FIG. 5 is a SEM image of an oriented PBS monofilament suture fiber after implantation at a rabbit subcutaneous site for 4 weeks. The image shows a smooth surface with no surface pitting or localized erosion of the surface at a 400× magnification.

It has been discovered that oriented fibers of PBS and copolymers thereof have prolonged tensile strength retention when implanted in vivo, as shown in Examples 16 and 15. FIG. 5 is a SEM of an oriented fiber that has been explanted after 4 weeks. Surprisingly, the surface of the fiber shows little if any noticeable surface pitting or localized surface erosion at a 400× magnification. The result is surprising in view of the known surface erosion and pitting of fibers derived from other resorbable fibers. The finding makes it possible to use the fibers in applications where prolonged strength retention is required. The lack of surface erosion is particularly important for strength retention of small diameter fibers where pitting of the surface of the fiber can rapidly decrease strength retention. The fibers are also useful in applications where high initial tensile strength is required. Example 16 clearly shows that an oriented fiber, when implanted in vivo, does not lose a significant amount of tensile strength in the first 4 weeks. The study described in Example 15 further demonstrates that a mesh made from oriented fiber of PBS or copolymer thereof retains 74.1% of its strength after 12 weeks indicating prolonged strength retention of the fibers. Analysis of the weight average molecular weights of the implanted fibers after 4 and 12 weeks in these studies shows that the fiber is degrading. The weight average molecular weight of the suture fiber in Example 16 decreases 7.3% to 92.7% of the initial value at 4 weeks, and the weight average molecular weight of the fiber in the mesh decreases 25.9% to 74.1% of the initial value at 12 weeks. It is also clear that there is good correlation between the weight average molecular weight loss of oriented fibers of PBS and copolymers thereof in vitro, shown in Example 12, with the in vivo data shown in Examples 15 and 16. This good correlation is further evidence that the oriented fibers resist surface pitting or surface erosion.

In a preferred embodiment, the weight average molecular weight of the fibers of PBS or copolymer thereof decrease 3 to 15% over a 4-week period in vivo, 5% to 15% over an 8-week time period, or 10-35%, more preferably 10-30%, over a 12-week time period, under physiological conditions, in vivo. The percent mass loss of the fibers is preferably between 0% and 5% over a 4-week period, under physiological conditions, in vivo.

In an embodiment, the monofilament fibers used to prepare sutures, suture meshes, braids, and tapes have a tensile strength between 400 MPa and 2,000 MPa, and more preferably greater than 500 MPa, 600 MPa, 700 MPa or 800 MPa, and less than 1,200 MPa. Preferably the monofilament fibers used to prepare the sutures, suture meshes and tapes have a Young's Modulus between 600 MPa and 5 GPa, but preferably at least 800 MPa, 1 GPa or 2 GPa. It has been found that the high Young's Modulus of the fiber prevents the suture from forming pig tails, or curling, during suturing. In another preferred embodiment, the monofilament fibers used to prepare sutures, suture meshes, braids, and tapes have a melting temperature over 100° C., and preferably 105° C. to 120° C.

In an embodiment, sutures prepared from the monofilament fibers of PBS or copolymers thereof have knot pull tensile strengths of 200 MPa to 1,000 MPa, and more preferably knot pull tensile strengths greater than 300 MPa, 400 MPa and 500 MPa, but less than 800 MPa. In an even more preferred embodiment, the knot pull tensile strengths of the sutures are from 300 MPa to 600 MPa.

The monofilament fibers of poly(butylene succinate) and copolymers thereof may also be used to prepare high strength monofilament sutures, hybrid sutures of monofilament and multifilament fibers that have good pliability, high knot strength, and can be securely knotted with low profile knot bundles (i.e. secured with a few throws). In one embodiment, the monofilament fibers may be processed into resorbable high strength sutures and suture anchors that can be used, for example, in rotator cuff repair procedures. These sutures and anchors are particularly useful for shoulder, elbow, wrist, hand hip, knee, ankle, and foot repairs, including tendon and ligament repairs, as well as in soft tissue approximation, ligation of soft tissue, abdominal closure, and plastic surgery procedures such as lift and suspension procedures, including face and breast lift procedures and breast reconstruction. The monofilament sutures and suture anchors (including soft suture anchors) may incorporate one or more needles, be transparent or dyed, and if desired, braided as part of a suture or suture anchor, or braided into flat tapes.

Accordingly, in the context of sutures, the present invention also provides subject matter defined by the following numbered paragraphs:

Paragraph 1. An absorbable suture, wherein the suture has a diameter between 0.02 and 0.9 mm, and wherein the suture is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The suture of Paragraph 1, wherein the suture is a monofilament suture, and wherein the suture has a tensile strength from 400 MPa to 2,000 MPa.

Paragraph 3. The suture of Paragraph 2, wherein the suture has a tensile strength greater than 500 MPa, 600 MPa, 700 MPa or 800 MPa.

Paragraph 4. The suture of Paragraphs 1 to 3, wherein the suture has a knot pull tensile strength of 200 MPa to 1,000 MPa.

Paragraph 5. The suture of Paragraph 4, wherein the suture has a knot pull tensile strength greater than 300 MPa, 400 MPa, or 500 MPa.

Paragraph 6. The suture of Paragraphs 1 to 5, wherein the suture has an elongation at break of 15 to 50%.

Paragraph 7. The suture of Paragraphs 1 to 6, wherein the suture has a Young's Modulus between 600 MPa and 5 GPa.

Paragraph 8. The suture of Paragraph 7, wherein the suture has a Young's Modulus between 1 and 3 GPa.

The monofilament fibers of poly(butylene succinate) and copolymers thereof may also be used to prepare barbed sutures. The barbs may be incorporated into the suture to physically engage with the tissue and allow the suture to pass the tissue in one direction, while resisting passage in the opposing direction.

It has been discovered that multifilament fiber of poly(butylene succinate) and copolymers thereof may be used to prepare high strength multifilament sutures, hybrid sutures of monofilament and multifilament fibers that have excellent pliability, prolonged strength retention, high knot strength, good drape, and can be securely knotted forming soft knot bundles with a low profile. Example 3 discloses one method that can be used to produce high strength multifilament of PBS or copolymers thereof suitable for use in these applications.

Multifilament yarns of PBS and copolymers thereof may be processed into resorbable high strength sutures and suture anchors that can be used in rotator cuff repair procedures. Currently, these procedures are repaired with permanent sutures because existing resorbable sutures degrade too quickly. In contrast to existing resorbable sutures, sutures prepared with the high tenacity yarn of the present invention not only provide high initial strength to stabilize a repair under a significant load, but also lose strength slowly allowing the repair of the soft tissues. The high strength sutures may also be used in bone anchors, suture anchors, and soft suture anchors. These sutures and anchors are particularly useful for shoulder, elbow, wrist, hand hip, knee, ankle, and foot repairs, including tendon and ligament repairs, as well as in lift and suspension procedures. The bone anchors, suture anchors and soft suture anchors may incorporate one or more needles, yarns of different colors, and if desired, flat braided sections. The ability to use resorbable high tenacity sutures, suture anchors, bone anchors, and soft suture anchors for procedures such as rotator cuff repair eliminates longer-term complications that can arise from foreign bodies, such as permanent sutures. These sutures may be used, for example, in soft tissue approximation, anastomosis, suspension and lift procedures, and for other applications in plastic surgery.

In one preferred embodiment, the yarns of poly(butylene succinate) and copolymers thereof may be used to prepare high strength braided sutures wherein the breaking load of the sutures is between 1N and 270N, or 40N and 270N. In a particularly preferred embodiment, the high tensile strength braided sutures comprising poly(butylene succinate) and copolymers thereof have a tensile strength retention in vivo under physiological conditions of at least 40% after implantation for 4-6 months.

Suture braids may be produced from the yarns with US Pharmacopeia (USP) suture sizes of 12-0, 11-0, 10-0, 9-0, 8-0, 7-0, 6-0, 5-0, 4-0, 3-0, 2-0, 0, 1, 2, 3, 4, and 5, and meet the USP knot-pull tensile strengths or breaking loads for these sizes. In another embodiment, the suture braids may be oversized in diameter in order to meet USP knot-pull tensile strengths or breaking loads. For example, the diameter of the suture braids may be oversized by up to 0.3 mm, preferably 0.2 mm, more preferably 0.1, and even more preferably 0.05 mm. The sutures may be needled and/or contain loops at either end.

In another embodiment, the yarns of poly(butylene succinate) and copolymers thereof and monofilaments of poly (butylene succinate) and copolymers thereof, may be used to prepare flat suture tapes, including flat braided suture tapes. These suture tapes are useful in approximation and/or ligation of soft tissue, and are particularly useful in procedures requiring broad compression and increased cut-through resistance. For example, the suture tapes can be used in shoulder and rotator cuff repair procedures such as acromioclavicular repairs, and restoration of labral height in instability repairs, as well as in ACL and PCL repair procedures. The suture tapes may have flat ends, tapered ends, needles at one or both ends of the suture tape, and comprise yarns with one or more different dyes.

Suture tapes disclosed herein may also be used as slings for tissue support, including slings for treatment of stress urinary incontinence.

In another embodiment, coatings may be applied to increase the lubricity of the braided sutures, and other fiber-based implants. These coatings include wax, natural and synthetic polymers such as polyvinyl alcohol, and spin finishes including polyethylene glycol sorbitan monolaurate, and polymers or oligomers of ethylene oxide, propylene oxide, PEG400, PEG40 Stearate, Dacospin and Filapan. These coatings are preferably applied so the braided suture has a coating weight of less than 6 wt. %, more preferably less than 3 wt. %, and even more preferably less than 2 wt. %. It is preferred that the coatings readily leave the surface of the braided suture or fiber-based device in vivo, for example, by degradation or dissolution (for example if the coating is water-soluble.)

In another embodiment, a coating may be applied to the surface of the suture in order to slow degradation and increase strength retention in vivo. For example, the suture may be coated with another polymer, preferably a slowly degrading polymer or composition, or coated with wax. For example, the suture may be coated with polycaprolactone to slow degradation, and prolong strength retention further.

Braids (including suture tapes and suture braids) made from high tenacity yarns of poly(butylene succinate) and copolymers thereof are preferably prepared by coating the yarn with spin finish, twisting or plying the yarn, and winding onto bobbins. Preferred spin finishes are polyethylene glycol sorbitan monolaurate and polyethylene glycol. The bobbins are then placed on a braider. The number of picks per inch may be increased to improve the fineness of the braid, as desired. The number of picks per inch can range from 5 to 100, and preferably 30 to 60. In some embodiments, cores of monofilament, yarn, or multiple plied yarn strands may be incorporated into the center of the braid. Alternatively, the braids may be prepared without cores. For example, to produce hollow braids.

In an embodiment, the yarns and monofilament fibers of poly(butylene succinate) and copolymers thereof may be used to prepare mesh sutures that can spread the load placed on re-apposed tissues, and thereby reduce suture pull-through (cheese wiring effect) and wound dehiscence. The mesh sutures may be threaded through tissue, the mesh anchored in tissue under tension to re-appose soft tissue, and the needle removed. The use of mesh instead of suture fiber to re-appose tissues increases the strength of the repair. The porosity of the mesh is designed to allow the in-growth of tissue into the mesh.

The mesh sutures comprise a suture needle and a mesh component. The mesh component comprises fibers of poly (butylene succinate) and copolymers described herein, and preferably monofilament fibers of poly(butylene succinate) and copolymers thereof. The mesh component is an interlaced structure of fibers, preferably monofilament fibers of poly(butylene succinate) and copolymers thereof. Preferably the mesh structure is formed by knitting, braiding and weaving of fibers comprising poly(butylene succinate) and copolymers thereof, and most preferably monofilament fibers. The cross-section of the mesh component may be an ellipse, half-ellipse, circle, half-circle, gibbous, rectangle, square, crescent, pentagon, hexagon, concave ribbon, convex ribbon, H-beam, I-beam or dumbbell-shaped. Alternatively, the mesh component may assume these shapes as it is passed through tissue. Preferably, the mesh component flattens as it is passed through tissue. The mesh component may also have a cross-sectional profile that varies over the length of the mesh. For example, part of the cross-section of the mesh may be tubular, and another part non-tubular. In embodiments, the mesh component has a cross-section greater than the cross-section of the needle. However, in a preferred embodiment, the mesh component has the same cross-section as the suture needle, and more preferably a cross-section with dimensions that are no more than ±25% of the cross-section of the suture needle. The mesh preferably has pores with average diameters ranging from 5 µm to 5 mm, and more preferably 50 µm to 1 mm. The width of the mesh is preferably from 1 mm to 20 mm, more preferably 1 mm to 10 mm, and even more preferably 1 mm to 7.8 mm. The width may vary along the length of the mesh. In an embodiment, the mesh may have an elasticity similar to the tissue at the site of implantation. For example, in the case of the repair of abdominal tissue, the mesh suture preferably has the same elasticity, or a similar elasticity to abdominal tissue. In another embodiment, the elasticity of the mesh is designed to permit even greater tension to be applied to the re-apposed tissues in order to keep the re-apposed tissue approximated to one another. Preferably, the mesh suture will stretch less than 30%, and more preferably less than 20%. It is also desirable that the mesh has sufficient flexibility to allow it to be passed through tissues with tight curvatures. In a preferred embodiment, the mesh suture has a stiffness less than 50 Taber Units (TU), more preferably less than 10 TU, and even more preferably less than 2 TU or 0.8 TU. In yet another embodiment, the mesh suture has an in vivo tensile strength retention under physiological conditions of at least 75% at 4 weeks, more preferably at least 80% at 4 weeks, and even more preferably at least 65% at 12 weeks.

The sutures, braids, suture tapes, mesh sutures, meshes, patches (such as, but not limited to, hernial patches and/or repair patches for the repair of abdominal and thoracic wall defects, inguinal, paracolostomy, ventral, paraumbilical, scrotal or femoral hernias, hiatal hernias, for muscle flap reinforcement, for reinforcement of staple lines and long incisions, for reconstruction of pelvic floor, including treatment of pelvic organ prolapse, including treatment of cystocele, urethrocele, uterine prolapse, enterocele and repair of rectal or vaginal prolapse, for suture and staple bolsters, for urinary or bladder repair, or for pledgets), and circular knits made from the high tenacity yarns and monofilament fibers of poly(butylene succinate) and copolymers thereof may be used in ligament and tendon repairs, hernia repairs, pelvic floor reconstruction, pelvic organ prolapse repair, Bankart lesion repair, SLAP lesion repair, acromion-clavicular repair, capsular shift/capsulolabral reconstruction, deltoid repair, Labral repair of the shoulder, Capsular/Labral Repairs of the Hip, rotator cuff tear repair, biceps tenodesis, foot and ankle medial/lateral repair and reconstruction, mid- and forefoot repair, Hallux valgus reconstruction, metatarsal ligament/tendon repair and reconstruction, Achilles tendon repair, ulnar or radial collateral ligament reconstruction, lateral epicondylitis repair, biceps tendon reattachment, knee extra-capsular repair, iliotibial band tenodesis, patellar tendon repair, VMO advancement, knee joint capsule closure, hand and wrist collateral ligament repair, scapholunate ligament reconstruction, tendon transfers in phalanx, volar plate reconstruction, acetabular labral repair, anterior ligament repair, spinal repair, fracture fixation, cardiovascular surgery, general surgery, gastric surgery, bowel surgery, abdominoplasty, plastic, cosmetic and reconstructive surgery including lift procedures, forehead lifting, brow lifting, eyelid lifting, facelift, neck lift, breast lift, lateral canthopexy, elevation of the nipple, breast reconstruction, breast reduction, breast augmentation, mastopexy, cystocele and rectocele repair, low anterior resection, urethral suspension, obstetrics and gynecological surgery, Nissen Fundoplication, myomectomy, hysterectomy, sacrolpopexy, cesarean delivery, general soft tissue approximation and ligation, wound closure including closure of deep wounds and the reduction of wide scars and wound hernias, hemostasis, anastomosis, abdominal closure, reinforcement of suture repairs, laparoscopic procedures, partial nephrectomy, vascular grafting, and implantation of cardiac rhythm management (CRM) devices, including pacemakers, defibrillators, generators, neurostimulators, ventricular access devices, infusion pumps, devices for delivery of medication and hydration solutions, intrathecal delivery systems, pain pumps, and other devices to provide drugs or electrical stimulation to a body part.

B. Mesh Products

The discovery that fibers of PBS and copolymers thereof can be prepared with high initial tensile strengths, and prolonged strength retention, has made it possible to develop mesh implants in particular for use in surgical procedures requiring prolonged strength retention, including prolonged burst strength retention. Notably, the fibers may be prepared with suitable properties for forming surgical meshes.

As discussed above, it has been discovered that fibers of PBS and copolymers thereof can be prepared that do not degrade in the first 4 weeks, preferably the first 12 weeks, by surface erosion, which can introduce defects and cause pitting of the surfaces of the fibers. Pitting of fibers is detrimental to the burst strength of a mesh formed from fibers, particularly when the diameters of the fibers are small. The absence of pitting makes it possible to produce meshes of PBS and copolymers thereof with more predictable rates of degradation than other meshes such as biologic meshes made from animal or human tissues, collagen or other absorbable polymer meshes that undergo surface pitting.

It has also been discovered that meshes can be formed from PBS and copolymers thereof that have improved dimensional stability after implantation. As shown in Example 15 and Table 8, meshes comprising PBS and copolymers thereof remain dimensionally stable following implantation for at least 4 weeks, and more preferably for at least 12 weeks. This is a surprising result in view of comparative data obtained for a mesh made from a different material shown in Table 9. The finding is particularly significant when the mesh is used in procedures where it is undesirable for the mesh to shrink and place additional tension on the mesh or surrounding tissue. Thus, mesh derived from PBS and copolymers thereof, preferably comprising monofilament or multifilament oriented fibers, and preferably knit or woven mesh, is particularly suitable for use in procedures such as hernia repair, breast reconstruction, mastopexy, tissue lifting, treatment of stress urinary incontinence, pelvic organ prolapse repair, including treatment of cystocele, urethrocele, uterine prolapse, vaginal fault prolapse, enterocele and rectocele, and other pelvic floor reconstruction. Porous meshes comprising PBS and copolymers thereof are particularly suitable for applications where it is desirable to obtain tissue in-growth, such as in hernia repair, breast reconstruction, treatment of stress urinary incontinence with slings, and pelvic floor reconstruction or repair, including treatment of pelvic organ prolapse, including treatment of cystocele, urethrocele, uterine prolapse, vaginal fault prolapse, enterocele and rectocele.

It has also been discovered that meshes made from PBS and copolymers thereof do not curl after implantation in vivo. This is another improvement since it prevents curled edges from potentially damaging nearby tissues.

In one embodiment, mesh products may be produced from the high tenacity yarns and high tensile strength monofilaments of poly(butylene succinate) and copolymers thereof, for example, by warp or weft knitting processes. In a particularly preferred embodiment, the high strength monofilament fibers of poly(butylene succinate) and copolymers thereof can be knitted or woven to make mesh products. In one embodiment, monofilament knitted mesh can be prepared using the following procedure. Forty-nine (49) spools of high strength poly(butylene succinate) or copolymer thereof monofilament is mounted on a creel, aligned side by side and pulled under uniform tension to the upper surface of a "kiss" roller. The "kiss" roller is spinning while semi-immersed in a bath filled with a 10% solution of polyethylene glycol sorbitan monolaurate, polyethylene glycol, or other suitable lubricant. The lubricant is deposited on the surface of the sheet of fiber. Following the application of the lubricant, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll ready for scouring. The poly(butylene succinate) or copolymer thereof monofilament mesh is then scoured ultrasonically with water, and may be (i) heat set (for example in a hot conductive liquid bath or an oven), and then (ii) washed with a 70% aqueous ethanol solution.

In an embodiment, the meshes made from monofilaments, multifilaments, or combinations thereof, of poly(butylene succinate) or copolymers thereof have one or more of the following properties: (i) a suture pullout strength of at least 5 N, 10 N, or at least 20 N, or 0.5-20 kgf (ii) a burst strength of 0.1 to 100 kgf, more preferably between 1 to 50 kgf, and even more preferably 5 to 25 kgf, or greater than 0.1 kPa, (iii) a thickness of 0.05-5 mm, (iv) an areal density of 5 to 800 g/m$^2$, (v) pores with pore diameters between 5 µm to 5 mm, or more preferably between 100 µm to 1 mm, (vi) Taber stiffness of at least 0.01 Taber Stiffness units (TSU), preferably 0.1-19 Taber Stiffness units, and more preferably 0.01-1 Taber Stiffness units (vii) a degradation rate in phosphate buffered saline at 37° C. wherein the weight average molecular weight of the mesh decreases between 10% and 30% over a 12-week time period, (viii) a degradation rate in vivo under physiological conditions wherein the burst strength of the mesh decreases less than 20% at 4 weeks, or wherein the burst strength of the mesh decreases less than 35% at 12 weeks, (ix) tear resistance of 0.1 to 40 kgf, and more preferably 1 to 10 kgf, (x) pore size between 0.001 to 10 mm$^2$, or more preferably between 0.01 to 1 mm$^2$, (xi) elongation at 16 N/cm of 5 to 50%, or more preferably 5 to 20%, and (xii) a residual textile processing lubricant content of less than 0.5 wt %, and more preferably less than 0.1 wt %, or a content of less than 0.5 wt %, or less than 0.1 wt %, of polyethylene glycol sorbitan monolaurate or polyethylene glycol.

Preparation of monofilament mesh implants prepared with different diameters of PBS-malic acid copolymer monofilament fibers are described in Example 22. The meshes have the following property ranges: monofilament diameters from 0.106 to 0.175 mm, burst strength 8.9-21.9 kgf, elongation at 16 N/cm of 11.1-15.4%, suture pull-out strength in the machine direction of 1.4-3.9 kgf, suture pull-out strength in the cross-machine direction of 1.1-4.5 kgf, tear resistance in the machine direction of 2.0-2.9 kgf, tear resistance in the cross-machine direction of 1.4-4.0 kgf, stiffness in the machine direction of 0.05 to 0.2 TSU, stiffness in the cross-machine direction of 0.06-0.24 TSU, pore sizes of 0.07-0.125 mm$^2$ and 0.48-0.59 mm$^2$, thickness of 0.38-0.62 mm, and areal density of 50-130 g/m$^2$. The residual level of lubricant (Tween-20) on the meshes after processing and washing of the meshes was 0.036-0.069 wt %.

In a preferred embodiment, the monofilament or multifilament meshes have one or more of the following properties: (i) a suture pullout strength of 1 kgf to 20 kgf, (ii) a burst strength of 1 to 50 kgf, more preferably 5 to 30 kgf, (iii) a thickness of 0.1 to 1 mm, (iv) areal density of 50 to 300 g/m$^2$, and (v) pore diameter 100 µm to 1 mm. In another preferred embodiment, the monofilament or multifilament mesh of poly(butylene succinate) or copolymer thereof has substantially one or more of the following properties: a pore diameter of 500±100 µm, thickness of 0.4±0.3 mm, areal density of approx. 182±50 g/m$^2$, suture pullout strength of 5.6±2 kgf, and a burst strength of at least 3 kgf, and more preferably at least 6 kgf. In yet another embodiment, the monofilament mesh comprising poly(butylene succinate) or copolymer thereof has more than one size of pores, and preferably, two to six different pore sizes. For example, the monofilament mesh may have two different pore sizes wherein the first average pore size is between 0.05 mm and 0.2 mm, and the second pore size is between 0.4 mm and 0.8 mm.

In another embodiment, the meshes made from monofilaments, multifilaments, or combinations thereof, of poly(butylene succinate) or copolymers thereof have a mass of from 0.05 to 150 grams, preferably 0.1 to 50 grams, and more preferably 1 to 35 grams, and/or a total filament surface area of from 0.1 to 125 cm$^2$ per cm$^2$ of mesh. For example, when used in surgical procedures involving the breast, such as in breast lift, mastopexy, breast reconstruction, breast augmentation or breast reduction procedures, the meshes typically have a mass of from 1 to 20 grams and/or a total filament surface area of from 0.5 to 20 cm$^2$ per cm$^2$ of mesh. When used in hernia repair, such as laparoscopic inguinal hernia repair, the meshes typically have a mass of from 0.1 to 15 grams and/or a total filament surface area of from 0.5 to 25 cm$^2$ per cm$^2$ of mesh. When used in ventral hernia repair, the meshes typically have a mass of from 1 to 150 grams.

In embodiments in which monofilament fibers of poly(butylene succinate) and copolymers thereof have been coated with a lubricant, such as polyethylene glycol sorbitan monolaurate, polyethylene glycol, prior to forming a mesh, the lubricant can be removed after formation of the mesh by scouring such that the residual level of lubricant remaining on the mesh is up to about 0.1% by weight of the mesh.

In one embodiment, the mesh can be combined with an anti-adhesion coating or film on one surface to make an implant. For example, the mesh may be coated on one side using a hydrogel barrier, such as the Sepra® coating, or using another hyaluronic acid coating. A particularly preferred mesh comprises oriented monofilament fibers of PBS or copolymer thereof coated on one side of the mesh with an anti-adhesion coating or film. Meshes coated with anti-adhesion coatings or films are particularly useful in hernia repair procedures to prevent adhesions to the visceral organs.

In another embodiment, the meshes of poly(butylene succinate) or copolymers thereof may comprise different sized fibers or other non-poly(butylene succinate) or copolymer thereof fibers, including multifilament, and fibers made from other absorbable or non-absorbable biocompatible polymers and hybrid meshes. Such meshes may be designed so that their fibers degrade at different rates in vivo.

Meshes comprising poly(butylene succinate) and copolymers thereof prepared as described herein may have a two-dimensional shape, including a polygon shape, including rectangular, square, triangle, and diamond shapes, a curved shape, including circular, semicircle, elliptical, and crescent shapes.

In yet another embodiment, the meshes described herein may be used to prepare three-dimensional implants, for example, implants that can be used in breast reconstruction, mastopexy, hernia repair, or in void filling (e.g. as a filling agent for use in plastic surgery to fill in defects). The three-dimensional shapes include cone, dome, partial dome, canoe, hemisphere, plug, and hemi-ellipsoid shapes. In one embodiment, these three-dimensional implants have shape memory that can be used to contour to the shape of an anatomical structure, or be used to confer shape to the patient's tissue. For example, these three-dimensional implants can be used in mastopexy and breast reconstruction procedures to confer shape to the host's breast tissue or form an anatomical shape of the breast. In one embodiment, these three-dimensional implants have shape memory that allows them to resume their three-dimension shape after delivery into the body (such as laparoscopic delivery), for example, through a trocar or similar delivery device. These three-dimensional implants can be used for laparoscopic inguinal hernia repair wherein the implant has a three-dimensional shape suitable to conform to the inguinal anatomy, and retain its shape following laparoscopic introduction. Suitable three-dimensional implants of poly(butylene succinate) and copolymers thereof may be manufactured by molding a two-dimensional monofilament mesh made from poly(butylene succinate) and copolymers thereof. In one process, the mesh may be molded using a split metal form consisting on an inwardly curving half and a mating outwardly curving half. The three-dimensional implant may be formed by draping the mesh over the inwardly curving half of the metal form, placing the outwardly curving half of the metal form other the mesh, clamping the split metal form together to form a block, and heating the block to mold the mesh. In another process, the three-dimensional implants may be plugs, preferably hernia plugs, made from meshes of poly(butylene succinate) and copolymers thereof.

In another embodiment, the three-dimensional implants comprising poly(butylene succinate) and copolymers thereof maybe implanted in the breast, preferably instead of breast implants. In a particularly preferred embodiment, the three-dimensional implants comprise pleats, chambers or compartments. Preferably the pleats, chambers and compartments are made with monofilament fibers of poly(butylene succinate) and copolymers thereof. The chambers or compartments may be filled with tissues during implantation, for example, the chambers or compartments may be filled with one or more of the following: blood or blood components, platelets, cells, including stem cells, protein, including collagen, fat, fascia and vascular pedicles or other tissue masses. In a particularly preferred embodiment, the three-dimensional implants may have the shape of a lotus flower or a funnel shape. In an even more preferred embodiment, the three-dimensional implants may have the shape of a lotus flower or funnel shape, and are made from monofilament fibers of poly(butylene succinate) or copolymer thereof.

Meshes comprising poly(butylene succinate) or copolymer thereof may also be prepared that are expandable. These meshes can be prepared so that the fibers of the meshes stretch or elongate so that the meshes can expand. The meshes may comprise fibers of poly(butylene succinate) or copolymer thereof that are unoriented, partially oriented or fully oriented. The meshes may also be designed to expand without the fibers of the meshes stretching. In one embodiment, the meshes may have a knit pattern that provides the mesh with the ability to stretch under force. For example, the mesh may comprise pores that can elongate under force, or loops that can shorten as force is applied. In another embodiment, the meshes may comprise a combination of stronger and weaker fibers, wherein the weaker fibers break when a force is applied allowing the meshes to stretch. Expandable meshes comprising poly(butylene succinate) or copolymer thereof are particularly suitable for use in breast reconstruction, more particularly in combination with the use of a tissue expander. The expandable meshes preferably comprise monofilament fibers made from poly(butylene succinate) and copolymers thereof.

Mesh implants comprising poly(butylene succinate) or copolymer thereof may be prepared for use in breast reconstruction, including mastopexy and augmentation, and other procedures to re-shape or reconstruct the breast, wherein the implant comprises a lower pole support that is placed on the lower pole of the breast which does not cover the nipple areola complex (NAC) of the breast. The implant may be used to confer shape to the breast. The implant may be used to support the breast. And the implant may be used to prevent or minimize ptosis. Preferably, the implant is sized to span the lower pole of the breast. In embodiments, the implant has a three-dimensional shape. The implant is preferably porous. Optionally, the implant may further comprise tabs for fixation of the implant, for example, by suturing or stapling. In an embodiment, the implant comprises a reinforced rim, at least on part of the periphery of the implant. In a preferred embodiment, the implant has a substantially 2-dimensional geometry that becomes a 3-dimensional geometry when the implant is secured to the breast. The lower pole support of the implant preferably comprises a monofilament mesh. The lower pole support of the implant may also comprise a non-woven, lattice, textile, patch, film, laminate, sheet, thermoform, foam, or web, or a molded, pultruded, machined or 3D-printed form. In a preferred embodiment, the implant comprises a polymeric composition of poly(butylene succinate) or copolymer thereof wherein the polymer chains have been aligned and the polymeric composition is partially or fully oriented. In a particularly preferred embodiment, the implant comprises fibers of poly(butylene succinate) or copolymer thereof wherein the fibers are partially or fully oriented.

Meshes comprising poly(butylene succinate) or copolymer thereof may also be prepared that have expandable or collapsible pores. Depending on the application, a mesh with expandable pores may be desired. For instance, if a collapsing pore design damages or irritates a tissue, an expanding pore design may be used. Expandable pores may be created by imparting a crimp or zig-zag in the fibers or by designing meshes with a negative Poisson's ratio or pores with auxetic geometries, such that under tension, the mesh pores expand rather than causing pore collapse. In embodiments, auxetic meshes may be formed from fibers or films of poly(butylene succinate) or copolymer thereof.

Mesh implants comprising poly(butylene succinate) or copolymer thereof may also be prepared for use in breast reconstruction, including mastopexy and augmentation, and other procedures to re-shape or reconstruct the breast, wherein the implant can be used to shape the entire breast. These implants may be prepared in a three-dimensional shape to cover the entire breast, or substantially all of the breast, except the NAC. An aperture may be introduced into the implant to accommodate the NAC. The implant may be shaped for placement under the skin and over the breast mound of a female breast. The implant may comprise an upper pole for placement on the upper pole of the breast, and a lower pole for placement on the lower pole of the breast. The aperture is preferably positioned on the implant so that it is able to angulate the NAC after implantation. Preferably, the aperture of the implant allows the NAC to be angulated superior to the nipple meridian reference. The diameter of the aperture for the NAC is preferably 2 to 6 cm. The mesh implant may optionally comprise one or more tabs for fixation of the implant. In a preferred embodiment, the implant is dimensioned so that the ratio of the volume of the upper pole of the mesh implant to the ratio of the volume of the lower pole of the mesh implant is less than 1. In another embodiment, the lower pole of the mesh implant has a convex shape, and the upper pole has a non-convex pole, optionally a concave or straight profile. In embodiments, the lower pole has a radius of 4 cm to 8 cm.

In a further embodiment, the meshes described herein may further comprise barbs, hooks, self-anchoring tips, micro-grips, fleece, reinforcement, and a reinforced outer edge or border.

In another embodiment, non-woven meshes may be prepared from the high tenacity yarns by entangling fibers using mechanical methods. For example, to prepare melt blown non-woven from PBS or a copolymer thereof, the molten polymer can be conveyed to a melt blowing die by a screw extruder. At the die, the polymer is extruded through many small holes to create a plurality of polymer filaments. These polymer filaments are stretched and attenuated by a stream of hot air and are accelerated toward the collection belt. Depending upon the processing conditions and the temperature and velocity of the air used to attenuate the fibers, the fibers may break into shorter filaments, or may remain intact to form longer, continuous filaments. During the stretching process, the fibers may entangle to form a random collection of filaments as they impact the moving collection drum called the take up screen or collector. If the fibers remain molten prior to hitting the collector, the fibers may fuse on the collection belt. Thus the non-woven material can be made of loosely entangled fibers with low cohesive strength, as opposed to a more cohesive mesh of fused fibers. After cooling, the non-woven material can be removed from the take up screen and may be collected on a separate take up roll.

The properties of the nonwovens can be tailored by selection of parameters such as fiber diameter, fiber orientation, and length of the fibers (for staple nonwovens). In a preferred embodiment, the non-woven meshes prepared from the high tenacity yarns have one or more of the following properties (i) a thickness of 0.1-5 mm, (ii) an areal density of 5 to 800 g/m$^2$, (iii) a suture pullout strength of greater than 10 N, and (iv) a burst strength that is able to withstand a pressure of at least 0.1 kPa, and/or a burst strength of 0.1 kgf to 25 kgf.

Non-wovens made from PBS polymers and copolymers thereof by melt-blown processes are characterized by their formation from fine fibers with average diameters ranging from 1 µm to 50 µm. These non-wovens are also characterized by their high burst strengths, as indicated above. The non-wovens possess properties that are desirable in preparing medical products, particularly implantable medical devices. For example, the non-wovens may be used to make partially or fully absorbable biocompatible medical devices, or components thereof. Such devices include those discussed elsewhere in the present application.

In another embodiment, a non-woven of PBS polymer or copolymer may be prepared by a dry spinning process. For example, the PBS polymer or copolymer is dissolved in a solvent to make a polymer solution. A suitable dry spinning apparatus may include a nozzle through which the polymer solution is injected into a stream of accelerated gas. A preferred set up comprises compressed air as the source of gas (controlled by a pressure regulator), a REGLO-Z digital pump drive equipped with a suction shoe pump head to control the injection rate of the polymer solution, a spraying apparatus that consists of concentric nozzles, and a solid surface or porous surface collector. The collector is positioned at a desired fixed distance from the nozzle. The spraying apparatus consists of an inner and a concentric outer nozzle, which creates a low pressure region near the orifice of the inner nozzle. Polymer strands are consistently shot to the collector due to the combination of the low pressure zone and stripping at the solution/gas interface. Solvent evaporates during the time the polymer strand hits the collector due to the high surface to volume ratio of the strands coupled with the high gas turbulence and temperature. A number of parameters can be varied to control the non-woven thickness, density and fiber sizes including, but not limited to, solution flow rate (ml/min), distance between the nozzle and the collector, needle configuration (including needle diameter and needle extrusion distance), temperature, choice of solvent, polymer molecular weight, collection time, and gas (e.g. air) pressure.

Non-wovens made from PBS polymers and copolymers thereof by dry spun processes can be characterized by their formation from fine fibers with average diameters ranging from 0.01 µm to 50 µm. Notably, the dry spun nonwovens may be produced with smaller fibers than the melt-blown non-wovens. The dry spun non-wovens are also characterized by their high burst strengths, exceeding 0.1 to 25 kgf, and molecular weights within 20% of the value of the polymer from which they are derived. Because these dry spun non-wovens can be produced without substantial loss of molecular weight, they can also have significant advantages over melt-blown non-wovens. This is of particular significance where it is desirable for a non-woven material to retain its integrity and strength in vivo for a longer period of time. For example, in tissue engineering it may be desirable for a non-woven scaffold to be present in vivo for a prolonged period of time to allow tissue in-growth and tissue maturation before the scaffold is absorbed. Premature absorption of the scaffold may result in immature tissue formation, and potentially failure of the implant device. Thus, because dry spun non-wovens can be prepared without substantial loss of polymer molecular weight, and the body requires longer periods of time to degrade PBS and copolymers thereof of higher molecular weight, a dry spun nonwoven may remain in vivo as a scaffold for longer than a melt blow non-woven.

In a further option for a dry spun process for producing non-wovens, the fibers may be collected on a moving or rotating collector instead of a stationary plate. This can improve the mechanical properties of the non-woven (for example, tensile strength). More particularly, for example, a rotating mandrel may be used as the collector. Collecting the fibers on a rotating mandrel aligns the fibers substantially in the machine direction. The alignment can be confirmed by SEM images, and by measurements of mechanical properties in each direction of the non-woven. Notably, increasing the rpm of the rotating mandrel results in a steady increase in the alignment, and results in a steady increase in the tensile strength of the non-woven in the machine direction (i.e. rotational direction) relative to the cross direction. Thus, it is possible to produce a non-woven device comprising dry spun fibers of PBS or copolymer thereof with anisotropic properties. Other methods to produce fibers and non-woven of PBS of copolymers thereof can be similarly employed to produce non-wovens with anisotropic properties.

In one preferred embodiment of such a process, the collector is positioned at a desired fixed distance from the nozzle. The spraying apparatus consists of an inner and a concentric outer nozzle, which creates a low pressure region near the orifice of the inner nozzle. Polymer strands are consistently shot to the collector due to the combination of the low pressure zone and stripping at the solution/gas interface. Solvent evaporates during the time the polymer strand leaves the nozzle and hits the collector due to the high surface to volume ratio of the strands coupled with the high gas turbulence and temperature. A number of parameters can be varied to control the non-woven thickness, density and fiber sizes including, but not limited to, solution flow rate (ml/min), distance between the nozzle and the collector, needle configuration (including needle diameter and needle extrusion distance), number of needles, temperature, choice of solvent, polymer molecular weight, polymer concentration in solution, collection time, gas (e.g. air) pressure and speed and/or circumference of the rotating collector plate. In some embodiments, the speed of the rotating collector plate is 10 rpm. In a preferred embodiment the speed of the rotating collector plate is greater than 50 rpm and more preferably, greater than 100 rpm.

Accordingly, the present application also provides a non-woven device comprising dry spun fibers of PBS or copolymer thereof with anisotropic properties, optionally wherein the non-woven form is formed into a medical implant or other medical device described herein. For example, the non-woven may have a ratio of the tensile strength in the machine direction to the tensile strength in the cross direction that is greater than 1.2. The non-woven may be made by dry spinning and collected on a rotating plate, cylinder or mandrel, for example as described above. The weight average molecular weight of the PBS or copolymer thereof may decrease less than 20% during the processing of the polymer or copolymer by this dry spun process.

In another embodiment of the invention, the high tenacity yarns of poly(butylene succinate) and copolymers thereof, may be knitted to produce circular knits. Circular knits comprising the high tenacity yarns may be used, for example, as vascular grafts. In one embodiment, a circular knit of the high tenacity yarns of poly(butylene succinate) and copolymers thereof may be produced using a single feed, circular weft knitting machine (Lamb Knitting Co., model ST3A/ZA).

In another preferred embodiment of the invention, it has been discovered that implantable meshes may also be formed by 3D printing. These meshes are particularly suitable for use in breast reconstruction, hernia repair, pelvic floor reconstruction, including treatment of pelvic organ prolapse, including treatment of cystocele, urethrocele, uterine prolapse, vaginal fault prolapse, enterocele and rectocele, and treatment of stress urinary incontinence using slings. Two different methods of 3D printing poly(butylene succinate) and copolymers thereof are described in Examples 9 and 10. FIG. 1 shows an image of a mesh that was 3D printed according to the method of Example 9. The high quality of the mesh is apparent from the image. The method is particularly suitable for forming three-dimensional mesh implants comprising PBS and copolymers thereof, including, for example, hernia plugs, and meshes with three-dimensional shapes that are designed to contour to the patient's anatomy or that have pores with defined shapes or sizes or with auxetic geometries that expand with tension. The method may also be used to prepare 3D meshes of PBS and copolymers thereof for breast reconstruction, include breast implants, expandable meshes, and full contour implants. In an embodiment, the 3D printed mesh implants comprising PBS or copolymers thereof have one or more of the following properties: burst strength of 1 kgf to 25 kgf, and more preferably 3 kgf to 10 kgf; thickness of 50 µm to 3 mm, and more preferably 100 µm to 800 µm; pore size between 75 µm and 5 mm; a total porosity of at least 50%, but less than 100%, and a weight average molecular weight of 25 kDa to 500 kDa, and more preferably 50 kDa to 300 kDa by GPC relative to polystyrene. In an embodiment, the 3D printed mesh comprising PBS and copolymers thereof are formed from unoriented PBS or copolymer thereof.

The meshes comprising PBS and copolymers thereof disclosed herein may be used in the following implants: wound closure device, patch (such as, but not limited to, hernial patches and/or repair patches for the repair of abdominal and thoracic wall defects, inguinal, paracolostomy, ventral, paraumbilical, hiatal, scrotal or femoral hernias, for muscle flap reinforcement, for reinforcement of staple lines and long incisions, for reconstruction of pelvic floor, for repair of rectal or vaginal prolapse, for repair of pelvic organ prolapse, including repair of cystocele, urethrocele, uterine prolapse, vaginal fault prolapse, enterocele and rectocele, for suture and staple bolsters, for urinary or bladder repair, or for pledgets), surgical meshes (including but not limited to surgical meshes for soft tissue implants for reinforcement of soft tissue, for the bridging of fascial defects, for a trachea or other organ patch, for organ salvage, for dural grafting material, for wound or burn dressing, or for a hemostatic tamponade; surgical mesh in the form of a mesh plug), wound healing device, device for tissue or suture line reinforcement, tracheal reconstruction device, organ salvage device, dural patch or substitute, nerve regeneration or repair device, hernia repair device, hernia mesh, hernia plug, inguinal hernia plug, device for temporary wound or tissue support, tissue engineering device, tissue engineering scaffold, guided tissue repair/regeneration device, anti-adhesion membrane or barrier, tissue separation membrane, retention membrane, sling, device for pelvic floor reconstruction, urethral suspension device, device for treatment of urinary incontinence, bladder repair device, void filling device, bone marrow scaffold, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, spinal fusion cage, devices with vascular applications, cardiovascular patch, intracardiac patching or for patch closure after endarterectomy, vascular closure device, intracardiac septal defect repair device, atrial septal defect repair device, patent foramen ovale closure device, left atrial appendage closure device, pericardial patch, vascular graft, myocardial regeneration device, periodontal mesh, guided tissue regeneration membrane for periodontal tissue, imaging device, anastomosis device, cell seeded device, controlled release device, drug delivery device, plastic surgery device, breast lift device, mastopexy device, breast reconstruction device, breast augmentation device, breast reduction device, devices for breast reconstruction following mastectomy with or without breast implants, facial reconstructive device, forehead lift device, brow lift device, eyelid lift device, face lift device, rhytidectomy device, rhinoplasty device, device for malar augmentation, otoplasty device, neck lift device, mentoplasty device, buttock lift device, cosmetic repair device, device for facial scar revision, a pouch, holder, cover, enclosure, or casing to partially or fully encase, surround or hold an implantable medical device, a cardiac rhythm management device, a pacemaker, a defibrillator, a generator, an implantable access system, a neurostimulator, a ventricular access device, an infusion pump, a device for delivery of medication and hydration solution, an intrathecal delivery system, a pain pump, or device that provides drug(s) or electrical stimulation to the body.

Accordingly, in the context of monofilament and multifilament fiber, suture, mesh suture, meshes, and slings, the present invention also provides subject matter defined by the following numbered paragraphs:

Paragraph 1. An implant comprising an oriented monofilament or multifilament fiber, wherein the fiber comprises a polymeric composition comprising a 1,4-butanediol unit and a succinic acid unit, and wherein the fiber has a knot pull tensile strength of 200 MPa to 1,000 MPa.

Paragraph 2. The implant of paragraph 1, wherein the implant is a suture.

Paragraph 3. The implant of paragraph 1, wherein the implant is a mesh suture.

Paragraph 4. The implant of paragraph 1, wherein the implant is a mesh, monofilament mesh, multifilament mesh, auxetic mesh or sling.

Paragraph 5. The implants of paragraphs 1-4, wherein the fiber has one or more of the following properties: (i) tensile strength of 400 MPa to 2,000 MPa, (ii) Young's Modulus of 600 MPa to 5 GPa, and (iii) elongation to break of 10 to 150%.

Paragraph 6. The implants of paragraphs 1-5, wherein the oriented fiber is produced by a method comprising the steps of: (a) spinning a multifilament fiber or monofilament fiber comprising the polymer composition, (b) one or more stages of drawing the multifilament fiber or monofilament fiber with an orientation ratio of at least 3.0 at a temperature of 50-70° C., (c) one or more stages of drawing the multifilament fiber or monofilament fiber with an orientation ratio of at least 2.0 at a temperature of 65-75° C., and (d) drawing the multifilament fiber or monofilament fiber with an orientation ratio greater than 1.0 at a temperature of 70-75° C.

Paragraph 7. The multifilament fiber or monofilament fiber of paragraph 6, wherein the order of the steps is (a) followed by (b) followed by (c) followed by (d).

Paragraph 8. The multifilament fiber or monofilament fiber of paragraph 6, wherein the multifilament fiber or monofilament fiber is drawn in a conductive liquid chamber.

Paragraph 9. The multifilament fiber or monofilament fiber of paragraph 6, further comprising the step of quenching the spun multifilament fiber or monofilament fiber prior to drawing in a conductive liquid chamber at a temperature of 50-70° C.

Paragraph 10. The multifilament fiber or monofilament fiber of paragraph 6, further comprising allowing the fiber to cool after quenching by passing the fiber between two godets.

Paragraph 11. The multifilament fiber or monofilament fiber of paragraph 6, wherein the multifilament fiber or monofilament fiber is spun in a temperature range of 60-230° C., 80-180° C., 80-175° C. or 80-170° C.

Paragraph 12. A method of forming the multifilament fiber or monofilament fiber of any one of paragraphs 1-11, wherein the fiber is produced by a method comprising the steps of: (a) spinning a polymeric composition comprising a 1,4-butanediol unit and a succinic acid unit to form a multifilament fiber or monofilament fiber comprising the polymeric composition, (b) one or more stages of drawing the multifilament fiber or monofilament fiber with an orientation ratio of at least 3.0 at a temperature of 50-70° C., (c) one or more stages of drawing the multifilament fiber or monofilament fiber with an orientation ratio of at least 2.0 at a temperature of 65-75° C., and (d) drawing the multifilament fiber or monofilament fiber with an orientation ratio greater than 1.0 at a temperature of 70-75° C.

Paragraph 13. The method of paragraph 12, wherein the multifilament fiber or monofilament fiber is drawn in a conductive liquid chamber.

Paragraph 14. The method of paragraphs 12 and 13, further comprising the step of quenching the spun multifilament fiber or monofilament fiber prior to drawing in a water bath at a temperature of 50-70° C.; and/or allowing the multifilament fiber or monofilament fiber to cool after quenching by passing the fiber between two godets, and/or further comprising drying the polymer composition prior to spinning so that the moisture content of the polymer composition is less than 0.1 wt %, less than 0.05 wt %, or less than 0.005 wt %.

Paragraph 15. The method of paragraph 14, wherein the multifilament fiber or monofilament fiber is spun in a temperature range of 60-230° C., 80-180° C., 80-175° C., or 80-170° C.

Paragraph 16. The method of paragraph 15, wherein: (a) the spun multifilament fiber or monofilament fiber is not cold quenched or cold stretched or (b) the sum of the orientation ratios is over 6.0, 6.5, 7.0, 7.5 or 8.0 and the multifilament fiber or monofilament fiber is drawn at temperatures between 50° C. and 90° C.

C. Absorbable Implants for Use in Breast Surgery

Absorbable implants for use in breast surgery that are made from PBS and copolymers thereof and which are designed to conform to, contour or shape the breast parenchyma and surrounding chest wall are disclosed herein. The implants may be used in breast reconstruction, mastopexy, breast augmentation, breast lifting, breast reduction, breast reconstruction following mastectomy with or without breast implants, and other procedures to re-shape or reconstruct the breast. These implants can be designed to support newly lifted breast parenchyma, and/or a silicone or saline breast implant, or a native tissue reconstruction from a tissue flap. The implants have initial mechanical properties sufficient to support a breast, with or without a breast implant, and allow the in-growth of tissue into the implant as the implant degrades. The implants are preferably porous. The implants also have a strength retention profile that allows the support of the breast to be transitioned from the implant to regenerated host tissue without any significant loss of support for the reconstructed breast. The implants have suture pullout strengths that can resist the mechanical loads exerted on the breast. The breast implants may be two-dimensional or three-dimensional, and may also be configured to deploy into a three-dimensional shape during implantation. For example, the implants may be rolled up or folded to allow delivery, and then deploy to form a three-dimensional shape during implantation. The implants may have shape memory. The implants may further comprise tabs to permit fixation after implantation. For example, the tabs may be sutured or stapled to the body to fixate the implants. Prior to implantation or following implantation, the implants may be coated or filled with one or more of the following: blood or blood components, platelets, cells, including stem cells, protein, including collagen, fat, lipoaspirate, fascia and vascular pedicles or other tissue masses. In an embodiment, the cells, tissues and materials may be injected into or onto the implants. The breast implants may incorporate bioactive agents, including antimicrobial agents, antibiotics, or anti-adhesion agents.

In an embodiment, the implants provide support for the lower pole of the breast. These implants may be used to confer a desirable shape to the breast. The implants may also be used to minimize ptosis.

In another embodiment, the implants are designed to re-shape or reconstruct the entire shape of the breast. These full contour breast implants contour both the shape of the lower pole and upper pole of the breast, and cover at least part of the upper and lower poles of the breast. In addition to conferring a desirable shape on the entire breast, the implants also help to minimize ptosis. The implants may also be used to angulate the nipple areola complex (NAC).

In one embodiment, the implants have a shape that: is conformable to the breast and chest wall without causing buckling or bunching; minimizing the need to trim the implant during surgery; and sculpturing the breast into the desired shape.

Absorbable implants are also disclosed with shape memory. These shape memory implants can be temporarily deformed, and can be delivered by minimally invasive techniques for mastopexy and/or breast reconstruction procedures. The implants can resume their preformed shapes after delivery into a suitably shaped tissue plane in the body. The shaped memory implants can confer a shape to the breast. In a preferred embodiment, the absorbable implants have an asymmetric shape.

Ideally, it would be preferable to use an absorbable implant for mastopexy and other breast reconstruction procedures that has a longer strength retention profile, and the demonstrated ability to regenerate healthy host tissue to support the breast. Such regenerated host tissue could replace or reinforce the ligamentous suspension system of the breast, acting as an artificial suspensory, and release the skin from the function of maintaining breast shape. The use of a prolonged strength retention absorbable implant to provide an even suspension of the breast instead of using sutures would also eliminate the formation of linear stress lines associated with suture only breast lift techniques, as well as eliminate the time required to adjust sutures to optimize appearance. It would also be desirable to use minimally invasive techniques in mastopexy and breast reconstruction procedures to implant these absorbable implants.

Furthermore, it would be desirable to provide the surgeon with a fully pre-shaped implant with shape memory and/or self-expansion capability that can be temporarily deformed to allow for implantation, and then resume its original preformed three-dimensional shape after placement in a suitably dissected tissue plane. The implant may be inserted in a folded, crimped, or constrained conformation. After insertion in a suitably shaped tissue plane, the implant would spring or open back into an opened conformation of its own volition and due to its inherent design. This procedure would be somewhat analogous in technique to a standard breast augmentation procedure, wherein a small (1 to 3 inch) incision is created at the inframammary fold (IMF). This incision is merely used by the surgeon as an access point through which the surgeon dissects a much larger tissue plane into which the implant is placed by deforming the implant and pushing it through the (small) incision.

It should be noted that such shape memory implants provide numerous important characteristics, including those in the following list. First, these shape memory implants would have the ability to be temporarily deformed, and then to open, unroll, or spring into a shape after they are delivered in vivo into a suitably shaped tissue plane. This property eliminates the need for the surgeon to unroll, for example, a flat mesh after implantation in vivo, and remove wrinkles in the mesh, and also further enables minimally invasive procedures. Second, the shape memory implants would be designed to confer shape to the breast unlike other implants previously disclosed that must be shaped or draped around the breast. Third, the shape memory implants are not suspension devices that are suspended from the upper pole region by, for example, sutures. Fourth, the shape memory implants are self-reinforced to allow the implants to spring into shape or deploy into an open conformation once implanted in vivo.

(i) Implants

In order to prevent recurrent breast ptosis and aid in shaping the breast parenchyma during a mastopexy or reduction procedure, implants made of PBS and copolymers thereof should have burst strength retention times longer than one to two months that over time can be replaced with regenerated host tissue, and that are able to support the lifted breast mound/parenchyma (including withstanding the forces exerted by any breast implant). The implant should: (i) have mechanical properties sufficient to support the breast, and any breast implant, while regenerated host tissue develops; (ii) allow predictable tissue in-growth as the implant slowly loses strength and is absorbed; (iii) have a burst strength retention profile that allows a transition from support by the implant to support by regenerated host tissue without any significant loss of support; (iv) have a shape and design that (a) is conformable to the breast and chest wall without buckling or bunching, (b) has sufficient suture pullout strength to resist the mechanical loads exerted on the reconstructed breast, (c) minimizes the need to trim the implant during surgery, and (d) sculpts or contours the breast into the desired shape; (v) optionally possess shape memory so that it can be temporarily deformed to allow for implantation and resume its original preformed three-dimensional shape essentially unaided; (vi) optionally have a 3-dimensional shape that substantially represents the shape of the lower pole of the breast, and (vii) optionally confer a shape to the breast.

Absorbable implants are described herein that are comprised of scaffolds, which over time can be replaced with regenerated host tissue that is able to support a surgically revised breast (including withstanding the forces exerted by any breast implant). The implants are made from PBS or copolymer thereof. Fibers comprising a polymeric composition comprising PBS or a copolymer thereof (preferably, fibers as described elsewhere in this application) can be converted into meshes and slings for breast reconstruction that allow some fibrous tissue ingrowth, and yet are soft, supple, and barely palpable once implanted.

The implants disclosed herein have mechanical properties that are sufficient to support the load of the breast, and the additional load of any breast implant, while regenerated host tissue develops. Following implantation, the implant scaffold structure allows a predictable in-growth of tissue as the implant slowly loses strength and is absorbed. The scaffold has a prolonged strength retention profile to ensure a smooth transition from support of the breast by the implant to support of the breast by regenerated host tissue without any significant loss of support. As such, the implant can maintain the ideal shape of the operated breast that was assembled during surgery.

A major advantage of these implants over existing mesh assisted breast surgery and specifically mastopexy is that a regenerated tissue that is strong enough to prevent recurrent ptosis replaces the implants. This eliminates the problems and concerns associated with the use of permanent or partially absorbable meshes, such as contraction, long-term chronic inflammatory and foreign body response and allows for long-term changes in breast volume that can result from pregnancy and weight gain or loss. The disclosed implants have major advantages over prior approaches that have used absorbable polygalactin 910 (VICRYL®) meshes. The latter meshes undergo very rapid loss of strength in vivo, and are completely absorbed in about 42 days. This rapid absorption process provides little time for a regenerated host tissue to form that can support the load on the breast. In contrast, the implants described herein which are formed from PBS, or copolymer thereof, have a prolonged strength retention profile, and in a preferred embodiment can maintain some residual strength for as much as one year. The prolonged presence of these implants provides an extended period for tissue in-growth into their scaffold structures, and a residual strength to prevent early recurrent ptosis while the regenerated tissue forms. Importantly, the in-grown tissue provides strength and support beyond the time of complete strength loss of the implant, thus demonstrating the implant's ability to provide a durable repair beyond its absorption timeframe.

In an embodiment, the absorbable implants are designed so that when manufactured, they are flat; however, when placed around a breast, they have a shape that conforms to the contours of the breast and chest wall without causing any buckling or bunching of the implant or tissue structures. The implants are designed to help sculpt the breast into the desired profile, and shaped to minimize the need to trim the implants during surgery. In a particularly preferred embodiment, the implants are asymmetric. In contrast, absorbable meshes used in existing approaches have generally been symmetric in shape. In a preferred embodiment, the asymmetric shaped implants are made from PBS, or copolymer thereof.

In another embodiment, the implants are designed to have suture pullout strengths high enough to resist the initial mechanical loads exerted by the breast, and to maintain sufficient pullout strength while tissue in-growth occurs. In contrast, polyglactin 910 (VICRYL®) mesh rapidly loses strength, and has negligible suture pullout strength after just a few days.

In a yet another embodiment, the implants made from PBS or copolymer thereof are preformed three-dimensional shapes with shape memory, designed to actively provide shape to the lower pole of the breast parenchyma. The implants can be temporarily deformed and resume their original preformed shapes after implantation into a suitably dissected tissue plane. The implants may aid in conferring a shape to the breast, and are self-reinforced.

(a) Properties of the Implants

The absorbable implants have been designed to support the mechanical forces acting on the breast during normal activities at the time of implantation, and to allow a steady transition of mechanical forces to regenerated host tissues that can also support those same mechanical forces once the implant has degraded. Design of the implant includes selection of the absorbable material, and its form (such as mesh, film, foam), degree of orientation, and molecular weight. This will also determine factors such as surface area and porosity. At rest, the load exerted on a large breast weighing, for example, 1 kg, is 9.8 Newtons (N). During exercise where vertical acceleration can reach 2-3 g, or in extreme exercise peak at around 6 g, the force on the breast could rise to nearly 60 N. In a preferred embodiment, the absorbable implants can withstand a load of at least 5 N, more preferably of at least 15 N, and even more preferably of at least 60 N.

Since the implants are absorbable, it is beneficial that the implants be replaced with regenerated host tissue strong enough to support the breast. In some embodiments, it is beneficial that the implants contain a porous scaffold that can allow tissue in-growth, and the formation of a regenerated tissue strong enough to support the breast after the implant is degraded and absorbed. In an embodiment, the scaffold structure of the implant has pore diameters that are at least 50 µm, more preferably at least 100 µm, and most preferably over 250 µm.

When the implant scaffold has been completely replaced by regenerated host tissue, it must be able to support the breast. The force per area that the regenerated tissue needs to be able to withstand to prevent recurrent ptosis depends upon the size of the reconstructed breast, activity level of the patient, and any additional force exerted by a breast implant. In an embodiment, the regenerated tissue supporting the reconstructed breast can withstand a pressure of at least 0.1 kPa, more preferably at least 1 kPa, and even more preferably at least 5 kPa. In an even more preferred embodiment, the combination of the implant and the regenerating tissue forming in the implant scaffold can also withstand a pressure of at least 0.1 kPa, more preferably at least 1 kPa, and even more preferably at least 5 kPa.

In a particularly preferred embodiment, the absorbable implants are sutured in place. This means that although in theory the load exerted by the breast is spread out over the implant, the entire force of the breast tissue is shared among the points of attachment of the implant to the body. A major advantage is that the absorbable implants disclosed herein possess a high suture pullout strength that allows a heavy breast to be supported with a limited number of anchoring sites. The high suture pullout strength can be obtained for example, as a result of selection of the absorbable material, molecular weight, orientation, form (such as monofilament mesh or film), and porosity.

In a preferred embodiment, an implant made of PBS or copolymer thereof is anchored to the chest wall at four or more places in order to support the breast. This strategy distributes the load over multiple attachment points. In a particularly preferred embodiment, the suture pullout strength of the absorbable implant is greater than 10 N, and more preferably greater than 20 N.

The implant can be designed either so that it stretches equally in each direction, or it may stretch more in some directions than in other directions. The ability of the implant to stretch can allow the surgeon to place tension on the breast during implantation. However, in order to maintain support for the breast following surgery, it is critical that after the implant is implanted, the implant, the regenerated host tissue, and any transitional structures, cannot stretch significantly. In an embodiment, the implant cannot stretch more than 30% of its original length in any direction. This property is imparted on the implant for example as a result of the degree of orientation of the absorbable material comprising PBS or a copolymer thereof, and also the weave or knit pattern if it is a textile.

It is particularly important that the surgeon is able to contour the breast parenchyma with the implant. It is also desirable that the implant is not palpable through the skin once implanted. The implants have been designed so that they are pliable, yet can remodel with increased in-plane stiffness over time to keep the breast in the desired shape. In a preferred embodiment, the implants are compliant and have a Taber stiffness that is less than 100 Taber Stiffness Units, more preferably less than 10 Taber Stiffness Units, and even more preferably less than 1 Taber Stiffness Unit.

The intrinsic property of the absorbable material, the fiber knit pattern, fiber size, degree of orientation and relaxation of the polymer imparts on the implant the desired Taber Stiffness.

In a particularly preferred embodiment, the implant has properties that allow it to be delivered through a small incision. The implant may, for example, be designed so that it can be rolled or folded to allow delivery through a small incision. This minimally invasive approach can reduce patient morbidity, scarring and the chance of infection and speed the rate of recovery.

In another preferred embodiment, the implant has a three-dimensional shape and shape memory properties that allow it to assume its original three-dimensional shape unaided after it has been delivered through a small incision and into an appropriately sized dissected tissue plane. For example, the implant may be temporarily deformed by rolling it up into a small diameter cylindrical shape, delivered through a trocar or using an inserter, and then allowed to resume its original three-dimensional shape unaided in vivo. In addition, the implant may be squeezed in between the fingers to shorten the distance between the two furthest points of the implant in order to facilitate its delivery through an incision smaller than the width of the device.

(b) Reinforced Rim

Figure 19A:
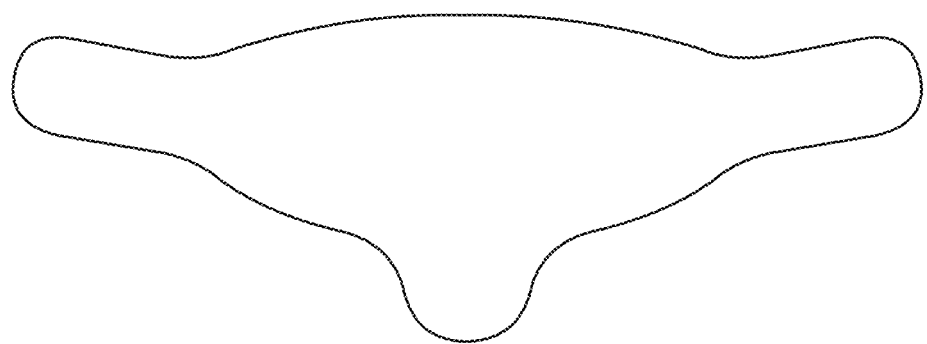
FIG. 19A shows a custom die to cut mesh and ribbing to size and create 3 fixation tabs.
Figure 19B:
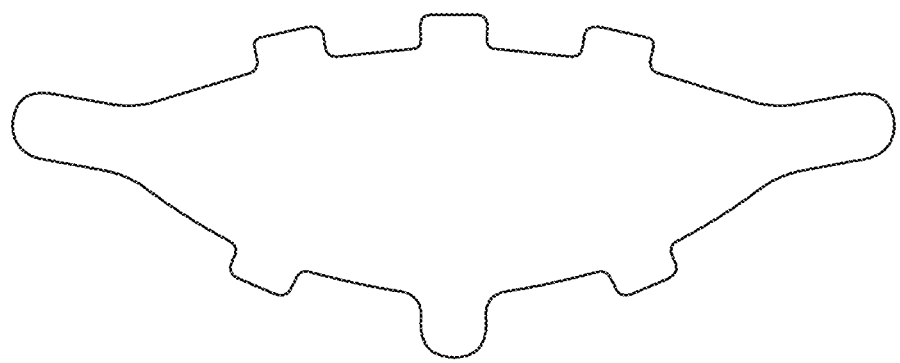
FIG. 19B shows custom die to cut mesh and ribbing to size and create 8 fixation tabs.
Figure 19C:
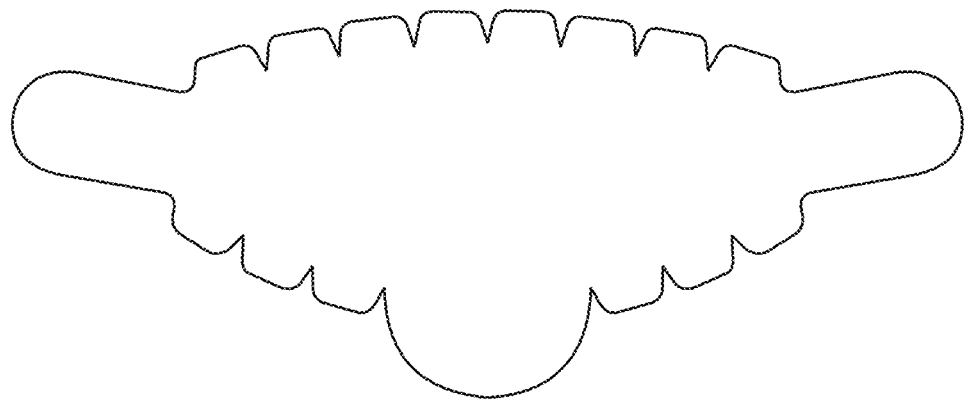
FIG. 19C shows custom die to cut mesh and ribbing to size and create 17 fixation tabs.
Figure 19D:
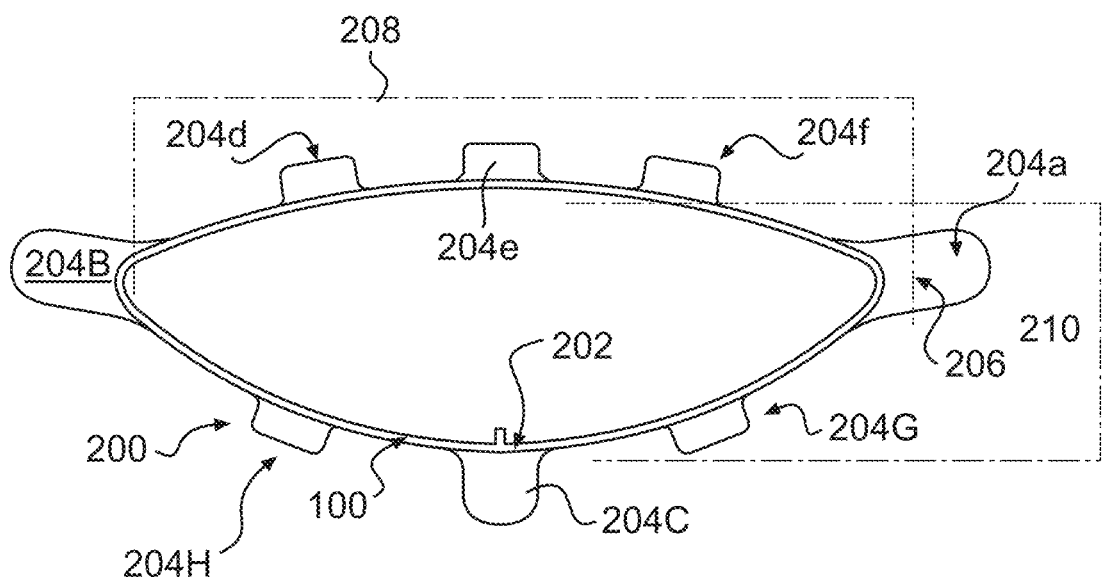
FIG. 19D shows a flat view of a three dimensional partial dome mesh implant (200) with eight fixation tabs (204a to 204h) and a uniform perimeter support ribbing (100) made from a polymeric extrudate, showing an upper section with an M-L distance (208) which is a measure of the width of the device, an IMF-NAC (Nipple Areolar Complex) NAC distance (210) which is a measure of the height of the device, an orientation mark (202) located in the lower section of the device, a lateral tab (204a), a medial tab (204b), an IMF central tab (204c), additional tabs (204d, 204e, 204f, 204g and 204h) and a rounded edge (206) to reduce stress in the implant.

Referring to FIG. 19D, the implants may have a three dimensional shape and include a scaffold which has an upper section, a lower section, medial side, lateral side, and an outlying border.

Figure 19E:
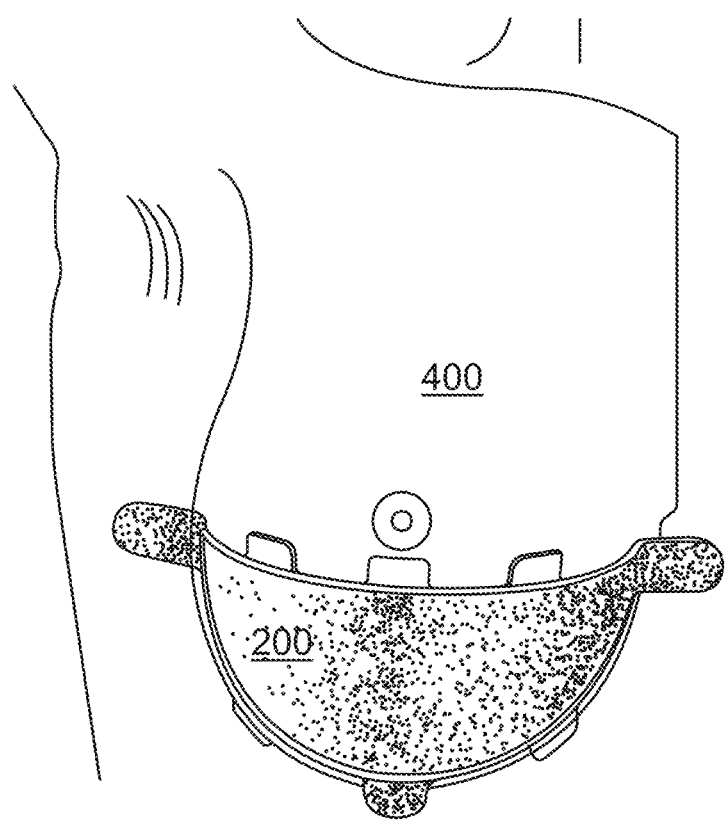
FIG. 19E shows the device 200, placed on a breast 400.
Figure 20A:
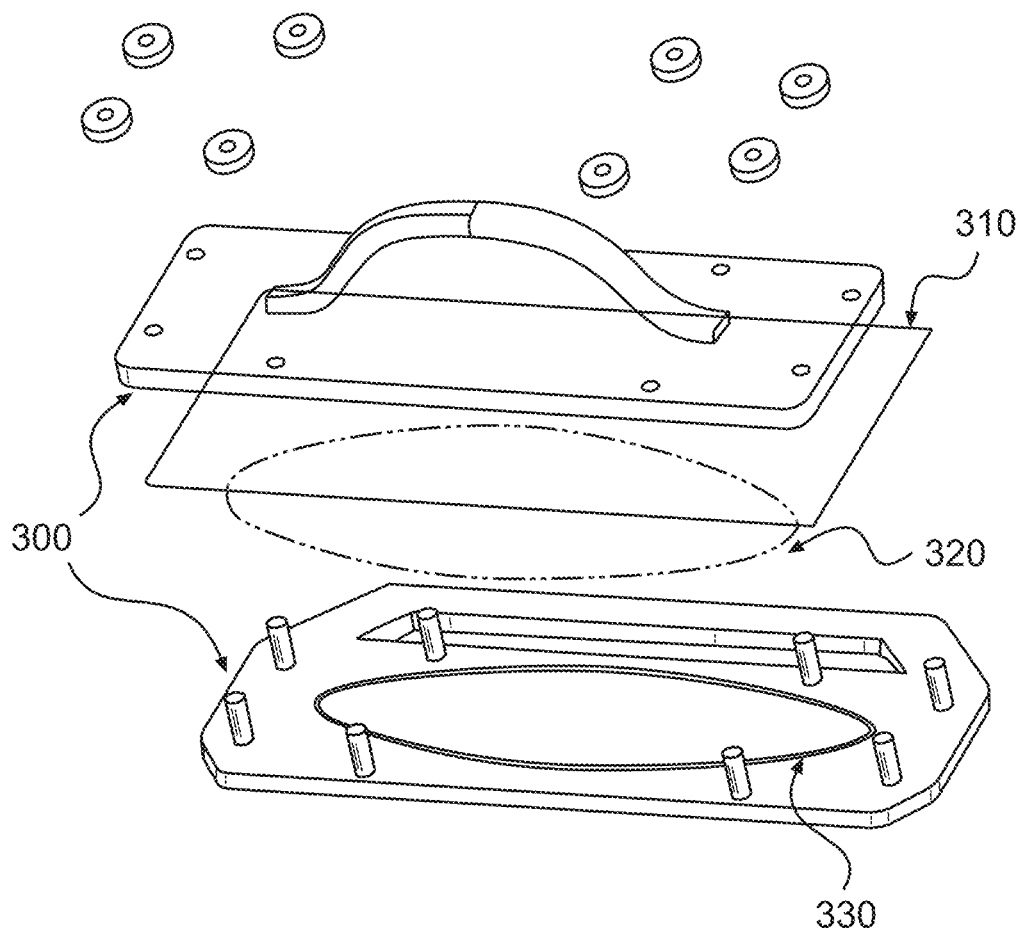
FIG. 20A is a diagram of a split metal form (300) used to attach scaffold material (310) to a ring of extrudate (320). The ring of extrudate is placed in a semicircular groove (330) in one half of the split metal form.
Figure 20B:
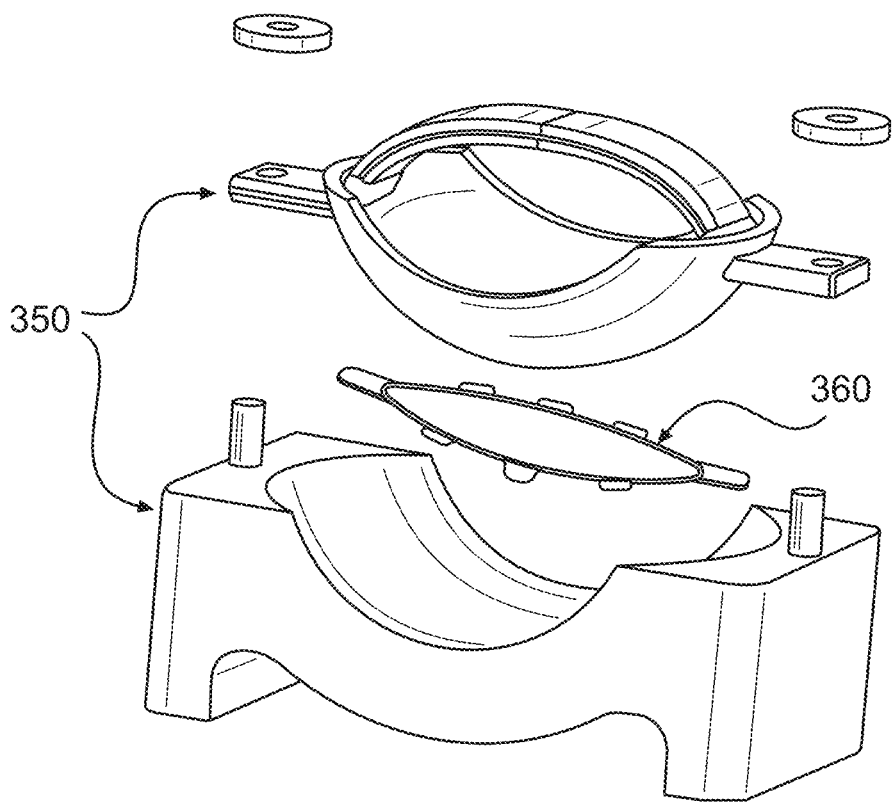
FIG. 20B is a diagram of a split metal form (350) with an inwardly curving half and a mating outwardly curving half, which is used to make implants that can assume a three-dimensional shape unaided. A material (360) to be molded is sandwiched in the split metal mold.

The rim of the implants described herein is preferably resorbable and reinforced. In some embodiments, the rim has an offset elliptical (American football) shape. In this embodiment, the top and bottom half of the rim are composed of circular arcs with collinear centers (FIG. 19E). The upper section can have a curvature range from 10-15 cm, and the lower section can have a curvature range from 21-25.5 cm. The arcs can be designed so that the ratio of their curvature radii follows the golden ratio rule described below in the sub-section entitled "Three-dimensional shaped implants". In some preferred embodiments, the rim has rounded edges. Rounded edges help to eliminate stresses in the implant. The rim edge radius can be for example, 0.6 cm for a small sized implant, 0.7 cm for a medium sized implant and 0.8 cm for a large sized implant.

The outer rim of the implant can be strengthened with a ring/ribbing. For example, the outlying border can be reinforced by a continuous or interrupted ring of: filament, thread, strand, string, fiber, yarn, wire, film, tape, tube, fabric, felt, mesh, multifilament, or monofilament. In a preferred embodiment, the implant is formed from a monofilament mesh with an outlying border reinforced by a continuous ring of monofilament, preferably, a monofilament of PBS or copolymer thereof, for example as described elsewhere in this application. To minimize palpability after implantation while performing the functions above, the rim is made out of a resorbable material with diameter not exceeding 2.0 mm.

To help reduce the amount of material used to make the rim while delivering the stiffness needed for maintaining the 3D shape, the rim can be designed using a decreasing (negative gradient) diameter from the IMF-central position towards the medial and lateral edges.

Ribbing around the edge of the implant that can be either one-sided or two sided and/or with a profile that changes. The support rib can be included along the perimeter of the implant or in the mid dome of the implant, continuously or intermittently (interrupted) for example, a number of ribbing lengths shorter than the perimeter of the device, can be placed intermittently along the perimeter of the device. The number of ribs and spacing used for interrupted placement can be selected as desired. The rib can be of uniform cross-sectional radius or it can have decreasing cross-sectional radius (i.e., a profile that changes).

Figure 18A:
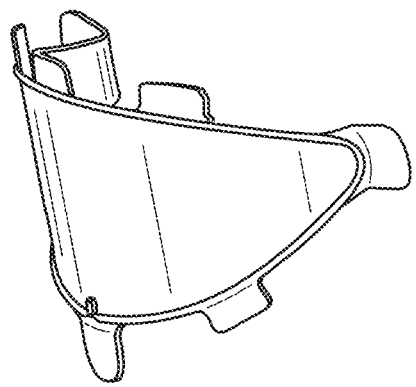
FIG. 18A shows unidirectional curvature for a 3D implant.
Figure 18B:
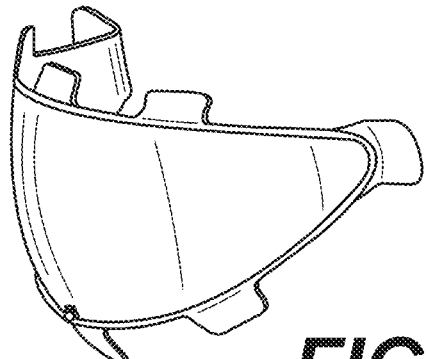
FIG. 18B shows bidirectional curvature for a 3D implant.
Figure 18C:
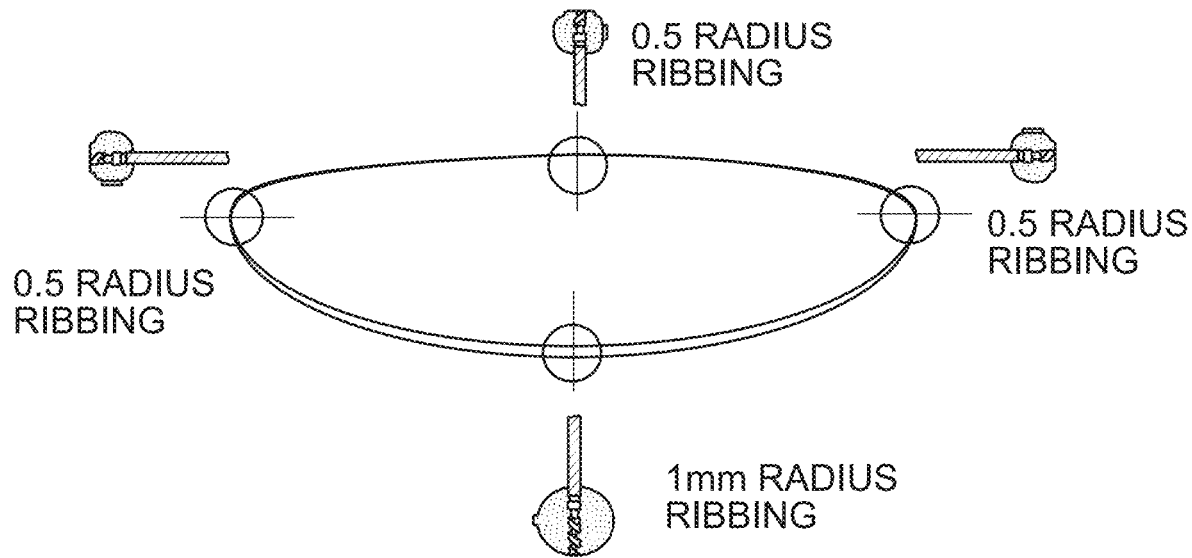
FIG. 18C shows perimeter support ribbing with decreasing radius of the ribbing.

An example of an implant with a three-dimensional partial dome shape that has been reinforced with ribbing is shown in FIG. 17, FIGS. 18C and 19D. In FIG. 17, the partial dome shaped implant is reinforced with a continuous body ribbing along the perimeter (100 of the dome and in the mid-dome (102a and 102b) section. An example of an implant with a three-dimensional partial dome shape that has been reinforced with a continuous ribbing of decreasing cross-sectional radius is shown in FIG. 18C.

(c) Shapes and Applications

The implants can be prepared in sizes large enough to allow for their use in mastopexy and other breast reconstruction procedures such that they are wide enough to substantially span the width of a breast, and for the surgeon to cut and trim the implants, if and as necessary, to the required sizes and shapes. In one embodiment, the implants are cut and shaped so that they can be used in a mastopexy procedure (with or without a breast implant) or in any other breast reconstruction procedure. In a preferred embodiment, the implants are pre-cut and shaped so that they will conform to the anatomical shape of the reconstructed breast. In a preferred embodiment, the implants are pre-cut and shaped so that they will support and conform an autologous tissue flap surgically moved from one location to another in the same patient and to form the anatomical shape of the reconstructed breast. In another embodiment, the implants can be cut and shaped to reinforce breast tissues, and in particular so that there is no buckling or bunching of the implant. In still another embodiment, the implants are two-dimensional (i.e. flat), but can be formed around three-dimensional shapes without any buckling or bunching of the implant.

In yet another embodiment, the implants are designed so that they can help to sculpt breast parenchyma into the desired shape. In a particularly preferred embodiment, the implants have anatomical shapes, three-dimensional shapes, and/or asymmetric shapes. These shapes minimize the need to cut or trim the implant during use, and also minimize any buckling or bunching of the implant.

Non-limiting examples of a support include a mesh, a set of strips, a fabric, a woven construct, a non-woven construct, a knitted construct, a braided construct, a porous scaffold, a porous film including laminated and perforated film, a nanospun, electrospun, or melt-blown construct. Options to produce such products from PBS or copolymers thereof are disclosed elsewhere in this application.

The implants may be shaped into an anatomical shape, two-dimensional shape, three-dimensional shape, and/or asymmetric shapes, minimizing any buckling or bunching of the implant upon placement.

The implants can incorporate one or more tabs to accommodate suture throws or other anchoring devices for the fixation of the implant to the patient's tissues. These tabs can be placed in order to improve the implant's ability to conform and shape to the breast, as well as to adapt to the chest wall. In particular, these tabs can be incorporated with appropriate spacing into the implant so that they amplify the implant's ability to bend and stretch around the lower curvature (lower pole) of the breast without causing bunching, kinking, folding or wrinkling of the implant. The width of the tabs can optionally range from 1 cm to 3 cm and the length from 2 to 4 cm and can range in number from 1 to 20. For example, the implants can have 2, 3, 4, 5, 6, 7, 8, 9, 10, 11, 12, 13, 14, 15, 16, 17, 18, 19 or 20 tabs. Referring to FIG. 19D, the implant can include three tabs (204e, 204d and 204f) in the upper section, three tabs 204c, 204h and 204g in the lower section, one tab 204b in the medial section and one tab 204a in the lateral section of the device.

Breast Implants for Lower Pole Support

Implants comprising poly(butylene succinate) or copolymer thereof may be prepared for use in breast reconstruction, including mastopexy and augmentation, and other procedures to re-shape or reconstruct the breast, wherein the implant comprises a lower pole support that is placed on the lower pole of the breast which does not cover the nipple areola complex (NAC) of the breast. The implant may be used to confer shape to the breast or the tissue flap used to reconstruct the breast. The implant may be used to support the breast or reconstructed breast. And the implant may be used to prevent or minimize ptosis. Preferably, the implant is sized to span the lower pole of the breast. In embodiments, the implant has a three-dimensional shape. The implant is preferably porous. Optionally, the implant may further comprise tabs for fixation of the implant, for example, by suturing or stapling. In an embodiment, the implant comprises a reinforced rim, at least on part of the periphery of the implant. In a preferred embodiment, the implant has a substantially 2-dimensional geometry that becomes a 3-dimensional geometry when the implant is secured to the breast. The lower pole support of the implant may comprise a non-woven, lattice, textile, patch, film, laminate, sheet, thermoform, foam, or web, or a molded, pultruded, machined or 3D-printed form. In one embodiment, the lower pole support of the implant preferably comprises a monofilament mesh. In a preferred embodiment, the implant comprises a polymeric composition of poly(butylene succinate) or copolymer thereof wherein the polymer chains have been aligned and the polymeric composition is partially or fully oriented. In a particularly preferred embodiment, the implant comprises fibers of poly(butylene succinate) or copolymer thereof wherein the fibers are partially or fully oriented. In an embodiment, the breast implant comprising a lower pole support has one or more of the following properties: (i) a polymer or copolymer with a weight average molecular weight of 10,000 to 400,000 Da, and more preferably 50,000 to 200,000 Da; (ii) burst strength of 0.1 to 100 kgf, or more preferably 1 to 50 kgf, and even more preferably 5 to 30 kgf; (iii) porosity, with average pore diameters of at least 25 microns, more preferably at least 75 microns, and preferably less than 2 mm, with a particularly preferred average pore size of 100 μm to 1 mm; (iv) a resistance to stretching, in one or more dimensions of the implant, a distance of more than 30% of the original dimension of the implant when a load of 1 kg is placed on the implant; (v) an areal density of 5 to 800 gram/m$^2$; (vi) when the implant is placed on the breast, an implant dimension of 8 to 20 cm measured from the medial side to the lateral side of the breast; (vii) implant dimension of 5 to 14 cm measured from the inferior to the superior position of the breast; and (viii) fiber or strut average diameters or widths, when present, of 1 micron to 5 mm, more preferably 10 micron to 1 mm, and even more preferably 50 microns to 500 microns when the implant comprises fibers or struts. In another embodiment, the implant may comprise one or more tabs wherein the one or more tabs each have a suture pullout strength of at least 10 N, but less than 1,000 N. In other embodiments, the implant may comprise fibers, wherein the fibers have one or more of the following properties: (i) a tenacity of 1 to 12 grams per denier; (ii) a tensile strength of 400 MPa to 2,000 MPa, and more preferably a tensile strength greater than 500 MPa, 600 MPa, 700 MPa or 800 MPa, but less than 1,200 MPa; (iii) a Young's Modulus of at least 600 MPa, and less than 5 GPa, but more preferably greater than 800 MPa, 1 GPa, 1.5 GPa, and 2 GPa; (iv) an elongation to break of 10-150%, and more preferably 10-50%; and (v) fiber diameter of 1 micron to 5 mm, more preferably 10 micron to 1 mm, and even more preferably 50 micron to 500 micron.

Full Contour Breast Implants

Implants comprising poly(butylene succinate) or copolymer thereof may also be prepared for use in breast reconstruction, including mastopexy and augmentation, and other procedures to re-shape or reconstruct the breast, wherein the implant can be used to shape part or all of the upper and lower poles of the breast or the entire breast. As used herein, a "full contour breast implant" means an implant that can be used to contour both the upper pole and the lower pole of the breast, wherein at least part of the implant covers the upper and lower poles of the breast. These full contour breast implants may be prepared in a three-dimensional shape to cover the entire breast, or substantially all of the breast, except the NAC. An aperture may be introduced into the implant to accommodate the NAC. The implant may be shaped for placement under the skin and over the breast mound of a female breast. The implant may comprise an upper pole for placement on the upper pole of the breast, and a lower pole for placement on the lower pole of the breast. The aperture is preferably positioned on the implant so that it is able to angulate the NAC after implantation. Preferably, the aperture of the implant allows the NAC to be angulated superior to the nipple meridian reference. The diameter of the aperture for the NAC is preferably 2 to 6 cm. The implant may be used to confer shape to the breast. The implant may be used to support the breast or the reconstructed breast. And the implant may be used to prevent or minimize ptosis. Preferably, the implant is sized to span the entire breast. In an embodiment, the implant comprises a reinforced rim, at least on part of the periphery of the implant. The full contour breast implant may comprise a non-woven, lattice, textile, patch, film, laminate, sheet, thermoform, foam, or web, or a molded, pultruded, machined or 3D-printed form. In one embodiment, the full contour breast implant preferably comprises a monofilament mesh. In a preferred embodiment, the implant comprises a polymeric composition of poly(butylene succinate) or copolymer thereof wherein the polymer chains have been aligned and the polymeric composition is partially or fully oriented. In a particularly preferred embodiment, the implant comprises fibers or struts of poly(butylene succinate) or copolymer thereof wherein the fibers or struts are partially or fully oriented. In a preferred embodiment, the full contour breast implant is dimensioned so that the ratio of the volume of the upper pole of the implant to the ratio of the volume of the lower pole of the implant is less than 1. In another embodiment, the lower pole of the implant has a convex shape, and the upper pole has a non-convex pole, optionally a concave or straight profile. In embodiments, the lower pole of the implant has a radius of 4 cm to 8 cm. In another embodiment, the full contour breast implants have one or more of the following properties: (i) a polymer or copolymer with a weight average molecular weight of 10,000 to 400,000 Da, and more preferably 50,000 to 200,000 Da; (ii) burst strength of 0.1 to 100 kgf, or more preferably 1 to 50 kgf, and even more preferably 5 to 30 kgf; (iii) porosity, with average pore diameters of at least 25 microns, more preferably at least 75 microns, and preferably less than 2 mm, with a particularly preferred average pore size of 100 µm to 1 mm; (iv) a resistance to stretching, in one or more dimensions of the implant, a distance of more than 30% of the original dimension of the implant when a load of 1 kg is placed on the implant; (v) an areal density of 5 to 800 gram/m$^2$; (vi) a medial to lateral distance between the implant's medial and lateral edges, when the implant is placed on the breast, of 10 to 20 cm (measured from the medial edge to the lateral edge of the breast implant); (vii) a longitudinal distance between the implant's lowest and highest points, when the implant is placed on the breast, of 12 to 22 cm (measured from the inferior position at the inframammary fold to the superior position (where the breast meets the chest wall); and (viii) fiber or strut average diameters or widths, when present, of 1 micron to 5 mm, more preferably 10 micron to 1 mm, and even more preferably 50 microns to 500 microns when the implant comprises fibers or struts. In another embodiment, the full contour breast implant may comprise one or more tabs wherein the one or more tabs each have a suture pullout strength of at least 10 N, but less than 1,000 N. In other embodiments, the full contour breast implant may comprise fibers, wherein the fibers have one or more of the following properties: (i) a tenacity of 1 to 12 grams per denier; (ii) a tensile strength of 400 MPa to 2,000 MPa, and more preferably a tensile strength greater than 500 MPa, 600 MPa, 700 MPa or 800 MPa, but less than 1,200 MPa; (iii) a Young's Modulus of at least 600 MPa, and less than 5 GPa, but more preferably greater than 800 MPa, 1 GPa, 1.5 GPa, and 2 GPa; (iv) an elongation to break of 10-150%, and more preferably 10-50%; and (v) fiber diameter of 1 micron to 5 mm, more preferably 10 micron to 1 mm, and even more preferably 50 micron to 500 micron.

Asymmetric Implants

Figure 6:
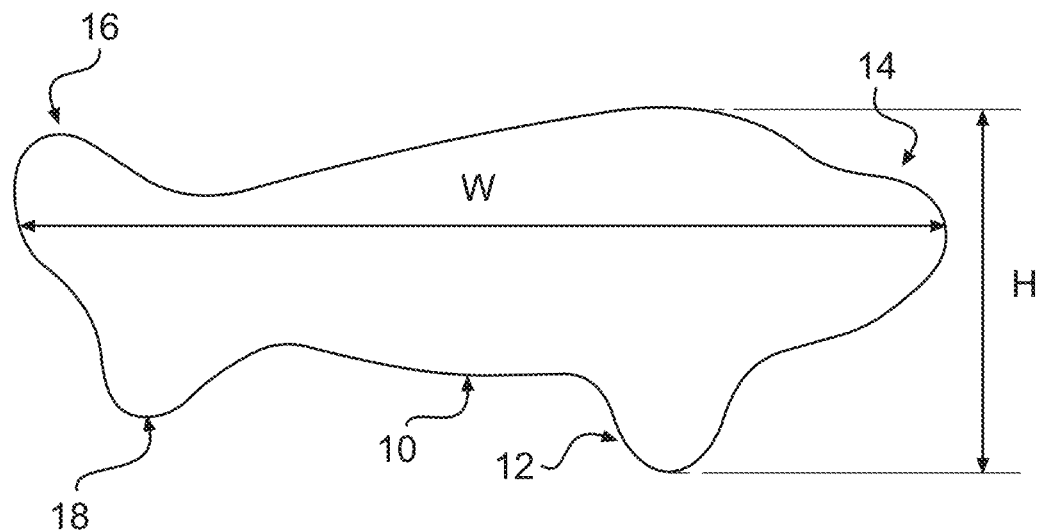
FIG. 6 is a diagram of an asymmetric implant for breast reconstruction with a teardrop shape and additional tabs (12, 14, 16, 18).

In one embodiment shown in FIG. 6, a body 10 of the asymmetric implant is shaped into a teardrop. This shape helps to prevent the implant from buckling or bunching, minimizes the need to cut or shape the implant during surgery, provides a low profile to avoid coverage of the nipple-areolar complex, and facilitates sculpturing the breast to create enhanced cleavage. Tabs 12, 14, 16, 18 or other shapes can also protrude from the teardrop, for example, to accommodate suture throws or other anchoring devices, maximize load distributions, and further shape the contours of the reconstructed breast. These tabs also allow the implant to contour tightly to the breast mound without forming wrinkles or folds. In a preferred embodiment, the width to height ratio of the teardrop ranges from a ratio of 10:1 to 1.5:1, and is more preferably 5:2. For example, the width (W) of the teardrop implant (shown in FIG. 6) can be about 25 cm and the height (H) of the teardrop shown in FIG. 6) can be 10-11 cm as. (The width of the teardrop is the longest distance measured between any two points, and the height of the teardrop is the longest distance measured perpendicular to the width.)

With reference to FIG. 6, four tabs are shown extending from body 10. Two tabs 12, 14 are shown extending from a base or wider portion of the teardrop, and an additional two tabs 16, 18 are shown extending from the narrow or tip portion of the tear drop. The tabs are shown in an asymmetric arrangement. Tabs assist with contouring to the breast tissue, and providing a platform for fastening the implant to tissue. Although four tabs are shown in FIG. 6, the body 10 may include more or less than four tabs. Preferably, the implant includes at least 4 tabs.

As described herein, the implant combines various features to optimize mechanical properties. For example, various combinations of implant body shapes, tab shapes, tab locations, number of tabs, thickness of body, type of material, and material processing result in increased mechanical properties including but not limited to increased suture pull out strength, increased breast load, increased stiffness, and increased load after several months (e.g. increased load after 78 weeks).

The implant may be installed in either breast. The implant shown in FIG. 6 is suited for a mastopexy procedure.

In a particularly preferred embodiment, the teardrop can incorporate seam lines that can be embossed to project the two-dimensional structure of the implant into a three-dimensional structure that accentuates the breast contouring.

Figure 7:
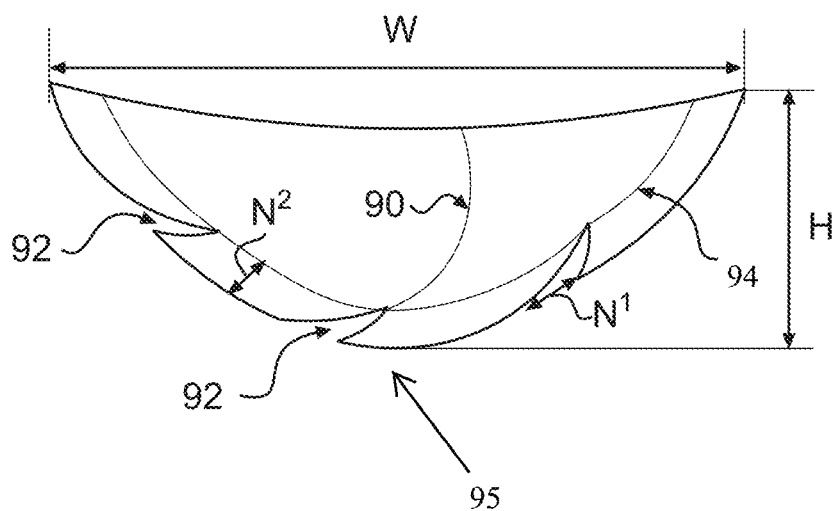
FIG. 7 shows a diagram of an asymmetric two-dimensional implant (95) for use in reconstruction of the right breast with a width (W), height (H), a mid-body curved support (90), and tabs (94) to allow the implant to stretch over the breast mound without bunching.

In another embodiment, the asymmetric implant is shaped as shown in FIG. 7, and used to reconstruct a right breast. An implant with a shape that is the mirror image of FIG. 7 may be used to reconstruct a left breast. The implant optionally has a curved mid-body support (90) to improve breast mound contouring and support, cut notches (92) and tabs (94) to minimize stress concentrations and allow the implant to stretch over the breast mound with minimal bunching. The notched sections may, if desired, be stitched closed to create a three-dimensional cup shape. In an embodiment, the implant has a width (W) between 22 and 30 cm, a height (H) between 7.5 and 11 cm, a perimeter notch gap (N$^1$) between 0.5 and 4 cm, and a tab width (N$^2$) between 1 and 2 cm.

Figure 8:
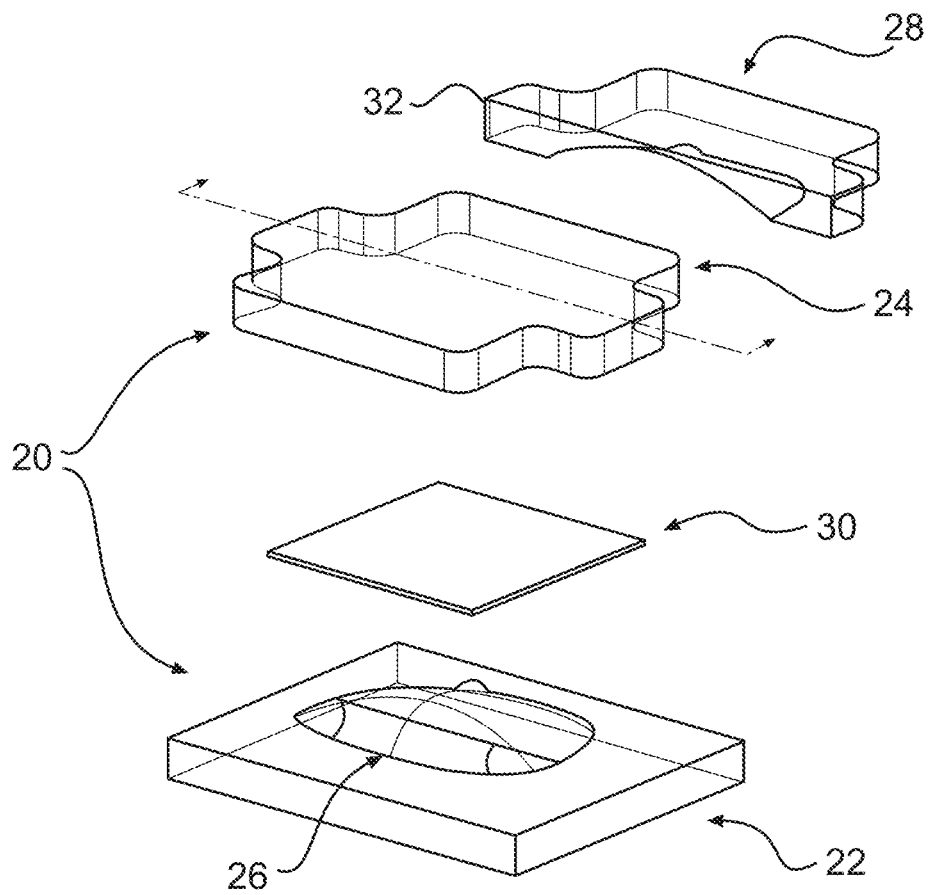
FIG. 8 is a diagram of a split metal form (20), including an inwardly curving half (22) and a mating outwardly curving half (28) with a semicircular groove (26) in the outlying border of the inwardly curving half (22), which is used to make implants that can assume a three-dimensional shape unaided. A line in the outwardly curving half (24) designated by the letters "AA" denotes the position of a cross-section view (32) of the outwardly curving half of the mold (24). A material (30) to be molded is sandwiched in the split metal mold.

The implants of FIGS. 6 and 7 can be manufactured using a metal form and standard manufacturing techniques. FIG. 8 is a diagram of a split metal form (20), including an inwardly curving half (22) and a mating outwardly curving half (24) with a semicircular groove (26) in the outlying border of the inwardly curving half (22), which is used to make implants that can assume a three-dimensional shape unaided. A line in the outwardly curving half designated by the letters "AA" denotes the position of a cross-section view (32) of the outwardly curving half of the mold (24). A material (30) to be molded is sandwiched in the split metal mold.

When the shape of the three-dimensional implant is substantially a hemi-ellipsoid, the dimensions of the implant may be defined by the tri-axial dimensions "a", "b" and "c" shown in FIGS. 9A and 9B. In a preferred embodiment, the ranges of these dimensions are preferably "a" from 2 to 10 cm, "b" from 3 to 10 cm, and "c" from 2.5 to 12 cm.

Shaped Implants

One embodiment of a two-dimensional implant is shown in FIG. 10. The upper region (40) of the implant has a larger footprint than the lower region (or tab) (46) of the implant, and is designed to support the breast parenchyma by spreading the load to key anchoring points. The implant features deep in cuts (48) that allow the lower region (or tab) (42) to fold at the IMF (i.e. at the dashed line in FIG. 10) and give shape to the IMF without bunching of the implant. The implant shown in FIG. 10 also incorporates rounded corners (e.g. (46)) to eliminate stress concentrations in the implant. In a preferred embodiment, the width (W) of the implant shown in FIG. 10 is between 18 cm and 36 cm, and the height (H) of the implant is between 6 cm and 14 cm.

Figure 11:
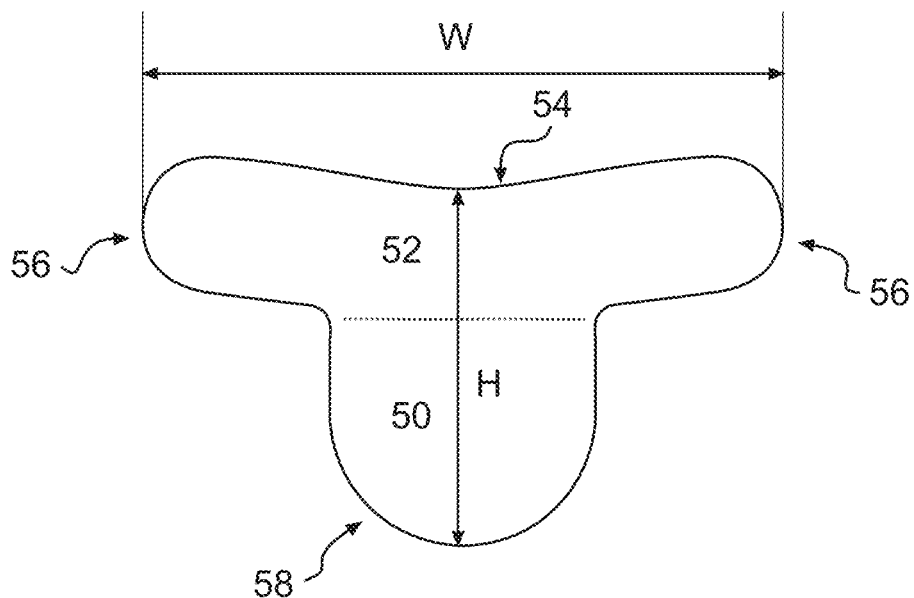
FIG. 11 is a diagram of a two-dimensional implant for breast reconstruction designed to support the breast mound that features a curved upper line (54) to improve breast mound conformity, a short right to left span to anchor the scaffold to the breast mound, and an oblong lower tab (50) with rounded corners to support the vertical pillar or fold under the IMF to provide shape and support to the breast.

Another embodiment of a two-dimensional implant is shown in FIG. 11. The upper region (52) of the implant also has a larger footprint than the lower region (or tab) (50) of the implant, and is also designed to support the breast parenchyma by spreading the load to key anchoring points. Instead of incorporating deep in cuts, the implant has a curved upper line (54) to allow the implant to conform and support the breast parenchyma without the implant bunching. The implant shown in FIG. 11 also incorporates rounded corners (56) and (58) to eliminate stresses in the implant. An oblong-shaped tab (50) allows the implant to fold at the IMF (i.e. at the dashed line in FIG. 11) and give shape to the IMF and support to the vertical pillar. In contrast to the implant shown in FIG. 10, the implant shown in FIG. 11 has a shorter width or span from left to right to anchor the implant on the breast mound. In a preferred embodiment, the width (W) of the implant shown in FIG. 11 is between 10 cm and 26 cm, and the height (H) of the implant is between 6 cm and 14 cm.

Figure 12:
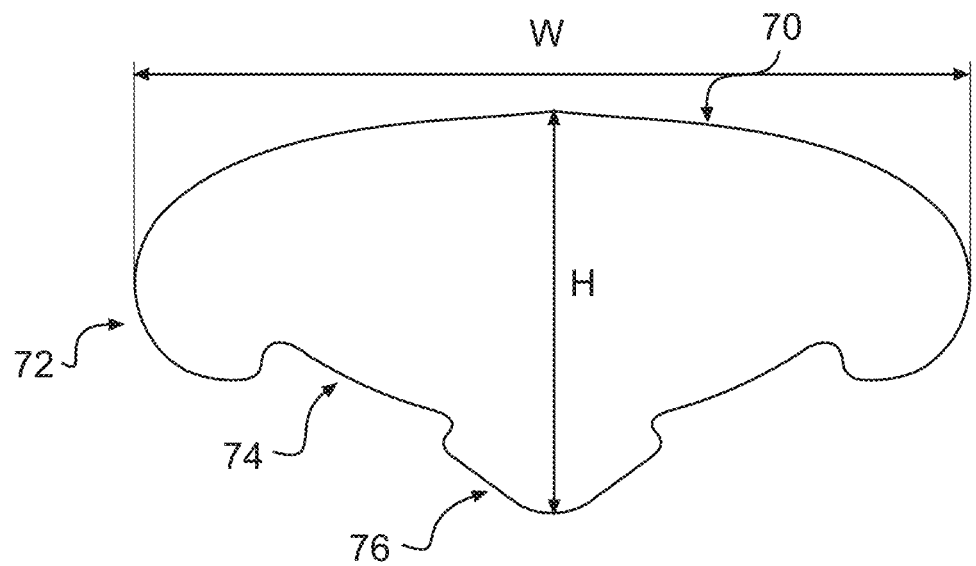
FIG. 12 is a diagram of an implant (70) for breast reconstruction designed to support the breast mound and distribute the load to specific anchoring positions. The two-dimensional implant features a wide right to left curved span to provide sling support defined by width "W", and insets (74) between anchor tabs (72 and 76) on the lower side to conform to the shape of the IMF without bunching of the implant.

A further embodiment of the two-dimensional implant is shown in FIG. 12. The implant has a curved upper line (70) (like the implant of FIG. 11) to allow the implant to conform to the breast without bunching, and a wide left to right span (like the implant of FIG. 10) to facilitate sling support of the breast parenchyma. The implant has a bottom tab (76) to anchor the implant and support the breast vertical pillar, and side tabs (e.g. (72)) separated from the bottom tab (76) with inset cuts to allow the implant to flex between tabs and form a curved IMF. The implant also features rounded corners to eliminate stress concentrations in the implant. In a preferred embodiment, the width (W) of the implant shown in FIG. 12 is between 18 cm and 34 cm, and the height (H) of the implant is between 8 cm and 16 cm.

The implants may also be crescent-shaped, rectangular or any other shape. As a crescent shape, the implant can transition from a first low profile or rolled configuration to a deployed shape. The implant can also be a canoe-like body including walls and a cavity formed therein. The cavity serves to accommodate the breast parenchyma when deployed. The implant can be configured as a sheet, a solid sheet, or as a discontinuous layer such as a mesh.

Figure 13:
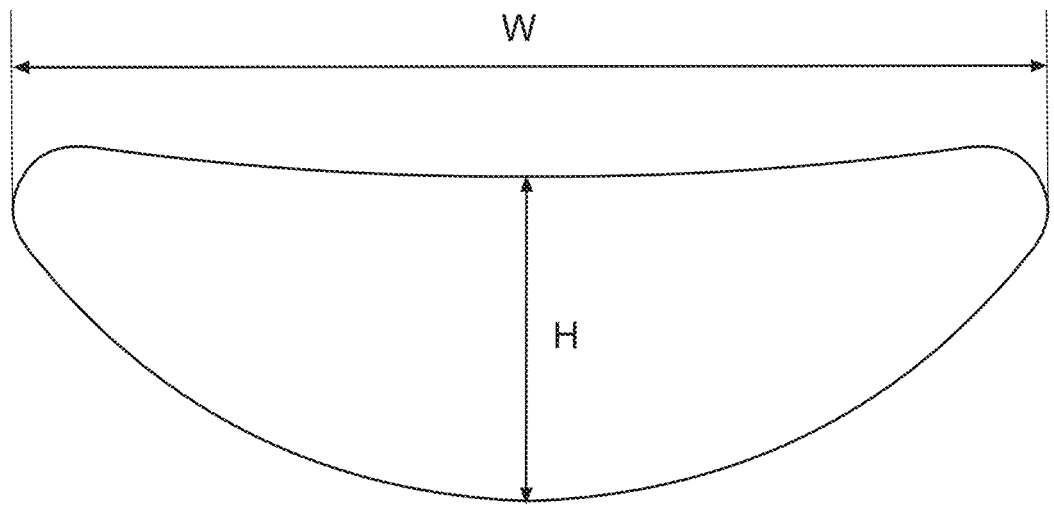
FIG. 13 shows an example of a two-dimensional crescent shaped implant with a width (W) and height (H).

An example of a crescent shaped implant is shown in FIG. 13. In a preferred embodiment, the crescent shaped implant has a width (W) of 10 to 25.5 cm, and a height (H) of 5 to 11 cm.

Figure 14:
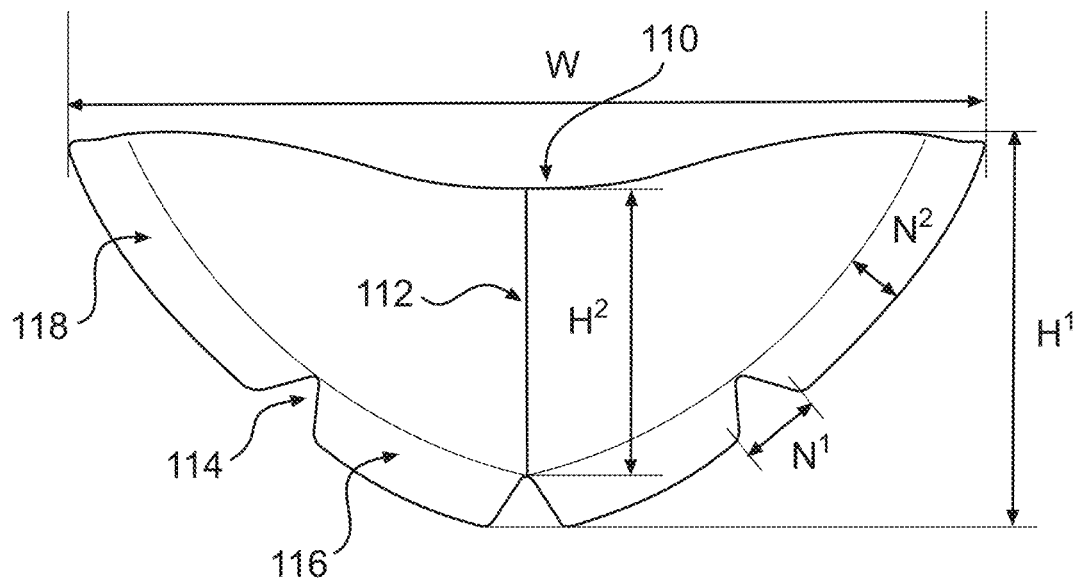
FIG. 14 shows a diagram of a two-dimensional implant for breast reconstruction of width (W) and height ($H^1$) with a recess (110) for the nipple areola complex, an option for mid-body support (112), and tabs (116) and (118) to allow the implant to stretch over the breast mound without bunching.

Another example of an implant with an upper curving profile is shown in FIG. 14. The two-dimensional implant incorporates a recess (110) for the nipple areola complex (NAC), an option for mid-body support (112), and notches (114) that create tabs (116) and (118) so that the implant can be stretched over the breast mound without bunching of the implant. The notched sections may also be stitched closed to create a three-dimensional cup shape. The mid-body support (112) may be stitched or embossed to create a hinge or crease. In an embodiment, the implant has a width (W) between 22 and 30 cm, a height ($H^1$) between 8.5 and 13 cm, a height ($H^2$) between 6.5 and 11 cm, a perimeter notch gap ($N^1$) between 0.5 and 4 cm, and a tab width ($N^2$) between 1 and 2 cm.

Three-Dimensional Shaped Implants

The disclosed implants include embodiments with a three-dimensional shape that is designed to provide additional predetermined contour to the host's breast tissue or an anatomical structure of the breast.

The implants can have unidirectional or bidirectional curvature. For example, the implant can be designed with two characteristic radii or curvatures: a medial-lateral (M-L) curvature in the M-L plane (See FIG. 18A) and an IMF-Nipple Areolar Complex NAC curvature in the IMF-NAC plane (FIGS. 18B, and 19E). Preferably, the IMF-NAC curvature is less pronounced than M-L curvature, i.e. wider radius. In a preferred embodiment, the curvature for the M-L curvature ranges from 7.5 to 10 cm, and for the IMF-NAC, it ranges from 11 to 20 cm. The ratio of the M-L curvature radius to that of the IMF-NAC ranges is preferably selected to range between 1.5 (=3/2) and 2 (=2/1). The most preferred ratio should be close to 1.61 (golden ratio) to which the ratio of consecutive numbers of the Fibonacci series converges.

Figure 15A:
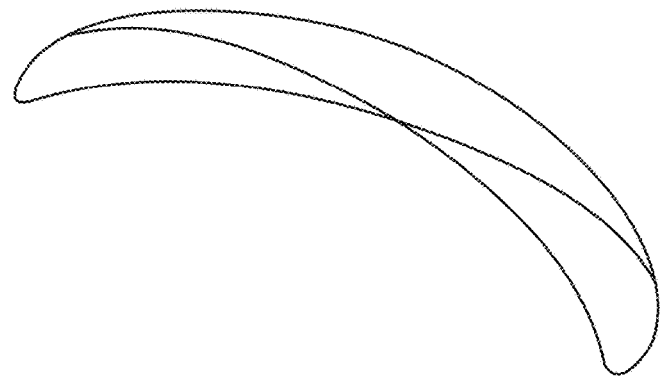
FIGS. 15A to 15C show diagrams of a three-dimensional implant for breast reconstruction.
Figure 15B:
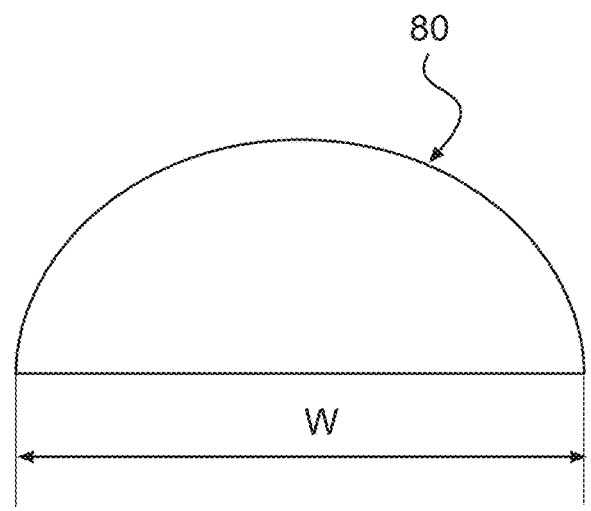
Figure 15C:
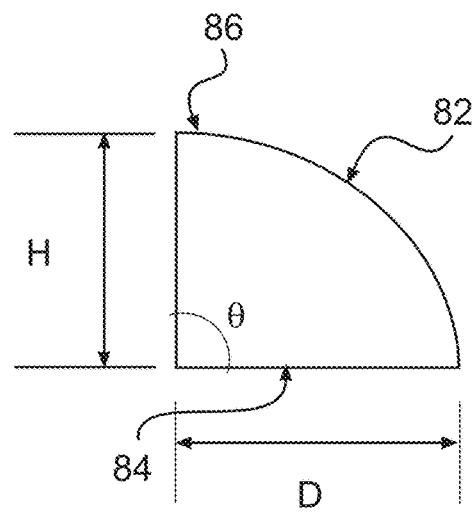

In an embodiment shown in FIG. 15, the implant has a three-dimensional partial dome shape (i.e. FIG. 15A) that allows the implant to capture, contour, and support the breast parenchyma, and distribute the load to key anchoring positions. The ability of the implant to capture and contour the breast parenchyma (i.e. the 3D implant mates and molds with the 3D breast mound) reduces surgery time. In common with the implants of FIGS. 10 and 11, the implant of FIG. 15A-C has rounded corners to eliminate stress concentrations in the implant and prevent bunching of the implant. In a preferred embodiment, the width (W) of the implant shown in FIG. 15B is between 12 and 24 cm, the height (H) measured from the floor or base (84) of the dome to the highest point (86) shown in FIG. 15C is between 2 and 10 cm, and the depth (D) of the dome shown in FIG. 15C is between 2.5 cm and 10 cm. The angle θ shown in FIG. 15C is preferably between 30 and 90°.

Figure 16A:
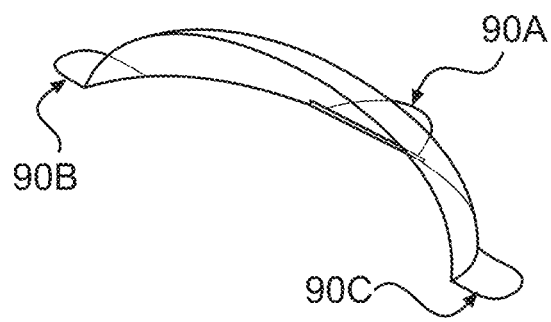
FIGS. 16A to 16C show a three-dimensional dome shaped implant.
Figure 16B:
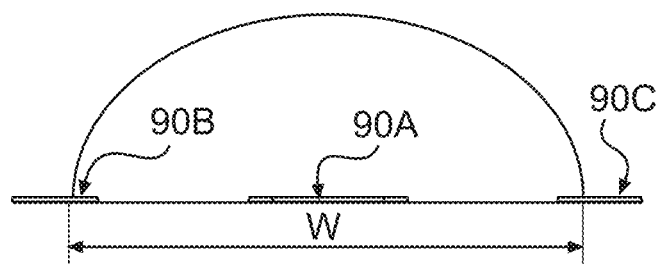
Figure 16C:
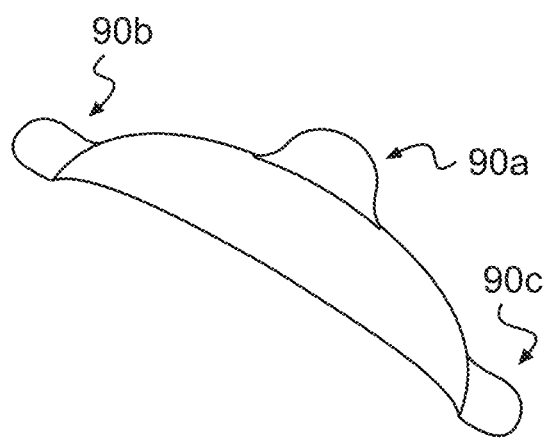

In a preferred embodiment, tabs may be added to the implant shown in FIG. 15A-C, for example, as shown in FIG. 16A-B. The number of tabs can be varied as desired. In the embodiment shown in FIG. 16A, the partial dome implant includes 3 tabs (90a, 90b and 90c), placed at the bottom of the implant (i.e. in the middle, 90a) and at the right and left sides (90b and 90c). Other embodiments show an implant with 8 tabs, which can include an orientation mark for placement (FIG. 19D). In a preferred embodiment, the width (W) of the implant shown in FIGS. 16A-D is between 12 and 24 cm, the height (H) measured from the floor or base of the dome (92) to the highest point (94) shown in FIG. 16D is between 2 and 10 cm, and the depth (D) of the dome shown in FIG. 16D is between 2.5 cm and 10 cm. The angle θ shown in FIG. 13D is preferably between 30° and 90°. Optionally, a support rib can be added to the inner surface of the partial dome implants shown in FIGS. 15 and 16 to provide added support and, if necessary, rigidity, or to add shape retention to the implant (for example, to allow minimally invasive delivery of the implant). An example of an implant with a three-dimensional partial dome shape that has been reinforced with ribbing is shown in FIG. 17. In this example, the partial dome shaped implant is reinforced with body ribbing along the perimeter (100) of the dome and in the mid-dome (102a and 102b) section.

Implants with Shape Memory

The three-dimensional shaped implants disclosed herein for use in breast surgery include implants that have shape memory. The shape memory allows the implant to be temporarily deformed, delivered by a minimally invasive method, and resume its preformed three-dimensional shape once placed across the lower pole of the breast. A particularly preferred three-dimensional shape comprises an outwardly curving exterior, and an inwardly curving interior. An even more preferred three-dimensional shape is self-reinforced and comprises an outwardly curving exterior, an inwardly curving interior, and an outlying border that is reinforced by a continuous or interrupted ring. The continuous or interrupted ring allows the implant to assume the desired three-dimensional shape unaided even if the three-dimensional shape has been temporarily deformed, for example, by rolling it into a small diameter cylinder or manipulating it into some other configuration. The three-dimensional shapes with shape memory may vary in shape and size. Shapes include, but are not limited to, hemispheres, hemi-ellipsoids, domes or similar kinds of shapes. The sizes of the three-dimensional shapes with shape memory vary, and range, for example, from a width of 8 to 20 cm at the base, more preferably 8 to 17 cm at the base, and a height or radius of curvature of 5 to 10 cm. In an embodiment, the width of the three-dimensional shape is designed to be 1 to 2 cm less than the width of the patient's breast after mastopexy. In another embodiment, the height of the three-dimensional shape is 0.5 to 2 cm less than the patient's nipple-IMF distance after mastopexy.

Non-limiting examples of materials comprising PBS and/or copolymers thereof that may be used to make these three-dimensional shaped implants with shape memory include meshes (e.g. monofilament and multifilament knitted meshes), strips, fabrics, woven constructs, non-woven constructs, knitted constructs, braided constructs, porous scaffolds, laminates, nanospuns, electrospuns, dry spuns, or melt-blown constructs, filaments, threads, strands, strings, fibers, yarns, wires, films, tapes, felts, multifilaments and monofilaments, for example using techniques as described elsewhere in the present application.

In one embodiment, the methods used to impart shape, contour or 3-dimensional properties to an implant for breast tissue, are used to create alternative shapes designed to conform to or provide shape to different anatomies such as the tissue of the pelvic floor or the abdominal cavity. While the sizes, dimensions and curvatures of these alternative tissues may differ, the overall approach is similar. Those skilled in the art will recognize that the methods described here to produce implants for breast surgery can be applied to other soft tissue anatomies that require the strength, support or contouring of an absorbable, shaped implant. These implants may be constructed of materials comprising PBS and copolymers thereof.

(d) Coatings to Stimulate Cell Attachment and in-Growth

The implants disclosed herein for use in breast surgery can be coated, derivatized, or modified with other agents in order to improve wettability, water contact angle, cell attachment, tissue in-growth, and tissue maturation.

In one embodiment, the implants can contain cellular adhesion factors, including cell adhesion polypeptides. As used herein, the term "cell adhesion polypeptides" refers to compounds having at least two amino acids per molecule that are capable of binding cells via cell surface molecules. The cell adhesion polypeptides include any of the proteins of the extracellular matrix which are known to play a role in cell adhesion, including fibronectin, vitronectin, laminin, elastin, fibrinogen, collagen types I, II, and V, as well as synthetic peptides with similar cell adhesion properties. The cell adhesion polypeptides also include peptides derived from any of the aforementioned proteins, including fragments or sequences containing the binding domains.

In another embodiment, the implants can incorporate wetting agents designed to improve the wettability of the surfaces of the implant structures to allow fluids to be easily adsorbed onto the implant surfaces, and to promote cell attachment and or modify the water contact angle of the implant surface. Examples of wetting agents include polymers of ethylene oxide and propylene oxide, such as polyethylene oxide, polypropylene oxide, or copolymers of these, such as PLURONICS®. Other suitable wetting agents include surfactants or emulsifyers.

(e) Therapeutic, Prophylactic and Diagnostic Agents

The implants disclosed herein for use in breast surgery may contain bioactive agents, for example as described elsewhere in this application (e.g. Section II, C).

In a preferred embodiment, an implant for use in breast surgery may contain one or more agents that improve cell attachment, tissue in-growth, and tissue maturation. The implants can contain active agents designed to stimulate cell in-growth, including growth factors, cellular differentiating factors, cellular recruiting factors, cell receptors, cell-binding factors, cell signaling molecules, such as cytokines, and molecules to promote cell migration, cell division, cell proliferation and extracellular matrix deposition. Such active agents include fibroblast growth factor (FGF), transforming growth factor (TGF), platelet derived growth factor (PDGF), epidermal growth factor (EGF), granulocyte-macrophage colony stimulation factor (GMCSF), vascular endothelial growth factor (VEGF), insulin-like growth factor (IGF), hepatocyte growth factor (HGF), interleukin-1-B (IL-1 B), interleukin-8 (IL-8), and nerve growth factor (NGF), and combinations thereof.

Other bioactive agents include antimicrobial agents, in particular antibiotics, disinfectants, oncological agents, anti-scarring agents, anti-inflammatory agents, anesthetics, small molecule drugs, anti-angiogenic factors and pro-angiogenic factors, immunomodulatory agents, and blood clotting agents.

The bioactive may be proteins such as collagen and antibodies, peptides, polysaccharides such as chitosan, alginate, polysaccharides such as hyaluronic acid and derivatives thereof, nucleic acid molecules, small molecular weight compounds such as steroids, inorganic materials such as hydroxyapatite, or complex mixtures such as platelet rich plasma. Suitable antimicrobial agents include: bacitracin, biguanide, trichlosan, gentamicin, minocycline, rifampin, vancomycin, cephalosporins, copper, zinc, silver, and gold. Nucleic acid molecules may include DNA, RNA, siRNA, miRNA, antisense or aptamers.

Diagnostic agents include contrast agents, radiopaque markers, or radioactive substances which may be incorporated into the implants.

The implants may also contain allograft material and xenograft materials.

In yet another preferred embodiment, the implants may incorporate systems for the controlled release of the therapeutic or prophylactic agents.

(ii) Methods of Manufacturing Implants for Use in Breast Surgery

A variety of methods can be used to manufacture the implants, and their scaffold structures. The breast implants may be prepared from fiber, mesh, non-woven, lattice, patch, film, laminate, thermoform, tube, foam, web, molded, pultruded, machined or 3D-printed forms. The breast implants may be prepared by one or more of the following methods: casting, solvent casting, solution spinning, solution bonding of fibers, melt processing, extrusion, melt extrusion, melt spinning, fiber spinning, orientation, relaxation, annealing, injection molding, compression molding, machining, machining of extrudate, lamination, foaming, dry spinning, knitting, weaving, crocheting, melt-blowing, film formation, film blowing, film casting, membrane forming, electrospinning, thermoforming, pultrusion, centrifugal spinning, molding, tube extrusion, spunbonding, spunlaiding, nonwoven fabrication, entangling of staple fibers, fiber knitting, weaving and crocheting, mesh fabrication, coating, dip coating, laser cutting, barbing, barbing of fibers, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, and printing using a binding solution and granules of powder.

Preferably, the methods used to construct the implants provide implants that can: (i) withstand a load of at least 5 N, (ii) support a pressure of at least 0.1 kPa, and (iii) hold a suture with a pullout strength exceeding 10 N.

The methods disclosed herein may use one or more split metal forms with a semi-circular groove, a support component material and a shape memory component material.

The shape memory component material, if present, can be selected from a filament, thread, strand, string, fiber, yarn, wire, film, tape, tube, fabric, felt, mesh, multifilament, or monofilament.

The support component material can in some embodiments be porous. Non-limiting examples of support component materials include a mesh, a set of strips, a fabric, a woven construct, a non-woven construct, a knitted construct, a braided construct, a porous scaffold, a porous film including laminated and perforated film, a nanospun, electrospun, or melt-blown construct. For example, scaffolds can include fibers, films or non-wovens. The scaffolds can be made using processes such as spinning, molding or 3D printing.

In one embodiment, the porous scaffolds are prepared using a process that incorporates particulate leaching (for example, as described elsewhere in this application). This process allows the size and porosity of the scaffold to be controlled by careful selection of the size of the leachable material and its distribution. The scaffolds can be prepared by dispersing particles of the leachable material in a solution of a biocompatible absorbable polymer, wherein the leachable material is not soluble in the polymer solvent. In a preferred embodiment, the leachable particle materials have a diameter of at least 25 µm, and more preferably greater than 50 µm. The leachable particles must be non-toxic, easily leached from the polymer, non-reactive with the polymer, and biocompatible (in case residues are left in the scaffold after leaching). In a preferred embodiment, the leachable particles are water soluble, and can be leached from the polymer solution with water. Examples of suitable particles include salts such as sodium chloride, sodium citrate, and sodium tartrate, proteins such as gelatin, and polysaccharides such as agarose, starch and other sugars. Examples of suitable solvents for the polymers include tetrahydrofuran, dioxane, acetone, chloroform, and methylene chloride. In a particularly preferred embodiment, an implant comprising a porous scaffold is formed from PBS or copolymer thereof by adding salt particles (100-180 µm diameter) to a solution of the polymer in dioxanone (10% wt/vol), allowing the solvent to evaporate, pressing the mixture using a hydraulic press with heated platens, and leaching out the salt particles after the polymer has crystallized.

In another embodiment, a process that includes phase separation is used to form the porous scaffold. The size of the pores can be selected by varying parameters such as the solvent, and the concentration of the polymer in the solvent. Suitable solvents include tetrahydrofuran, dioxane, acetone, chloroform, and methylene chloride. In a particularly preferred embodiment, a cast solution of PBS dissolved in dioxane (3% wt/vol) is frozen at −26° C. to precipitate the polymer, and the solvent sublimated in a lyophilizer to form a phase separated porous PBS scaffold.

In a further embodiment, the scaffolds can be prepared from films comprising PBS or a copolymer thereof. The films may be made, for example, by either solvent casting or melt extrusion. Method of making films of PBS or copolymers thereof are discussed elsewhere in this application. The films can be un-oriented, or more preferably oriented in one or more directions (e.g. discussed elsewhere in this application) so that they have sufficient mechanical properties to support the breast, and provide prolonged strength retention. In order to allow tissue in-growth, the films are preferably rendered porous or attached to other porous components. Suitable methods for making the films porous include punching or laser drilling holes in the films, or cutting slits or holes in the films. In a particularly preferred embodiment, porous scaffolds are prepared by melt extrusion of PBS films, and holes are cut, punched or drilled in the films.

In still another embodiment, the scaffold can comprise thermally bonded fibers comprising PBS or copolymer thereof. The thermally bonded fibers can be produced by melt extrusion using a multi-holed die. This process allows the diameter of the fibers, the porosity of the scaffold, and the thickness of the scaffold to be controlled by selection of parameters such as the diameter of the die holes, the distance between the die and collector plate, and the collection time. In a preferred embodiment, the thermally bonded fiber scaffold has one or more of the following properties (i) a thickness of 0.1-5 mm, (ii) an areal density or basis weight of 5 to 800 g/m$^2$, (iii) a suture pullout strength of greater than 10 N, and (iv) is able to withstand a pressure of at least 0.1 kPa.

The scaffolds can also be formed from structures comprising non-wovens of PBS or copolymers thereof that have been prepared by entangling fibers using mechanical methods. Method of making non-wovens of PBS or copolymers thereof are discussed elsewhere in this application. The properties of the nonwovens can be tailored by selection of parameters such as fiber diameter, fiber orientation, and length of the fibers (for staple nonwovens). In a preferred embodiment, the scaffolds comprising non-wovens have one or more of the following properties (i) a thickness of 0.1-5 mm, (ii) an areal density of 5 to 800 g/m$^2$, (iii) a suture pullout strength of greater than 10 N, and (iv) is able to withstand a pressure of at least 0.1 kPa.

The scaffolds comprising PBS, or copolymer thereof, may also be formed directly from solution by spinning processes. In these processes, solutions are pumped or forced through dies, and fibers are collected after removal of the polymer solvent. The fiber diameters and porosities of the scaffolds can be controlled by appropriate selection of parameters such as the polymer molecular weight, solvent, polymer concentration, temperature, pump pressure or force, die configuration, and the diameter of the holes in the die. In the case of wet spinning, the choice of coagulation non-solvent may be used to control fiber diameter and scaffold porosity and morphology. In a preferred embodiment, the solution spun scaffolds have (i) a thickness of between about 0.5 and 5 mm, (ii) a weight of between 5 and 800 g/m$^2$, (iii) a suture pullout strength of greater than 10 N, and (iv) are able to withstand a pressure of at least 0.1 kPa.

In yet another embodiment, the scaffolds can be prepared from monofilament fibers, multifilament fibers, or a combination of these fibers, formed from PBS or copolymers thereof. Method of making monofilament fibers, multifilament fibers, or a combination thereof, from PBS or copolymers thereof, are discussed elsewhere in this application. For example, melt extrusion and solution spinning processes can be used to form these fibers. In a preferred embodiment, the scaffolds are woven or knitted from the pre-formed fibers. The scaffolds may be produced by weaving, or either warp or weft knitting processes, however, a warp knit is preferred in order to minimize the stretching of the scaffold structure. In a preferred embodiment, the scaffold woven or knitted from mono or multifilament fibers has one or more of the following properties: (i) stretches less than 30% of the scaffold's original length in any direction, (ii) has a suture pullout strength of at least 10 N, and (iii) can withstand a pressure of at least 0.1 kPa. In a particularly preferred embodiment, the scaffold is made from PBS monofilament fibers, PBS multifilament fibers, or a combination of these fibers, and has an areal density of 5 to 800 g/m². The implant can also be prepared by combining a woven or knitted construct formed from PBS or a copolymer thereof, with a film formed from PBS or a copolymer thereof.

In still another embodiment, the scaffolds comprising PBS, or a copolymer thereof, may be prepared by methods that include 3D printing (also known as additive manufacturing). This method is particularly useful in the manufacture of specific shapes since the desired shape can be made directly without the need for further cutting or trimming. Methods of 3D printing of PBS or copolymers thereof, are discussed elsewhere in this application.

In still a further embodiment, the scaffolds comprising PBS, or a copolymer thereof, may be prepared by molding. In these processes, polymer may be directly molded into a scaffold, or the polymer may be first converted into another form (such as a mesh, film, non-woven, laminate, electrospun fabric, foam, thermoform or combinations thereof), and then the form molded, or two methods may be used to form a scaffold that has varying stiffness. In a preferred embodiment, three-dimensional shapes with shape memory are prepared by molding a monofilament mesh into a shape designed to confer shape to the host's breast tissue or form an anatomical shape of the breast. Such shapes include those with an outwardly curving exterior and inwardly curving interior, and optionally contain an outlying border that is reinforced by a continuous or interrupted ring that allows the three-dimensional scaffold to be temporarily deformed and resume a three-dimensional shape. (Such shapes have shape memory.)

The implants of FIGS. 6 and 7 can be optionally manufactured using a metal form and standard manufacturing techniques. FIG. 8 is a diagram of a split metal form (20), including an inwardly curving half (22) and a mating outwardly curving half (24) with a semicircular groove (26) in the outlying border of the inwardly curving half (22), which is used to make implants that can assume a three-dimensional shape unaided. A line in the outwardly curving half (24) designated by the letters "AA" denotes the position of a cross-section view (32) of the outwardly curving half of the mold (20). A material (30) to be molded is sandwiched in the split metal mold.

The implants of FIG. 19D can also be manufactured using a metal form and standard manufacturing techniques. FIG. 19A is a diagram of a split metal form (300) that incorporates a semicircular groove in one half of the mold that can be used to attach ribbing (320) to a scaffold material (310). FIG. 19B is a diagram of a second split metal form (350) that can be used to make implants that can assume a three-dimensional shape unaided from the molded forms (360) of ribbing attached to scaffold material. In a preferred embodiment, the implants shown in FIG. 19D have rounded edges (206) to reduce stress in the implants, reduce palpability, reduce bunching of the implant and to minimize patient discomfort.

Shapes with outwardly curving exteriors and inwardly curving interiors may, for example, be prepared using a split metal form consisting of an inwardly curving half and a mating outwardly curving half as shown in FIG. 8. One skilled in the art will understand that the size and shape of the split metal form can be varied in order to provide different three-dimensional shapes that can confer shape to a patient's breast, or other soft tissue structure present in the pelvic floor or the abdominal cavity. In a preferred embodiment, the inwardly curving half of the metal form contains a semicircular groove in the outlying border that will accommodate a continuous or interrupted ring of filament, thread, strand, string, fiber, yarn, wire, film, tape, tube, fabric, felt, mesh, multifilament or monofilament. In a particularly preferred embodiment the groove will accommodate a monofilament, preferably a monofilament extrudate. The semicircular groove is cut into the outlying border of the inwardly curving half such that the ring of material, for example, a monofilament, will protrude from the groove. In an alternative embodiment, the groove may be cut into the outwardly curving half instead of the inwardly curving half. In still other embodiments, the groove may be cut into both halves of the split metal form. A three-dimensional shape with an inwardly curving interior, outwardly curving exterior, and reinforced outlying border is prepared by placing, for example, a filamentous or other extrudate in the semicircular groove of the inwardly curving half so that it forms a ring, draping a polymeric material such as a monofilament mesh over the inwardly curving half of the metal form, placing the mating outwardly curving half of the metal form over the polymeric material, and clamping the two halves of the split metal form together to form a block. The block is then heated, cooled in such a way as to heat set the material inside the mold, then the mold is disassembled, and the three-dimensional shape removed and trimmed as necessary to form a smooth outlying border. In an embodiment, the block is heated uniformly, preferably by heating with hot water, and cooled uniformly, preferably by cooling with ambient temperature water.

In a preferred embodiment, partial dome shape implants with natural proportions and a better fit to natural breast curves may be prepared by controlling the curvatures (feature 26) of the mold shown in FIG. 8. The curvatures have two radii: a transversal (in transverse plane) curvature radius which may range from 7 to 10 cm and a sagittal (in sagittal plane) curvature radius which may range from 11 to 20 cm. Furthermore, the values of the transversal curvature radius, henceforth referred to as TCR, and the sagittal curvature radius, henceforth referred to as SCR, can preferably be selected such that the ratio TRC/SCR is specifically between 1.5 and 2, and more preferably close to the golden ratio value of 1.61. This specific relationship between TRC and SRC results in a partial dome shape with natural proportions and a better fit to natural breast curves.

In a preferred embodiment, the three-dimensional shape is made from a PBS monofilament mesh, and a PBS monofilament extrudate. The temperature of the hot water is set such that the ring is either pressed or melted into the outlying border to reinforce the outlying border. A ring of polymer, derived, for example, from a monofilament extrudate of a polymer composition comprising PBS or a copolymer thereof, or poly-4-hydroxybutyrate or copolymer thereof, may be used to reinforce the outlying border of the scaffold, so that the scaffold can be temporarily deformed for implantation, and will then resume its three-dimensional shape when released in a suitably dissected tissue plane. However, if a ring/ribbing is not used to reinforce the edge of the material (such as a monofilament mesh), the material may not be able to resume a three-dimensional shape.

In another embodiment, the implants comprise retainers, such as barbs or tacks, so that the implant can be anchored to the chest wall without the use of additional suture. For example, the three-dimensional implants may contain retainers in their outlying borders to anchor the implants to the tissue.

The implants can be cut or trimmed with scissors, blades, other sharp cutting instruments, or thermal knives in order to provide the desired shapes. For example, a custom die can be used to cut the mesh along the fused ribbing. Examples of custom dies that can be used to create up to 17 tabs are shown in FIGS. 19A (3 tabs), 19B (8 tabs) and 19C (17 tabs). The implants can also be cut into the desired shapes using laser-cutting techniques. This can be particularly advantageous in shaping fiber-based implants because the technique is versatile, and importantly can provide shaped products with sealed edges that do not shed cut loops or debris produced in the cutting process.

The processes described herein to produce the scaffolds can also be used in combination. For example, a woven construct could be combined with a non-woven construct to make a scaffold. In a preferred embodiment, a scaffold can be reinforced with a monofilament or multifilament fiber. In a particularly preferred embodiment, the implants can be reinforced at anchor points to provide, for example, increased suture pullout strength.

(iii) Methods of Implanting

The implants are most suited to use in mastopexy or mastopexy augmentation procedures, wherein the skin of the lower pole is dissected away from the breast and eventually tightened to provide a more appealing breast contour. However, the implants may also be used in other procedures such as revision procedures following the removal of a breast implant, and breast reconstruction procedures following mastectomy, particularly where it is desirable to retain the position of a silicone or saline breast implant or tissue expander. For example, the implants may be used on the lateral side of a patient's breast to properly retain a breast implant, or to cover a breast implant. The implants may also be used in conjunction with expanders in breast reconstruction procedures to give additional support for the skin surrounding an expander, and to create a pocket for a breast implant. They may also be implanted to cover any defects in the major pectoralis muscle, after insertion of breast implants, in patients undergoing breast reconstruction where the muscle has been compromised as a result of breast cancer and mastectomy.

Any current mastopexy technique may be used to achieve a breast lift with the implants using any appropriate skin resection pattern, provided it preserves the functional integrity of the mammary structures. The implants can also be implanted using minimally invasive techniques such as those disclosed by U.S. Patent Application No. 20120283826 to Moses et al.

The chosen method will depend upon the extent of breast ptosis and a number of other factors. The four main techniques for mastopexy are the: crescent mastopexy, donut (or Benelli) mastopexy, lollipop (or vertical) mastopexy, and anchor (or Weiss or Wise) mastopexy. In the crescent mastopexy, a semi-circular incision is made on the upper side of the areolar, and a crescent shaped piece of breast tissue removed. This procedure is typically used for patients with only mild ptosis where a good lift can be achieved by removing excess skin on the upper breast, and suturing the skin back in order to elevate the areolar nipple complex. In one embodiment, the implants can be implanted after further dissection and/or resection to provide additional support for the upper breast tissue.

The implants can also be implanted during a donut or Benelli mastopexy. In this procedure, a donut shaped piece of breast skin is removed from around the areolar with an inner incision line following the perimeter of the areolar, and an outer incision line circling the areolar further out. In one embodiment, the implant(s) can be inserted after further dissection to support the lift, and a purse string suture used to approximate the breast skin back to the areolar.

In both the lollipop and anchor mastopexy procedures, incisions are made around the areolar complex. In the lollipop procedure, a vertical incision is made in the lower breast from the areolar to the inframammary fold (IMF), and in the anchor mastopexy procedure an incision is made across the inframammary fold in addition to the vertical incision used in the lollipop procedure. The lollipop procedure is generally used for patients with moderate ptosis, whereas the anchor procedure is normally reserved for patients with more severe ptosis. These two procedures can be performed with or without breast implant augmentation. In both procedures, breast tissue may be resected, and the resected edges sutured together to create a lift. Prior to suturing the resected tissue, the implants can be implanted to support the breast, and to decrease the forces on the resected skin and suture line after closure. In a particularly preferred procedure, the implants are positioned to support the breast parenchyma or silicone or saline breast implant, and to minimize the weight of the breast on the skin and suture line. In an even more preferred procedure, the suture line is closed with minimal or no tension on the wound to minimize scar formation.

In a preferred embodiment, when sutured in place, the implants provide support, elevation and shape to the breast by anchoring of the implants at one or more locations to the tissue, muscle, fascia or the bones of the chest or torso. In a particularly preferred embodiment, the implants are sutured to the pectoralis fascia or the clavicle. The implants may also be sutured to the chest wall or fascia, and in a particularly preferred embodiment, the implants may be sutured to the chest wall so that they provide slings for support of the lifted breast or breast implant.

The teardrop implant of FIG. 6 is designed to be implanted with the wider section positioned medially for primary load support, and the tapered section positioned on the side of the chest near the arm for lateral support and to direct the breast to the cleavage area. Thus in a preferred embodiment, the implant is asymmetric, and has a precise geometric form. The implant may be anchored first in the medial position using the two suture tabs located in the wider section of the implant, and then the tapered end of the implant subsequently anchored, preferably under tension. Tabs are shown in FIG. 6 having a length to width ratio ranging from about 1:1 to 1:2. However, the shape and size of the tabs may vary widely and are only intended to be limited as recited in the appended claims.

In a preferred embodiment, the three-dimensional implants with shape memory are implanted using minimally invasive techniques into a suitably dissected tissue plane to confer shape to the breast. These implants may, for example, be rolled up into a small cylindrical shape, placed inside a tubular inserter, and implanted through a small incision, such as a standard size incision at the inframammary fold that is usually used for breast augmentation. Once released in vivo, these implants will resume their original three-dimensional shapes, and may be moved into position, for example, to confer shape to the host's breast tissue or an anatomical shape of the breast. In one preferred embodiment, the implant is delivered by employing an IMF incision used as the entry point for dissection, along with a periareolar incision, in a mastopexy procedure. Once skin removal and dissection is complete, a three-dimensional shape memory implant can be deployed in vivo and allowed to resume its preformed three-dimensional shape. The relative rigidity of the self-reinforcing three-dimensional implant allows the implant to remain in place. One skilled in the art will appreciate that these three-dimensional implants can also be delivered by other minimally invasive methods as well as using more traditional open surgery techniques.

Accordingly, in the context of implants for use in breast surgery, the present invention also provides subject matter defined by the following numbered paragraphs:

Paragraph 1. An absorbable implant for plastic surgery procedures comprising a porous biodegradable polymeric scaffold formed into an anatomical shape, two-dimensional shape, three-dimensional shape, and/or asymmetric shapes, minimizing any buckling or bunching of the implant upon placement,
wherein the porous biodegradable scaffold is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The implant of Paragraph 1, wherein the suture pullout strength of the absorbable implant is greater than 10 N, and more preferably greater than 20 N.

Paragraph 3. The implant of Paragraph 1 or 2, wherein the scaffold can support a pressure of at least 0.1 kPa.

Paragraph 4. The implant of any of Paragraphs 1-3, wherein the absorbable implant can withstand a load of at least 5 N, more preferably of at least 15 N, and even more preferably of at least 60 N.

Paragraph 5. The implant of any of Paragraphs 1-4, wherein the scaffold has an average pore diameter of at least 50 µm.

Paragraph 6. The implant of any of Paragraphs 1-5, wherein the implants are compliant and the bending stiffness of the scaffold is less than 100 gram cm (100 Taber Stiffness Units), more preferably less than 10 Taber Stiffness Units, and even more preferably less than 1 Taber Stiffness Unit.

Paragraph 7. The implant of any of Paragraphs 1-6, wherein the scaffold cannot stretch more than 30% of its original length.

Paragraph 8. The implant of any of Paragraphs 1-7 wherein the scaffold has two or more of the properties selected from the group consisting of the bending stiffness of the scaffold is less than 100 gram cm, the scaffold cannot stretch more than 30% of its original length, and the scaffold can withstand a load of at least 5 N, wherein the suture pullout strength of the absorbable implant is greater than 10 N, and more preferably greater than 20 N.

Paragraph 9. The implant of any of Paragraphs 1-8 which, when implanted is infiltrated with the host's cells and undergoes a controlled resorption such that the implant is replaced with regenerated host tissue.

Paragraph 10. The implant of any of Paragraphs 1-9, wherein the regenerated host tissue can support a load of at least 5 N after 78 weeks in vivo.

Paragraph 11. The implant of any of Paragraphs 1-9, wherein the implant after implantation and infiltration of host tissue can withstand a pressure of at least 0.1 kPa.

Paragraph 12. The implant of any of Paragraphs 1-9, wherein the implant retains at least 20% of its initial burst strength 12 weeks after implantation.

Paragraph 13. The implant of any of Paragraphs 1-12, wherein the implant further comprises one or more bioactive agents.

Paragraph 14. The implant of any of Paragraphs 1-3, wherein the implant further comprises one or more coatings, additives or therapeutic, prophylactic or diagnostic agents.

Paragraph 15. The implant of any of Paragraphs 1-14, wherein the implant can be stretched up to 30% in one or more directions to place tension on the host tissue.

Paragraph 16. The implant any of Paragraphs 1-15, wherein the implant is designed to contour to the host's tissue without forming wrinkles or bunching.

Paragraph 17. The implant of any of Paragraphs 1-16, wherein the implant does not interfere with radiographic imaging.

Paragraph 18. The implant of any of Paragraphs 1-17, wherein the implant has been sterilized by ethylene oxide, steam, hydrogen peroxide, nitrogen dioxide, chlorine dioxide, peracetic acid, electron beam, or gamma-irradiation.

Paragraph 19. The implant of any of Paragraphs 1-18, wherein the implant is deployed into an anatomical shape after implantation.

Paragraph 20. The implant of Paragraph 19, wherein the implant comprises seam lines or is embossed to help the implant conform to an anatomical shape.

Paragraph 21. The implant of any of Paragraphs 1-20, wherein the implant is used in facial plastic surgery procedures.

Paragraph 22. The implant of any of Paragraphs 1-20, wherein the implant is used in breast surgery procedures, including mastopexy and breast reconstruction.

Paragraph 23. The implant of Paragraph 22, wherein the implant is a two-dimensional shape designed to contour to the breast mound or breast parenchyma without buckling, bunching, or folding over itself.

Paragraph 24. The implant of Paragraph 22, wherein the scaffold is fixed to breast tissue so that the scaffold forms a supporting structure for the breast mound or breast parenchyma.

Paragraph 25. The implant of Paragraph 22, wherein the scaffold is fixed to breast tissue and secured to the fascia.

Paragraph 26. The implant of Paragraph 22, wherein the implant is asymmetric.

Paragraph 27. The implant of Paragraph 26, wherein the body of the implant has a teardrop shape.

Paragraph 28. The implant of Paragraph 27, wherein the teardrop has a width to height ratio ranging from 10:1 to 1.5 to 1,
wherein the width of the teardrop is the longest distance measured between any two points, and
wherein the height of the teardrop is the longest distance measured perpendicular to the width.

Paragraph 29. The implant of Paragraph 27, wherein the teardrop shape comprises additional tabs around its edges for fixation of the implant to the body.

Paragraph 30. The implant of Paragraph 22, wherein the implant is used to prevent medial, lateral and inferior displacement of a breast implant.

Paragraph 31. The implant of Paragraph 22, wherein the implant is suitable for use in conjunction with a tissue expander.

Paragraph 32. The implant of Paragraph 31, wherein the implant is used to reinforce a pocket for a breast implant.

Paragraph 33. The implant of Paragraph 22, wherein the implant is used to cover any tissue defects in the breast or surrounding muscle.

Paragraph 34. The implant of Paragraph 22, wherein the implant redistributes the volume of the breast.

Paragraph 35. The implant of Paragraph 23, wherein the implant has a shape selected from one or more of the following: (i) substantially the shape of FIG. 9 wherein the width (W) of the implant is between 18 cm and 36 cm, and the height (H) of the implant is between 6 cm and 14 cm; (ii) substantially the shape of FIG. 10 wherein the width (W) of the implant is between 10 cm and 26 cm, and the height (H) of the implant is between 6 cm and 14 cm; (iii) substantially the shape of FIG. 11 wherein the width (W) of the implant is between 18 cm and 34 cm, and the height (H) of the implant is between 8 cm and 16 cm; (iv) substantially the shape of FIG. 15 wherein the width (W) of the implant is between 10 to 25.5 cm, and the height (H) of the implant is between 5 to 11 cm; (v) substantially the shape of FIG. 16 wherein the implant has a width (W) between 22 and 30 cm, a height ($H^1$) between 8.5 and 13 cm, a height ($H^2$) between 6.5 and 11 cm, a perimeter notch gap ($N^1$) between 0.5 and 4 cm, and a tab width ($N^2$) between 1 and 2 cm; and (vi) substantially the shape of FIG. 17 wherein the implant has a width (W) between 22 and 30 cm, a height (H) between 7.5 and 11 cm, a perimeter notch gap ($N^1$) between 0.5 and 4 cm, and a tab width ($N^2$) between 1 and 2 cm.

Paragraph 36. The implant of Paragraph 23, wherein the implant can fold at the IMF upon placement with minimal buckling or bunching of the implant.

Paragraph 37. The implant of Paragraph 36 wherein the implant folds at the IMF upon placement to give shape to the IMF.

Paragraph 38. The implant of any of Paragraphs 1-37 wherein the scaffold has a three-dimensional shape designed to contour to the breast mound or breast parenchyma without buckling, bunching, or folding over itself.

Paragraph 39. The implant of Paragraph 38 wherein the scaffold has a partial dome shape.

Paragraph 40. The implant of Paragraph 39 wherein the scaffold has substantially the shape shown in FIG. 12 wherein the width (W) of the implant is between 12 and 24 cm, the height (H) measured from the floor or base of the dome to the highest point is between 2 and 10 cm, the depth (D) of the dome is between 2.5 cm and 10 cm, and the angle θ is preferably between 30° and 90°.

Paragraph 41. The implant of Paragraph 38 wherein the implant further comprises one or more of the following: tabs and support ribs.

Paragraph 42. The implant of any of Paragraphs 1-41 wherein the scaffold has a three-dimensional shape and shape memory, and is designed to confer shape to the breast.

Paragraph 43. The implant of Paragraph 42 wherein the implant can be temporarily deformed to allow for implantation through an incision that is shorter than the width of the implant, and resume its original conformation after implantation.

Paragraph 44. The implant of Paragraph 42 or 43 wherein the scaffold comprises an outwardly curving exterior, and an inwardly curving interior.

Paragraph 45. The implant of Paragraph 44 wherein the outlying border of the scaffold is reinforced.

Paragraph 46. The implant of Paragraph 45 wherein the outlying border is reinforced by a continuous or interrupted ring of: filament, thread, strand, string, fiber, yarn, wire, film, tape, tube, fabric, felt, mesh, multifilament, or monofilament, optionally formed from the PBS or copolymer thereof.

Paragraph 47. The implant of any of Paragraphs 1-46 wherein the scaffold is formed from a mesh, non-woven, woven, film, laminate, electrospun fabric, foam, thermoform, or combinations thereof.

Paragraph 48. The implant of Paragraph 47 wherein the scaffold comprises a monofilament mesh.

Paragraph 49. The implant of Paragraph 46 wherein the scaffold comprises a monofilament mesh with an outlying border reinforced by a continuous ring of monofilament.

Paragraph 50. The implant of Paragraph 42 wherein the three-dimensional shape has a shape selected from one from the group consisting of a hemisphere, a hemi-ellipsoid, a dome, a partial dome, a shape with a width of 8 to 20 cm at the base, a shape with a height or radius of curvature of 5 to 14 cm, a shape with a width that is 1 to 2 cm less than the width of the patient's breast when measured prior to surgery, and a shape with a height that is 0.5 to 5 cm less than the patient's nipple-IMF distance after mastopexy.

Paragraph 51. The implant of any one of Paragraphs 1 to 50, wherein the scaffold comprises PBS.

Paragraph 52. The implant of any one of Paragraphs 1 to 51, wherein the implant has been manufactured by one or more processes selected from the group consisting of particular leaching, phase separation, film formation, thermal forming, thermal or solution bonding of fibers, entanglement of staple fibers, solution spinning, weaving, knitting, three-dimensional printing, and cutting using scissors, blades, thermal knives, or lasers.

Paragraph 53. A method of manufacturing the implant of any one of Paragraph 1-52, using one or more processes selected from the group consisting of particular leaching, phase separation, film formation, thermal or solution bonding of fibers, entanglement of staple fibers, solution spinning, melt extrusion, weaving, knitting, three-dimensional printing, and cutting using scissors, blades, thermal knives, or lasers.

Paragraph 54. A method of forming the scaffold of Paragraph 42, the method comprising the steps of: providing a split metal form consisting of an inwardly curving half and a mating outwardly curving half wherein there is a semicircular groove in the outlying border of the inwardly curving half; placing a filament, thread, strand, string, fiber, yarn, wire, film, tape, tube, fabric, felt, mesh, multifilament, or monofilament in the semicircular groove so that it forms a ring around the outlying border of the inwardly curving half; draping a polymeric material over the inwardly curving half of the metal form; placing the mating outwardly curving half of the metal form over the polymeric material, and clamping the two halves of the split metal form together to form a block; heating the block; cooling the block; disassembling and removing the polymeric shape from the block, and trimming the outlying border of the compressed extrudate.

Paragraph 55. The method of Paragraph 54 wherein the semicircular groove is in the outlying border of the outwardly curving half of the metal form instead of the inwardly curving half, and a filament, thread, strand, string, fiber, yarn, wire, film, tape, tube, fabric, felt, mesh, multifilament, or monofilament is placed in the groove on the outwardly curving half of the metal form.

Paragraph 56. The method of any one of Paragraphs 54 and 55 wherein the scaffold is a monofilament mesh.

Paragraph 57. The method of any one of Paragraphs 54 to 56, wherein the monofilament mesh comprises PBS or copolymer thereof, and a monofilament extrudate of PBS or copolymer is used to reinforce the outlying border.

Paragraph 58. The method of Paragraphs 57 wherein the block is heated using hot water at 56° C. for 5 minutes, and cooled by placing in a water bath at ambient temperature.

Paragraph 59. A method of implanting the implant of Paragraph 22, wherein the implant is anchored at one or more locations to the pectoralis fascia to lift the breast.

Paragraph 60. A method of implanting the implant of Paragraph 22, wherein the implant is attached to a flap below the areolar-nipple complex, rotated to enhance the anterior projection of the breast, and fixed to the anteropectoral fascia.

Paragraph 61. The method of any one of Paragraphs 59 or 60, wherein the implants are sutured, tacked, or stapled to the fascia.

Paragraph 62. A method of delivering the implants of any of Paragraphs 22, 38, and 42 wherein the implant is delivered by a minimally invasive technique.

Paragraph 63. A method of implanting the implant of any of Paragraphs 22, 38 or 42 using a crescent, donut, lollipop, or anchor mastopexy procedure.

Paragraph 64. A method of delivering the implants for any one of Paragraphs 1 to 52, wherein the implant is temporarily deformed, and delivered using an inserter device into a dissected tissue plane.

Paragraph 65. The method of any of Paragraphs 1 and 22-50 wherein the implant is delivered using an inserter device through an IMF incision.

Paragraph 66. An implant for securing a breast of a patient in a lifted position or contouring a patient's breast, the implant having a three-dimensional shape and comprising a support component with an upper section, a lower section, medial side, lateral side, and an outlying border and comprising a shape memory component with rounded edges, wherein the implant, support component, and/or outlying border is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 67. The implant of Paragraph 66 wherein the support component comprises a mesh, a set of strips, a fabric, a woven construct, a non-woven construct, a knitted construct, a braided construct, scaffold, a porous film, a nanospun, electrospun, or melt-blown construct.

Paragraph 68. The implant of Paragraph 67, wherein the support component comprises a thin mesh defining a body and plurality of tabs extending therefrom; wherein the shape memory component comprises a rib extending along a perimeter of the body of the mesh and wherein the rib urges the body to assume a three dimensional predetermined shape following release from a constrained shape.

Paragraph 69. The implant of Paragraph 66 or 68 wherein the implant assumes a preformed shape.

Paragraph 70. The implant of Paragraph 66 or 68 wherein the three-dimensional shape has a shape selected from the group consisting of a partial dome, dome, hemisphere, hemi-ellipsoid, a canoe shape a shape with a width of 8 to 20 cm at the base, a shape with a height or radius of curvature of 5 to 14 cm, a shape with a width that is 1 to 2 cm less than the width of the patient's breast when measured prior to surgery, and a shape with a height that is 0.5 to 5 cm less than the patient's nipple-IMF distance after mastopexy.

Paragraph 71. The implant of Paragraph 66 wherein buckling or bunching of the implant is minimized upon placement.

Paragraph 72. The implant of Paragraph 66 wherein the shape memory component is a continuous or interrupted ring forming an outlying border to which the prosthetic material is attached.

Paragraph 73. The implant of Paragraph 66 wherein the shape memory component has continuous dimensions or wherein the shape memory component has variable dimensions.

Paragraph 74. The implant of Paragraph 71 wherein the dimensions of the shape memory component decrease from the middle of the implant towards the medial and lateral sides of the implant.

Paragraph 75. The implant of Paragraph 66 wherein the implant further comprises one or more tabs radially extending from the outlying border.

Paragraph 76. The implant of Paragraph 73 wherein the implant comprises between two and twenty tabs.

Paragraph 77. The implant of Paragraph 74 wherein the implant has a medial tab and a lateral tab.

Paragraph 78. The implant of Paragraph 75 wherein there are one to eighteen tabs placed between the medial and lateral tabs.

Paragraph 79. The implant of Paragraph 76 wherein there are three tabs placed on each of the upper and lower sections between the medial and lateral tabs.

Paragraph 80. The implants of any one of Paragraphs 73-77 wherein the tabs have widths of 1-3 cm, and lengths of 2-4 cm.

Paragraph 81. The implant of Paragraph 73 further comprising a plurality of sutures extending through said tabs and for securing the tabs to supportive tissue.

Paragraph 82. The implant of Paragraph 66 or 68 further comprising one or more orientation marks.

Paragraph 83. The implant of Paragraph 66 further comprising ribbing in the upper and lower sections of the scaffold.

Paragraph 84. The implant of Paragraph 66 wherein the implant has unidirectional or bidirectional curvature.

Paragraph 85. The implant of Paragraph 82 wherein the curvature is either in the medial to lateral plane, or in the plane perpendicular to the medial to lateral plane, or in both planes.

Paragraph 86. The implant of Paragraph 68, wherein the rib is fused to the mesh.

Paragraph 87. The implant of Paragraph 85, wherein the rib comprises an absorbable material.

Paragraph 88. The implant of Paragraph 68, wherein the body comprises a rounded corner.

Paragraph 89. The implant of Paragraph 87, a tab extends from the rounded corner.

Paragraph 90. The implant of Paragraph 68 comprising a plurality of upper tabs spaced between a medial tab and a lateral tab.

Paragraph 91. The implant of Paragraph 66 wherein the rounded edges of the shape memory component are at the medial and lateral sides of the implant.

Paragraph 92. The implant of Paragraph 66 wherein the shape memory component is made from a filament, thread, strand, string, fiber, yarn, wire, film, tape, tube, fabric, felt, mesh, multifilament, or monofilament.

Paragraph 93. The implant of Paragraph 66 wherein the scaffold comprises a mesh, monofilament mesh, multifilament mesh, strips, fabrics, woven constructs, non-woven constructs, knitted constructs, braided constructs, porous scaffolds, laminates, nanospuns, electrospuns, dry spuns, or melt-blown constructs, filaments, threads, strands, strings, fibers, yarns, wires, films, tapes, felts, foams, multifilaments and monofilaments.

Paragraph 94. The implant of Paragraph 66 wherein either the scaffold or the shape memory component is resorbable, or wherein both the scaffold and the shape memory component are resorbable.

Paragraph 95. The implant of any of Paragraphs 66-94 wherein the scaffold is made from a polymeric composition comprising PBS or a copolymer thereof.

Paragraph 96. The implant of any of Paragraphs 66-95 wherein the shape memory component is made from a polymeric composition comprising PBS or a copolymer thereof.

Paragraph 97. The implant of any of Paragraphs 66-96, wherein the scaffold is made from a monofilament knitted mesh of a polymeric composition comprising PBS or a copolymer thereof and the shape memory component is made from an extrudate of a polymeric composition comprising PBS or a copolymer thereof.

Paragraph 98. The implant of any of Paragraphs 66-97 wherein the implant is replaced in vivo with regenerated host tissue that can support a reconstructed breast.

Paragraph 99. The implant of any of Paragraph 66-97 wherein the implant cannot stretch more than 30% in any direction.

Paragraph 100. An implant for use in breast surgery, wherein the implant is shaped for placement under the skin and over the breast mound of a female breast, wherein the implant comprises an upper pole for placement on the upper pole of the breast, a lower pole for placement on the lower pole of the breast, and an aperture for the nipple areola complex (NAC), and wherein the aperture is positioned on the implant to angulate the NAC after implantation, and optionally wherein the implant further comprises one or more tabs for fixation of the implant, and wherein the implant is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 101. The implant of Paragraph 100, wherein the upper pole and the lower pole comprise the polymeric composition.

Paragraph 102. The implant of Paragraph 100 and 101, wherein the implant has one or more of the following properties: (i) a ratio of the volume of the upper pole to the lower pole of less than 1, (ii) an aperture for the NAC positioned to angulate the NAC superior to the nipple meridian reference line, (iii) a convex lower pole and non-convex upper pole, (iv) a lower pole radius of 4 cm to 8 cm, (v) an aperture for the NAC with a diameter of 2 to 6 cm, and (vi) an upper pole that has a concave or straight profile.

Paragraph 103. The implant of Paragraphs 100 to 102, wherein the implant comprises a mesh, and wherein the mesh has one or more of the following properties: (i) a burst strength between 0.5 kgf and 50 kgf, (ii) a suture pullout strength of 1-20 kgf, (iii) pores with average diameters of 25 μm to 2 mm, (iv) a melt temperature of 115° C.±15° C., (v) oriented fibers, and (vi) an areal density of 5-800 g/cm².

Paragraph 104. The implants of Paragraphs 100 to 103, wherein the implant is a breast reconstruction implant, a mastopexy implant, an implant used in breast augmentation or reduction, or a tissue regeneration implant.

Paragraph 105. A method of forming the implants of Paragraphs 100 to 104, wherein the method comprises the steps of (i) preparing a 3-dimensional mold in the shape of the implant, (ii) molding a two-dimensional construct into a three-dimensional shape using the 3-dimensional mold, (iii) removing the molded shape from the mold, and, (iv) optionally cutting an aperture in the molded three-dimensional shape.

Paragraph 106. The method of Paragraph 105, wherein the two-dimensional construct is a monofilament mesh or 3D-printed mesh.

Paragraph 107. The method of Paragraph 106, wherein the mesh is trimmed, optionally to form one or more tabs for fixation of the implant in vivo.

Paragraph 108. An implant for use in breast surgery, wherein the implant comprises a lower pole support for the breast, wherein the lower pole support does not cover the NAC of the breast, and wherein the lower pole support is sized to span the lower pole of the breast, and optionally wherein the lower pole support further comprises one or more tabs for fixation of the implant, and wherein the implant is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 109. The implant of Paragraph 108, wherein the implant further comprises one or more of the following: (i) a three-dimensional configuration, (ii) a porous construction, (iii) tabs for fixation of the implant, (iv) a reinforced rim at least on part of the periphery of the implant, and (v) a substantially 2-dimensional geometry that becomes a 3-dimensional geometry when the implant is secured to the breast.

Paragraph 110. The implant of Paragraphs 108 and 109, wherein the lower pole support comprises a fiber, mesh, monofilament mesh, non-woven, lattice, textile, patch, film, laminate, sheet, thermoform, foam, web, molded, pultruded, machined or 3D-printed form.

Paragraph 111. The implants of Paragraphs 107 to 110, wherein the implant comprises a mesh, and wherein the mesh has one or more of the following properties: (i) a burst strength between 0.5 kgf and 50 kgf, (ii) a suture pullout strength of 1-20 kgf, (iii) pores with average diameters of 25 μm to 2 mm, (iv) a melt temperature of 115° C.±15° C., (v) oriented fibers, and (vi) an areal density of 5-800 g/cm².

Paragraph 112. The implants of Paragraphs 108 to 111, wherein the implant is a mastopexy implant, an implant used in breast augmentation or reduction, a tissue regeneration implant, or a breast reconstruction implant.

Paragraph 113. A method of forming the implant of Paragraph 66, the method comprising the steps of: providing a first split metal mold comprising two halves and having a semicircular groove in one half of the mold; placing a shape memory component material selected from the group consisting of a filament, thread, strand, string, fiber, yarn, wire, film, tape, tube, fabric, felt, mesh, multifilament, or monofilament in the semicircular groove so that it forms a ring; placing a support component material between the molding halves, and clamping the two halves of the split metal mold together to form a block; heating the block at a temperature between 50° C. and 70° C.; cooling the block at a temperature between 0° C. and 25° C.; disassembling and removing a molded shape from the block; cutting the molded shape to remove unwanted shape memory material and mesh; placing the cut molded shape form in a second split metal mold consisting of an inwardly curving half and an outwardly curving half; clamping the halves of the mold together to form a block; heating the block at a temperature between 40°

C. and 52° C.; cooling the block at a temperature between 0° C. and 25° C.; disassembling and removing the implant.

Paragraph 114. The method of Paragraph 113 wherein the scaffold material and extrudate are made from a polymeric composition comprising PBS or a copolymer thereof.

Paragraph 115. A method of implanting the implant of Paragraph 66, wherein the implant is anchored at one or more locations to the pectoralis fascia and/or serratus anterior fascia to lift the breast, or wherein the implant is attached to a flap below the areolar-nipple complex, rotated to enhance the anterior projection of the breast, and fixed to the anteropectoral fascia, and wherein the implants are sutured, tacked, or stapled to the fascia.

Paragraph 116. A method of implanting the implant of Paragraph 66 wherein the implant is delivered by a minimally invasive technique.

Paragraph 117. The method of Paragraph 116 wherein the implant is rolled into a small diameter cylindrical shape, delivered using an inserter or by hand, and allowed to resume its three-dimensional shape.

Paragraph 118. The implant of Paragraphs 1 to 117, wherein the implant comprises an absorbable, polyester comprising monomers that have pKa(s) greater than 4.19 or that have hydrolytic degradation products with pKa(s) greater than 4.19.

Paragraph 119. The implant of Paragraphs 1 to 118, wherein the implant comprises PBS or copolymer thereof and the implant contains pores that expand under tension or have an auxetic design so that the porous implant has a negative Poisson's ratio.

D. Expandable Breast Implants

Breast implants comprising poly(butylene succinate) or copolymer thereof may also be prepared that are expandable. These implants can be prepared so that the implants stretch or elongate in one or more directions when a stretching force is applied to the implant. The percentage expansion may be calculated using the formula: % Expansion=(Dimension of implant after expansion–Dimension of implant prior to expansion)/Dimension of implant prior to expansion. These expandable implants are particularly useful in breast reconstruction. For example, these expandable implants can be used in combination with a tissue expander. The expandable implants may be sutured to the detached edge of the patient's pectoralis major muscle to function as a pectoralis extender, and used to form a sling for a tissue expander. Force applied by the tissue expander will cause the expandable implants to stretch which is useful in creating a pocket in the breast, for example, for a silicone or saline breast implant during reconstruction following mastectomy. In an embodiment, the expandable implants can be expanded with a tissue expander by inflating the tissue expander with 1 to 150 cc of fluid or gas on one or more occasions. In another embodiment, the expandable implants are expanded or stretched by subjecting them to a force of 0.2 to 22 N/cm, more preferably 0.6 to 12 N/cm, and even more preferably 1 to 9 N/cm. In a particularly preferred embodiment, the expandable implants can be stretched in one or more directions between 31% and 100% of the implant's original dimensions in the one or more directions by stretching the implant with a force of 0.2 to 22 N/cm, more preferably 0.6 to 12 N/cm, and even more preferably 1 to 9 N/cm. In another embodiment, the expandable implants are expanded using a tissue expander with a force of 0.2 to 22 N/cm, more preferably 0.6 to 12 N/cm, and even more preferably 1 to 9 N/cm. The expandable implants may also be used in other breast surgery procedures. For example, the expandable implant can be implanted during a mastopexy procedure. In an embodiment, the expandable implant can provide support during a breast lift procedure. For example, the implant can provide support for the lower pole of the breast. The expandable implant may have a two-dimensional or three-dimensional shape. The expandable implant may include an aperture or cutout to accommodate the NAC. In an embodiment, the expandable implant may be shaped for placement under the skin and over part, or substantially all, of the breast mound of a female breast. The expandable implant may be used to confer shape to the breast. The expandable implant may be used to prevent or minimize ptosis. In one embodiment, the expandable implant is sized to span the entire breast. In another embodiment, the expandable implant is sized for attachment to the detached edge of the patient's pectoralis muscle. In yet another embodiment, the expandable implant may be dimensioned so that it at least partially covers a breast augmentation implant such as a silicone or saline breast implant when implanted in the body. The expandable implant may comprise a non-woven, lattice, textile, patch, film, laminate, sheet, thermoform, foam, or web, or a molded, pultruded, machined or 3D-printed form. In one embodiment, the expandable breast implant preferably comprises a monofilament mesh, and preferably a monofilament warp knit mesh. Preferred monofilament meshes have one of the following knit patterns: Diamond, Diamond Plus, Crotchet, Del., Marquisette, Marquisette Plus and Marlex. In a preferred embodiment, the implant comprises a polymeric composition of poly(butylene succinate) or copolymer thereof wherein the polymer chains have been aligned and the polymeric composition is partially or fully oriented. In an embodiment, the implant comprises fibers or struts of poly(butylene succinate) or copolymer thereof wherein the fibers or struts are unoriented, partially or fully oriented, or a combination thereof. In an embodiment, the expandable implant initially becomes stronger when the implant is expanded or stretched. For example, the implant may become stronger after stretching by a tissue expander. Preferably, the expandable implant is resorbable, and is replaced in vivo by in-grown tissue. In another embodiment, the expandable breast implants may comprise one or more tabs wherein the one or more tabs each have a suture pullout strength of at least 10 N, but less than 1,000 N. In another embodiment, the expandable breast implants may comprise pores that have an auxetic design that expand under tension, rather than get smaller or collapse, preventing the mesh pores from compressing and possibly damaging the tissue that forms within them. The expandable breast implants preferably have one or more of the following properties: (i) a thickness of 0.5 to 5 mm, more preferably a thickness of 1 to 4 mm, and even more preferably a thickness of 2 to 3 mm; (ii) dimensions of 5 cm×15 cm to 15 cm to 30 cm; average pore sizes of 25 microns to 5 mm, and more preferably 75 microns to 1 mm; (iii) suture tabs with suture pullout strengths of 10 gf to 20 kgf; and an ability to be expanded in one or more dimensions of the implant between 31% and 100% when a force of 0.2 to 22 N/cm, more preferably 0.6 to 12 N/cm, and even more preferably 1 to 9 N/cm is applied to the implant; (iv) an ability to be expanded one or more times in vivo within 4 months of implantation, more preferably within 2-3 months of implantation, and even more preferably within 10 days of implantation; and (v) porosity, with average pore diameters of at least 25 microns, more preferably at least 75 microns, and preferably less than 2 mm, with a particularly preferred average pore size of 100 µm to 1 mm.

In an embodiment, the expandable breast implant comprises elements comprising poly(butylene succinate) or copolymer thereof that can be expanded when a force is applied, for example, a force applied by a tissue expander or by a surgeon stretching the implant. The elements may be all the same, or different. For example, the expandable breast implant may comprise unoriented or partially oriented fibers or struts that can be stretched when subjected to a force. The fibers or struts may comprise poly(butylene succinate) or copolymer thereof. In one embodiment, the unoriented or partially oriented fibers or struts become more oriented, at least initially, when a force is applied to stretch the fibers or struts, and optionally the implant's tensile strength or burst strength increases when a force is applied to stretch the implant.

In another embodiment, the expandable breast implant comprises elements that do not initially stretch when a force is applied to stretch the implant, or at least do not stretch more than 30% when a force is initially applied, but instead the elements of the implant move relative to each other when a force is applied resulting in an expanded implant. Preferably, the force applied to these expandable breast implants is 0.2 to 22 N/cm. For example, the expandable implant may be a mesh knitted from fibers comprising poly(butylene succinate) or copolymer thereof, and the positions of the fibers in the mesh can change relative to each other to allow expansion of the mesh without the fibers stretching more than 30% of their original lengths. In one embodiment, the implant may comprise pores that can elongate when the implant is subject to a stretching force. Preferably, the fibers are oriented. In an embodiment, the expandable implants comprising fibers of poly(butylene succinate) and copolymers thereof have knit patterns that allow the implants to expand 31-100% in one or more directions without the fibers stretching more than 30% of their original lengths.

In another embodiment, the expandable breast implants comprising poly(butylene succinate) or copolymer thereof comprise sacrificial and non-sacrificial elements. In this embodiment, the sacrificial elements will yield or be broken when a force is applied to expand the implant before the non-sacrificial elements will yield, substantially yield, or be broken, when a force is applied. The sacrificial elements, non-sacrificial elements or both the sacrificial and non-sacrificial elements may comprise poly(butylene succinate) or copolymer thereof. When the sacrificial elements of the expandable implants yield or break, the implant can be expanded to the extent permitted by the non-sacrificial element or the remaining resistance of the sacrificial elements. The amount of expansion will also depend upon the force applied to expand the implant. Preferably, these implants can expand 31-100% in one or more directions when a force of 0.2 to 22 N/cm is applied to the implant. In an embodiment, the sacrificial elements of the expandable implant may be fibers or struts, wherein the fibers or struts can be more easily stretched than non-sacrificial elements of the implant, or the sacrificial fibers or struts can be broken or degraded in vivo before the non-sacrificial elements of the implant. In an embodiment, the sacrificial fibers or struts degrade faster in vivo than the non-sacrificial elements of the implant. In one embodiment, the sacrificial and non-sacrificial elements of the expandable implants are prepared from poly(butylene succinate) or copolymer thereof, wherein the sacrificial elements, for example the sacrificial fibers or struts, have a lower weight average molecular weight than the non-sacrificial elements (for example, non-sacrificial fibers or struts). In another embodiment, the sacrificial and non-sacrificial elements of the expandable implants are prepared from poly(butylene succinate) or copolymer thereof, and the cross-section of the sacrificial elements is less than that of the non-sacrificial elements. For example, the sacrificial and non-sacrificial elements may both be fibers, wherein the diameter of the sacrificial fibers is less than the diameter of the non-sacrificial fibers. In another example, the sacrificial and non-sacrificial elements may both be struts, wherein the cross-section of the sacrificial struts is less than the cross-section of the non-sacrificial struts. In another embodiment, the sacrificial and non-sacrificial elements of the expandable implants are prepared from poly(butylene succinate) or copolymer thereof, and the polymer or copolymer of the sacrificial elements is less oriented than the polymer or copolymer of the non-sacrificial elements. For example, the sacrificial and non-sacrificial elements may both be fibers or struts comprising poly(butylene succinate) or copolymer thereof, but the fibers or struts of the sacrificial elements are less oriented than the fibers or struts of the non-sacrificial elements. In another embodiment, the sacrificial and non-sacrificial elements of the expandable implants are prepared from poly(butylene succinate) or copolymer thereof, and the sacrificial elements degrade in vivo before the non-sacrificial elements. In one embodiment, the sacrificial and non-sacrificial elements of the expandable implants are prepared from poly(butylene succinate) or copolymer thereof, wherein the sacrificial elements, for example sacrificial fibers or struts, have a lower tensile strength than the non-sacrificial elements, for example non-sacrificial fibers or struts. In an embodiment, the expandable breast implants comprise sacrificial and non-sacrificial elements wherein the sacrificial elements have a short tensile strength retention and the non-sacrificial elements have a prolonged tensile strength retention. A short tensile strength retention is preferably a 50% strength retention at 1-12 weeks, and a prolonged tensile strength retention is preferably a 50% strength retention at 4-24 months. In an embodiment, the sacrificial and non-sacrificial elements are fibers or struts, wherein the sacrificial elements have one or more of the following properties: (i) elongation to break of 100-1,000%, (ii) tensile strength of 30-300 MPa, (iii) Young's Modulus of 70-400 MPa, and (iv) average diameter or cross-sectional width of 10-500 microns; and wherein the non-sacrificial elements have one or more of the following properties: (i) elongation to break of 10-100%, (ii) tensile strength of 301-1,300 MPa, (iv) Young's Modulus of 401 MPa to 5 GPa, and average diameter or cross-sectional width of 10-1,000 microns.

In an embodiment, the expandable breast implants are manufactured by melt or solvent spinning, extrusion, molding, pultrusion or 3D printing. In an embodiment, an expandable implant may be knitted as a spacer fabric with sacrificial fibers knitted on the front and back beds, and non-sacrificial fibers knitted as a spacer layer with an accordion profile running between the sacrificial fibers on the front and back beds. The sacrificial fibers preferably have a lower tensile strength, lower tensile strength retention, or yield more easily than the non-sacrificial fibers. When a stretching force is applied to the spacer fabric, the sacrificial fibers of the spacer fabric either yield or break allowing the implant to extend. During extension, the width of the accordion profile is reduced, and at least initially, the non-sacrificial fibers of the accordion profile limit the total extension of the implant. In another embodiment, the expandable breast implant may comprise loops of non-sacrificial fibers, zig-zagging non-sacrificial fibers, or crimped, wavy or curly non-sacrificial fibers that straighten when a stretching force is applied to the implant allowing the implant to expand, but to a limited extent. In yet another embodiment, the expandable implants may comprise oriented fibers that have been fused to unoriented struts, or oriented mesh that has been fused to unoriented struts. These implants may be prepared, for example, by directly printing the struts on the oriented fibers or mesh using 3D printing. In these implants, the struts serve as sacrificial elements, and the oriented fibers or mesh serve as non-sacrificial elements. Examples of ways to construct expandable breast implants with sacrificial and non-sacrificial elements are shown in Table A. The sacrificial and non-sacrificial elements disclosed in Table A may comprise poly(butylene succinate) or copolymer thereof.

TABLE A

| # | Non-sacrificial element | Sacrificial element | Implant construction |
|---|---|---|---|
| 1 | Oriented mesh | Unoriented struts | Struts 3D printed on mesh |
| 2 | Oriented mesh | Grid of unoriented struts | Struts fused to mesh |
| 3 | Oriented mesh | Parallel lines of struts | Struts fused to mesh |
| 4 | Large diameter fiber | Small diameter fiber | Knit or woven fabric, including spacer fabric |
| 5 | Wavy large diameter unoriented fiber | Grid of small diameter unoriented fiber | Wavy fiber sewn into grid |
| 6 | Oriented mesh | Unoriented and partially oriented fiber | Unoriented or partially oriented fiber inlaid in oriented mesh |
| 7 | Oriented mesh | Oriented fiber with smaller diameters than mesh fibers | Unoriented fiber inlaid in oriented mesh |
| 8 | Wavy oriented fiber | Lattice with small diameter unoriented struts | Wavy fiber inserted or sewn in lattice |
| 9 | Wavy unoriented fiber | Lattice of small diameter unoriented struts | Wavy fiber inserted or sewn in lattice |
| 10 | Wavy oriented fiber | Spunlaid or spunbond | Wavy fiber inserted or sewn in spunlaid or spunbond |

In embodiments, the pores in the absorbable implants comprising poly(butylene succinate) or copolymer thereof can be designed such that they have an auxetic design and thus get larger under tension, rather than collapsing. In a simple example, a film of poly(butylene succinate) or copolymer thereof with an auxetic design is made by cutting multiple small, parallel off-set slits through the film (like a fenestrated skin graft). Under tension orthogonal to the direction of the slits, the film will elongate and the slits will expand to create elliptical or spherical pores that get larger under tension, rather than collapsing as the pores in a typical fabric would. Such expanded pores may be desirable to prevent the collapse of the pores resulting in possible damage to the tissue within the pores. Such a film may have a negative Poisson's ratio and may get thicker under tension, rather than the more typical behavior of most materials that get thinner under tension, like a rubber band or balloon. Fibrous scaffolds comprising poly(butylene succinate) or copolymer thereof, or 3D printed scaffolds comprising poly(butylene succinate) or copolymer thereof may be designed with auxetic pores that expand under tension.

Accordingly, in the context of expandable breast implants for use in breast surgery, the present invention also provides subject matter defined by the following numbered paragraphs:

Paragraph 1. An absorbable expandable breast implant for plastic surgery procedures, wherein the implant has pores, and wherein the pores have an average diameter between 10 μm and 2 mm, and wherein the implant is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The implant of Paragraph 1, wherein the implant has one or more of the following properties: (i) a thickness of 0.5 to 5 mm, more preferably a thickness of 1 to 4 mm, and even more preferably a thickness of 2 to 3 mm; (ii) dimensions of 5 cm×15 cm to 15 cm to 30 cm; average pore sizes of 25 microns to 5 mm, and more preferably 75 microns to 1 mm; (iii) suture tabs with suture pullout strengths of 10 gf to 20 kgf; and an ability to be expanded in one or more dimensions of the implant between 31% and 100% when a force of 0.2 to 22 N/cm, more preferably 0.6 to 12 N/cm, and even more preferably 1 to 9 N/cm is applied to the implant; (iv) an ability to be expanded one or more times in vivo within 4 months of implantation, more preferably within 2-3 months of implantation, and even more preferably within 10 days of implantation; and (v) porosity, with average pore diameters of at least 25 microns, more preferably at least 75 microns, and preferably less than 2 mm, with a particularly preferred average pore size of 100 μm to 1 mm.

Paragraph 3. The implant of Paragraphs 1 and 2, wherein the implant comprises fibers of poly(butylene succinate) and copolymers thereof that have knit patterns that allow the implants to expand 31-100% in one or more directions without the fibers stretching more than 30% of their original lengths.

Paragraph 4. The implant of Paragraphs 1 and 2, wherein the implant comprises sacrificial and non-sacrificial elements, optionally wherein the elements are fibers or struts.

Paragraph 5. The implant of Paragraph 4, wherein the sacrificial elements: (i) can be more easily stretched than the non-sacrificial elements; (ii) can be broken in vivo before the non-sacrificial elements; (iii) degrade faster in vivo than the non-sacrificial elements; (iv) have a lower weight average molecular weight than the non-sacrificial elements: (v) have a smaller cross-section or diameter than the non-sacrificial elements: (vi) are less oriented than the non-sacrificial elements; (vii) have a lower tensile strength than the non-sacrificial elements; or (viii) have a shorter tensile strength retention than the non-sacrificial elements.

Paragraph 6. The implant of Paragraphs 4 and 5, wherein the sacrificial elements have one or more of the following properties: (i) elongation to break of 100-1,000%, (ii) tensile strength of 30-300 MPa, (iii) Young's Modulus of 70-400 MPa, and (iv) average diameter or cross-sectional width of 10-500 microns; and wherein the non-sacrificial elements have one or more of the following properties: (i) elongation to break of 10-100%, (ii) tensile strength of 301-1,300 MPa, (iv) Young's Modulus of 401 MPa to 5 GPa, and average diameter or cross-sectional width of 10-1,000 microns.

Paragraph 7. The implant of Paragraph 1, wherein the implant comprises one or more of the following: mesh, monofilament mesh, oriented monofilament mesh, non-woven, lattice, textile, patch, film, laminate, sheet, thermoform, foam, or web, or a molded, pultruded, machined or 3D-printed form.

Paragraph 8. The implant of Paragraph 1, wherein the tensile strength of the implant initially increases upon expansion of the implant.

Paragraph 9. The implant of Paragraphs 1 to 8, wherein the implant is a breast reconstruction implant, a tissue regeneration implant, an implant used in conjunction with a tissue expander, a mastopexy implant, or an implant used to reconstruct the breast following mastectomy.

Paragraph 10. The implant of Paragraphs 1 to 9, comprising poly(butylene succinate) or copolymer thereof, wherein the implant has pores with auxetic design that can expand when the implant is under tension.

Paragraph 11. A method of forming the implant of Paragraph 4, wherein the implant is knitted as a spacer fabric with sacrificial fibers knitted on the front and back beds, and non-sacrificial fibers knitted as a spacer layer with an accordion profile running between the sacrificial fibers on the front and back beds.

Paragraph 12. A method of using the implants of Paragraphs 1 to 9, wherein the implants are implanted, and expanded in vivo with a tissue expander.

E. Tissue Regeneration Breast Implants

In an embodiment, the implants comprising poly(butylene succinate) or copolymer thereof may be used to regenerate breast tissue. The implants may be used instead of conventional silicone and saline breast implants so that the patient's breasts are made of breast tissue, and preferably do not comprise synthetic materials. The implants may be used to augment or reduce the size of the breast, shape the breast, or be used to replace conventional silicone and saline breast implants. In this manner, the implants can be used in one embodiment to produce an augmented breast, reduced breast size, or re-shaped breast, without the use of a permanent breast implant. In a preferred embodiment, the implants may be used as tissue regeneration implants, wherein the implant is implanted in the breast and breast tissue is regenerated while the implant degrades. The implants may be used in the breast as void fillers. In particular, the implants may be used as void fillers that support the in-growth of breast tissue as the implants degrade. Preferably, the implants are porous to allow cell in-growth. Preferably, the implants are three-dimensional. Implantation of the implant in the breast may result in the formation of a natural breast made up entirely of tissue, preferably the patient's own tissue. In a preferred embodiment, these implants may be loaded or coated with one or more of the following: blood or blood components, platelets, cells, fat cells, autologous cells, stem cells, adipose cells, fibroblast cells, protein, collagen, gel, hydrogel, hyaluronic acid, fat, autologous fat, injectable fat, lipoaspirate, fascia, antimicrobial, antibiotic or a bioactive agent. These cells and materials may be added to the implant prior to implantation, and or added to the implant after implantation. In an embodiment, the cells and materials may be added to the implant before or after implantation by injection. The implant may further comprise one or more chambers or compartments. In an embodiment, the one or more chambers or compartments may be filled with cells and or a tissue mass, preferably a living tissue mass, and even more preferably a vascular pedicle. In another embodiment, the implants may comprise pleats. In a particularly preferred embodiment, the implants may have the shape of a lotus flower, a funnel shape, or other structural shape preferably with a high surface area. In an even more preferred embodiment, the three-dimensional implants may have the shape of a lotus flower or funnel shape.

In an embodiment, the implants for regeneration of breasts and breast tissue, may be formed from scaffolds comprising poly(butylene succinate) and copolymers thereof. The implants may have one or more of the following properties: (i) a polymer or copolymer with a weight average molecular weight of 10,000 to 400,000 Da, and more preferably 50,000 to 200,000 Da; (ii) porosity, with average pore diameters of at least 25 microns, more preferably at least 75 microns, and preferably less than 5 mm, with a particularly preferred average pore size of 100 μm to 1 mm; (iii) an areal density of 5 to 800 gram/m$^2$; (iv) a volume of 50 to 800 cc, and more preferably 150 to 800 cc; (v) a projection from the chest wall ranging from 3 to 15 cm, and more preferably 4 to 10 cm, when the implant is placed on the chest wall of the patient; (vi) a width or diameter at the base of the implant of 7 to 20 cm, and more preferably 9 to 17 cm, when the base of the implant is placed on the chest wall of the patient; (vii) a hemi-spherical dome, round, or anatomical shape, or shape of a silicone or saline breast implant; and (viii) average fiber diameters of 10 microns to 1 mm, when the implant comprises fibers, and optionally fibers with one or more of the following properties: (a) a tenacity of 1 to 12 grams per denier; (b) a tensile strength of 30 MPa to 2,000 MPa; (c) a Young's Modulus of at least 300 MPa, and less than 5 GPa, but more preferably less than 3 GPa; and (d) an elongation to break of 20-800%.

In an embodiment, the implants for regeneration of breasts and breast tissue comprising poly(butylene succinate) and copolymers thereof are manufactured by one or more of the following methods: melt casting, solvent casting, solution spinning, solution bonding of fibers, melt processing, extrusion, melt extrusion, melt spinning, fiber spinning, orientation, relaxation, annealing, injection molding, compression molding, foaming, dry spinning, knitting, weaving, crocheting, melt-blowing, electrospinning, thermoforming, pultrusion, centrifugal spinning, molding, spun-bonding, spunlaiding, nonwoven fabrication, entangling of staple fibers, fiber knitting, weaving and crocheting, mesh fabrication, pore forming, lyophilization, stitching, calendering, freeze-drying, phase separation, particle leaching, thermal phase separation, leaching, 3D printing, fused filament fabrication, fused pellet deposition, melt extrusion deposition, selective laser melting, printing of slurries and solutions using a coagulation bath, and printing using a binding solution and granules of powder. In a particularly preferred method, the implants comprise scaffolds formed from fibers of poly(butylene succinate) or copolymer thereof, and more preferably from knitted, woven or non-woven constructs comprising fibers of poly(butylene succinate) or copolymer thereof. In another preferred embodiment, the implants are 3D printed from poly(butylene succinate) or copolymer thereof.

Accordingly, in the context of implants that regenerate breast tissue for use in breast surgery, the present invention also provides subject matter defined by the following numbered paragraphs:

Paragraph 1. An absorbable breast implant for use in breast surgery to support or regenerate breast tissue, wherein the implant comprises pores, and wherein the pores have an average dimeter or width of 10 μm to 2 mm, and wherein the implant is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The implant of Paragraph 1, wherein the implant has one or more of the following properties: (i) a polymer or copolymer with a weight average molecular weight of 10,000 to 400,000 Da, and more preferably 50,000 to 200,000 Da; (ii) porosity, with an average pore size of 100 μm to 1 mm; (iii) an areal density of 5 to 800 gram/m$^2$; (iv) a volume of 50 to 800 cc, and more preferably 150 to 800 cc; (v) a projection from the chest wall ranging from 3 to 15 cm, and more preferably 4 to 10 cm, when the implant is placed on the chest wall of the patient; (vi) a width or diameter at the base of the implant of 7 to 20 cm, and more preferably 9 to 17 cm, when the base of the implant is placed on the chest wall of the patient; (vii) a hemi-spherical dome, round, anatomical or three-dimensional shape, or shape of a silicone or saline breast implant; and (viii) average fiber diameters of 10 microns to 1 mm, when the implant comprises fibers, and optionally fibers with one or more of the following properties: (a) a tenacity of 1 to 12 grams per denier; (b) a tensile strength of 30 MPa to 2,000 MPa; (c) a Young's Modulus of at least 300 MPa, and less than 5 GPa, but more preferably less than 3 GPa; and (d) an elongation to break of 15-800%.

Paragraph 3. The implant of Paragraphs 1 and 2, wherein the implant further comprises one or more of the following: blood or a blood component, platelets, cells, fat cells, autologous cells, stem cells, adipose cells, fibroblast cells, protein, collagen, gel, hydrogel, hyaluronic acid, fat, autologous fat, injectable fat, lipoaspirate, fascia, antimicrobial, antibiotic or a bioactive agent.

Paragraph 4. The implant of Paragraphs 1 and 2, wherein the implant further comprises one or more compartments or chambers.

Paragraph 5. The implant of Paragraph 4, wherein the one or more compartments or chambers is filled with a vascular pedicle or other tissue mass.

Paragraph 6. The implant of Paragraphs 1 to 5, wherein the implant comprises one or more of the following: mesh, monofilament mesh, oriented monofilament mesh, non-woven, lattice, textile, patch, film, laminate, sheet, thermoform, foam, or web, or a molded, pultruded, machined or 3D-printed form.

Paragraph 7. The implant of Paragraph 6, wherein the implant comprises a mesh, monofilament mesh or oriented mesh derived from fiber, and the total fiber surface area of the mesh is 10 to 400 cm$^2$ per cm$^2$ of mesh.

Paragraph 8. The implant of Paragraphs 1 to 7, wherein the implant comprises pleats, a lotus flower shape, or a funnel shape.

Paragraph 9. The implants of Paragraphs 1 to 8, wherein the implant is a breast reconstruction implant, mastopexy implant, implant used in breast augmentation or reduction, implant used as a void filler, implant used as a scaffold for fat grafting or tissue regeneration implant.

Paragraph 10. The implants of Paragraphs 1 to 9, wherein the implant comprises an absorbable polyester comprising monomers or hydrolytic degradation products with pKa(s) greater than 4.19.

Paragraph 11. The implants of Paragraphs 1 to 10, wherein the implant comprises an absorbable polyester and pores with an auxetic design that expand under a tensile load.

Paragraph 12. A method of implanting the implants of Paragraphs 1 to 8, wherein the implants are coated with one or more of the following prior to implantation or following implantation: blood or a blood component, platelets, cells, fat cells, autologous cells, stem cells, adipose cells, fibroblast cells, protein, collagen, gel, hydrogel, hyaluronic acid, fat, autologous fat, injectable fat, lipoaspirate, fascia, antimicrobial, antibiotic or a bioactive agent.

Paragraph 13. A method of augmenting the breast of a patient, wherein the implants of Paragraphs 1 to 11 are secured on the breast mound of the patient.

Paragraph 14. The method of Paragraph 12, comprising coating or injecting into the implant one or more of the following: autologous fat, fat lipoaspirate, injectable fat, adipose cells, fibroblast cells, stem cells, gel, hydrogel, hyaluronic acid, collagen, antimicrobial, antibiotic or a bioactive agent.

F. Orthopedic Implants

In an embodiment, orthopedic implants may be prepared from polymeric compositions comprising poly(butylene succinate) and copolymers thereof. Optionally, these implants may comprise one or more of the following: a ceramic, bioceramic, medical glass, bio-active glass, and calcium salt, and may comprise an antimicrobial or an antimicrobial and a ceramic, bioceramic, medical glass, bio-active glass, and or calcium salt. In one embodiment, implants may be formed from poly(butylene succinate) and copolymers thereof, optionally with ceramic, medical glass or bio-active glass present, that include screws, bone screws, interference screws, pins, ACL screws, clips, clamps, nails, medullary cavity nails, bone plates, bone substitutes, including porous bone plates, bone putty, tacks, fasteners, suture fastener, rivets, staples, fixation devices, bone void fillers, suture anchors, bone anchors, meniscus anchors, meniscal implants, intramedullary rods and nails, antibiotic beads, joint spacers, interosseous wedge implants, osteochondral repair devices, spinal fusion devices, spinal fusion cage, bone plugs, cranioplasty plugs, plugs to fill or cover trephination burr holes, orthopedic tape, including knitted and woven tape, and devices for treatment of osteoarthritis. These implants may further comprise an antimicrobial agent, including an antibiotic. The orthopedic implants comprising PBS or copolymer thereof may further comprise a radiopaque material or radiopaque marker.

The polymeric compositions used to prepare the orthopedic implants preferably comprise poly(butylene succinate) or copolymer thereof with a weight average molecular weight of 10 to 400 kDa, and more preferably 50 to 200 kDa.

Examples of ceramics that can be blended in the polymeric compositions include: tricalcium phosphate (alpha and beta forms of tricalcium phosphate (TCP)), biphasic calcium phosphate (BCP), hydroxylapatite, calcium sulfate, calcium carbonate, and other calcium phosphate salt-based bioceramics. In a preferred embodiment, the ceramics are resorbable. Bio-active glasses may also be blended into the polymeric compositions. Examples of bio-active glasses include bioactive glasses composed of $SiO_2$, $Na_2O$, $CaO$ and $P_2O_5$ in specific proportions.

Examples of calcium salts that can be incorporated into the polymeric compositions include: calcium carbonate, calcium sulfate, calcium phosphate, calcium orthophosphate, dicalcium phosphate, octacalcium phosphate, amorphous calcium phosphate, biphasic calcium phosphate, hydroxyapatite, and tricalcium phosphate (TCP), including α-TCP and β-TCP.

Alternatives to ceramics that may be incorporated into the implants include demineralized bone (DMB) harvested from human or animal donors and processed to remove the inorganic minerals. This includes materials from which the mineral bone has been removed, leaving behind the collagen bone matrix and stimulatory matrix components.

The polymeric compositions of poly(butylene succinate) and copolymers thereof may be blended with 1-70% by weight of the ceramic, medical glass, bio-active glass, or DMB, including 5, 10, 15, 20, 25, 30, 35, 40, 45, 50, 55, 60 and 65% by weight, and more preferably 20-60% by weight of the ceramic, medical glass, bio-active glass, or DMB. In a preferred embodiment, the compositions comprise beta-TCP, alpha-TCP, or a combination thereof with average particle sizes of 0.1 to 500 microns.

The orthopedic implants comprising polymeric compositions of poly(butylene succinate) and copolymers thereof may further comprise bioactive agents. In an embodiment, these compositions may comprise DMB, medical glass, bio-active glass, antimicrobial agents, and preferably antibiotics. In another embodiment, the orthopedic implants may comprise poly(butylene succinate) or copolymer thereof with ceramic, medical glass, or bio-active glass, and an antimicrobial agent, preferably an antibiotic.

It has been discovered that implants can be made from the compositions of poly(butylene succinate) and copolymers thereof with high stiffness and torsional strength making the implants suitable for use in orthopedic implants.

In one embodiment, the orthopedic implants may be produced by injection molding. For example, injection molded implants of PBS and copolymers thereof may be formed using an Arburg model 221 injection molder using the following conditions: barrel temperature of the molder increasing from 70° C. at the feed zone to 170° C. at the end of the barrel; and mold temperature of 32° C. After molding, the implants may be dried in a vacuum oven at room temperature for 48 hours, and tensile properties determined using an MTS test machine with a 2 inch/min cross head speed. Representative tensile properties of implants formed by this method are as follows: Young's Modulus 0.66 GPa (96,600 psi), Yield Strength 49.2 MPa (7,140 psi) and Break Stress of 71.7 MPa (10,400 psi). Notably, the polymeric compositions comprising poly(butylene succinate) and copolymers thereof, with or without ceramic, may be injection molded with only a 0-20% loss of intrinsic viscosity, more preferably only a 0-10% loss of intrinsic viscosity, and even more preferably only a 0-5% loss of intrinsic viscosity, indicating that little loss of molecular weight occurs during injection molding. In an embodiment, orthopedic implants are formed from compositions comprising poly(butylene succinate) and copolymers thereof, wherein the weight average molecular weight of poly(butylene succinate) and copolymers thereof decreases less than 20%, and more preferably less than 10%, upon melt processing of the polymer or copolymer to form the orthopedic implant.

In other embodiments, the orthopedic implants may be prepared from fiber, monofilament or multifilament fiber or yarn, mesh, non-woven, lattice, patch, particle, film, laminate, thermoform, tube, foam, web, molded, pultruded, machined or 3D-printed forms. The orthopedic implants may be prepared by one or more of the following methods: casting, solvent casting, solution spinning, solution bonding of fibers, melt processing, extrusion, melt extrusion, melt spinning, fiber spinning, orientation, relaxation, annealing, injection molding, compression molding, machining, machining of extrudate, lamination, particle formation, microparticle, macroparticle and nanoparticle formation, foaming, dry spinning, knitting, weaving, crocheting, melt-blowing, film forming, film blowing, film casting, membrane forming, electrospinning, thermoforming, pultrusion, centrifugal spinning, molding, tube extrusion, spunbonding, spunlaiding, nonwoven fabrication, entangling of staple fibers, fiber knitting, weaving and crocheting, mesh fabrication, coating, dip coating, laser cutting, barbing, barbing of fibers, punching, piercing, pore forming, lyophilization, stitching, calendering, freeze-drying, phase separation, particle leaching, thermal phase separation, leaching, latex processing, gas plasma treatment, emulsion processing, 3D printing, fused filament fabrication, fused pellet deposition, melt extrusion deposition, selective laser melting, printing of slurries and solutions using a coagulation bath, and printing using a binding solution and granules of powder.

In another embodiment, orthopedic implants may be prepared with fibers of the polymeric compositions, preferably wherein the orthopedic implants are self-reinforced with the fibers. Preferably, the fibers are oriented. The oriented fibers may be monofilament, multifilament, or yarns.

(i) Screws and Interference Screws

In an embodiment, the orthopedic implants may be screws, and in a preferred embodiment the orthopedic implants may be interference screws or bone screws. Polymeric compositions comprising poly(butylene succinate) or copolymer thereof may be used to prepare the screws and interference screws. Example 8 discloses the manufacture of an interference screw by injection molding. The torsional strength of screws made from PBS and copolymer thereof is preferably between 10 Ncm and 18 Ncm. An example of an interference screw made from a PBS copolymer with a torsional strength of 15.0 Ncm is shown in Example 8. In comparison, a commercially available interference screw, the Arthrex Biointerference Screw, comprising poly-L-lactic acid, failed at an average torque of 12.1 Ncm. The torsional strength of an implant comprising a polymeric composition of PBS or copolymer thereof may be further increased by blending the polymeric compositions with a ceramic, medical glass or bio-active glass prior to injection molding. A suitable ceramic is tri-calcium phosphate. Suitable blend ratios are 10-50 wt. % ceramic. Interference screws prepared with a ceramic may have torsional strengths of at least 10-20 Ncm. Example 8 demonstrates how the torsional strength of an interference screw comprising poly(butylene succinate) copolymer can be increased from 15.0 Ncm to 18.2 Ncm when the copolymer is blended with a ceramic, namely beta-tri-calcium phosphate (beta-TCP). In an embodiment, screws, including interference screws and/or bone screws, comprising poly(butylene succinate) or copolymers thereof, have one or more of the following properties: torsional strengths of 10 to 20 Ncm, melting temperatures of 115±15° C., yield strengths of 0.03 to 3 GPa, and a weight average molecular weight that decreases by one or more of the following: 5-20% over a 4-8 week time period, 20-35% over a 12-week time period, or 35-50% over a 26-week time period under physiological conditions when the screw, interference screw, or bone screw, is implanted in vivo.

(ii) Meniscal Implants

In an embodiment, the orthopedic implants may be meniscal implants, including meniscus anchors. Polymeric compositions comprising poly(butylene succinate) or copolymer thereof may be used to prepare the meniscal implants and meniscus anchors. For example, the orthopedic implants may replace the meniscus anchors used in the Smith & Nephew Fast Fix 360 meniscus repair system. The meniscus anchors may comprise one or more holes, preferably two holes. Suture, either permanent suture or absorbable suture, may be threaded through the one or more holes of the meniscus anchor. A preferred suture size for this purpose is size 2/0, but may be from size 5/0 to size 1. In a preferred embodiment, a meniscus repair system comprises two meniscus anchors connected with suture, or threaded on suture. Preferably, the meniscus anchors of the repair system can be secured in place at the implant site to repair the meniscus with suture using a sliding knot. The meniscus anchor(s) may be loaded into a delivery device in order to deliver them to the implant site. The delivery device may comprise a needle designed to penetrate the meniscus. The meniscus anchor may be prepared by injection molding, for example, using the conditions described above. Alternatively, the meniscus anchor may be formed by pultrusion and machining, or by machining of extrudate. The meniscus anchor may be formed directly with one or more holes, or one or more holes may be drilled in a subsequent step. The meniscus anchor may have any shape and size that provides a secure and safe meniscus repair. In one embodiment, the meniscus anchor is a rectangular cuboid. In a preferred embodiment, the meniscus anchor has a length of 3 to 20 mm, more preferably 4 to 10 mm, and even more preferably 5 to 7 mm. In an embodiment, the meniscus anchor has a width of 0.3 to 5 mm, and more preferably 1-2 mm, and a depth of 0.3 to 5 mm, and more preferably 1-2 mm. In an embodiment, the meniscus anchors comprise poly(butylene succinate) or copolymers thereof, and have one or more of the following properties: Young's Modulus of 0.03 to 5 GPa, more preferably 0.1 to 4 GPa, yield strength of 0.02 to 2 GPa, more preferably 0.2 to 1.0 GPa, a melt temperature of 115° C.±20° C., weight average molecular weight of the PBS polymer or copolymer thereof of 10 to 400 kDa, more preferably 50 to 200 kDa, and a weight average molecular weight of the PBS polymer or copolymer that decreases by one or more of the following: 5-20% over a 4-8 week time period, 20-35% over a 12-week time period, or 35-50% over a 26-week time period, under physiological conditions when the meniscus anchor is implanted in vivo. In another embodiment, the meniscus anchor may further incorporate one or more of the following: ceramic, antimicrobial and an antibiotic.

(iii) Suture Anchors (Bone Anchors)

In an embodiment, the orthopedic implants may be suture anchors (otherwise referred to as bone anchors). Suture anchors are medical devices that are commonly used in orthopedic surgery to fix soft tissues, such as ligaments and tendons, to bone. The anchors are inserted into bone, and normally include an eyelet, such as a hole or a loop, through which a suture can be passed to allow attachment of the suture to the anchor. The anchor is usually implanted into a pre-drilled hole, and is typically designed so it screws into bone or is of a shape and size that engages with the bone using an interference fit. The polymeric compositions comprising poly(butylene succinate) or copolymer thereof may be used to form the anchor component of a suture anchor. In another embodiment, the polymeric compositions may further comprise ceramic, bioceramic, medical glass, bio-active glass, and or a bioactive agent. Suitable bioactive agents include antimicrobials, particularly antibiotics. In an embodiment, the anchors may be manufactured from the polymeric compositions by injection molding as described above.

In an embodiment, the suture anchors comprise poly (butylene succinate) or copolymers thereof, and have one or more of the following properties: Young's Modulus of 0.03 to 5 GPa, more preferably 0.1 to 1 GPa, yield strength of 0.02 to 2 GPa, more preferably 0.2 to 1.0 GPa, a melt temperature of 115° C.±20° C., PBS polymer or copolymer weight average molecular weight of 10 to 400 kDa, and more preferably 50 to 200 kDa, and a weight average molecular weight of the PBS polymer or copolymer that decreases by one or more of the following: 5-20% over a 4-8 week time period, 20-35% over a 12-week time period, or 35-50% over a 26-week time period under physiological conditions when the suture anchor is implanted in vivo. In another embodiment, the suture anchors may further incorporate one or more of the following: ceramic, medical glass, bio-active glass, antimicrobial and an antibiotic. In a preferred embodiment, the polymer or copolymer comprises 10-60% weight ceramic.

(iv) Bone Plates

In an embodiment, the orthopedic implants may be bone plates. Polymeric compositions comprising poly(butylene succinate) or copolymer thereof may be used to prepare the bone plates. The bone plates may be used for internal fixation, for example, to repair bone fractures or delivery of a bioactive agent. The bone plates may be used to immobilize the fracture at the facture site. The bone plates may be used to reduce movement at the fracture site, and between bone segments. The bone plates may also be used to reduce a fracture gap, or bridge a bone defect. The bone plates may be used to hold fractured bone or bone segments in position. The bone plates may relieve tensile stresses at the fracture site. The bone plates may also be used to induce some compressive stress at the fracture site. Compressive stress at the fracture site can help to speed up healing. The bone plates are preferably resorbable, and offer an improvement over non-absorbable bone plates such as stainless steel plates that can provide excessive stress-shielding to bone leading to a slow repair, or even osteoporosis. The resorbable bone plates reduce the problems associated with stress-shielding of the bone and fracture by initially provide stress-shielding at the fracture site, but resorbing over time and exposing the bone and fracture to increased tensile stresses as the fracture repairs. The resorbable bone plates are also not as stiff as metal bone plates, such as stainless steel plates, and therefore can improve fracture healing by preventing excessive stress shielding during the early days of repair. Thus, the resorbable bone plates have a more optimal stiffness to promote initial healing, and then degrade to prevent undesired outcomes resulting from prolonged stress-shielding. The resorbable bone plates also allow restoration of vascularity in the area of the bone which can be prevented when permanent bone plates are used. The resorbable bone plates may also be contoured as necessary for fixation which is difficult to achieve with very stiff stainless steel plates. In a preferred embodiment, the bone plates are molded or 3D-printed, and more preferably the bone plates are injection molded.

In comparison to existing resorbable polymers, the bone plates have a unique combination of prolonged tensile strength retention necessary to sustain loads during the bone-healing process, yet prevent long-term stress-shielding. In an embodiment, the bone plates comprise poly (butylene succinate) or copolymers thereof, and have one or more of the following properties: a polymer or copolymer weight average molecular weight that decreases by one or more of the following: 5-20% over a 4-8 week time period, 20-35% over a 12-week time period, or 35-50% over a 26-week time period under physiological conditions, in vivo. In another embodiment, the bone plates may have one or more of the following properties: Young's Modulus of 0.03 to 5 GPa, more preferably 0.1 to 3 GPa, yield strength of 0.02 to 2 GPa, more preferably 0.2 to 1.0 GPa, and a melt temperature of 115° C.±20° C. In another embodiment, the bone plates comprise an absorbable polyester with monomer(s) or hydrolytic degradation products with pKa(s) greater than 4.19. In another embodiment, the bone plates may further incorporate one or more of the following: ceramic, bioceramic, medical glass, bio-active glass, antimicrobial and an antibiotic. In a preferred embodiment, the bone plates comprise 10-60% by weight of ceramic or bioceramic.

In an embodiment, the bone plates are fixated to bone, preferably using screws, pins or wires. In a preferred embodiment, the bone plates may have pre-drilled holes. The pre-drilled holes may be used to fixate the bone plates, for example, using screws.

There is no particular limitation on the use of the bone plates. The bone plates may be used in the repair or healing of weight bearing and non-weight bearing bones, osteofixation, and in osteotomy and bone grafting procedures, however, they are preferably used in non-weight bearing applications, including the mid-facial skeleton and mandible. The bone plates are particularly suitable for use in oral, facial and maxillofacial applications, including fixation of the craniofacial and midfacial skeletons, and zygomatic fractures, mandibular fractures, naso-orbito-ethmoidal fractures, periorbital rim fractures, symphysial fractures, as well as for reconstruction procedures, stabilization of osteotomies, and orthognathic surgery.

(v) Bone Fillers, Substitutes and Putty

In an embodiment, the orthopedic implants may be bone fillers, bone substitutes or bone putty. Polymeric compositions comprising poly(butylene succinate) or copolymer thereof may be used to prepare the bone fillers, substitutes and putty. The bone filler, bone substitute and bone putty implants may be used in procedures where bone re-growth is desired or bone healing is desired, and may be implanted for treatment of a bone defect instead of using autogenous or allogenous bone. For example, these implants may be used in applications such as spinal fusions, fixation of fractures, oncologic surgery, traumatology, revision prosthetic surgery, spinal surgery, and in periodontal surgery. The implants may be used alone or in conjunction with other materials, including bone graft, bone promoting agents, including osteoconductive and osteoinductive agents, ceramics, bioceramics, DMB, medical glass, bio-active glass, and bioactive agents, including anti-microbials and antibiotics, including gentamycin, ciprofloxin and vancomycin. In a preferred embodiment, the polymeric compositions comprising poly (butylene succinate) or copolymer thereof may be used as carrier vehicles, for example, as carrier vehicles for delivery of osteoconductive or osteoinductive materials. In embodiments, the bone fillers, bone substitutes and bone putty may comprise the polymeric compositions and one or more of the following: bone graft, including autograft, allograft and xenograft, demineralized bone matrix, platelet rich plasma, cells, stem cells, ceramics, including hydroxyapatite, tricalcium phosphates (TCP), including α-TCP and β-TCP, calcium sulfate, calcium phosphate, medical glass, bio-active glass, collagen, fibrin, alginate, gelatin, RGD peptides, hydrogels, and growth factors, including bone morphogenic proteins.

In embodiments, the bone fillers, substitutes and putty are formed so that they are easily molded, for example as a workable paste, and may be shaped during surgery to fit contours and may be easily molded into bone defects. In an embodiment, the bone fillers, substitutes and putty may be injected into a bone defect or implant site in need of repair. In embodiments, the bone fillers, substitutes and putty may be formulated so that they have a short setting time. In an embodiment, the bone fillers, substitutes and putty comprise the polymeric compositions wherein the polymeric compositions are present in the form of fibers, preferably between 0-2 cm in length, and more preferably 0.1-0.5 mm in length. In another embodiment, the weight average molecular weight of the polymers in the polymeric compositions is from 1,000-400,000, more preferably 10,000-250,000 Da. The polymeric compositions may be formed into bone fillers, substitutes and putty by methods including, but not limited to, particulate leaching, for example, salt leaching, phase separation, including thermally induced phase separation, foaming, solvent processing, and melt processing. Preferably, the bone fillers, substitutes and putty are formed in a porous form.

(vi) Intramedullary Rods and Nails

In an embodiment, the orthopedic implants may be intramedullary rods, also known as intramedullary nails. The intramedullary rods may be inserted into the medullary cavity of a bone, preferably a long bone of the body. The intramedullary rods are preferably used to treat fractures of the bone, preferably fractures of the long bones. Polymeric compositions comprising poly(butylene succinate) or copolymer thereof may be used to prepare the intramedullary rods. These resorbable implants offer an improvement over intramedullary rods made from metal since they will provide reinforcement and stabilization to the bone during healing of a fracture, but then degrade. In contrast, intramedullary rods made from metals can cause osteoporosis, and can require a second operation for their removal.

In an embodiment, the intramedullary rods may have one or more of the following properties: Young's Modulus of 0.03 to 5 GPa, more preferably 0.1 to 3 GPa, yield strength of 0.02 to 2 GPa, more preferably 0.2 to 1.0 GPa, and a melt temperature of 115° C.±20° C. The rods preferably comprise PBS or copolymer thereof with a weight average molecular weight of 10 to 400 kDa, and more preferably 50 to 200 kDa.

In another embodiment, the polymeric compositions used to prepare the intramedullary rods may further comprise one or more of the following: ceramic, bioceramic, medical glass, bio-active glass, calcium salt and a bioactive agent. Suitable bioactive agents include antimicrobials, particularly antibiotics. The polymeric compositions may contain 5-60% by weight of a ceramic or bioceramic. In an embodiment, the rods may be manufactured from the polymeric compositions by injection molding or pultrusion. In another embodiment, the intramedullary rods may be manufactured using fibers of the polymeric compositions to reinforce the rods.

(vii) Bone Plugs and Cranioplasty Plugs

In an embodiment, the orthopedic implants may be bone plugs, cranioplasty plugs or plugs to cover trephination burr holes. In an embodiment, these plugs may be used to cover trephination burr holes, for example, following neurosurgery. Polymeric compositions comprising poly(butylene succinate) or copolymer thereof may be used to prepare the bone plugs and cranioplasty plugs. The weight average molecular weight of the PBS polymer or copolymer in the implant is preferably 10 to 400 kDa, and more preferably 50 to 200 kDa. These resorbable implants are preferably porous, and preferably can be rapidly infiltrated with marrow, blood, and nutrients for bone growth. The bone plugs and cranioplasty plugs may further comprise one or more of the following: ceramic, DMB, medical glass, bio-active glass, bioceramic, calcium salt and a bioactive agent, including antimicrobial agents and antibiotics. In an embodiment, the polymer or copolymer comprises 10 to 60% weight ceramic or bioceramic. The bone plugs can be manufactured by melt processing, for example, by injection molding. Alternatively, the bone plugs can be manufactured by solution processing, for example by salt leaching and phase separation, including thermally induced phase separation. In a particularly preferred embodiment, the bone plugs are prepared by 3D printing.

Preferably, the percentage porosity of the plugs is selected to allow rapid tissue ingrowth and remodeling of the plug into bone. Percent porosities of 10-90% are preferred, more preferably 20-80% and most preferably 30-70%. The sizes of the pores are selected to allow rapid tissue ingrowth and remodeling into bone. Pore sizes of 0.01 to 5 mm are preferred, more preferably 0.02 to 5 mm and most preferably 0.05 to 5 mm. The pore volumes are selected to allow rapid tissue ingrowth and remodeling into bone. Pore volumes of 0.0001 to 25 mm$^2$ are preferred, more preferably 0.0004 to 25 mm$^2$ and most preferably 0.0025 to 25 mm$^2$.

(viii) Antibiotic Beads

In an embodiment, the orthopedic implants may be antibiotic beads. The antibiotic beads may be used to deliver antibiotic following orthopedic procedures, for example, by incorporation of the beads into a bone filler, a bone substitute, a putty, a bone cement (including adhesives and/or structural fillers) or other orthopedic implant. In another embodiment, the beads may be placed within the bone cavity as a prophylactic to infection prior to inserting another orthopedic device, such as the stem of an artificial replacement joint. The antibiotic beads are useful for delivering a high concentration of antibiotic to the implant site, and in the vicinity of the implant. The antibiotic beads are particularly useful for delivery of a high concentration of antibiotic to a severely infected site. Polymeric compositions comprising poly(butylene succinate) or copolymer thereof may be used to prepare the antibiotic beads. In an embodiment, the weight average molecular weight of the PBS polymer or copolymer thereof is 5 to 400 kDa, and more preferably 10 to 250 kDa. Examples of antibiotics that may be incorporated into the beads are given in Section II.C Bioactive Agents. Preferred antibiotics include vancomycin, gentamycin, metronidazole, and tobramycin.

In embodiments, the antibiotic beads may be prepared by molding of the polymeric compositions. In a particularly preferred embodiment, the antibiotic beads are porous. Porous antibiotic beads can be prepared, for example, by foaming of the polymeric compositions, and molding. Beads may be produced using solution techniques such as oil-in-water emulsions or water-in-oil-in-water triple emulsions. Beads may also be produced by melt extrusion techniques such as underwater pelletization. Porosity can be induced in such beads by including a foaming agent during compounding or pelletization. Beads may also be prepared through a combination of techniques such as particle reduction followed by spherification to form spherical beads in a heated non-solvent or oil.

Although a preferred use of the antibiotic beads is in orthopedic applications, the antibiotic beads disclosed herein may be used in other applications, particularly where infections exist or there is a possibility of infection occurring. In embodiments, the antibiotic beads may be used in wound management, for example, in the treatment of ulcers, and also in embolization procedures.

(ix) Joint Spacers

In an embodiment, the orthopedic implants may be joint spacers or interpositional spacers for placement between the bones of a joint. Polymeric compositions comprising poly (butylene succinate) or copolymer thereof may be used to prepare the joint spacers. The PBS polymer of copolymers thereof preferably have a weight average molecular weight of 10 to 400 kDa, and more preferably 50 to 200 kDa. The implants may be inserted in joints, particularly degenerative joints, joints requiring resurfacing, and in joints of patients with osteoarthritis or rheumatoid arthritis. The joint spacers offer an improvement over other surgical options by preserving more joint tissue, and eliminating the need to remove bone.

In a preferred embodiment, the joint spacers are implanted in the carpometacarpal joint of the thumb between the trapezial bone and the first metacarpal bone. In another preferred embodiment, the joint spacers are implanted in the scaphotrapeziotrapezoid (STT) joint. The joint spacers are designed to separate the bone edges of the joint.

In embodiments, the joint spacers may have a "T" or "L" shape, where the vertical portion separates the bone edges when the spacer is inserted into the joint, and the horizontal portion stabilizes the joint. Preferably, the joint spacers can be trimmed prior to implantation or post-implantation. The joint spacers may be fixated after implantation with, for example, screws, pins or sutures.

The joint spacers are preferably porous, and preferably allow tissue in-growth. In embodiments, the joint spacers are made from textiles comprising the polymeric compositions, including woven, knitted and non-woven textiles. The joint spacers may also be made by 3D-printing, and from foams and other porous constructs.

The percentage porosity of the spacer is selected to preferentially allow rapid tissue ingrowth into the spacer and remodeling. Percent porosities of 10-90% are preferred, more preferably 20-80% and most preferably 30-70%. The sizes of the pores preferentially allow rapid tissue ingrowth and remodeling. Pore sizes of 0.01 to 5 mm are preferred, more preferably 0.02 to 5 mm and most preferably 0.05 to 5 mm. The pore volumes are selected to preferentially allow rapid tissue ingrowth and remodeling. Pore volumes of 0.0001 to 25 mm$^2$ are preferred, more preferably 0.0004 to 25 mm$^2$ and most preferably 0.0025 to 25 mm$^2$.

(x) Interosseous Wedge

In an embodiment, the orthopedic implants may be interosseous wedge implants. The interosseous wedge implants may be used in an opening osteotomy procedure, wherein the implants are inserted into an osteotomy site. In an embodiment, the interosseous wedge implants may be inserted into an osteotomy of the tibia or femur. For example to relieve pressure on the knee joint. However, their use is not limited to the tibia or femur, and may include other bones including other long bones. Polymeric compositions comprising poly(butylene succinate) or copolymer thereof may be used to prepare the interosseous wedge implants. The PBS polymer or copolymer preferably has a weight average molecular weight of 10 to 400 kDa, and more preferably 50 to 200 kDa. The interosseous wedge implants are preferably resorbable, and preferably the interosseous wedge implants are porous. In embodiments, the porosity (the amount of void space) of the interosseous wedge implant is at least 30% by volume, and more preferably at least 50% by volume. The interosseous wedge implants will preferably allow bone in-growth, and be replaced after implantation with new bone. In a preferred embodiment, the interosseous wedge implants have a wedge shape, or slice shape, however, the interosseous wedge implants may further comprise a plate to allow fixation to bone. The interosseous wedge implants may be fixated in place, for example, with screws or more preferably with a bone plate and screws.

The interosseous wedge implants may further comprise one or more of the following: ceramic, bioceramic, medical glass, bio-active glass, DMB, calcium salt, bio-active glass, bone graft, osteoconductive and osteoinductive materials, collagen, antimicrobial and antibiotic. In an embodiment, the PBS polymer or copolymer contains 10 to 60% weight ceramic or bioceramic.

The interosseous wedge implants may be prepared by melt processing, for example, by molding, including injection molding. Alternatively, the implants may be prepared by solution processing, for example, by salt leaching and phase separation, including thermally induced phase separation. In a preferred embodiment, the interosseous wedge implants are prepared by 3D printing.

At time of implantation, the interosseous wedge preferably has a compressive yield load greater than that of the bone at the implantation site to prevent deformation under relevant loads. This load strength will depend on the repair site as load bearing applications in the knee may be different, for instance, than in the foot, arm, elbow or hand.

(xi) Tendon and Ligament Repair and Replacement

In embodiments, PBS and copolymers thereof can be formed into implants for the repair or replacement of tendons and ligaments. Suitable implants may be fabricated from high strength fibers of PBS and copolymer thereof. Preferably, the fibers are oriented. Suitable implants may be formed from monofilament fibers, multifilament fibers, and braids thereof. In embodiments, the implants comprise the fibers formed into cords, cables, ribbons, tapes or braids. The implants preferably have prolonged strength retention, and retain at least 65% of their initial strength at 12 weeks post-implantation. In embodiments, the size of the implant for the repair or replacement of tendons and ligaments fabricated from fibers of PBS and copolymer thereof is sized to match the size (length, width and thickness) of the ligament or tendon that it will replace. For example, an implant to replace the anterior cruciate ligament (ACL) may be designed with a diameter of 6 to 12 mm. In embodiments, the implant for the repair or replacement of tendons and ligaments may have a tensile load at break in the range of 10 to 1,600 N. In embodiments, the implant may further comprise a biologic component. For example, the implant may further comprise allograft, xenograft, acellular tissue matrix, or a collagen-containing tissue. In embodiments, the implant may be formed from a sheath of the biologic component surrounding fibers of PBS or copolymer thereof.

In embodiments, the implants are designed for repair or replacement of the ACL, and have one or more of the following properties: failure load of 1200-2400 N, stiffness 150-300 N/mm, failure stress of 18-28 MPa, strain at failure of 20-35%, and a modulus of elasticity of 75-180 MPa.

(xv) Cartilage Repair and Replacement

In embodiments, PBS and copolymers thereof may be formed into implants for the repair or replacement of cartilage. In embodiments, the PBS or copolymers thereof may be formed into porous scaffolds for cartilage repair or replacement. In embodiments, the porous scaffolds are three-dimensional. In embodiments, the porous scaffolds have average pore diameters larger than 50 microns, more preferably larger than 100 microns, and even more preferably larger than 200 microns, but less than 5 mm. In embodiments, the porosity of the implant is between 25% and 70%, and more preferably between 35% and 60%. In embodiments, the volume occupied by PBS or copolymer thereof is 30% to 75%. In embodiments, the implants further comprise cells. In embodiments, the cells may be selected from one or more of the following: autologous cells, stems cells, progenitor cells, fibroblasts, chondrocytes, mesenchymal stem cells, embryonic stem cells, amniotic fluid-derived stem cells, and autologous adult stems cells. In embodiments, the implants further comprise a bioactive agent.

Accordingly, in the context of orthopedic implants, the present invention also provides subject matter defined by the following numbered paragraphs:

Paragraph 1. An orthopedic implant comprising a polymeric composition,
(a) wherein the polymeric composition comprises a 1,4-butanediol unit and a succinic acid unit and optionally, isotopically enriched;
(b) wherein the orthopedic implant has one, two, or more properties selected from the group consisting of: a Young's modulus from 0.03 to 5 GPa, a melting point of 115° C.±15° C., a yield strength of 0.02 to 2 GPa, a torsional strength of 5 Ncm to 50 Ncm, and a weight average molecular weight of the polymeric composition of 10 to 400 kDa or 50 to 200 kDa; hydrolytic degradation products with pKa(s) greater than 4.19;
(c) optionally, wherein the weight average molecular weight of the polymeric composition decreases 5% to 20% over a 4 to 8-week time period, or 20-35% over a 12-week time period, or 35-50% over a 26-week time period under physiological conditions, in vivo.

Paragraph 2. The orthopedic implant of Paragraph 1, wherein the polymeric composition: (i) excludes urethane bonds, (ii) is not prepared with a diisocyanate, (iii) comprises 1-500 ppm of one or more, or all, of the following: silicon, titanium and zinc, (iv) excludes tin, or (v) is not a blend of two or more polymers.

Paragraph 3. The orthopedic implant of Paragraph 1, wherein: (a) the polymeric composition further comprises one or more of the following: a second diacid unit, a second diol unit, 1,3-propanediol, 2,3-butanediol, ethylene glycol, 1,5-pentanediol, glutaric acid, adipic acid, terephthalic acid, malonic acid, and oxalic acid; (b) the polymeric composition further comprises one or more of the following: branching agent, cross-linking agent, chain extender agent, and reactive blending agent; or (c) the polymeric compositions further comprise a hydroxycarboxylic acid unit, optionally wherein the hydroxycarboxylic acid unit has two carboxyl groups and one hydroxyl group, two hydroxyl groups and one carboxyl group, three carboxyl groups and one hydroxyl group, or two hydroxyl groups and two carboxyl groups.

Paragraph 4. The orthopedic implant of Paragraph 3, wherein the branching agent, cross-linking agent, or chain extender unit is selected from one or more of the following: malic acid, maleic acid, fumaric acid, trimethylol propane, trimesic acid, citric acid, glycerol propoxylate, and tartaric acid.

Paragraph 5. The orthopedic implant of Paragraph 1, wherein the polymeric compositions comprise succinic acid-1,4-butanediol-malic acid copolyester, succinic acid-1,4-butanediol-citric acid copolyester, succinic acid-1,4-butanediol-tartaric acid copolyester, succinic acid-1,4-butanediol-malic acid copolyester further comprising citric acid, tartaric acid, or a combination thereof, succinic acid-adipic acid-1,4-butanediol-malic acid copolyester, succinic acid-adipic acid-1,4-butanediol-citric acid copolyester, succinic acid-adipic acid-1,4-butanediol-tartaric acid copolyester, or succinic acid-adipic acid-1,4-butanediol-malic acid copolyester further comprising citric acid, tartaric acid, or combinations thereof.

Paragraph 6. The orthopedic implant of Paragraphs 1 to 5, wherein the polymeric composition further comprises one or more of the following: a ceramic, a bioceramic, DMB, medical glass and a bio-active glass.

Paragraph 7. The orthopedic implant of Paragraph 6, wherein the ceramic, bioceramic, DBM, medical glass or bio-active glass is incorporated into the polymeric composition in an amount of 1-70 weight percent.

Paragraph 8. The orthopedic implants of Paragraphs 1-7, wherein the implants further comprise a bioactive agent.

Paragraph 9. The orthopedic implants of Paragraph 8, wherein the bioactive agent is an antimicrobial or antibiotic.

Paragraph 10. The orthopedic implants of Paragraphs 1-9, wherein the implant comprises a fiber, mesh, non-woven, lattice, patch, particle, film, laminate, thermoform, tube, foam, web, molded, pultruded, machined or 3D-printed form.

Paragraph 11. The orthopedic implant of Paragraphs 1 to 9, wherein the orthopedic implant is an interference screw, bone screw, meniscal anchor, meniscus repair device, meniscus regeneration device, pin, screw, bone plate, nail, intramedullary rod or nail, tack, fastener, suture fastener, rivet, staple, fixation device for an implant, tissue engineering device, tissue engineering scaffold, guided tissue repair/regeneration device, bone void filler, bone substitute, bone putty, bone marrow scaffold, clip, clamp, bone graft substitute, suture anchor, bone anchor, ligament repair device, ligament augmentation device, anterior cruciate ligament repair device, tendon repair device, rotator cuff repair device, articular cartilage repair device, osteochondral repair device, spinal fusion device, spinal fusion cage, bone plug, cranioplasty plug, plug to cover or fill a trephination burr hole, antibiotic bead, joint spacer, interosseous wedge, device for treatment of osteoarthritis, cell seeded device, cell encapsulation device, targeted delivery devices, diagnostic devices, rods, devices with biocompatible coatings, prosthetics, controlled release device, or a drug delivery device.

Paragraph 12. The orthopedic implant of Paragraph 11, wherein the implant comprises first and second meniscal anchors derived from the polymeric composition, and suture connecting the first and second meniscal anchors.

Paragraph 13. The orthopedic implant of Paragraph 12, wherein the implant further comprises an element that can fixate the position of the suture relative to the first and second meniscal anchors.

Paragraph 14. The orthopedic implant of Paragraph 13, wherein the element is a knot, a slip knot or a retainer.

Paragraph 15. A device for delivering the orthopedic implant of Paragraphs 12 to 14, wherein the device comprises a cannula, and the first and second meniscal anchors and suture connecting the first and second meniscal anchors are located within the cannula, and may be passed from the cannula.

Paragraph 16. The orthopedic implant of Paragraph 11, wherein the implant is a screw, interference screw or bone screw, and wherein the screw, interference screw or bone screw, has a torsional strength from 10 Ncm to 50 Ncm.

Paragraph 17. The orthopedic implant of Paragraph 11, wherein the implant is a suture anchor, and the suture anchor is connected to a suture comprising poly(butylene succinate) or copolymer thereof.

Paragraph 18. A mesh for use in orthopedic applications formed from a polymeric composition comprising a 1,4-butanediol unit and a succinic acid unit, optionally wherein the units are isotopically enriched, wherein the mesh has a suture pullout strength of 1-20 kgf and an areal density of 5-800 g/cm$^2$.

Paragraph 19. The mesh of Paragraph 18, wherein the polymeric composition further comprises a hydroxycarboxylic acid unit.

Paragraph 20. The mesh of Paragraph 19, wherein the hydroxycarboxylic acid unit is malic acid, tartaric acid or citric acid.

Paragraph 21. The meshes of Paragraph 18-20, wherein the polymeric composition has a melting temperature of 115±15° C.

Paragraph 22. A method of forming the orthopedic implants of Paragraphs 1-9 and Paragraphs 11-17, comprising melt processing the polymeric composition, wherein the method comprises heating the polymeric composition to a temperature between 50° C. and 220° C., and optionally wherein the polymeric composition retains at least 80%, or at least 90% of its weight average molecular weight during processing.

Paragraph 23. The method of Paragraph 22, wherein the moisture content of the polymeric composition prior to heating is less than 2,000 ppm, or less than 500 ppm.

Paragraph 24. The method of Paragraph 22, wherein the polymeric composition further comprises a ceramic, medical glass or bio-active glass in an amount between 1-70 wt. %.

Paragraph 25. The method of Paragraph 22, wherein the polymeric composition further comprises a hydroxycarboxylic acid unit, and wherein the weight average molecular weight of the polymeric composition increases during heating of the polymeric composition.

Paragraph 26. The method of Paragraph 25, wherein the hydroxycarboxylic acid is malic acid, citric acid or tartaric acid.

Paragraph 27. The method of Paragraphs 22-26, wherein the orthopedic implants are injection molded, and the temperature of the mold is from 0° C. to 60° C.

Paragraph 28. The method of Paragraphs 22-26, wherein the orthopedic implants are 3D printed, optionally by selective laser melting, melt extrusion deposition, fixed pellet deposition or fused filament deposition.

Paragraph 29. The method of Paragraphs 22-26, wherein the polymeric composition is melt extruded, melt-blown, melt-spun, compression molded, laminated, foamed, thermoformed, pultruded, molded, or spun-bonded.

Paragraph 30. The method of Paragraph 29, wherein the polymeric composition is melt extruded to form a yarn or fiber, wherein the yarn or fiber is produced by a method comprising the steps of: (a) spinning the polymeric composition to form a multifilament yarn or monofilament fiber, (b) one or more stages of drawing the multifilament yarn or monofilament fiber with an orientation ratio of at least 3.0 at a temperature of 50-70° C., (c) one or more stages of drawing the multifilament yarn or monofilament fiber with an orientation ratio of at least 2.0 at a temperature of 65-75° C., and (d) drawing the multifilament yarn or monofilament fiber with an orientation ratio greater than 1.0 at a temperature of 70-75° C.

Paragraph 31. The method of Paragraph 30, wherein the yarn or fiber is drawn in a conductive liquid chamber.

Paragraph 32. The method of Paragraph 30, wherein the multifilament yarn or monofilament fiber is spun in a temperature range of 60-230° C., 80-180° C., 80-175° C., or 80-170° C.

Paragraph 33. A method of forming the orthopedic implants of Paragraphs 1-9 and Paragraphs 11-17, comprising solution processing the polymeric composition, wherein the method comprises dissolving the polymeric composition in a solvent, and optionally wherein the polymeric composition retains at least 80%, or at least 90% of its weight average molecular weight during processing.

Paragraph 34. The method of Paragraph 33, wherein the polymeric composition is dry spun, foamed, fabricated into a non-woven or particles, or processed by centrifugal spinning.

Paragraph 35. A method of using the orthopedic implants of Paragraphs 1-17, wherein the implant is implanted in the body.

The present application also discloses an implantable device for osteo and osteochondral or connective tissue repair comprising a matrix formed from a polymeric composition, the matrix including a series of channels communicating between the upper and lower surface of the device which are effective to allow passage of cells and nutrients through the device, wherein:
- (a) the polymeric composition comprises a 1,4-butanediol unit and a succinic acid unit and are optionally, isotopically enriched;
- (b) optionally, the polymeric composition has one, two, or more properties selected from the group consisting of: a Young's modulus from 0.03 to 5 GPa, a melting point of 115° C.±15° C., a yield strength of 0.02 to 2 GPa, a torsional strength of 5 Ncm to 50 Ncm, and a weight average molecular weight of the polymeric composition of 10 to 400 kDa or 100 to 250 kDa; and
- (c) optionally, wherein the weight average molecular weight of the polymeric composition decreases 5% to 20% over a 4 to 8-week time period, or 20-35% over a 12-week time period, or 35-50% over a 26-week time period under physiological conditions, in vivo.

In certain embodiments, the implantable device for osteo and osteochondral or connective tissue repair: (i) may have a porosity of the device ranging from between 25 and 70%; (ii) the channels may be formed in a resorbable matrix and optionally, the matrix may comprise fibers, braids or a textile, optionally comprising the polymeric composition, which is structure aligned substantially parallel to the axis of the device, and further optionally the matrix may be knitted, braided, woven, embroidered, or extruded; (iv) the matrix or channels may be formed by stereolithography, drilling, molding or extrusion; (v) the device may be cylindrical, for example a cylinder with a diameter of between 1 and 20 mm; (vi) the surface of the channels may be coated with a medical glass, bio-active glass, bioceramic, such as a bioceramic selected from α-tricalcium phosphate (TCP), β-TCP, a combination of α- and β-TCP, calcium sulfate, calcium carbonate, or a calcium phosphate salt-based bioceramic, and optionally wherein a region of the device or channels is not coated with bioceramic; (vii) a polymer gel may be impregnated into the device, such as a polymer gel that is comprised of hyaluronic acid or carboxymethylcellulose, or a polymer gel that contains a particulate bioceramic; (viii) a bioactive agent may be added to the device immediately prior to implantation in the patient, for example wherein the bioactive agent is autologous bone marrow aspirate or platelet rich plasma. In a preferred embodiment, the implantable device for osteo and osteochondral or connective tissue repair comprises a resorbable matrix that is a textile structure comprising braided resorbable polymeric fibers with the axis of the braids aligned substantially parallel to the axis of the device and including a series of channels communicating between the upper and lower surface of the device which are effective to allow passage of cells and nutrients through the device.

G. Hernia Repair Devices

As discussed elsewhere in the present application, hernia repair devices, including meshes, may be prepared from polymeric compositions comprising poly(butylene succinate) or copolymers.

The present application further discloses that resorbable polymeric compositions comprising poly(butylene succinate) or copolymers can be processed into fibers, converted into textile constructs such as knitted and woven meshes, and subsequently formed into three-dimensional shapes suitable for tissue reinforcement and hernia repair.

The three-dimensional shapes may be temporarily deformed to allow their implantation by minimally invasive methods, and will then resume their original three-dimensional shape.

More specifically, resorbable three-dimensional implants formed from polymeric compositions comprising poly(butylene succinate) or copolymer, that can be temporarily deformed, implanted by minimally invasive means, and resume their original shape in vivo, have been developed. These implants are particularly suitable for use in minimally invasive procedures for tissue reinforcement, the repair of hernias, and applications where it is desirable for the implant to contour in vivo to an anatomical shape, such as the inguinofemoral region. In the preferred embodiment, the implants are made from meshes of PBS mono- or copolymer monofilament that have reinforced outlying borders that allow the meshes to form three-dimensional shapes that can be temporarily deformed. These implants can resume three-dimensional shapes after being temporarily deformed that contour to the host's tissue or an anatomical shape, for example, in the repair of a hernia, and particularly a hernia in the inguinofemoral region. The implants can contour to the host's tissue for example, of the inguinofemoral region, without the implants wrinkling, bunching or folding.

Monofilament meshes of PBS or copolymer thereof can be molded into three-dimensional shapes that can be temporarily deformed, and will resume their original three-dimensional shape provided the outlying border of the three-dimensional shape has been reinforced. In a preferred embodiment, the outlying border is reinforced using a ring of unoriented PBS fiber extrudate or PBS copolymer fiber extrudate.

Certain additives may be incorporated into PBS polymer, copolymers and blends thereof prior to converting these compositions into three-dimensional structures. Preferably, these additives are incorporated during the compounding process to produce pellets that can be subsequently processed into fibers suitable for making the three-dimensional shapes. In another embodiment, the additives may be incorporated using a solution-based process. In a preferred embodiment, the additives are biocompatible, and even more preferably the additives are both biocompatible and resorbable. Suitable additive include those discussed elsewhere in the present application and/or may be one or more of nucleating agents, plasticizers, contrast agents, radiopaque markers and radioactive substances.

If desired, the PBS polymer and copolymers thereof used to make the three-dimensional shapes may incorporate bioactive agents. These bioactive agents may be added during the formulation process, during pelletization or blending, or may be added later to the fibers or meshes. Suitable bioactifve agents include those discussed elsewhere in the present application and include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, anesthetics, hormones, antibodies, growth factors, extracellular matrix or components thereof (fibronectin, laminin, vitronectin), integrins, antibiotics, steroids, hydroxyapatite, silver particles or silver ions, vitamins, non-steroidal anti-inflammatory drugs, chitosan and derivatives thereof, alginate and derivatives thereof, collagen, hyaluronic acid and derivatives thereof, allograft material, xenograft material, and ceramics. Representative materials include proteins, peptides, sugars, polysaccharides, nucleotides, oligonucleotides, lipids, lipoproteins, nucleic acid molecules such as antisense molecules, aptamers, siRNA, and combinations thereof.

Accordingly, in the context of hernia repair devices, the present invention also provides subject matter defined by the following numbered paragraphs:

Paragraph 1. A reinforced absorbable three-dimensional implant comprising monofilament and/or multifilament fibers, or a porous film, for hernia repair or pelvic floor repair procedures, including treatment of pelvic organ prolapse, including treatment of cystocele, urethrocele, uterine prolapse, vaginal fault prolapse, enterocele and rectocele, that can be temporarily deformed and unaided assumes its original three-dimensional shape, wherein the monofilament and/or multifilament fibers, or a porous film, is formed from a polymeric composition that comprises a 1,4-butanediol unit and a succinic acid unit and optionally, is isotopically enriched, and preferably wherein the polymeric composition that comprises a 1,4-butanediol unit and a succinic acid unit is a composition as defined by any of the claims of the present application.

Paragraph 2. The implant of Paragraph 1 comprising braided, woven or knitted fibers.

Paragraph 3. The implant of Paragraph 1 wherein the implant is contoured to fit to a patient's tissue.

Paragraph 4. The implant of Paragraph 3 having minimal buckling, bunching or wrinkling upon placement in a patient.

Paragraph 5. The implant of Paragraph 1 wherein the implant is securable in a patient without fixation.

Paragraph 6. The implant of Paragraph 5 wherein the implant further comprises barbs, fleece, hooks, self-fixating tips, anchoring devices, or micro-grips.

Paragraph 7. The implant of Paragraph 1 wherein the implant further comprises tabs, attachment portions, or straps, and/or sutures with or without needles for fixing the implant to the patient's tissues.

Paragraph 8. The implant of Paragraph 1 wherein the implant can be deformed into a delivery device for placement by a minimally invasive method.

Paragraph 9. The implant of Paragraph 1 shaped to conform to the inguinal anatomy.

Paragraph 10. The implant of Paragraph 1 for laparoscopic or open surgical repair of inguinal hernias.

Paragraph 11. The implant of Paragraph 1 wherein the implant is porous.

Paragraph 12. The implant of Paragraph 1 wherein the implant comprises an outwardly curving exterior, and an inwardly curving interior.

Paragraph 13. The implant of Paragraph 12 wherein the outlying border of the implant is reinforced so that the implant assumes a shape contoured to the patient's inguinal anatomy after being temporarily deformed.

Paragraph 14. The implant of Paragraph 13 wherein the outlying border is reinforced by a continuous or interrupted ring of: filament, thread, strand, string, fiber, yarn, wire, film, tape, tube, fabric, felt, mesh, multifilament, monofilament, or fiber extrudate.

Paragraph 15. The implant of any one of Paragraphs 1 to 14 wherein the implant comprises a monofilament, multifilament or hybrid mesh.

Paragraph 16. The implant of Paragraph 15 wherein the implant comprises a monofilament mesh with an outlying border reinforced by a continuous ring of monofilament.

Paragraph 17. The implant of any one of Paragraph 1 to 16 wherein the implant comprises a PBS or copolymer thereof.

Paragraph 18. The implant of Paragraph 17 wherein the implant is made from PBS or copolymer thereof.

Paragraph 19. The implant of Paragraph 18 comprising monofilament fibers of PBS or a copolymer thereof having one or more of the following properties:
(i) diameters ranging from 10 µm to 1 mm;
(ii) orientation;
(iii) tensile strength between 400 MPa and 1200 MPa;
(iv) elongation to break of 10% to 50%; and
(v) Young's Modulus of less than 5.0 GPa, and preferably at least 600 MPa, at least 1 GPa, or at least 2 GPa, but less than 3 GPa.

Paragraph 20. The implant of claim 18 wherein the implant has one or more of the following properties:
(i) a suture pullout strength of at least 10 N, or at least 20 N;
(ii) a burst strength greater than 0.1 kPa;
(iii) pore diameters of at least 50 µm; and
(iv) a Taber stiffness of at least 0.01 Taber stiffness units.

Paragraph 21. The implant of any one of Paragraphs 1 to 20 comprising one or more of the following: plasticizer, nucleant, dye, medical marker, bioactive agent, therapeutic agent, diagnostic agent, prophylactic agent.

Paragraph 22. The implant of Paragraph 21 comprising one or more of contrast agent, radiopaque marker, radioactive substance, hyaluronic acid or derivative thereof, collagen, hydroxyapatite, or absorbable polymer comprising one or more the following monomeric units: glycolic acid, lactic acid, trimethylene carbonate, p-dioxanone, and caprolactone.

Paragraph 23. A method of forming the implant of any of Paragraphs 1 to 22, the method comprising the steps of:
providing a split metal form consisting of an inwardly curving half and a mating outwardly curving half wherein there is a semicircular groove in the outlying border of the inwardly curving half; placing a filament, thread, strand, string, fiber, yarn, wire, film, tape, tube, fabric, felt, mesh, multifilament, monofilament or fiber extrudate in the semicircular groove so that it forms a ring around the outlying border of the inwardly curving half,
wherein the filament, thread, strand, string, fiber, yarn, wire, film, tape, tube, fabric, felt, mesh, multifilament, monofilament or fiber extrudate is preferably formed from a polymeric composition that comprises a 1,4-butanediol unit and a succinic acid unit and optionally, is isotopically enriched, and more preferably wherein the polymeric composition that comprises a 1,4-butanediol unit and a succinic acid unit is a composition as defined by any of the claims of the present application;
draping an absorbable mesh comprising monofilament fibers or a porous film over the inwardly curving half of the metal form,
wherein the monofilament fibers or a porous film is preferably formed from a polymeric composition that comprises a 1,4-butanediol unit and a succinic acid unit and optionally, is isotopically enriched, and more preferably wherein the polymeric composition that comprises a 1,4-butanediol unit and a succinic acid unit is a composition as defined by any of the claims of the present application;
placing the mating outwardly curving half of the metal form over the absorbable mesh or porous film, and clamping the two halves of the split metal form together to form a block;
heating the block;
cooling the block;

removing the absorbable three-dimensional shaped implant from the block;

trimming the outlying border; and optionally forming barbs, fleece, hooks, self-fixating tips, anchoring devices or micro grips on one side of the implant.

Paragraph 24. The method of Paragraph 23 wherein the semicircular groove is in the outwardly curving half of the metal form instead of the inwardly curving half, and a filament, thread, strand, string, fiber, yarn, wire, film, tape, tube, fabric, felt, mesh, multifilament, monofilament or fiber extrudate is placed in the groove on the outwardly curving half of the metal form.

Paragraph 25. The methods of either of Paragraph 23 or 24 wherein the absorbable mesh is a monofilament mesh.

Paragraph 26. The method of Paragraph 25 wherein the monofilament mesh comprises PBS or copolymer thereof, and a monofilament fiber extrudate of PBS or copolymer thereof, or poly-4-hydroxybutyrate or copolymer thereof, is used to reinforce the outlying border.

Paragraph 27. The method of Paragraph 26 wherein the block is heated using
(i) hot water at 56° C. for 5 minutes and cooled by placing in a water bath at ambient temperature, or
(ii) conduction, convection or radiant heating and cooling to ambient temperature.

Paragraph 28. The method of Paragraph 25 wherein welding is used to reinforce the outlying border.

Paragraph 29. The method of Paragraph 23 wherein the mesh comprises loops that are shaved to form barbs, fleece, hooks, self-fixating tips, anchoring devices or micro grips.

Paragraph 30. The method of any one of Paragraphs 23 to 29 wherein the implant is sterilized and packaged.

Paragraph 31. A method of using any of the implants of any one of Paragraph 1 to 22, wherein the implants are implanted in the body after being temporarily deformed.

Paragraph 32. The method of Paragraph 31, wherein the implant is delivered by a minimally invasive technique.

Paragraph 33. The method of Paragraph 32 wherein the implant is delivered laparoscopically for repair of an inguinal hernia H. Other Implants In an embodiment, absorbable stents may be prepared from poly(butylene succinate) or copolymers thereof by first producing a tubular stent blank. Tubes may be prepared by melt extrusion, injection molding, solvent dipping, or similar processes that yield a tube with consistent wall thickness of approximately 0.001 to 0.500 mm. The stent structure may be cut into the blank using mechanical or laser processes to remove material from selected areas of the tube blank. The stent may be delivered to a location of the body and deployed by balloon expansion, or removed from a sheath in the body and allowed to self-deploy if the stent is self-expanding. The stent structure provides support to the adjacent tissue and/or delivers therapeutic agents that may be included in the stent material or coated onto its surface.

In another embodiment, microbeads may be prepared from poly(butylene succinate) or copolymers thereof using solvent techniques or melt processing approaches. The microbeads may contain a therapeutic agent and may deliver that agent to the tissue after injection into the tissue. The beads may also be used to occlude a blood vessel or provide additional volume to the tissue.

In embodiments, poly(butylene succinate) or copolymer thereof may be used to prepare theranostic agents, or multifunctional agents, for example, for diagnosis and therapy. In embodiments, poly(butylene succinate) or copolymer thereof may be combined with agents capable of providing image contrast, and that are also able to generate heat upon near-infrared laser irradiation. For example, composites of poly(butylene succinate) or copolymer thereof with metal particles, such as gold. In embodiments, the composites are nanoparticles or microparticles.

In a further embodiment, staple line reinforcement material may be prepared from the poly(butylene succinate) or copolymers thereof using methods to prepare medical textiles such as knitting, weaving, or non-woven processes. Alternatively, the staple line reinforcement materials may be produced from porous foams of poly(butylene succinate) or copolymers thereof. The staple line reinforcing material may be used to provide a backing material to weakened or friable tissue that could not reliably support a surgical staple or suture. In this way, the staple line reinforcement material may also function as a pledget or backing material for a surgical suture. Additionally, the staple line reinforcing material may also be used to seal a tissue and prevent leakage of air, blood or other body fluids during a surgical repair. This can facilitate a procedure allowing a surgeon to more quickly, consistently and reliably make a surgical resection, staple line reinforcing material repair, or anastomosis to tissues such as the lungs, blood vessels, bowel or similar tissues.

In another embodiment, absorbable clips for tissue ligation may be prepared from poly(butylene succinate) or copolymers thereof using melt processing techniques such as injection molding or 3D printing. The absorbable clips may be used when a permanent clip is not desired or to treat a temporary condition. Absorbable clips or cuffs may be useful to prevent or stop bleeding, to restrict flow of material or liquid through a vessel. Bariatric clips or cuffs may be preferred for treating obesity or eating disorders and may be preferred over permanent, invasive surgeries.

In yet another embodiment, absorbable filters to trap blood clots may be prepared from the poly(butylene succinate) or copolymers thereof. Such vena cava filters may be preferred over permanent metal or polymer filters as they could obviate the need for a second procedure to remove the filter after the need for the filter has passed.

I. Embolization

In embodiments, particles of poly(butylene succinate) and copolymers thereof may be prepared for use as embolization agents. Such agents may be preferable in certain applications because the particles will degrade, and leave no foreign body behind after embolization has been achieved. The embolization particles may comprise other components such as imaging, contrast, or dyes, cell adhesion factors, anti-angiogenic agents, and/or drugs (that can be eluted and used for example in chemoembolization for the treatment of cancers).

In embodiments, the embolization particles have diameters ranging from 10 µm to 2,000 µm, and can be formed in the form of dry powder or suspended in solution. The particles may be further sieved into more narrowly defined size ranges, for example, with distributions in sizes between the particles of 10-300 µm, and more preferably 10-200 µm. The exact size ranges required for each procedure can be readily determined by those skilled in the art.

In embodiments, the particles for embolization remain sufficiently long to achieve embolization. In embodiments, the particles for embolization remain long enough to allow tissue in-growth at the embolization site, and permanent embolization. In embodiments, the particles remain for at least 2 weeks, more preferably at least 4 weeks, and even more preferably at least 12 weeks at the embolization site.

In embodiments, the particles may comprise a dye, imaging agent, contrast agent, cell-adhesion factor, anti-angiogenic agent, and/or drug. Cell adhesion promoters include, but are not limited to, CM dextran, collagen, DEAE dextran, gelatin, glucosaminoglycans, fibronectin, lectins, polycations, and natural biological or synthetic cell adhesion agents. Examples of dyes that can be used to make direct visualization of the particles in vivo possible, include, but are not limited to, Cibacron Blue and Procion Red HE-3B. Examples of imaging agents, include, but are not limited to, magnetic resonance imaging agents such as erbium, gadolinium and magnetite. Examples of contrast agents that can be used include, but are not limited to, barium or iodine salts, iodipamide, and amino-3-triiodo-2, 4, 6-benzoic acid, or iodine containing contrast agents such as iopamidol (Isovue), iohexol (Omnipaque), iopromide (Ultravist), ioversol (Optiray) and or ioxilan (Oxilan).

In embodiments, the embolization particles are prepared by an oil in water emulsion technique. In embodiments, the particles may be formed by dissolving poly(butylene succinate) or copolymer thereof in a suitable solvent, such as methylene chloride, to form a polymer solution, slowly adding the solution with rapid stirring to an aqueous solution of polyvinyl alcohol, and allowing the methylene chloride to evaporate. After the solvent has evaporated, the stirring is stopped, and the particles comprising poly(butylene succinate) or copolymer thereof collected. The particles may be washed, for example, with water. The particles may be sieved to select specific particle size ranges. Particle size may also be controlled by stirring at different speeds, for example, stirring more slowly to form larger particles, and stirring faster to form smaller particles. In embodiments, an overhead stirrer may be used to form the particles, and the RPM of the stirrer set at speeds from 100 to 1,000 RPM. Particle size may also be controlled by adjusting the concentration of the polymer solution. In embodiments, the concentration of the polymer solution is 0.1 to 40 wt/vol %, and more preferably 1 to 20 wt/vol %. In embodiments, the concentration of the aqueous solution of polyvinyl alcohol is 0.1 to 10 wt/vol %, and more preferably 0.1 to 1 wt/vol %.

In embodiments, the embolization particles are prepared by cutting fibers of poly(butylene succinate) or copolymer thereof into defined lengths. In embodiments, fiber of poly(butylene succinate) or copolymer thereof with a diameter of 50 to 500 μm, and more preferably 200-300 μm, is cut into lengths of 50-500 μm, and more preferably 100-300 μm, to create small embolization particles.

In embodiments, the embolization particles are prepared by extruding poly(butylene succinate) or copolymer thereof underwater using a palletization process.

In embodiments, the embolization particles are sterilized by exposure to ethylene oxide gas, peracetic acid, hydrogen peroxide, nitrogen dioxide, chlorine dioxide, gamma-irradiation or electron beam.

In embodiments, the particles may be suspended without forming agglomerates prior to use. In embodiments, the particles are administered for embolization as an injectable suspension with a suitable liquid carrier, for example, a physiologically acceptable liquid carrier. In embodiments, the particles are suspended in a saline solution, aqueous solution, solutions containing density modifying agents, or solution containing sugars. These solutions may also comprise marking agents, contrast agents, imaging agents, or therapeutic drugs. In embodiments, the saline solution has a concentration of 0.1-5 wt/vol %.

In embodiments, embolization is achieved by administering to a human or animal an injectable suspension comprising an effective amount of the particles. The diameters of the particles are preferably 10 μm to 2,000 μm. The size of the dose of the particles will vary with the nature, type, location and severity of the condition to be treated and the route of administration. As well as with the age, weight and response of the patient. In embodiments, an effective amount of particles for embolization may range from a few dozen particles to a few hundred particles. In embodiments, embolization particles with given size ranges are administered to a human or animal, for example, particle size ranges of 300-500 μm, 500-700 μm and 700-900 μm. Any suitable route may be used to administer the particles, including parenteral, subcutaneous or intramuscular, provided that it provides the patient with an effective dose at the desired target or location. A preferred route of administration is to the arteries using a catheter.

Conditions and disease states that may be prevented or treated using the embolization particles include, but are not limited to, solid tumors, vascular malformations, and hemorrhagic events or processes. With respect to tumors, the embolization particles may be used to suppress pain, to limit blood loss occurring during surgical intervention following embolization, or to bring on tumoral necrosis and to either avoid or minimize the necessity of surgical intervention. With respect to vascular malformations, the embolization particles may be used to normalize the blood flow to "normal" tissues, to aid in surgery and to limit the risk of hemorrhage. For hemorrhagic events or processes, the embolization particles may be used to reduce blood flow and to promote cicatrization of the arterial opening(s). In addition, the embolization particles may be used as a pre-surgical treatment in order to decrease the blood flow in blood rich organs (e.g., the liver) prior to surgical intervention. Examples of specific conditions that may be prevented or treated by the embolization particles include, but are not limited to: uterine tumors or fibroids; small intestinal hemorrhage, such as that associated with stress ulcer; surgical drain; anastomosis; tuberculous ulcer and nonspecific ulcer; symptomatic hepatic arteriovenous malformation (AVM); primary colorectal cancer; hepatocellular carcinomas; liver metastases; bone metastases; melanomas; cancers of the head or neck; and intracranial meningiomas.

J. Implants Comprising Polymeric Compositions Comprising 1,4-butanediol and a Diacid with a pKa Greater than 4.19

In embodiments, implants are derived from polymeric compositions comprising 1,4-butanediol and a diacid, wherein the diacid has a pKa greater than 4.19. These polymeric compositions form less acidic degradation products in vivo as the polymeric compositions are degraded when compared to many other absorbable polymers, such as polyglycolic acid (PGA), polylactic acid (PLA), poly-L-lactic acid (PLLA), and poly-lactic-co-glycolic acid copolymer (PLGA). The latter polymers breakdown in vivo releasing glycolic acid and or lactic acid. The pKa's of these acids are 3.83 and 3.86, respectively, which is lower than 4.19 (i.e. glycolic acid and lactic acid are stronger acids). Acidic degradation products are not desirable for implants since they can cause local tissue irritation, toxicity, aseptic sinus formation, tissue damage or necrosis at the site of the implant and it is preferred to have less acidic degradation products such as polymeric compositions derived from 1,4-butanediol and a diacid with a pKa greater than 4.19 to avoid such adverse tissue reactions. In embodiments, the diacids with pKa greater than 4.19 are selected from succinic acid, adipic acid, and glutaric acid. In embodiments, the polymeric compositions further comprise a hydroxycarboxylic acid unit. In embodiments, the hydroxycarboxylic acid unit has two carboxyl groups and one hydroxyl group, two hydroxyl groups and one carboxyl group, three carboxyl groups and one hydroxyl group, or two hydroxyl groups and two carboxyl groups. In embodiments, the hydroxycarboxylic acid is malic acid. In embodiments, the implant comprises a monofilament or multifilament fiber derived from the polymeric composition, (a) wherein the multifilament yarn has one or more properties selected from the group consisting of: a tenacity greater than 4 grams per denier but less than 14 grams per denier, an elongation to break of between 15% and 50%, and a denier per filament between 1 and 10; and (b) wherein the monofilament fiber has one or more properties selected from the group consisting of: a tensile strength between 400 MPa and 1200 MPa, a Young's Modulus of less than 5.0 GPa, and an elongation to break of 10% to 50%. In embodiments, the implant comprises a textile derived from the polymeric composition, wherein the textile has one or more of the following properties: (i) a burst strength of 0.1 to 100 kgf, (ii) a suture pullout strength of at least 5 N, or 0.5-20 kgf, an areal density of 5 to 800 g/m$^2$, (iii) a thickness of 0.05-5 mm, (iv) pores with average pore diameters between 5 μm and 5 mm, (v) a Taber stiffness of 0.01-19 TSU, (vi) a tear resistance of 0.1 to 40 kgf, and (vii) a pore size between 0.001 to 10 mm$^2$. In embodiments, the textile is selected from one of the following: mesh, monofilament mesh, multifilament mesh, non-woven, woven mesh, braid, tape, and knitted mesh. In embodiments, the textile is derived by melt-blowing, dry spinning, wet spinning, entangling staple fibers, knitting, weaving, braiding or crocheting of fibers, centrifugal spinning, electrospinning, spun-laiding, spun-bonding, 3D printing, and melt extrusion. In embodiments, the implant is a hernia mesh, breast reconstruction mesh, mastopexy mesh, mesh used as a void filler, a three-dimensional mesh, tendon or ligament repair or replacement device, or a sling. In embodiments, the implant is an orthopedic implant, and the implant has one or more of the following properties: (i) a Young's Modulus of 0.03-5 GPa, (ii) a yield strength of 0.02-2 GPa, or a (iii) torsional strength of 10-20 Ncm.

Accordingly, in the context of implants comprising polymeric compositions comprising 1,4-butanediol and a diacid with a pKa greater than 4.19, the present invention also provides subject matter defined by the following numbered paragraphs:

Paragraph 1. An implant derived from a polymeric composition, wherein the polymeric composition comprises a 1,4-butanediol unit and a diacid unit, wherein the diacid has a pKa greater than 4.19.

Paragraph 2. The implant of paragraph 1, wherein the diacid is selected from the following: succinic acid, adipic acid, and glutaric acid.

Paragraph 3. The implant of paragraph 1, wherein the polymeric composition further comprises a hydroxycarboxylic acid unit.

Paragraph 4. The implant of paragraph 3 wherein the hydroxycarboxylic acid unit has two carboxyl groups and one hydroxyl group, two hydroxyl groups and one carboxyl group, three carboxyl groups and one hydroxyl group, or two hydroxyl groups and two carboxyl groups.

Paragraph 5. The implant of paragraph 1, wherein the implant comprises a monofilament or multifilament fiber derived from the polymeric composition, (a) wherein the multifilament yarn has one or more properties selected from the group consisting of: a tenacity greater than 4 grams per denier but less than 14 grams per denier, an elongation to break of between 15% and 50%, and a denier per filament between 1 and 10; and (b) wherein the monofilament fiber has one or more properties selected from the group consisting of: a tensile strength between 400 MPa and 1200 MPa, a Young's Modulus of less than 5.0 GPa, and an elongation to break of 10% to 50%.

Paragraph 6. The implant of paragraph 1, wherein the implant comprises a textile derived from the polymeric composition, and wherein the textile has one or more of the following properties: (i) a burst strength of 0.1 to 100 kgf, (ii) a suture pullout strength of at least 5 N, or 0.5-20 kgf, (iii) an areal density of 5 to 800 g/m$^2$, (iv) a thickness of 0.05-5 mm, (v) pores with average pore diameters between 5 μm and 5 mm, (vi) a Taber stiffness of 0.01-19 TSU, (vii) a tear resistance of 0.1 to 40 kgf, and (viii) a pore size between 0.001 to 10 mm$^2$.

Paragraph 7. The implant of paragraph 6, wherein the textile is selected from one of the following: mesh, monofilament mesh, multifilament mesh, non-woven, woven mesh, braid, tape, and knitted mesh.

Paragraph 8. The implant of paragraph 7, wherein the textile is derived by melt-blowing, dry spinning, wet spinning, entangling staple fibers, knitting, weaving, braiding or crocheting of fibers, centrifugal spinning, electrospinning, spun-laiding, spun-bonding, 3D printing, and melt extrusion.

Paragraph 9. The implant of paragraph 7, wherein the implant is a hernia mesh, breast reconstruction mesh, mastopexy mesh, mesh used as a void filler, a three-dimensional mesh, tendon or ligament repair or replacement device, or a sling.

Paragraph 10. The implant of paragraph 1, wherein the implant is an orthopedic implant, and wherein the implant has one or more of the following properties: (i) a Young's Modulus of 0.03-5 GPa, (ii) a yield strength of 0.02-2 GPa, or a (iii) torsional strength of 10-20 Ncm.

Paragraph 11. The implant of paragraph 10, wherein the orthopedic implant is a screw, interference screw, pin, meniscal implant, osteochondral implant, suture anchor, bone plate, bone filler or substitute, intramedullary rod, bone plug, cranioplasty plug, joint spacer, or interosseous wedge.

Paragraph 12. A method of forming the implant of paragraph 1, wherein the implant is produced by a method comprising the steps of: (a) preparing the polymeric composition by polymerization of 1,4-butanediol and a diacid, wherein the diacid has a pKa greater 4.19, (b) processing the polymeric composition to form the implant using one of the following methods: melt extrusion, injection molding, melt foaming, film extrusion, melt blowing, melt spinning, compression molding, lamination, thermoforming, molding, spun-bonding, non-woven fabrication, tube extrusion, fiber extrusion, 3D printing, molding, injection molding, compression molding, solvent casting, solution processing, solution bonding of fibers, dry spinning, wet spinning, film casting, pultrusion, electrospinning, centrifugal spinning, coating, dip coating, phase separation, particle leaching, leaching, latex processing, printing of slurries and solutions using a coagulation bath, printing using a binder solution and granules of powder, entangling staple fibers, knitting, weaving, braiding or crocheting of fibers, spun-laiding, and spun-bonding.

Paragraph 13. The method of paragraph 12, wherein the diacid is selected from the group: succinic acid, adipic acid, and glutaric acid.

Paragraph 14. The method of paragraph 12, wherein the polymeric composition further comprises a hydroxycarboxylic acid unit.

Paragraph 15. The method of paragraph 14, wherein the hydroxycarboxylic acid unit has two carboxyl groups and one hydroxyl group, two hydroxyl groups and one carboxyl group, three carboxyl groups and one hydroxyl group, or two hydroxyl groups and two carboxyl groups.

Paragraph 16. The method of paragraph 15, wherein the hydroxycarboxylic acid unit is selected from the group: malic acid, citric acid, and tartaric acid.

Paragraph 17. The method of paragraph 12, wherein the implant comprises a monofilament or multifilament fiber derived from the polymeric composition, and wherein the monofilament or multifilament fiber is produced by a method comprising (a) spinning the polymeric composition to form a multifilament fiber or monofilament fiber, and (b) one or more stages of drawing the multifilament fiber or monofilament fiber with an orientation ratio of at least 3.0 at a temperature of 50-70° C.

Paragraph 18. The method of paragraph 17, wherein (a) the multifilament fiber has one or more properties selected from the group consisting of: a tenacity greater than 4 grams per denier but less than 14 grams per denier, an elongation to break of between 15% and 50%, and a denier per filament between 1 and 10; and (b) the monofilament fiber has one or more properties selected from the group consisting of: a tensile strength between 400 MPa and 1200 MPa, a Young's Modulus of less than 5.0 GPa, and an elongation to break of 10% to 50%.

Paragraph 19. The method of paragraph 17, wherein the implant comprises a textile, and wherein the textile is produced by a method comprising knitting or weaving the monofilament fiber or multifilament fiber to form the textile.

Paragraph 20. The method of paragraph 19, wherein the textile has one or more of the following properties: (i) a burst strength of 0.1 to 100 kgf, (ii) a suture pullout strength of at least 5 N, or 0.5-20 kgf, (iii) an areal density of 5 to 800 g/m$^2$, (iv) a thickness of 0.05-5 mm, (v) pores with average pore diameters between 5 µm and 5 mm, (vi) a Taber stiffness of 0.01-19 TSU, (vii) a tear resistance of 0.1 to 40 kgf, and (viii) a pore size between 0.001 to 10 mm$^2$.

Paragraph 21. The method of paragraph 12, wherein the implant is an orthopedic implant, and wherein the implant is formed by molding or 3D printing and has one or more of the following properties: (i) a Young's Modulus of 0.03-5 GPa, (ii) a yield strength of 0.02-2 GPa, or a (iii) torsional strength of 10-20 Ncm.

Paragraph 22. The method of paragraph 21, wherein the implant is formed by exposing the polymeric composition to a temperature between 70° C. and 170° C.

K. Melt Processed, Unoriented and Oriented Implants Comprising PBS and Copolymers Thereof In embodiments, oriented and unoriented implants, and melt processed implants comprising polymeric compositions of PBS and copolymers thereof with specific weight average molecular weights, and optionally specific polydispersity ranges, have been developed. These weight average molecular weight ranges and optionally polydispersity ranges have been selected based on the ability to process the polymeric compositions, the properties of the implants, and the degradation behavior of the implants in vivo.

It has been discovered that PBS and copolymers thereof should preferably have a weight average molecular weight range of 75,000 to 250,000 Da, more preferably 150,000 to 250,000 Da, and even more preferably 160,000 to 200,000 Da in order that the melt viscosity of the polymer or copolymer is not too high or too low for melt processing, to ensure that the melt processed implant has a sufficiently high weight average molecular weight to provide useful mechanical properties for implant applications, and to ensure that the melt processed implant retains strength sufficiently long in vivo. In embodiments, melt processed implants comprise a polymeric composition, wherein the polymeric composition comprises a 1,4-butanediol unit and a succinic acid unit, and the weight average molecular weight of the polymeric composition is 75,000 to 250,000 Da, more preferably 150,000 to 250,000 Da, and even more preferably 160,000 to 200,000 Da. In embodiments, the polymeric composition has a weight average molecular weight of 75,000 to 250,000 Da, 150,000 to 250,000 Da or 160,000 to 200,000 Da and a polydispersity of between 1 and 10, more preferably between 2 and 8, and even more preferably between 4 and 8. In embodiments, the melt processed implants derived from the polymeric compositions with a weight average molecular weight of 75,000 to 250,000 Da, 150,000 to 250,000 Da or 160,000 to 200,000 Da, and a polydispersity between 1 and 10, 2 and 8, or 4 and 8, have one or more of the following properties: (i) a tensile strength of 400 MPa to 2,000 MPa, (ii) Young's Modulus of 600 MPa to 5 GPa, (iii) elongation to break of 10 to 150%, (iv) tenacity greater than 4 grams per denier but less than 14 grams per denier, an elongation to break of between 15% and 50%, and a denier per filament between 1 and 10 when the implant is a multifilament yarn, (v) tensile strength between 400 MPa and 1200 MPa, a Young's Modulus of less than 5.0 GPa, and an elongation to break of 10% to 50% when the implant is a monofilament fiber, (vi) a burst strength of 0.1 to 100 kgf, suture pullout strength of at least 5 N, or 0.5-20 kgf, areal density of 5 to 800 g/m$^2$, thickness of 0.05-5 mm, pores with average pore diameters between 5 µm and 5 mm, Taber stiffness of 0.01-19 TSU, tear resistance of 0.1 to 40 kgf, and pore size between 0.001 to 10 mm$^2$, when the implant is a textile, including a mesh, monofilament mesh, multifilament mesh, woven mesh, or nonwoven. In embodiments, the melt processed implants are formed by melt extrusion, melt blowing, melt spinning, film extrusion, tube extrusion, spunbonding, fused filament fabrication, fused pellet deposition, and melt extrusion deposition. In embodiments, the melt processed implants are oriented after melting processing. In embodiments, oriented implants comprise a polymeric composition, wherein the polymeric composition comprises a 1,4-butanediol unit and a succinic acid unit, and the weight average molecular weight of the polymeric composition is 75,000 to 250,000 Da, more preferably 150,000 to 250,000 Da, and even more preferably 160,000 to 200,000 Da. In embodiments, the polymeric composition has a weight average molecular weight of 75,000 to 250,000, 150,000 to 250,000 Da, or 160,000 to 200,000 Da and a polydispersity of between 1 and 10, more preferably between 2 and 8, and even more preferably between 4 and 8. In embodiments, the oriented implants derived from the polymeric compositions with a weight average molecular weight of 75,000 to 250, 000, 150,000 to 250,000 Da or 160,000 to 200,000 Da, and a polydispersity between 1 and 10, 2 and 8, or 4 and 8, have one or more of the following properties: (i) a tensile strength of 400 MPa to 2,000 MPa, (ii) Young's Modulus of 600 MPa to 5 GPa, (iii) elongation to break of 10 to 150%, (iv) tenacity greater than 4 grams per denier but less than 14 grams per denier, an elongation to break of between 15% and 50%, and a denier per filament between 1 and 10 when the implant is a multifilament yarn, (v) tensile strength between 400 MPa and 1200 MPa, a Young's Modulus of less than 5.0 GPa, and an elongation to break of 10% to 50% when the implant is a monofilament fiber, (vi) a burst strength of 0.1 to 100 kgf, suture pullout strength of at least 5 N, or 0.5-20 kgf, areal density of 5 to 800 g/m$^2$, thickness of 0.05-5 mm, pores with average pore diameters between 5 µm and 5 mm, Taber stiffness of 0.01-19 TSU, tear resistance of 0.1 to 40 kgf, and pore size between 0.001 to 10 $mm^2$, when the implant is a textile, including a mesh, monofilament mesh, multifilament mesh, woven mesh, or nonwoven. In embodiments, the oriented implants are formed by melt processing followed by orientation. In embodiments, the implants are oriented by stretching the polymeric composition in one or more directions. In embodiments, the melt processed implants or oriented implants may be a: suture, barbed suture monofilament suture, braided suture, mesh suture, surgical meshes (including but not limited to surgical meshes for soft tissue implants for reinforcement of soft tissue, for the bridging of fascial defects, for a trachea or other organ patch, for organ salvage, for dural grafting material, for wound or burn dressing, or for a hemostatic tamponade; or surgical mesh in the form of a mesh plug), surgical tape, wound closure device, resorbable wound closure materials such as suturing and stapling materials, patch (such as, but not limited to, hernial patches and/or repair patches for the repair of abdominal and thoracic wall defects, inguinal, paracolostomy, ventral, paraumbilical, scrotal or femoral hernias, for muscle flap reinforcement, for reinforcement of staple lines and long incisions, for reconstruction of pelvic floor, for repair of rectal or vaginal prolapse, for suture and staple bolsters, for urinary or bladder repair, or for pledgets), wound healing device, wound dressing, burn dressing, ulcer dressing, skin substitute, hemostat, tracheal reconstruction device, organ salvage device, dural patch or substitute, nerve regeneration or repair device, hernia repair device, hernia repair mesh, hernia plug, inguinal hernia plug, device for temporary wound or tissue support, tissue engineering device, tissue engineering scaffold, guided tissue repair/regeneration device, anti-adhesion membrane or barrier, tissue separation membrane, retention membrane, sling, device for pelvic floor reconstruction, device for treatment of pelvic organ prolapse, urethral suspension device, device for treatment of urinary incontinence, device for treatment of stress urinary incontinence, bladder repair device, bulking or filling device, bone marrow scaffold, bone plate, fixation device for an implant, ligament repair device or augmentation device, orthopedic device, anterior cruciate ligament repair device, tendon repair device or augmentation device, rotator cuff repair device, meniscus repair or regeneration device, articular cartilage repair device, osteochondral repair device, spinal fusion device, spinal fusion cage, devices with vascular applications, cardiovascular patch, intracardiac patching or for patch closure after endarterectomy, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, imaging device, cochlear implant, anastomosis device, cell seeded device, cell encapsulation device, targeted delivery devices, diagnostic devices, rods, devices with biocompatible coatings, prosthetics, controlled release device, drug delivery device, plastic surgery device, breast lift device, mastopexy device, breast reconstruction device, breast augmentation device, breast reduction device, breast implant, devices for removal, reshaping and reorienting breast tissue, devices for breast reconstruction following mastectomy with or without breast implants, facial reconstructive device, forehead lift device, brow lift device, eyelid lift device, face lift device, rhytidectomy device, thread lift device, device to lift and support sagging areas of the face, brow and neck, rhinoplasty device, device for malar augmentation, otoplasty device, neck lift device, mentoplasty device, buttock lift device, cosmetic repair device, device for facial scar revision, device for lifting tissues, screw, bone screw, interference screw, pin, ACL screw, clip, clamp, nail, medullary cavity nail, bone plate, bone substitute, including porous bone plate, tack, fastener, suture fastener, rivet, staple, fixation device, bone void filler, suture anchor, bone anchor, meniscus anchor, meniscal implant, intramedullary rod and nail, joint spacer, interosseous wedge implant, osteochondral repair device, spinal fusion device, spinal fusion cage, bone plug, cranioplasty plug, plug to fill or cover a trephination burr hole, orthopedic tape, including knitted and woven tape, and device for treatment of osteoarthritis.

It has been discovered that polymeric compositions comprising PBS and copolymers thereof should preferably have a weight average molecular weight range of 20,000 to 250,000 Da, and optionally a polydispersity of between 1 and 10, more preferably between 2 and 8, and even more preferably between 4 and 8 in order to be able to process the polymeric composition into a useful unoriented implant. When the unoriented implant has a weight average molecular lower than 20,000 Da, the implants have little strength, and in vivo lose integrity too quickly. When the implant has a weight average molecular weight higher than 250,000 Da, degradation times are undesirably prolonged. Processing of the polymeric compositions with weight average molecular weights higher than 250,000 Da also becomes challenging. In embodiments, unoriented implants comprise a polymeric composition, wherein the polymeric composition comprises a 1,4-butanediol unit and a succinic acid unit, and the weight average molecular weight of the polymeric composition is 20,000 to 250,000 Da. In embodiments, the polymeric composition has a weight average molecular weight of 20,000 to 250,000 Da and a polydispersity of between 1 and 10, and more preferably between 2 and 8, and even more preferably between 4 and 8. In embodiments, the unoriented implants derived from polymeric compositions with a weight average molecular weight of 20,000 to 250,000 Da, and a polydispersity between 1 and 10, 2 and 8, or 4 and 8, have one or more of the following properties: (i) a tensile strength of 30 to 60 MPa, (ii) an elongation to break of 40 to 200%, (iii) a Young's Modulus of 0.03 to 5 GPa, or 0.3 to 0.5 GPa, (iv) a yield strength of 0.02 to 2 GPa, and (v) a torsional strength of 10-20 Ncm. In embodiments, the unoriented implants are formed by molding, injection molding, compression molding, solvent casting, 3D printing, solution processing, solution bonding of fibers, dry spinning, film casting, lamination, thermoforming, pultrusion, electrospinning, centrifugal spinning, coating, dip coating, phase separation, particle leaching, leaching, latex processing, printing of slurries and solutions using a coagulation bath, or printing using a binder solution and granules of powder. In embodiments, the unoriented implants may be a: suture, barbed suture monofilament suture, braided suture, mesh suture, surgical meshes (including but not limited to surgical meshes for soft tissue implants for reinforcement of soft tissue, for the bridging of fascial defects, for a trachea or other organ patch, for organ salvage, for dural grafting material, for wound or burn dressing, or for a hemostatic tamponade; or surgical mesh in the form of a mesh plug), surgical tape, wound closure device, resorbable wound closure materials such as suturing and stapling materials, patch (such as, but not limited to, hernial patches and/or repair patches for the repair of abdominal and thoracic wall defects, inguinal, paracolostomy, ventral, paraumbilical, scrotal or femoral hernias, for muscle flap reinforcement, for reinforcement of staple lines and long incisions, for reconstruction of pelvic floor, for repair of rectal or vaginal prolapse, for suture and staple bolsters, for urinary or bladder repair, or for pledgets), wound healing device, wound dressing, burn dressing, ulcer dressing, skin substitute, hemostat, tracheal reconstruction device, organ salvage device, dural patch or substitute, nerve regeneration or repair device, hernia repair device, hernia repair mesh, hernia plug, inguinal hernia plug, device for temporary wound or tissue support, tissue engineering device, tissue engineering scaffold, guided tissue repair/regeneration device, anti-adhesion membrane or barrier, tissue separation membrane, retention membrane, sling, device for pelvic floor reconstruction, device for treatment of pelvic organ prolapse, urethral suspension device, device for treatment of urinary incontinence, device for treatment of stress urinary incontinence, bladder repair device, bulking or filling device, bone marrow scaffold, bone plate, fixation device for an implant, ligament repair device or augmentation device, anterior cruciate ligament repair device, tendon repair device or augmentation device, rotator cuff repair device, meniscus repair or regeneration device, articular cartilage repair device, osteochondral repair device, spinal fusion device, spinal fusion cage, devices with vascular applications, cardiovascular patch, intracardiac patching or for patch closure after endarterectomy, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, imaging device, cochlear implant, anastomosis device, cell seeded device, cell encapsulation device, targeted delivery devices, diagnostic devices, rods, devices with biocompatible coatings, prosthetics, controlled release device, drug delivery device, plastic surgery device, breast lift device, mastopexy device, breast reconstruction device, breast augmentation device, breast reduction device, breast implant, devices for removal, reshaping and reorienting breast tissue, devices for breast reconstruction following mastectomy with or without breast implants, facial reconstructive device, forehead lift device, brow lift device, eyelid lift device, face lift device, rhytidectomy device, thread lift device, device to lift and support sagging areas of the face, brow and neck, rhinoplasty device, device for malar augmentation, otoplasty device, neck lift device, mentoplasty device, buttock lift device, device for lifting tissue, cosmetic repair device, device for facial scar revision, orthopedic device, screw, bone screw, interference screw, pin, ACL screw, clip, clamp, nail, medullary cavity nail, bone plate, bone substitute, including porous bone plate, tack, fastener, suture fastener, rivet, staple, fixation device, bone void filler, suture anchor, bone anchor, meniscus anchor, meniscal implant, intramedullary rod and nail, joint spacer, interosseous wedge implant, osteochondral repair device, spinal fusion device, spinal fusion cage, bone plug, cranioplasty plug, plug to fill or cover a trephination burr hole, orthopedic tape, including knitted and woven tape, and device for treatment of osteoarthritis.

Accordingly, in the context of melt processed, unoriented, and oriented implants, the present invention also provides subject matter defined by the following numbered paragraphs:

Paragraph 1. An implant comprising a polymeric composition, wherein the polymeric composition comprises a 1,4-butanediol unit and a succinic acid unit, wherein:
(a) the polymeric composition has a weight average molecular weight of 75,000 to 250,000 Da, and
(b) the implant has been formed by melt processing of the polymeric composition.

Paragraph 2. The implant of paragraph 1, wherein the polymeric composition has a weight average molecular weight of 150,000 to 250,000 Da or 160,000 to 200,000 Da.

Paragraph 3. The implant of paragraphs 1 and 2, wherein the polymeric composition has a polydispersity between 1 and 10.

Paragraph 4. The implant of paragraph 3, wherein the polymeric composition has a polydispersity between 2 and 8, or 4 and 8.

Paragraph 5. The implant of paragraphs 1-4, wherein the implant has one or more of the following properties: (i) a tensile strength of 400 MPa to 2,000 MPa, (ii) Young's Modulus of 600 MPa to 5 GPa, (iii) elongation to break of 10 to 150%, (iv) tenacity greater than 4 grams per denier but less than 14 grams per denier, an elongation to break of between 15% and 50%, and a denier per filament between 1 and 10 when the implant is a multifilament yarn, (v) tensile strength between 400 MPa and 1200 MPa, a Young's Modulus of less than 5.0 GPa, and an elongation to break of 10% to 50% when the implant is a monofilament fiber, (vi) a burst strength of 0.1 to 100 kgf, suture pullout strength of at least 5 N, or 0.5-20 kgf, areal density of 5 to 800 g/m$^2$, thickness of 0.05-5 mm, pores with average pore diameters between 5 μm and 5 mm, Taber stiffness of 0.01-19 TSU, tear resistance of 0.1 to 40 kgf, and pore size between 0.001 to 10 mm$^2$, when the implant is a textile, including a mesh, monofilament mesh, multifilament mesh, woven mesh, or nonwoven.

Paragraph 6. The implants of paragraphs 1-5, wherein the implants are formed by melt extrusion, melt blowing, melt spinning, film extrusion, tube extrusion, spunbonding, fused filament fabrication, fused pellet deposition, and melt extrusion deposition.

Paragraph 7. The implants of paragraphs 1-6, wherein the implants are oriented after melt processing.

Paragraph 8. The implants of paragraph 7, wherein the implants have one or more of the following properties: (i) a tensile strength of 400 MPa to 2,000 MPa, (ii) Young's Modulus of 600 MPa to 5 GPa, (iii) elongation to break of 10 to 150%, (iv) tenacity greater than 4 grams per denier but less than 14 grams per denier, an elongation to break of between 15% and 50%, and a denier per filament between 1 and 10 when the implant is a multifilament yarn, (v) tensile strength between 400 MPa and 1200 MPa, a Young's Modulus of less than 5.0 GPa, and an elongation to break of 10% to 50% when the implant is a monofilament fiber, (vi) a burst strength of 0.1 to 100 kgf, suture pullout strength of at least 5 N, or 0.5-20 kgf, areal density of 5 to 800 g/m$^2$, thickness of 0.05-5 mm, pores with average pore diameters between 5 μm and 5 mm, Taber stiffness of 0.01-19 TSU, tear resistance of 0.1 to 40 kgf, and pore size between 0.001 to 10 mm$^2$, when the implant is a textile, including a mesh, monofilament mesh, multifilament mesh, woven mesh, or nonwoven.

Paragraph 9. The implants of paragraphs 1-8, wherein the implant is selected from the group comprising: suture, surgical mesh, mesh suture, surgical tape, hernia repair device, breast reconstruction device, mastopexy implant, sling, ligament or tendon repair device, cardiovascular patch, and device for lifting tissues.

Paragraph 10. An implant comprising a polymeric composition, wherein the polymeric composition comprises a 1,4-butanediol unit and a succinic acid unit, wherein:
(a) the polymeric composition has a weight average molecular weight of 20,000 to 250,000 Da, and
(b) the polymeric composition has not been oriented during processing of the implant.

Paragraph 11. The implant of paragraph 10, wherein the polymeric composition has a weight average molecular weight of 50,000 to 250,000 Da or 75,000 to 200,000 Da.

Paragraph 12. The implant of paragraphs 10 and 11, wherein the polymeric composition has a polydispersity between 1 and 10.

Paragraph 13. The implant of paragraph 12, wherein the polymeric composition has a polydispersity between 2 and 8, or 4 and 8.

Paragraph 14. The implant of paragraphs 10-13, wherein the implant has one or more of the following properties: (i) a tensile strength of 30 to 60 MPa, (ii) an elongation to break of 40 to 200%, (iii) a Young's Modulus of 0.03 to 5 GPa, or 0.3 to 0.5 GPa, (iv) a yield strength of 0.02 to 2 GPa, and (v) a torsional strength of 10-20 Ncm.

Paragraph 15. The implants of paragraphs 10-14, wherein the implants are formed by molding, injection molding, compression molding, solvent casting, 3D printing, solution processing, solution bonding of fibers, dry spinning, film casting, lamination, thermoforming, pultrusion, electrospinning, centrifugal spinning, coating, dip coating, phase separation, particle leaching, leaching, latex processing, printing of slurries and solutions using a coagulation bath, or printing using a binder solution and granules of powder.

Paragraph 16. The implants of paragraphs 10-15, wherein the implant is selected from the group comprising: orthopedic implant, screw, bone screw, interference screw, pin, ACL screw, clip, clamp, nail, medullary cavity nail, bone plate, bone substitute, including bone plate, tack, fastener, suture fastener, rivet, staple, fixation device, bone void filler, suture anchor, bone anchor, meniscus anchor, meniscal implant, intramedullary rod and nail, joint spacer, interosseous wedge implant, osteochondral repair device, spinal fusion device, spinal fusion cage, bone plug, cranioplasty plug, plug to fill or cover a trephination burr hole, orthopedic tape, including knitted and woven tape, and device for treatment of osteoarthritis, surgical mesh, hernia mesh, mastopexy mesh, breast reconstruction mesh, sling, device to lift tissue, and drug delivery device.

Paragraph 17. A method of forming the implant of paragraphs 1 and 10, wherein the polymeric composition is heated in a temperature range of 60-230° C., 80-180° C., 80-175° C. or 80-170° C.

Paragraph 18. The method of paragraph 17, wherein the implant is an oriented monofilament or oriented multifilament fiber and is produced by a method comprising the steps of: (a) spinning the polymeric composition to form a multifilament fiber or monofilament fiber, and (b) one or more stages of drawing the multifilament fiber or monofilament fiber with an orientation ratio of at least 3.0 at a temperature of 50-70° C.

Paragraph 19. The method of paragraph 17, wherein the implant is 3D printed, and the method further comprises: (a) drying the polymeric composition to a moisture content of less than 0.1 wt % prior to heating the polymeric composition, (b) heating the polymeric composition to a temperature between 60° C. and 230° C. in a 3D printer, and (c) printing the polymeric composition to form the implant.

Paragraph 20. The method of paragraph 17, wherein the implant is molded, and the method further comprises: heating the polymeric composition to a temperature between 70° C. and 170° C., and allowing the polymeric composition to cool in a mold to form the implant, optionally wherein the temperature of the mold is between 5° C. and 50° C.

Paragraph 21. A method of forming the implant of paragraph 10, wherein the method comprises dissolving or slurrying the polymeric composition in a suitable solvent selected from one or more of the following: methylene chloride, chloroform, dichloroethane, tetrachloroethane, trichloroethane, dibromomethane, bromoform, tetrahydrofuran, acetone, THF, ethyl acetate, dimethylformamide, 1,4-dioxane, DMF and DMSO, and either (i) casting the solution or slurry of the polymeric composition and allowing the solvent to evaporate to form the implant, (ii) spinning the solution or slurry of the polymeric composition into a coagulation bath to form the implant, (iii) printing the solution or slurry of the polymeric composition with a 3D printer to form the implant, or (iv) electrospinning, dry spinning or centrifugally spinning the solution or slurry to form an implant on a collector.

V. Methods of Delivering Implants Made from Poly(Butylene Succinate) and Copolymers Thereof The implants made from poly(butylene succinate) and copolymers thereof may be implanted using conventional open surgical techniques, but may also be implanted using minimally invasive techniques. In one embodiment, high strength sutures are implanted using arthroscopic techniques. In a particularly preferred embodiment, the high strength sutures and suture tapes are used for arthroscopic repair of shoulders, elbows, wrists, spine, hips, knees, ankles and feet, including ligament and tendon repair. In another embodiment, meshes, webs, and lattices made from high strength monofilaments and high tenacity yarns, or by 3D printing of poly(butylene succinate) and copolymers thereof may be implanted using laparoscopic techniques. In a preferred embodiment, meshes, webs and lattices are implanted for the repair of hernias, and lift procedures, using laparoscopic techniques and other minimally invasive techniques.

In a particularly preferred embodiment, the implants may be used in any current mastopexy technique to achieve a breast lift using any appropriate skin resection pattern. The chosen method will depend upon the extent of breast ptosis and a number of other factors. The four main techniques for mastopexy are the: crescent mastopexy, donut (or Benelli) mastopexy, lollipop (or vertical) mastopexy, and anchor (or Weiss or Wise) mastopexy. In the crescent mastopexy, a semi-circular incision is made on the upper side of the areolar, and a crescent shaped piece of breast tissue removed. This procedure is typically used for patients with only mild ptosis where a good lift can be achieved by removing excess skin on the upper breast, and suturing the skin back in order to elevate the areolar nipple complex. In one embodiment, the implants can be implanted after further dissection and/or resection to provide additional support for the upper breast tissue.

The implants can also be implanted during a donut or Benelli mastopexy. In this procedure, a donut shaped piece of breast skin is removed from around the areolar with an inner incision line following the perimeter of the areolar, and an outer incision line circling the areolar further out. In one embodiment, the implant(s) can be inserted after further dissection to support the lift, and a purse string suture used to approximate the breast skin back to the areolar.

In both the lollipop and anchor mastopexy procedures, incisions are made around the areolar complex. In the lollipop procedure, a vertical incision is made in the lower breast from the areolar to the inframammary fold, and in the anchor mastopexy procedure an incision is made across the inframammary fold in addition to the vertical incision used in the lollipop procedure. The lollipop procedure is generally used for patients with moderate ptosis, whereas the anchor procedure is normally reserved for patients with more severe ptosis. These two procedures can be performed with or without breast implant augmentation. In both procedures, breast tissue may be resected, and the resected edges sutured together to create a lift. Prior to suturing the resected tissue, the implants can be implanted to support the breast, and to decrease the forces on the resected skin and suture line after closure. In a particularly preferred procedure, the implants are positioned to support the breast parenchyma or implant, and to minimize the weight of the breast on the skin and suture line. In an even more preferred procedure, the suture line is closed with minimal or no tension on the wound to minimize scar formation.

In a preferred embodiment, when sutured in place, the implants provide support, elevation and shape to the breast by anchoring of the implants at one or more locations to the tissue, muscle, fascia or the bones of the chest or torso. In a particularly preferred embodiment, the implants are sutured to the pectoralis fascia or the clavicle. The implants may also be sutured to the chest wall or fascia, and in a particularly preferred embodiment, the implants may be sutured to the chest wall so that they provide slings for support of the lifted breast or breast implant.

In embodiments, the microparticle compositions comprising poly(butylene succinate) or copolymer thereof may be administered to a human or animal in the form of injectable microparticle suspensions. For example, microparticle suspensions may be administered to a human or animal via a subcutaneous or intramuscular route. In other embodiments, the microparticle suspensions may be administered to a human or animal via infusions, surgical procedures, catheterization procedures, and other medical-device interventions. Routes of administration can include any relevant medical, clinical, surgical, procedural, and/or parenteral route of administration including, but not limited to, intravenous, intraarterial, intramuscular, intraperitoneal, subcutaneous, intradermal, infusion, subconjunctive, and intracatheter (e.g., aurologic delivery), as well as administration via external scopic techniques such as, for example, arthroscopic or endoscopic techniques. The compositions can be administered to specific locations (e.g., local delivery) including intrathecal, intracardiac, intraosseous (bone marrow), stereotactic-guided delivery, infusion delivery, CNS delivery, stereo-tactically administered delivery, orthopedic delivery (for example, delivery to joints, into bone and/or bone defects, cardiovascular, inter- and intra- and para-ocular (including intravitreal and scleral and retrobulbar and sub-tenons delivery), as well as delivery to any multitude of other sites, locations, organs, etc.

In embodiments, suspensions of the microparticle compositions may be administered using needles with sizes of 16 G to 31 G, more preferably 19 G to 30 G, and even more preferably 19 G to 21 G, wherein "G" refers to the gauge or gauge number of the needle. The compositions can also be administered through a larger diameter tube, catheter, trocar, infusion tubing, or endoscopy/arthroscopic tubes. Catheters generally have a diameter between about 0.03 inches and 0.5 inches (rated as 3 Fr to 30 Fr, where 3 Fr is approximately 1 mm). Devices with diameters up to about 0.75 inches may also be used to deliver the microparticles.

In embodiments, the microparticle compositions are administered in aqueous vehicles containing a viscosity-modifying agent and/or a surfactant. In embodiments, suspensions of the microparticle composition in the injection vehicles may have a concentration level in the range of about 10-40 wt. % (percent solids).

Modifications and variations of the invention described herein will be obvious to those skilled in the art and are intended to come within the scope of the appended claims.

The present invention will be further understood by reference to the following non-limiting examples.

EXAMPLES

Example 1: Monofilament Melt Extrusion of Succinic Acid-1,4-Butanediol-Malic Acid Copolyester with Two Stage Orientation in Convective Chambers to Produce Monofilament Fiber for Implants Succinic acid-1,4-butanediol-malic acid copolyester (Tepha lot 180333) with weight average molecular weight of 184 kDa, Tm=115° C., (melt flow rate (MFR) at 190° C./2.16 kgf of 5 g/10 min) was dried under vacuum overnight to less than 0.01% (w/w) water. Dried pellets of the polymer were fed into an extruder barrel of an AJA (Alex James Associates, Greer, S. C.) ¾" single screw extruder (24:1 L:D, 3:1 compression) equipped with a Zenith type metering pump (0.16 cc/rev) and a die with a single hole spinneret (0.026", 2:1 L:D) under a blanket of nitrogen. The 4 heating zones of the extruder were set at 75° C., 165° C., 180° C. and 180° C. The extruder was fitted with a quench bath filled with water at 35° C. and set up with an air gap of 10 mm between the bottom of the spinneret and the surface of the water. Two 2-roll godets were positioned after the quench bath, followed by two sets of longitudinal hot convection chamber/2-roll godet combination. The temperatures of the hot convection chambers were set between 60° to 80° C., followed by 2-roll godets then a horizontal winder. Pellets of the copolyester were allowed to enter the heated extruder barrel, molten polymer passed through the barrel, entered a heated block followed by a metering pump then a single hole spinneret. The block, metering pump and the spinneret die were maintained at a constant temperature, preferably 180° C. Pump discharge pressure was kept below 1500 psi by controlling the temperatures and the speed of the metering pump. The resulting spun extrudate filament was free from all melt irregularities. The extrudate was quenched in a water bath, drawn through longitudinal ovens and wound on a horizontal tension controlled Sahm winder. The results of 3 trials with in-line orientation and shown in Table 1, together with the result of a fourth trial where the fiber was not oriented in-line, but rather off-line and 10 days after it had been extruded. From inspection of Table 1, it will be evident that the conditions used to prepare the monofilament fiber resulted in fiber with a tensile strength in the range of 434-518 MPa.

TABLE 1

Properties of monofilament fibers made from PBS copolymer derived from 2-stage orientation in convection ovens

| Trial | #1 | #2 | #3 | #4 |
|---|---|---|---|---|
| Orientation | Online | Online | Online | Offline |
| Delay | None | None | None | 10 days |

TABLE 1-continued

Properties of monofilament fibers made from PBS copolymer
derived from 2-stage orientation in convection ovens

| Trial | #1 | #2 | #3 | #4 |
|---|---|---|---|---|
| Godet 1 (m/min) | 3.3 | 3.3 | 3.3 | 3.3 |
| Hot Chamber 1 (° C) | 62 | 62 | 70 | 70 |
| Godet 2 (m/min) | 18.6 | 18.6 | 18.5 | 15 |
| Hot Chamber 2 (° C) | 75 | 75 | 80 | 80 |
| Godet 3 (m/min) | 22 | 21 | 23 | 22.5 |
| Orientation ratio (total) | 6.67 | 6.36 | 6.97 | 6.82 |
| Fiber Diameter (mm) | 0.178 | 0.182 | 0.183 | 0.172 |
| Tensile Strength (MPa) | 452 | 449 | 434 | 518 |
| Break Elongation (%) | 46 | 67 | 41 | 24 |

Example 2: Monofilament Melt Extrusion of Succinic Acid-1,4-Butanediol-Malic Acid Copolyester with Multi Stage Incremental Orientation in Conductive Chambers to Produce Monofilament Fiber for Implants Succinic acid-1,4-butanediol-malic acid copolyester (Tepha lot 180333) with weight average molecular weight of 184 kDa, Tm=115° C., (MFR 190° C., 2.16 kg, 5 g/10 min) was dried under vacuum overnight to less than 0.01% (w/w) water. Dried pellets of the polymer were fed under a blanket of nitrogen into the extruder barrel of a 2½" American Kuhne single screw extruder (30:1 L:D, 3:1 compression) equipped with a Zenith type metering pump model HPB917, a die with 0.5 mm—8 hole spinneret and 8 heat zones. The 8 heating zones of the extruder were set between 40° C. and 200° C. The extruder was fitted with a quench bath filled with water at 35-70° C. and set up with an air gap of 10 mm between the bottom of the spinneret and the surface of the water. Two 5-roll godets were positioned after the quench bath, followed by three sets of hot conduction chambers fed by godets in order to orient the fiber in multiple stages. The temperatures of the hot chambers were set up between 50° to 90° C. temperature. Another godet was positioned after the last chamber, and then a multi-position Sahm winder. The results from three trials to produce monofilament fiber with diameter of 0.166-0.169 mm are shown in Table 2A. In comparison to the results shown in Table 1, the use of multi-stage incremental orientation of the fiber and conductive chambers instead of standard conventional non-liquid chambers resulted in monofilament fiber with substantially higher tensile strengths of 779-883 MPa.

TABLE 2A

Properties of monofilament fibers made from PBS copolymer derived
from multi-stage orientation in conductive liquid chambers

| Trial | #1 | #2 | #3 |
|---|---|---|---|
| Orientation | Online | Online | Online |
| Godet 1&2 (m/min) | 3.6 | 3.6 | 1 |
| Hot Chamber 1 (° C.) | 55 | 55 | 60 |
| Godet 3 (m/min) | 14 | 14 | 3.7 |
| Hot Chamber 2 (° C.) | 80 | 80 | 65 |
| Godet 4 (m/min) | 28 | 28.3 | 7.7 |
| Hot Chamber 3 (° C.) | 85 | 85 | 65 |
| Godet 5 (m/min) | 30 | 29.7 | 8.22 |
| Orientation Ratio | 8.3 | 8.25 | 8.2 |
| Diameter (mm) | 0.169 | 0.166 | 0.167 |
| Tensile Strength (MPa) | 779 | 752 | 883 |

TABLE 2A-continued

Properties of monofilament fibers made from PBS copolymer derived
from multi-stage orientation in conductive liquid chambers

| Trial | #1 | #2 | #3 |
|---|---|---|---|
| Break Elongation (%) | 24 | 23.7 | 23 |
| Young's Modulus (GPa) | 2.8 | n.d. | n.d. |

Table 2B shows tensile property data for four additional sizes of PBS copolymer monofilament fibers.

| Diameter (mm) | Cross-sectional area (mm$^2$) | Load (kgf) | Stress (MPa) | Break Elongation (%) |
|---|---|---|---|---|
| 0.106 | 0.0088 | 0.642 | 707 | 20.4 |
| 0.130 | 0.0133 | 0.908 | 667 | 21.3 |
| 0.175 | 0.0241 | 1.699 | 690 | 26 |
| 0.37 | 0.1075 | 7.975 | 729 | 25 |

Example 3: Multifilament Extrusion of Succinic Acid-1,4-Butanediol-Malic Acid Copolyester to Prepare Implants Succinic acid-1,4-butanediol-malic acid copolyester (Tepha lot 180333) with weight average molecular weight of 184 kDa, Tm=115° C., (melt flow rate (MFR) at 190° C./2.16 kgf of 5 g/10 min), was dried under vacuum overnight to less than 0.01% (w/w) water. Dried pellets of the polymer were fed into an extruder barrel of an AJA (Alex James Associates, Greer, S. C.) ¾" single screw extruder (24:1 L:D). The extrusion barrel contained 4 heating zones, a metering pump and a spin pack assembly. The pellets were gravity fed into a chilled feeder section and introduced into the extruder with temperature profile set as follows: Chimney 40° C.-100° C., Spinneret 170° C.±30° C., Pump 170° C.±30° C., Block 170° C.±30° C., Zone 4 160° C.±40° C., Zone 3 150° C.±40° C., Zone 2 120° C.±50° C., Zone 1 30° C.-40° C., Feed Zone: Ambient temperature. The heated and homogenized melted resin from the extruder was fed into a heated metering pump (melt pump), and from the melt pump the extruded resin was fed into the heated block and the spinneret assembly. The spinneret had 30 holes with a capillary diameter of 0.200 millimeters and a L/D ratio of 2:1. (The spinneret may also be configured in other alternative manners. For example, the spinneret can be configured with capillary diameters from 0.150 to 0.300 millimeters (6 mil to 12 mil) and 15, 120 and 240 holes, as well as higher and lower diameters and numbers of holes.) Processing temperature profile ranges from 35° C. to 250° C. were used with pressures ranging from 200 to 5,000 psi in the barrel and 200 to 5,000 psi in the spin pack. As the molten filaments exited the spin pack they passed through a heated chimney collar that was 6-12 inches long and ranged in temperature from 40° C. to 100° C., and then through an air quench box. The spin pack was suspended vertically above a yarn take-up roll at a distance sufficient to allow crystallization of the molten filaments and application of spin finish lubricant. A spin finish solution of 25% polyethylene 25 glycol 400 (PEG400) in water was used to hold the filaments together to form a yarn bundle. The speed of the yarn take-up rolls (typically 3-18 meters per minute) was set in proportion to the flow rate of the molten filament to control the denier of the as spun yarn bundle. The as spun yarn bundle was then conveyed to a Lessona winder for offline later orientation or conveyed to a take-up roll for inline orientation on a series of cold and heated godet pairs and separator rolls. The spin finish can be reactivated by rewetting the yarn bundle with pure water, and the yarn drawn at ratios from 5 to 14× and temperatures ranging from 50° C. to 90° C. The tenacity and denier of the multifilament yarn produced is shown in Table 3.

TABLE 3

Properties of Multifilament Fibers made from PBS Copolymer Prepared by Melt Extrusion

| Number of Filaments | Denier | Load (Kg) | Break Elongation (%) | Tenacity (gpd) |
|---|---|---|---|---|
| 15 | 60 ± 10 | 0.50 ± 0.05 | 16% | 8.3 |
| 30 | 63 ± 10 | 0.79 ± 0.04 | 20% | 12.5 |
| 30 | 152 ± 10 | 1.55 ± 0.07 | 21% | 10.2 |
| 60 | 309 ± 10 | 2.80 ± 0.10 | 24% | 9.1 |

Example 4: Preparation of Multifilament Sutures

Oriented yarn produced according to Example 3 and with properties shown in Table 3 was braided using 8 and 16 carrier Steeger braiding equipment to form the braid constructions shown in Table 4. The mechanical properties of the high strength braided sutures, determined according to USP 24, are also shown in Table 4. The examples include a braid formed as a tape (shown as the last example in Table 4.

TABLE 4

Mechanical Properties of Braids and Tapes Prepared from PBS Copolyester

| | | | | Mechanical Properties | | |
|---|---|---|---|---|---|---|
| Lot Number | Braid Construction | | | Diameter (mm) | Tensile strength, (Kg) | Break elongation (%) |
| | Core denier | Sheath denier | Pick count | | | |
| TE18-008 | 2 × 152 | 16 × 152 | 48 | 0.608 | 26.5 | 39 |
| TE18-010 | 3 × 63 | 16 × 63 | 58 | 0.380 | 14.2 | 31 |
| TE18-010 | 1 × 60 | 8 × 60 | 49 | 0.246 | 4.3 | 26 |
| TE18-021 Tape Suture | 13 × 6 × 126 denier | | 17 | 0.5 × 3.0* | 62 | 40 |

*Tape dimensions of 0.5 mm thickness and 3.0 mm width

Example 5: Preparation of a Knitted Monofilament Mesh Implants

Monofilament fiber (USP suture size 5/0) prepared according to the method of Example 2 was processed into knitted mesh according to the following procedure. Monofilament fibers from 49 spools were mounted on a creel, aligned side by side and pulled under uniform tension to the upper surface of a "kiss" 10" roller. The "kiss" roller was spun while semi-immersed in a bath filled with a 10% solution of TWEEN® 20 lubricant. The TWEEN® 20 lubricant was deposited on the surface of the sheet of monofilament fibers. Following the application of TWEEN® 20, the sheet of fiber was passed into a comb guide and then wound on a warp beam. A warp is a large wide cylinder onto which individual fibers are wound in parallel to provide a sheet of fibers. Next, warp beams were converted into a finished mesh fabric by means of interlocking knit loops. Eight warp beams were mounted in parallel onto tricot machine let-offs and fed into the knitting elements at a constant rate determined by the 'runner length'. Each individual monofilament fiber from each beam was fed through a series of 20 dynamic tension elements down into the knitting 'guides'. Each fiber was passed through a single guide, which was fixed to a guide bar. The guide bar directed the fibers around the needles forming the mesh fabric structure. The mesh fabric was then pulled off the needles by the take down rollers at a constant rate of speed determined by the fabric 'quality'. The mesh fabric was then taken up and wound onto a roll and scored ultrasonically with water, heat set in hot water, and then washed with a 70% aqueous ethanol solution. The knitted mesh produced with monofilament fiber from Example 2 had the following properties (as shown in Table 11 at time 0): burst strength of 22.668 kgf, thickness of 0.683 mm, and Taber Stiffness of 0.116.

Example 6: Preparation of Knitted Multifilament Mesh Implants

Spools of multifilament fiber prepared according to the method of Example 3 were processed into knitted multifilament mesh using the method described in Example 5.

Example 7: Injection Molded Implants

Injection molded implants of succinic acid-1,4-butanediol-malic acid copolyester (Tepha lot 180333) with weight average molecular weight of 184 kDa, Tm=115° C., were prepared using an Arburg model 221 injection molder using the following conditions. The barrel temperature of the molder was increased from 70° C. at the feed zone to 170° C. at the end of the barrel. The mold temperature was maintained at 32° C. After molding, the implants were dried in a vacuum oven at room temperature for 48 hours, and tensile properties determined using an MTS test machine with a 2 inch/min cross head speed. Representative tensile properties of the implants were as follows: Young's Modulus 0.66 GPa (96,600 psi), Yield Strength 49.2 MPa (7,140 psi) and Break Stress of 71.7 MPa (10,400 psi).

Example 8: Injection Molded Interference Screws for Use as Implants

Interference screws with a diameter of 7 mm and length of 20 mm were injection molded from succinic acid-1,4-butanediol-malic acid copolyester (Tepha lot 180333), and from the same copolyester after blending with 50 wt. % beta-TCP (tri-calcium phosphate). The screws were formed using a similar procedure to that described in Example 7. After injection molding of the screws, the intrinsic viscosity of the compositions was essentially identical to that of the starting materials, indicating little loss of weight average molecular weight during injection molding occurred. The torsional strength of the screws was determined by embedding the tip of the molded screws in epoxy resin and measuring the maximum torque achieved by the screwdriver before failure of the screws. The average of three screws tested for the copolyester alone gave a value for torsional strength of 15.0 Ncm. The testing was repeated for the screws prepared from the blend, and the average value was 18.2 Ncm. For comparison, a commercial Arthrex Biointerference screw for implantation composed of PLLA (poly-L-lactic acid) was also tested. The Arthrex Biointerference screw has an average failure torque of 12.1 Ncm.

Example 9: 3D Printed Implantable Mesh

A 3D printed mesh was prepared from succinic acid-1,4-butanediol-malic acid copolyester (Tepha lot 180333), with weight average molecular weight of 184 kDa, Tm=115° C., using melt extrusion deposition according to the following method. The mesh was printed using an ARBURG Free-Former machine consisting of a horizontal extruder feeding into a vertical ram extruder fitted with motion controlled needle plunger, 200 micron spinneret nozzle and a movable stage table. The extruder hopper was charged with 1½×3 mm sized polymer pellets with a moisture content of less than 2,000 ppm. The pellets were purged with dry nitrogen in the extruder hopper to maintain dryness. The temperature profile of the extruder was set between 45-180° C., and the residence time of the polymer in the extrusion system was maintained at less than 15 min/cm. The conditions resulted in the formation of very high quality printed mesh as shown in FIG. 1.

Example 10: 3D Printed Implantable Lattice

A 3D printed lattice was prepared from succinic acid-1, 4-butanediol-malic acid copolyester (Tepha lot 180333), with weight average molecular weight of 184 kDa, Tm=115° C., using selective laser melting (SLM). The SLM equipment consisted of a moving powder bed equipped with a reservoir for the polymer granules and a powder sweeper gate valve, and a laser source that can direct a laser beam on the powder bed and focus on a single polymer granule in the bed. The position of both the moving powder bed and laser beam were controlled by a computer that had been programmed with 3D CAD data to produce a lattice structure of the copolyester. The powder bed could be moved in the X-Y horizontal plane, and also in the Z axis vertical plane. The focal distance, the distance between the lens and surface of the powder was less than 50 cm. Prior to printing, the polymer was cryo-milled using liquid nitrogen, and sieved to produce granules with average sizes of 0.3 to 250 μm. The granules were placed in the powder reservoir, and a first layer of powder, 250 μm thick, was spread on the moving bed using the powder sweeper. The computer driven laser beam was focused on each polymer granule until it melted, shifting from one granule when it melted to the next granule. After printing of the first layer, a sweeper arm spread a second layer of polymer granules, the laser position was adjusted to focus on the granules, and laser firing started to form the second 3D layer. The process was repeated with successive layers until the lattice made of succinic acid-1, 4-butanediol-malic acid copolyester was formed.

Example 11: Endotoxin testing of Copolymer of Succinic acid and 1,4-Butanediol

Polymer pellets of succinic acid-1,4-butanediol-malic acid copolyester were tested for endotoxin content using the Bacterial Endotoxin Test (BET) Gel Clot method per USP <85>. Before testing, the pellets were sterilized by exposure to ethylene oxide gas. The extraction was performed at a ratio of 1 gram of polymer in 10 mL of endotoxin-free water; then, a 1:8 dilution of the sample extract was prepared and tested by the gel clot method. The results yielded <2.5 EU/g of polymer.

Example 12: In Vitro Degradation of an Implantable Mesh Prepared from Succinic acid-1,4-Butanediol-Malic acid Copolyester The in vitro degradation rate of an implantable mesh prepared from oriented monofilament fibers of succinic acid-1,4-butanediol-malic acid copolyester (prepared as described in Example 5) was studied by incubation of the mesh in phosphate buffered saline. The buffer solution contained 137 mM NaCl, 2.7 mM KCl, 9.8 mM phosphate and 0.05 wt % sodium azide and had pH 7.4 at 25° C. The prepared buffer solution was filtered through a 0.45 um filter (VWR Product #10040-470) prior to use. Mesh samples were sterilized by exposure to ethylene oxide gas. Samples (2×2 in.) were placed in sterile containers covered in buffer solution and incubated in a shaker incubator at 50 rpm and at a temperature of 37° C. Buffer media was monitored monthly and changed if the pH was outside of the targeted value 7.4+/−0.2. At prescribed time points, the samples were removed from the buffer and rinsed with deionized water to remove buffer salts. The samples were then tested for mechanical properties [including mesh burst strength (peak load) and strength retention] and weight average molecular weight retention of the polymer by gel permeation chromatography (as further described in Example 15). The in vitro degradation data is shown in Table 5.

TABLE 5

Mechanical and Mw data for PBS mesh samples made from oriented PBS monofilament fiber after incubation in phosphate buffered saline (pH 7.4) at 37° C.

| Time point (weeks) | Thick (mm) | Peak Load (kgf) | Std Dev (kgf) | Strength Retention (%) | Mw (kDa) | Std Dev (kDa) | Poly-dispersity | Mw Retention (%) |
| --- | --- | --- | --- | --- | --- | --- | --- | --- |
| 0 | 0.696 | 21.773 | 1.034 | 100.0 | 174 | 0.9 | 5.26 | 100.0 |
| 2 | 0.689 | 21.117 | 1.566 | 97.0 | 166 | 0.2 | 5.08 | 95.4 |
| 4 | 0.696 | 19.923 | 1.141 | 91.5 | 160 | 0.2 | 4.94 | 92.1 |
| 8 | 0.692 | 19.537 | 1.135 | 89.7 | 147 | 0.7 | 4.58 | 84.2 |
| 12 | 0.709 | 18.630 | 1.044 | 85.6 | 134 | 0.8 | 4.33 | 77.2 |
| 26 | 0.723 | 12.232 | 1.095 | 56.2 | 103 | 0.4 | 3.76 | 59.0 |
| 39 | 0.704 | 6.115 | 1.168 | 28.1 | 74 | 0.5 | 3.47 | 42.2 |
| 52 | 0.710 | 3.116 | 0.725 | 14.3 | 55 | 0.8 | 3.36 | 31.8 |
| 78 | 0.711 | 0.715 | 0.138 | 3.3 | 31 | 0.3 | 3.22 | 18 |

Example 13: In Vitro Degradation of an Implantable Suture Prepared from Succinic Acid-1,4-Butanediol-Malic Acid Copolyester The degradation rate of an implantable suture prepared from oriented monofilament fibers of succinic acid-1,4-butanediol-malic acid copolyester in vitro was studied by incubation of the suture in phosphate buffered saline. The initial properties of the suture are shown in Table 6, line 1 (t=0). The buffer solution contained 137 mM NaCl, 2.7 mM KCl, 9.8 mM phosphate and 0.05 wt % sodium azide and had pH 7.4 at 25° C. The prepared buffer solution was filtered through a 0.45 um filter (VWR Product #10040-470) prior to use. Suture samples were sterilized by exposure to ethylene oxide gas. Samples (12 in. length) were placed in sterile containers covered in buffer solution and incubated in a shaker incubator at 50 rpm and at a temperature of 37° C. Buffer media was monitored monthly and changed if the pH was outside of the targeted value 7.4+/−0.2. At prescribed time points, the samples were removed from the buffer and rinsed with deionized water to remove buffer salts. The samples were then tested for mechanical properties (tensile strength and tensile strength retention) and weight average molecular weight (Mw) retention of the polymer by gel permeation chromatography (as further described in Example 15). The in vitro degradation data is shown in Table 6.

TABLE 6

Mechanical and Mw data for oriented PBS suture samples after incubation in phosphate buffered saline (pH 7.4) at 37° C.

| Time point (weeks) | Peak Load (kgf) | Std Dev (kgf) | Break Elongation (%) | Strength Retention (%) | Mw (kDa) | Std Dev (Daltons) | Polydispersity | Mw Retention (%) |
|---|---|---|---|---|---|---|---|---|
| 0 | 1.793 | 0.007 | 25.133 | 100.0 | 174 | 0.2 | 4.86 | 100.0 |
| 2 | 1.801 | 0.009 | 25.120 | 100.4 | 167 | 0.8 | 4.93 | 96.2 |
| 4 | 1.810 | 0.010 | 25.364 | 100.9 | 163 | 0.5 | 4.84 | 93.6 |
| 8 | 1.772 | 0.020 | 25.311 | 98.8 | 156 | 1.5 | 5.78 | 89.4 |
| 12 | 1.736 | 0.021 | 24.866 | 96.8 | 145 | 0.6 | 4.85 | 83.1 |
| 26 | 1.571 | 0.057 | 24.917 | 87.6 | 114 | 0.9 | 4.85 | 65.3 |

Example 14: Elemental Analysis of Succinic Acid-1,4-Butanediol-Malic Acid Copolyester The elemental composition of the Succinic acid-1,4-Butanediol-Malic acid copolyester was analyzed by Inductively Coupled Plasma Mass Spectrometry (ICP) at Galbraith Laboratories Inc. This screening method provides semi-quantitative elemental composition of a material for most metal and non-metal elements lithium through uranium on the periodic table. The elements found in succinic acid-1,4-butanediol malic acid copolyester are shown in Table 7. The copolymer did not contain detectable heavy metals such as tin, which is sometimes used in the manufacture of resorbable polymers such as poly-glycolide, polylactide and poly-glycolide-co-lactide nor toxic metals such as cadmium, mercury, arsenic, chromium, or nickel. The following trace elements were detected: titanium 42 ppm, magnesium 31 ppm, and phosphorous 24 ppm.

TABLE 7

ICP-MS Analysis of a Poly(butylene succinate) Copolymer Mass Spec Semi-Quantitative Screen

| Element | Result | Element | Result |
|---|---|---|---|
| Lithium | <2 ppm | Indium | <2 ppm |
| Berylium | <2 ppm | Tin | <2 ppm |
| Boron | <20 ppm | Antimony | <2 ppm |
| Sodium | <20 ppm | Tellurium | <2 ppm |
| Magnesium | 31 ppm | Cesium | <2 ppm |
| Aluminum | <20 ppm | Barium | <2 ppm |
| Phosphorus | 24 ppm | Lanthanum | <2 ppm |
| Potassium | <20 ppm | Cerium | <2 ppm |
| Calcium | <20 ppm | Praseodymium | <2 ppm |
| Scandium | <2 ppm | Neodymium | <2 ppm |
| Titanium | 42 ppm | Samarium | <2 ppm |
| Vanadium | <2 ppm | Europium | <2 ppm |
| Chromium | <2 ppm | Gadolinium | <2 ppm |
| Manganese | <2 ppm | Terbium | <2 ppm |
| Cobalt | <2 ppm | Dysprosium | <2 ppm |
| Nickel | <2 ppm | Holmium | <2 ppm |
| Copper | <2 ppm | Erbium | <2 ppm |
| Zinc | <20 ppm | Thulium | <2 ppm |
| Gallium | <2 ppm | Ytterbium | <2 ppm |
| Arsenic | <2 ppm | Lutetium | <2 ppm |
| Selenium | <2 ppm | Hafnium | <2 ppm |
| Rubidium | <2 ppm | Tantalum | N/A |
| Strontium | <2 ppm | Tungsten | <2 ppm |
| Yttrium | <2 ppm | Rhenium | <2 ppm |
| Zirconium | <2 ppm | Iridium | <2 ppm |
| Niobium | <20 ppm | Platinum | <2 ppm |
| Molybdenum | <2 ppm | Mercury | <2 ppm |
| Ruthenium | <2 ppm | Thallium | <2 ppm |
| Rhodium | <2 ppm | Lead | <2 ppm |
| Palladium | <2 ppm | Bismuth | <2 ppm |
| Silver | <2 ppm | Thorium | <20 ppm |
| Cadmium | <2 ppm | Uranium | <2 ppm |

Example 15: Comparison of In Vivo Properties of an Implantable Mesh Prepared from Succinic Acid-1,4-Butanediol-Malic Acid Copolyester Versus an Implantable Mesh Prepared from Poly-4-Hydroxybutyrate The properties of a monofilament knitted mesh prepared from a copolymer of 1,4-butanediol and succinic acid units (the "PBS" mesh), as described in Example 5, were compared to a commercial mesh, the "GalaFLEX mesh (Galatea Surgical, Lexington, Mass.)" prepared from knitting of poly-4-hydroxybutyrate monofilament in an in vivo implantation study in rabbits. The weight average molecular weight of the PBS mesh fibers prior to implantation was 178 kDa. The PBS and GalaFLEX meshes were implanted in the dorsal, subcutaneous tissue of New Zealand White rabbits to evaluate the local tissue reaction, the degree of tissue in-growth and the changes in mechanical properties of the meshes over time in vivo. Twenty-four (24) female New Zealand White (NZW) rabbits were implanted with 6 mechanical (4×4 cm), 1 histological (2×2 cm), and 1 scanning electron microscopy (SEM) (2×2 cm) test articles per animal.

Prior to implantation, the rabbits (weighing at least 3.5 kg at implantation) were anesthetized by an intramuscular injection, followed by maintenance under isoflurane. Following anesthesia, the animals were injected subcutaneously with an analgesic. The surgical sites were prepared for implantation. An incision was made through the skin and the skin was dissected laterally by blunt dissection to create a pocket. Three individual mechanical samples (4×4 cm) and 1 histo/SEM sample (2×2 cm) were implanted on each side of each animal, for a total of 8 specimens per animal. The specimens were implanted by placing the mesh flat along the back of the animal without folding or rolling and fixated with a Prolene suture at each corner. The skin was closed and a bandage was applied. The animals were returned to their respective cages, monitored for recovery from the anesthetic, and then monitored daily for general health.

At 4, 8, 12 and 26 weeks, three rabbits were euthanized from each group. The skin was reflected, the subcutaneous tissues were examined and the area around each implant was dissected free. The implanted meshes were recovered by dissection from the surrounding tissue. The explants were processed for histological, biomechanical and polymer testing. At each time point, half of the 4×4 cm implanted meshes (n=9) were tested for mechanical properties including the in-grown tissue. The other samples (n=9), were designated for mesh-only analyses and were tested following collagenase digestion to remove ingrown tissue and evaluate the residual strength of the residual polymeric scaffold. In this way, the mechanical properties of the mesh alone could be measured and compared to that of the combination of mesh and tissue in the composite.

For the mesh-only samples, the in-grown tissue was removed from the explanted samples using enzymatic digestion with collagenase. Previous testing demonstrated no impact of the collagenase enzyme on the mesh mechanical properties or Mw properties. Individual explanted mesh specimens were placed in a 50 mL Falcon tube containing 25 mL collagenase (type I) solution (1.0 mg/mL) in TESCA buffer (50 mM TES, 2 mM calcium chloride, 10 mM $NaN_3$, pH 7.4, sterile filtered). The tube was placed in a shaker (50 rpm) and incubated at 37° C. overnight (~17 h) to digest and remove tissue attached to the mesh specimen. After the incubation was complete, the specimens were removed from the tubes, residual tissue was manually removed from the explant taking care not to damage the mesh, and the meshes were rinsed with distilled water followed by 70% ethanol. Mesh specimens were blotted dry using a lint-free wipe.

Samples were tested for dimensions, relative stiffness (Taber tester), burst strength and evaluated for surface morphology via SEM. Comparison was made to non-implanted (TO) articles (n=9/group). Polymer degradation was further evaluated by Gel Permeation Chromatography (GPC). The host tissue response and degree of tissue remodeling were evaluated histologically Burst Test, Stiffness & Molecular Weight (Mw) Retention of PBS Mesh The thickness of each sample was measured with a pro-gage thickness tester before testing for burst strength. The burst strength was measured using a universal testing machine (Q test Elite by MTS) fitted with a 1,000 N load cell according to test method ASTM D6797-02, Standard Test Method for Bursting Strength of Fabrics Constant-Rate-of-Extension (CRE) Ball Burst Test. The samples were clamped over the circular opening of the fixture and a ⅜ in. probe was lowered through the sample at 305 mm/min until failure. A pre-load setting of 0.05 kg was used to remove slack from the sample and register zero displacement. The load at failure (kgf) was recorded as the bursting strength.

After mechanical testing a portion of the mesh remnant was removed to measure the weight average molecular weight ($M_w$) by Gel Permeation Chromatography (GPC). Mw was measured relative to monodisperse polystyrene standards using a TOSOH HPLC with Refractive Index detector. Samples for GPC were prepared at 1 mg/ml in chloroform, 100 μl of the solutions were injected onto a Polymer Labs, PLgel column (5 micron, mixed C, 300×7.5 mm), and eluted at 1 ml/min in chloroform using a refractive index detector. The test results are summarized in Tables 8 to 12 below.

Tables 8 and 9 show the dimensions (length, width and area of the meshes) of the PBS mesh and GalaFLEX mesh prior to implantation, and after implantation for 4, 8, 12 and 26 weeks. The data shows a surprising difference between the two meshes. Although both are made with the same knit patterns and from similar sized monofilament fibers, the dimensions of the PBS mesh remain essentially constant following implantation whereas the dimensions of the GalaFLEX mesh change over time. It is thus apparent that the PBS mesh is dimensionally stable following implantation, and does not shrink following implantation. The area occupied by the mesh remains constant as shown by the relative area occupied by the PBS mesh in Table 8, as well as the mesh dimensions.

TABLE 8

Dimensional data for PBS Mesh Samples after Implantation Subcutaneously in Rabbit Tissue with In-grown Tissue Intact

| Time point (wks) | Length (mm) | SD (mm) | Width (mm) | SD (mm) | Area (mm²) |
|---|---|---|---|---|---|
| 0 | 39.2 | 0.2 | 39.8 | 0.2 | 1560 |
| 4 | 39.7 | 0.5 | 39.1 | 1.6 | 1550 |
| 8 | 40.3 | 0.9 | 39.7 | 0.8 | 1598 |
| 12 | 39.6 | 0.6 | 39.6 | 0.6 | 1566 |
| 26 | 40.4 | 1.0 | 40.0 | 0.7 | 1616 |

TABLE 9

Dimensional data for GalaFLEX Mesh Samples after Implantation Subcutaneously in Rabbit Tissue with In-grown Tissue Intact

| Time point (wks) | Length (mm) | SD (mm) | Width (mm) | SD (mm) | Area (mm²) |
|---|---|---|---|---|---|
| 0 | 43.3 | 0.9 | 43.1 | 1.1 | 1866 |
| 4 | 39.5 | 3.0 | 36.7 | 2.9 | 1448 |
| 8 | 40.4 | 2.8 | 36.6 | 3.9 | 1476 |
| 12 | 39.5 | 2.8 | 38.3 | 2.7 | 1513 |
| 26 | 40.7 | 1.5 | 38.6 | 3.3 | 1571 |

Table 11 shows that the burst strength of the explanted PBS mesh samples after tissue removal decreases over 26 weeks from 23.672 kgf to 12.779 kgf, representing a strength retention of 54%. Table 10 shows that tissue in-growth into the PBS mesh adds strength to the tissue-mesh composite and results in a greater burst strength at 26 weeks (19.003 kgf) than when compared to mesh alone after tissue removal (12.779 kgf). The same is true, but to a lesser degree, at intermediate time points of 8 and 12 weeks. It is apparent from this data, that the PBS mesh can support tissue in-growth, and that this tissue in-growth contributes an additional 6.224 kgf (19.003−12.779=6.224 kgf) or approximately 49% (6.224/12.779=0.49) to the burst strength of the mesh at 26 weeks post-implantation. Table 11 also shows that the stiffness of the PBS mesh (measured in Taber Stiffness Units) decreases slightly by approximately 10% throughout the 26-week implantation period even though the burst strength of the mesh decreases about 46% during this period. Comparison with Table 10 shows that the stiffness of the mesh-tissue composite increases by approximately 30% over the 26 week implantation time, demonstrating that the ingrown tissue increases the stiffness of the mesh-tissue composite.

TABLE 10

Mechanical Data for PBS Mesh Samples after Implantation Subcutaneously in Rabbit Tissue with In-grown Tissue Intact

| Time (wks) | Burst Strength (kgf) | SD (kgf) | Strength Reten. (%) | Thick (mm) | SD (mm) | Taber Stiffness | Rel. Stiffness |
|---|---|---|---|---|---|---|---|
| 0 | 23.672 | 1.000 | 100.0 | 0.603 | 0.005 | 0.276 | 100.0 |
| 4 | 22.975 | 0.897 | 97.1 | 0.667 | 0.054 | 0.308 | 111.6 |
| 8 | 23.660 | 1.457 | 100.0 | 0.727 | 0.076 | 0.272 | 98.5 |
| 12 | 22.725 | 1.691 | 96.0 | 1.056 | 0.299 | 0.343 | 124.4 |
| 26 | 19.003 | 2.853 | 80.3 | 1.167 | 0.509 | 0.355 | 128.7 |

TABLE 11

Mechanical data for PBS Mesh Samples after Implantation Subcutaneously in Rabbit Tissue after Tissue Digestion with Collagenase to Remove In-grown Fibrotic Tissue

| Time (wks) | Strength (kgf) | SD (kgf) | Strength Reten. (%) | Thick (mm) | SD (mm) | Taber Stiffness | Rel. Stiffness |
|---|---|---|---|---|---|---|---|
| 0 | 23.672 | 1.000 | 100.0 | 0.603 | 0.005 | 0.276 | 100.0 |
| 4 | 23.265 | 0.714 | 98.3 | 0.607 | 0.005 | 0.268 | 97.2 |
| 8 | 21.658 | 1.001 | 91.5 | 0.600 | 0.004 | 0.228 | 82.6 |
| 12 | 20.842 | 1.285 | 88.0 | 0.603 | 0.004 | 0.247 | 89.4 |
| 26 | 12.779 | 1.202 | 54.0 | 0.603 | 0.005 | 0.265 | 96.1 |

Table 12 shows the reduction in the weight average molecular weight (Mw) of the PBS polymer used to prepare the PBS mesh implant at 4 and 12 weeks compared to the initial Mw. The data demonstrates that the PBS mesh implant degrades in vivo, and that the retention of weight average molecular weight of the polymer is 89.7% at 4 weeks, and 72.5% at 12 weeks. The finding of the good retention of strength of the PBS mesh means that it is suitable for use in procedures requiring prolonged strength retention.

TABLE 12

Weight Average Molecular Weight (Mw) of PBS Mesh Samples after Implantation Subcutaneously in Rabbit Tissue after Tissue Digestion with Collagenase to Remove In-grown Fibrotic Tissue.

| Time (wks) | Mw (kDa) | SD (kDa) | Mw Retention (%) |
|---|---|---|---|
| 0 | 173 | 0.5 | 100.0 |
| 4 | 155 | 0.5 | 89.7 |
| 12 | 126 | 1.9 | 72.5 |

Biocompatibility and Histological of PBS Mesh

At 4 weeks, gross examination showed that the tissue had completely integrated into the pores of the mesh implants. Microscopically, marked tissue ingrowth into the implant material was noted at all 3 sites and consisted of new fibrous connective tissue, neovascularization, and inflammation extending into the spaces between implant material fibers (i.e. the mesh pores).

Under the conditions of this study, the PBS mesh and control P4HB mesh both caused the same tissue reaction—fibrosis with neovascularization and chronic inflammation when implanted into the subcutaneous tissue of rabbits for 4 to 26 weeks. Both materials were surrounded by a thin mature fibrosis capsule with diffuse infiltration of the materials by inflammatory cells and small amounts of fibrosis (collagen). There were minimal differences in the tissue reaction to the PBS mesh and control mesh. There was no evidence of infiltration of the tissue reaction into the individual fibers of the PBS or control mesh. However, a few of the fibers of the control article at 8, 12 and 26 weeks appeared to exhibit minor surface erosion with infiltration of the inflammatory cells into these areas. The tissue reaction to the PBS and control mesh were generally the same, except that the tissue reaction between the fibers of the PBS article was maturing faster than the tissue reaction between the fibers of the control mesh. There was slightly more neovascularization and immature fibrosis between the fibers of the control mesh, than the fibers of the PBS mesh. Overall, the tissue reaction within the PBS article and control mesh implant sites was normal and comparable for a 4 to 26 week mesh material that was implanted subcutaneously. Due to the structure of the mesh material, the tissue reaction would surround and infiltrate any open areas of the material. This occurred with both the PBS and control meshes. Comparable cellular infiltration, neovascularization and fibrosis (collagen) deposition was evident between the fibers of the PBS and control mesh over 26 weeks. There was limited evidence of fiber resorption and inflammatory cell infiltration into the PBS or control mesh fibers by 26 weeks.

Based on the Irritant Rank Score relative to the comparative control mesh (GalaFLEX mesh), the PBS test article was considered a non-irritant. and the PBS mesh considered to be biocompatible.

Example 16: Determination of the Strength Retention of a PBS Suture

Fiber, and its Local Tissue Reaction PBS oriented monofilament fiber samples (0.109±0.004 mm) (USP suture size 6/0) were implanted in the dorsal, subcutaneous tissue of New Zealand White rabbits to evaluate the local tissue reaction and the changes in mechanical properties of the fibers over time in vivo. Three (3) male New Zealand White (NZW) rabbits were implanted with 3 mechanical (9 in.), 1 histological/SEM (9 in.) test articles per animal.

Prior to implantation, the rabbits (weighing at least 3.5 kg at implantation) were anesthetized by an intramuscular injection, followed by maintenance under isoflurane. Following anesthesia, the animals were injected subcutaneously with an analgesic. The surgical sites were prepared for implantation. An incision was made cranially through the skin and a long forcep was tunneled through the subcutaneous tissue and parallel to the spine to exit caudally through a second skin incision. A single suture fiber was grasped by the forceps and pulled back into the tissue. This process was repeated to implant each fiber. Four test PBS suture fibers (3 mechanical samples and 1 histo/SEM sample) and four control monofilament fibers made of poly-4-hydroxybutyrate (TephaFLEX monofilament suture, Tepha, Inc. Lexington, Mass.) were implanted on each side of each animal, for a total of 8 specimens per animal. The skin was closed and a bandage was applied. The animals were returned to their respective cages, monitored for recovery from the anesthetic, and then monitored daily for general health.

At 4 weeks, all three rabbits were euthanized. The skin was reflected, the subcutaneous tissues were examined and the area around each implant was dissected free. The implanted sutures were recovered by dissection from the surrounding tissue. The explants were processed for histological, biomechanical and polymer testing. The explanted sutures (n=9) were tested for tensile mechanical properties. The other samples (n=3), were designated for histopathology.

Analysis of the local tissue reaction by histopathology demonstrated that the PBS suture was graded as a non-irritant relative to the comparative poly-4-hydroxybutyrate (TephaFLEX) suture control.

Tensile testing was performed on a Universal Testing Machine operating on the principle of constant rate of elongation of test specimen. The tensile testing machine was equipped with pneumatic fiber grips, using a pre-load setting of 0.05 kg. A gauge length of 138 mm and a strain rate of 300 mm/minute were used. During testing, the location of the break was recorded. Tensile strength retention was calculated from the tensile strength measurements.

After mechanical testing a portion of the suture remnant was removed to measure the weight average molecular weight ($M_w$) by Gel Permeation Chromatography (GPC). Mw was measured relative to monodisperse polystyrene standards using a TOSOH HPLC with Refractive Index detector as described above for mesh. The test results are summarized in Table 13. The results shown in Table 13 show the PBS monofilament suture retained 92.7% of its initial weight average molecular weight at 4 weeks post-implantation indicating that the suture had begun to degrade in vivo, but could retain substantial strength over a critical wound healing period.

TABLE 13

Mechanical and Weight Average Molecular Weight (Mw) data for PBS suture samples after subcutaneous implantation in rabbits

| Time point (weeks) | Peak Load (kgf) | Std Dev (kgf) | Break Elongation (%) | Strength Retention (%) | Mw (kDa) | Std Dev (kDa) | Mw Retention (%) |
|---|---|---|---|---|---|---|---|
| 0 | 1.771 | 0.034 | 24.063 | 100 | 172 | 1.5 | 100 |
| 4 | 1.749 | 0.044 | 25.694 | 99 | 159 | 0.8 | 92.7 |

Figure 4:
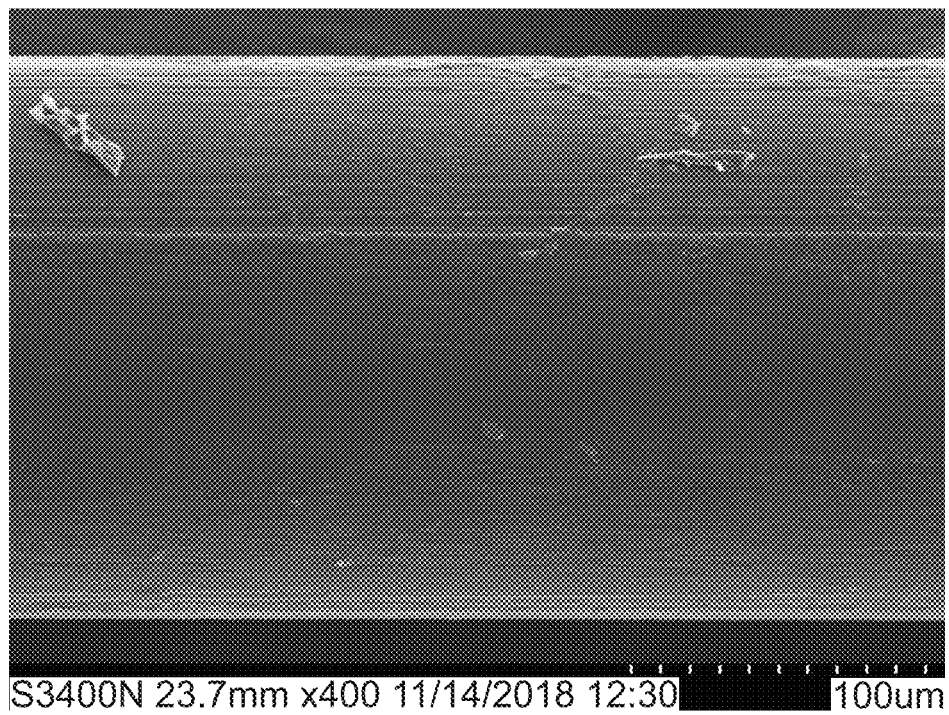
FIG. 4 is a SEM image of an oriented PBS monofilament suture fiber prior to implantation at a 400× magnification showing a smooth surface.

The subcutaneously implanted oriented PBS monofilament suture fiber was analyzed by SEM after it had been implanted for 4 weeks. The SEM image was compared to an unimplanted PBS suture fiber. SEM images were recorded with a 400× magnification. FIG. 4 shows the SEM image of the oriented PBS suture fiber prior to implantation. FIG. 5 shows the SEM image of the oriented PBS suture fiber after subcutaneous implantation for 4 weeks. Surprisingly, there is no evidence of surface erosion of the implanted PBS suture fiber after 4 weeks in vivo. The SEM image in FIG. 5 shows no evidence of surface erosion of the fiber.

Example 17: Preparation of a Poly(Butylene Succinate) Mesh Suture

A mesh suture was prepared using triaxial braiding from high strength monofilament PBS fibers. Spooled monofilament fibers of succinic acid-1,4-butanediol-malic acid copolyester extruded and oriented as described in Example 2 were unspooled and wound on braider bobbins. The bobbins were then loaded onto Herzog 4, 8, 16 and 24 carrier braiders. Additional spooled monofilament fiber was used to provide axial fiber in the mesh suture. The monofilament fibers were unspooled and threaded through the hollow axles of the horn gears, and all bobbin and axial fiber ends were pulled through the braiding ring to form the fell point. The braiders' bobbins were allowed to move along the braiding track, and the braid helix angle was adjusted to 15 degrees at 1 to 2 Picks Per Inch (PPI). The constructions (number of carriers and axial fibers used to prepare the hollow braids) and properties of the triaxial braided mesh sutures prepared with 100 µm, 150 µm, and 200 µm P4HB monofilament fiber are shown in Tables 14, 15 and 16. The tables show the outside (OD) and inside (ID) diameters of the mesh suture hollow braids. The width and thickness of the hollow braided mesh sutures were measured after the hollow braids had been squashed flat.

TABLE 14

Properties of Triaxial Hollow Braids Prepared with 100 µm PBS Monofilament Fibers

| Braider | | Hollow Triaxial Braid | | | | |
|---|---|---|---|---|---|---|
| | | Circular | | Flattened | | Tensile |
| # Carriers | # Pillar Fibers | OD (mm) | ID (mm) | Width (mm) | Thickness (mm) | Strength (N) |
| 4 | 2 | 0.8 | 0.4 | 1.2 | 0.4 | 47 |
| 8 | 4 | 1.0 | 0.6 | 1.5 | 0.4 | 99 |
| 12 | 6 | 1.3 | 0.9 | 2.0 | 0.4 | 149 |
| 16 | 8 | 1.7 | 1.2 | 2.6 | 0.4 | 200 |
| 24 | 12 | 2.8 | 2.2 | 3.4 | 0.4 | 297 |

TABLE 15

Properties of Triaxial Hollow Braids Prepared with 169 µm PBS Monofilament Fibers

| Braider | | Hollow Triaxial Braid | | | | |
|---|---|---|---|---|---|---|
| | | Circular | | Flattened | | Tensile |
| # Carriers | # Pillar Fibers | OD (mm) | ID (mm) | Width (mm) | Thickness (mm) | Strength (N) |
| 4 | 2 | 1.0 | 0.4 | 1.5 | 0.6 | 97 |
| 8 | 4 | 1.5 | 0.9 | 2.3 | 0.6 | 199 |
| 12 | 6 | 2.5 | 1.9 | 3.9 | 0.6 | 291 |

TABLE 15-continued

Properties of Triaxial Hollow Braids Prepared with 169 μm PBS Monofilament Fibers

| Braider | | Hollow Triaxial Braid | | | | Tensile |
|---|---|---|---|---|---|---|
| | | Circular | | Flattened | | |
| # Carriers | # Pillar Fibers | OD (mm) | ID (mm) | Width (mm) | Thickness (mm) | Strength (N) |
| 16 | 8 | 3.0 | 2.4 | 4.7 | 0.6 | 389 |
| 24 | 12 | 4.0 | 3.4 | 6.2 | 0.6 | 584 |

TABLE 16

Properties of Triaxial Hollow Braids Prepared with 200 μm PBS Monofilament Fibers

| Braider | | Hollow Triaxial Braid | | | | Tensile |
|---|---|---|---|---|---|---|
| | | Circular | | Flattened | | |
| # Carriers | # Pillar Fibers | OD (mm) | ID (mm) | Width (mm) | Thickness (mm) | Strength (N) |
| 4 | 2 | 1.1 | 0.3 | 1.7 | 0.8 | 129 |
| 8 | 4 | 1.6 | 0.8 | 2.5 | 0.8 | 259 |
| 12 | 6 | 2.5 | 1.7 | 3.9 | 0.8 | 389 |
| 16 | 8 | 3.5 | 2.7 | 5.4 | 0.8 | 518 |
| 24 | 12 | 5.0 | 4.1 | 7.8 | 0.8 | 778 |

Example 18: 3D Printing of a PBS-Malic Acid Copolymer Implant by Melt Extrusion Deposition (MED)

A PBS-malic acid copolymer implant was printed by MED using equipment having a horizontal extruder feeding into a vertical extruder fitted with a vertical plunger, and a movable stage. The extruder hopper was charged with PBS-malic acid copolymer pellets (160 kDa, by GPC relative to polystyrene standards), with a titanium catalyst content of 56 ppm, a diameter of about 2-3 mm and a moisture content of about 300 ppm. The pellets were kept dry in the hopper using a purge of air dried through a silica bed. The temperature profile of the horizontal extruder was set to about 30° C. in the build chamber; with the temperatures for the transition zone 1, zone 2; and zone 3 (extrusion zone) for various trials as shown in Table 17. The residence time of the polymer in the MED horizontal extruder was approximately 22 min/cm³. The diameter of the nozzle orifice of the vertical extruder was 0.2 mm and the drop printing frequency was about 50 drops/sec at the edge of the printed construct and about 240 drops/sec for the in-fill. Under these conditions, it was possible to print implants made from PBS-malic acid copolymer with good print quality. The weight average molecular weight, Mw, of the printed implants was measured by GPC and is also shown in Table 17. The Mw and polydispersity (PDI) were found to vary with the extrusion conditions used. As is evident from Table 17, the weight average molecular weight of the printed implants increased as the temperature was raised from 180° C. to 230° C.

TABLE 17

Properties of Implants made from PBS and Copolymers thereof Prepared Under Different Thermal Conditions by MED 3D Printing

| Description | Zone 1 | Zone 2 | Zone 3 | Mw (kDa) | PDI |
|---|---|---|---|---|---|
| Lot# 170065 (PBS-Malic Acid Copolymer Pellets) | | | | 160.4 | 2.97 |
| PBS Tn180 | 100 | 130 | 180 | 164.5 | 2.88 |
| PBS Tn190 | 110 | 140 | 190 | 170.0 | 2.96 |
| PBS Tn200 | 120 | 150 | 200 | 180.8 | 3.00 |
| PBS Tn210 | 130 | 160 | 210 | 190.7 | 3.09 |
| PBS Tn220 | 140 | 170 | 220 | 209.4 | 3.26 |
| PBS Tn230 | 160 | 190 | 230 | 192.1 | 3.27 |

Figure 21:
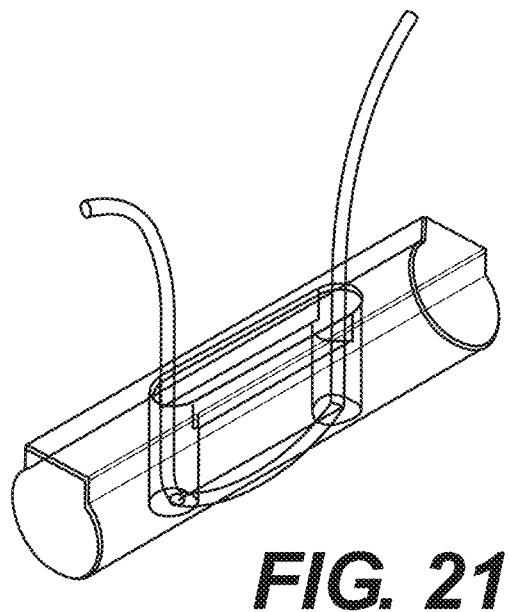
FIG. 21 is a diagram of a meniscal anchor prepared from PBS-malic acid copolymer by pultrusion and compression molding showing a size 2/0 suture threaded through two holes in the anchor.

Example 19: Pultrusion of a PBS-malic Acid Copolymer Anchor Implant for Meniscal Repair Polybutylene succinate-malic acid copolymer pellets with an average molecular weight of 174 kDa were extruded at 140° C. to form 3.0 mm diameter unoriented filaments (extrudate). The extrudate was axially pultruded at room temperature to form a constant cross-section rod using a controlled displacement machine through a 2.0 mm Die with a 60 transition angle. Pultrusion was performed with axial forces transmitted to the extrudate rod of 10 to 15 kN. Once tension was relieved, the pultruded rod was removed from the die by cutting both ends. The collected rods were then cut to approximately 2 mm in diameter and 10 mm in length. A compression mold having an anchor shape with 1×5 mm dimensions was used to mold the collected rods into anchors. The compression mold was heated between 45° C. to 50° C. to soften the polymer rod, and the rod was compressed by pushing it with a 2 mm hardened pin until a displacement of approximately 7 mm was completed. The compression molding rate ranged from 0.1 mm/min to 0.5 mm/min. The mold was allowed to cool to room temperature, and the molded part removed from the mold, and mechanically cut to a size of 1×5 mm. The molded part was annealed at 80° C. for 120 hr. Two holes of 0.4 mm diameter were then machined through the width of the rod at a distance of 1.4 mm from the ends of the anchor to allow insertion of a size 2-0 suture as shown in FIG. 21.

The pull through tensile strength of the rod was determined, according to ASTM D790-17 Standard part 7.5. The test samples measured 1.0 mm in diameter and 5.0 mm length. In the cross-section direction, the average maximum tensile strength of the anchor was 12.8 lbf.

Example 20: Monofilament Melt Extrusion of Succinic Acid-1,4-Butanediol-Malic Acid Copolyester with Multi Stage Incremental Orientation in Conductive Chambers to Produce Monofilament Fiber for Implants Monofilament fibers were made from PBS copolymers according to the method described in Example 2 with fiber diameters of 0.108, 0.165, 0.369 and 0.459 mm. The starting molecular weight of the copolymer was $M_w$=203,199 Da and $M_n$=28,905 Da, with a polydispersity of 7.03 for fibers produced with diameters of 0.108, 0.369 and 0.459 mm, and the starting molecular weight of the copolymer was $M_w$=194,104 Da and $M_n$=33,836 Da with a polydispersity of 5.74 for the fiber produced with a diameter of 0.165 mm. Molecular weights were determined by GPC relative to polystyrene standards. Tensile properties, including knot pull tensile strength, were determined, and are shown in Table 18. Knot pull tensile strength was determined using a universal mechanical tester according to the procedures described in US Pharmacopeia (USP) standard for testing tensile properties of surgical sutures (USP 881). The example shows that monofilament fibers of PBS or copolymers thereof can be produced with high tensile strengths and high knot pull tensile strengths using multi-stage orientation of melt extrudate.

TABLE 18

Properties of monofilament fibers made from PBS copolymer derived from multi-stage orientation in conductive liquid chambers

| | USP Suture size | | | |
|---|---|---|---|---|
| | 6-0 | 5-0 | 2-0 | 0 |
| Diameter (mm) | 0.108 | 0.165 | 0.369 | 0.459 |
| Load (kgf) | 0.684 | 1.783 | 7.860 | 11.329 |
| Tensile strength (kgf/mm$^2$) | 73.6 | 84.9 | 73.9 | 68.4 |
| Tensile strength (MPa) | 722 | 833 | 725 | 671 |
| Knot pull tensile strength (kgf/mm$^2$) | 52.1 | 52.2 | 37.6 | 36 |
| Knot pull tensile strength (MPa) | 511 | 512 | 369 | 353 |
| Break elongation (%) | 19.5 | 24.0 | 27.5 | 27.1 |
| Young's Modulus (GPa) | 2.09 | 2.19 | 1.88 | 2.14 |
| Molecular wt (Mw) of fiber (Da) | 206,591 | 185,456 | 203,738 | 212,634 |
| Molecular wt (Mn) of fiber (Da) | 29,555 | 30,858 | 26,667 | 29,739 |
| Polydispersity of fiber | 6.99 | 6.01 | 7.64 | 7.15 |

Example 21: Properties of Films Prepared from PBS-Malic Acid Copolymer Blended with Poly-4-Hydroxybutyrate PBS-malic acid copolymer was solution blended with poly-4-hydroxybutyrate (P4HB) in different mass ratios in chloroform, and the resultant blends cast to form films. After drying of the films, the films were melt pressed to a uniform thickness between heated platens, and dog bones were punched out of the films for tensile testing. The ratios of the PBS copolymer to P4HB are shown in Table 19, and the tensile properties were measured for the blends. The properties of the blends were compared to those of the PBS copolymer alone, and the P4HB homopolymer. As is evident from Table 19, the tensile modulus of the blends increased as the percentage of PBS copolymer in the blend increased. Breaking strength of the blends generally decreased as the percentage of PBS copolymer in the blend was increased, although the change was small when lower amounts of the PBS copolymer were present in the blend. Elongation at break of the films decreased as the percentage of the PBS copolymer in the blended film was increased. In addition to the results shown in Table 19, the following results were also observed: (i) a slight depression of the melting temperature of PBS copolymer and P4HB was observed in blends when the PBS copolymer was added to P4HB or vice versa, and (ii) crystallization of P4HB occurred faster and at a higher temperature when 10% PBS copolymer was added to P4HB. The results demonstrate that addition of PBS or copolymer thereof increases the crystallization rate of P4HB, which is useful in processing P4HB, for example, by melt spinning or injection molding.

TABLE 19

Properties of films prepared from blends of PBS-malic copolymer and P4HB

| | Percent PBS-malic copolymer in blend with P4HB | | | | | | |
|---|---|---|---|---|---|---|---|
| | 0 | 10 | 25 | 50 | 75 | 90 | 100 |
| Modulus (MPa) | 168 | 287 | 334 | 225 | 275 | 333 | 487 |
| Stress at Break (MPa) | 46 | 48 | 47 | 48 | 47 | 36 | 33 |
| Extension at Break (%) | 183 | 165 | 160 | 197 | 145 | 95 | 51 |

Example 22: Preparation of Knitted Monofilament Mesh Implants with Fibers of Different Diameters The method described in Example 5 was used to prepare knitted monofilament mesh implants of monofilament fiber produced from PBS-malic acid copolymer with 3 different diameter sizes (0.175, 0.13 and 0.106 mm) using the method disclosed in Example 2. Multiple samples of each fiber size were knit into mesh, and the average property values of the meshes were calculated for each fiber size, and are reported in Table 20. (MD is machine direction, CMD is cross-machine direction.) Elongation at 16 N/cm was measured using Standard Test Method for Bursting Strength of Fabrics Constant-Rate-of-Extension (CRE) Ball Burst Test. Tear resistance was measured by ASTM-D1938.

TABLE 20

Properties of Monofilament Meshes Prepared from PBS-Malic Copolymer Monofilament Fibers of Different Diameters

| Property | Mesh 1 | Mesh 2 | Mesh 3 |
|---|---|---|---|
| Monofilament Diameter (mm) | 0.175 | 0.13 | 0.106 |
| Burst Strength (kgf) | 21.863 | 11.616 | 8.964 |
| Elongation at 16 N/cm (%) | 15.41 | 11.14 | 12.52 |
| Suture pull-out strength (MD, kgf) | 3.86 | 2.08 | 1.424 |
| Suture pull-out strength (CMD, kgf) | 4.496 | 1.41 | 1.118 |
| Tear resistance (MD, kgf) | 2.919 | 1.46 | 2.01 |
| Tear resistance (CMD, kgf) | 4.022 | 2.53 | 1.43 |
| Stiffness (MD, TSU) | 0.201 | 0.091 | 0.055 |
| Stiffness (CMD, TSU) | 0.236 | 0.086 | 0.066 |
| Minor pore size (mm$^2$) | 0.125 | 0.12 | 0.07 |
| Major pore size (mm$^2$) | 0.589 | 0.514 | 0.485 |
| Thickness (mm) | 0.613 | 0.457 | 0.387 |
| Areal density (g/m2) | 129.85 | 67.2 | 50.18 |
| Tween-20 (wt %) | 0.036 | 0.069 | 0.064 |
| Polymer Mw (kDa) | 189 | 193 | 185 |

Example 23: Film Extrusion of Succinic Acid-1,4-Butanediol-Malic Acid Copolyester Succinic acid-1,4-butanediol-malic acid copolyester (Tepha lot 180333) with weight average molecular weight of 184 kDa, Tm=115° C., (melt flow rate (MFR) at 190° C./2.16 kgf of 5 g/10 min) was dried under vacuum overnight to less than 0.01% (w/w) water. Dried pellets of the polymer were fed into an extruder barrel of an American Khune 1½" single screw extruder (24:1 L:D, 3:1 compression) equipped with a Zenith type metering pump (0.16 cc/rev) and a Cloeren 14" MasterFlex™ 2100 extrusion die. The 4 heating zones of the extruder were set at 75° C., 165° C., 180° C. and 180° C. The Coloeren die was heated to 210° C. The film line with fitted with 3 chilled horizontal rolls stack set at a temperature of 20° C. and run at 1.4 meter per minute. Molten film was allowed to cast on the first, wrap around the middle roll and castoff the third roll. The resulting film measured 250 mm wide×1.5 mm thick. Dog bones were cut from the film and tensile properties measured. The results are shown in Table 21.

TABLE 21

Tensile data of PBS Copolymer film prepared by extrusion

| Dog bone Dimensions mm² | Tensile Break Kg | Tensile Stress MPa | Break Elongation % | Young's Modulus MPa |
|---|---|---|---|---|
| 1.5 × 5 | 33.4 | 43.20 | 146 | 949 |
| 1.5 × 5 | 35.67 | 46.64 | 86 | 989 |

We claim:

1. An implant comprising a polymeric composition, wherein the polymeric composition comprises a 1,4-butanediol unit and a succinic acid unit, wherein:
    (a) the polymeric composition has a weight average molecular weight of 75,000 to 250,000 Da,
    (b) the implant has been formed at least in part by melt processing of the polymeric composition; and
    (c) the implant is a mesh.

2. The implant of claim 1, wherein the polymeric composition has a weight average molecular weight of 150,000 to 250,000 Da.

3. The implant of claim 1, wherein the polymeric composition has a polydispersity between 1 and 10.

4. The implant of claim 3, wherein the polymeric composition has a polydispersity between 2 and 8.

5. The implant of claim 1, wherein the implant has one or more of the following properties:
    (i) a tensile strength of 400 MPa to 2,000 MPa,
    (ii) Young's Modulus of 600 MPa to 5 Gpa,
    (iii) elongation to break of 10 to 150%,
    (iv) tenacity greater than 4 grams per denier but less than 14 grams per denier, an elongation to break of between 15% and 50%, and a denier per filament between 1 and 10 when the implant comprises a multifilament yarn,
    (v) tensile strength between 400 MPa and 1200 MPa, a Young's Modulus of less than 5.0 Gpa, and an elongation to break of 10% to 50% when the implant comprises a monofilament fiber,
    (vi) a burst strength of 0.1 to 100 kgf, suture pullout strength of at least 5 N, or 0.5-20 kgf, areal density of 5 to 800 g/m², thickness of 0.05-5 mm, pores with average pore diameters between 5 μm and 5 mm, Taber stiffness of 0.01-19 TSU, tear resistance of 0.1 to 40 kgf, and pore size between 0.001 to 10 mm², when the implant is a monofilament mesh, multifilament mesh, woven mesh, or nonwoven mesh.

6. The implant of claim 1, wherein the implants are formed at least in part by melt extrusion, melt blowing, melt spinning, film extrusion, tube extrusion, spunbonding, fused filament fabrication, fused pellet deposition, or melt extrusion deposition.

7. The implant of claim 1, wherein the implants are formed, at least in part, by orienting the polymeric composition after melt processing.

8. The implants of claim 7, wherein the implants have one or more of the following properties:
    (i) a tensile strength of 400 MPa to 2,000 MPa,
    (ii) Young's Modulus of 600 MPa to 5 GPa,
    (iii) elongation to break of 10 to 150%,
    (iv) tenacity greater than 4 grams per denier but less than 14 grams per denier, an elongation to break of between 15% and 50%, and a denier per filament between 1 and 10 when the implant comprises a multifilament yarn,
    (v) tensile strength between 400 MPa and 1200 MPa, a Young's Modulus of less than 5.0 GPa, and an elongation to break of 10% to 50% when the implant comprises a monofilament fiber,
    (vi) a burst strength of 0.1 to 100 kgf, suture pullout strength of at least 5 N, or 0.5-20 kgf, areal density of 5 to 800 g/m², thickness of 0.05-5 mm, pores with average pore diameters between 5 μm and 5 mm, Taber stiffness of 0.01-19 TSU, tear resistance of 0.1 to 40 kgf, and pore size between 0.001 to 10 mm², when the implant is a monofilament mesh, multifilament mesh, woven mesh, or nonwoven mesh.

9. The implant of claim 1, wherein the implant is selected from the group comprising: surgical mesh, mesh suture, hernia repair device, breast reconstruction device, mastopexy implant, sling, ligament or tendon repair device, cardiovascular patch, and device for lifting tissues.

10. An implant comprising a polymeric composition, wherein the polymeric composition comprises a 1,4-butanediol unit and a succinic acid unit, wherein:
    (a) the polymeric composition has a weight average molecular weight of 20,000 to 250,000 Da, and
    (b) the polymeric composition has not been oriented during processing of the implant.

11. The implant of claim 10, wherein the polymeric composition has a weight average molecular weight of 50,000 to 250,000 Da.

12. The implant of claim 10, wherein the polymeric composition has a polydispersity between 1 and 10.

13. The implant of claim 12, wherein the polymeric composition has a polydispersity between 2 and 8.

14. The implant of claim 10, wherein the implant has one or more of the following properties:
    (i) a tensile strength of 30 to 60 MPa,
    (ii) an elongation to break of 40 to 200%,
    (iii) a Young's Modulus of 0.03 to 5 GPa,
    (iv) a yield strength of 0.02 to 2 GPa, and
    (v) a torsional strength of 10-20 Ncm.

15. The implant of claim 10, wherein the implant is formed at least in part by molding, injection molding, compression molding, solvent casting, 3D printing, solution processing, solution bonding of fibers, dry spinning, film casting, lamination, thermoforming, pultrusion, electrospinning, centrifugal spinning, coating, dip coating, phase separation, particle leaching, leaching, latex processing, printing of slurries and solutions using a coagulation bath, or printing using a binder solution and granules of powder.

16. The implant of claim 10, wherein the implant is selected from the group comprising: orthopedic implant, screw, bone screw, interference screw, pin, ACL screw, clip, clamp, nail, medullary cavity nail, bone plate, bone substitute, including bone plate, tack, fastener, suture fastener, rivet, staple, fixation device, bone void filler, suture anchor, bone anchor, meniscus anchor, meniscal implant, intramedullary rod and nail, joint spacer, interosseous wedge implant, osteochondral repair device, spinal fusion device, spinal fusion cage, bone plug, cranioplasty plug, plug to fill or cover a trephination burr hole, orthopedic tape, including knitted and woven tape, and device for treatment of osteoarthritis, surgical mesh, hernia mesh, mastopexy mesh, breast reconstruction mesh, sling, device to lift tissue, and drug delivery device.

* * * * *